United States Patent [19]
Chrusciel et al.

[11] Patent Number: 5,977,169
[45] Date of Patent: Nov. 2, 1999

[54] SUBSTITUTED TETRONIC ACIDS USEFUL FOR TREATING HIV AND OTHER RETROVIRUSES

[76] Inventors: Robert A. Chrusciel, 519 Cherryview Dr., Portage, Mich. 49002; Linda L. Maggiora, 4400 Glenrose Terrace, Kalamazoo, Mich. 49008; Suvit Thaisrivongs, 5659 Swallow, Kalamazoo, Mich. 49002; James M. Tustin, 7681 Cottonwood, Richland, Mich. 49083; Clark W. Smith, 6429 Torrington Rd., Kalamazoo, Mich. 49009; Ruben A. Tommasi, 1 Plantation Rd., Whitehouse Station, N.J. 07960; Paul A. Aristoff, 1650 Brookmoor La., Kalamazoo, Mich. 49002; Harvey I. Skulnick, 1745 Old Deer Run, Kalamazoo, Mich. 49009; W. Jeffrey Howe, 1021 Edgemoor Ave., Kalamazoo, Mich. 49008; Gordon L. Bundy, 7622 Ravenswood Dr., Portage, Mich. 49002

[21] Appl. No.: 08/604,937
[22] PCT Filed: Sep. 7, 1994
[86] PCT No.: PCT/US94/09533
§ 371 Date: Jul. 28, 1997
§ 102(e) Date: Jul. 28, 1997
[87] PCT Pub. No.: WO95/07901
PCT Pub. Date: Mar. 23, 1995

Related U.S. Application Data

[63] Continuation-in-part of application No. 08/238,820, May 6, 1994, abandoned, which is a continuation-in-part of application No. 08/123,029, Sep. 17, 1993, abandoned.

[51] Int. Cl.$^6$ .............. A61K 31/34; A61K 31/335; A61K 31/415; A61K 31/505
[52] U.S. Cl. .............. 514/473; 514/274; 514/278; 514/312; 514/314; 514/336; 514/382; 514/395; 514/397; 514/462; 514/471; 549/265; 549/313; 544/316; 546/16; 546/17; 546/284.4; 548/251; 548/304.7; 548/340.1
[58] Field of Search .................. 549/265, 313; 548/251, 304.7, 340.1; 546/16, 172, 284.4; 544/316; 514/274, 278, 312, 314, 336, 382, 395, 397, 462, 471, 473

[56] References Cited

FOREIGN PATENT DOCUMENTS

| | | |
|---|---|---|
| 0 202 589 A2 | 11/1986 | European Pat. Off. ...... C07D 307/62 |
| 0259707 | 3/1988 | European Pat. Off. .................. 307/60 |
| 0 365 329 | 4/1990 | European Pat. Off. ...... C07D 307/60 |
| 0 480 624 A1 | 4/1992 | European Pat. Off. .... C07D 295/088 |
| 0534907 | 3/1993 | European Pat. Off. .................. 31/365 |
| 4-211676 | 8/1992 | Japan . |
| 05043568 | 2/1993 | Japan ....................... 307/60 |
| 93/04055 | 3/1993 | WIPO ......................... C07D 307/60 |
| WO94/11361 | 5/1994 | WIPO ..................................... 309/38 |

OTHER PUBLICATIONS

Rehse, K., et al., *Arch. Pharm.*, 311, pp. 986–992 (1978).
Rehse, K., et al., *Arch. Pharm.*, 312, pp. 164–168 (1979).
Rehse, K., et al., *Arch. Pharm.*, 315, pp. 052–056 (1982).
*J. Synthetic Org. Chem.*, Japan, 44, 2, pp. 127–(1986).
Vekemans, J., et al., *Tetrahedron Letters*, 28, 20, pp. 2299–2300 (1987).
Roggo, B., et al.,*J. of Antibiotics*, 47, 2, pp. 136–142 (1994).
Roggo, B., et al.,*J. of Antibiotics*, 47, 2, pp. 143–147 (1994).
Lang, M., et al., *Arch. Pharm.*, 326, pp. 921–924 (1993).
CA, 91:68274b (1979).
CA, 98:119144p (1983).
CA, 90:185907a (1979).
CA, 90:114925u (1979).
CA, 55:16687, f.
Fell, S.C.M. et al, *J.C.S. Chem Comm.*, "Synthesis of 4–Substituted Tetronic Acids: Multicolanic Acid," pp. 81–2 (1979).
CA, 34:2378, f (1963).
CA, 118:45729r (1993).
Sibi, M.P. et al, *Synthetic Communications*, 22(6), "A Convenient Synthesis of 3–Alkyltetronic Acids from 3–Acyltetronic Acids," 809–816 (1992).
Arai, K., et al., *Chem. Pharm. Bull.*, 37(12), "Metabolites of *Penicillium italicum* Wehmer: Isolation and Structures . . . " 3229–3235 (1989).
Wakabayashi, H., et al., *Chemistry Letters*, "Synthesis of Optically Active Litsenolide C," 875–878 (1987).
Buck, J., et al, *J. Chem. Soc. Perkin Trans.* 1, "Directed Metallations of 4–Ethylidenetetronic Acid O–Methyl Ether . . . ," 2399–2405 (1985).
Wanwagenen, B.C. et al. *Tetrahedron*, 42(4), "Native American Food and Medicidnal Plans 7 . . . ," 1117–1122 (1986).
CA, 97:109463g (1982).

(List continued on next page.)

*Primary Examiner*—Amelia Owens
*Attorney, Agent, or Firm*—Thomas A. Wootton

[57] ABSTRACT

This invention comprises novel substituted tetronic acid type compounds, 2, 4(3H, 5H)-furandiones, that are useful for the inhibition of the HIV protease enzyme. The compounds may be useful for the treatment of a person with AIDS or AIDS related diseases. The compounds may be used in the attempt to retard the further replication of any retrovirus containing the aspartyl protease enzyme. Compounds are represented by the formula below.

Formula 1

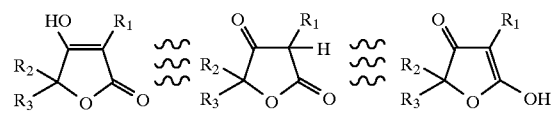

25 Claims, No Drawings

OTHER PUBLICATIONS

Anderson, J.R., et al, *J.C.S. Perkin I*, 1, "Metabolites of the Higher Fungi. Part 19[1] . . . " 215–221 (1982).

CA, 87:184299e (1977).

Damon, R.E., et al., *Tetrahedron Letters,* No. 32, "A General Synthesis of 2–Alkyl Tetronic Acids," 2749–2752 (1976).

Gudgeon, J.A., et al, *Bioorganic Chemistry,* 8, "The Structures and Biosynthesis of Multicolanic . . . " 311–322 (1979).

Gudgeon, J.A., et al, *J.C.S. Chem. Commun.,* "Use of Singly and Doubly Labelled $^{13}$C–Acetate . . . ," 636–638 (1974).

Sudo, R., et al, *J. Org. Chem.,* 32(6), "Synthesis of Carolic Acid," 1844–1846.

CA registry No. 6232–63–9 CA index name, 2,4(3H, 5H)–Furandione,3–(2–iminoethyl)–5–methyl–(8CI, 9CI).

CA, 63:13064, a (1965).

SUBSTITUTED TETRONIC ACIDS USEFUL FOR TREATING HIV AND OTHER RETROVIRUSES

The present application is a 371 (national phase) patent application of International Patent Application No. PCT/U.S.94/09,533, International Filing Date Sep. 7, 1994, which is a continuation-in-part patent application of U.S. patent application Ser. No. 08/238,820, filed May 6, 1994, now abandoned, which is a continuation-in-part patent application of U.S. patent application Ser. No. 08/123,029, filed Sep. 17, 1993, now abandoned.

BACKGROUND OF THE INVENTION

1. Field of the Invention

This invention comprises novel substituted tetronic acid type compounds, 2,4-(3H,5H)-furandiones, that are useful for the inhibition of the HIV protease enzyme. The compounds may be useful for the treatment of a person with AIDS or AIDS related diseases. The compounds may be used in the attempt to retard the further replication of any retrovirus containing the aspartyl protease enzyme.

2. Information Disclosure

WO 93/04055, published Mar. 4, 1993, inventor Dolak, Lester, et al. A tetronic acid useful for the inhibition of HIV-protease.

EP 0,259,707-A2 published Mar. 16, 1988, assigned to Takeda Chemical; Terao, Shinji et al., Hydroxybutenolide Derivatives useful for scavenging active oxygen species.

JP 05043568-A (90JP-202268) published Feb. 23, 1993, assigned to Takeda Chemical, disclosing tetronic acids used to treat inflammatory diseases.

Rehse, K., et al., "Anticoagulant Activity of 3,5-Disubstituted Tetronic Acids," *Arch. Pharm.* (Weinheim) Vol. 311, pp. 986–992 (1978).

Rehse, K., and Wagenknecht, J., "Mass Spectrometric Investigation of Anticoagulant 3-(1-Arylpropyl)-tetronic Acids," *Arch. Pharm.* (Weinheim), Vol. 312, pp. 164–168 (1979).

Rehse, K., et al., "Protein Binding of Drugs Determined by Continuous Ultrafiltration, III: Protein Binding of Anticoagulant Tetronic Acids," *Arch. Pharm.* (Weinheim) Vol. 315, pp. 052–056 (1982).

EP 0,534,907-A1, (92JP-276543) published Mar. 31, 1993, assigned to Nippon Zoki Pharmaceutical disclosing 2-(5H)-furanones to treat auto-immune diseases.

*J. Synthetic Org. Chem.* Japan, Vol. 44, No. 2, pp. 127—(1986),

Vekemans, J., "An Efficient Synthesis of (S)-5-Hydroxymethyl-2(5H)-Furanone" *Tetrahedron Letters,* Vol. 28, No. 20, pp. 2299–2300 (1987),

*J. Org. Chem.,* Vol. 46, pp. 2299—(1981),

Kokai Number Hei-4-211676, published Aug. 3, 1992; Yoji, Shirokura. A tetronic acid useful as a vasodilator.

Roggo, B. E., et al., "3-Alkanoyl-5-Hydroxymethyl Tetronic Acid Homologues and Resistomycin: New Inhibitors of HIV-1 Protease, I. Fermentation, Isolation and Biological Activity" *J. of Antibiotics,* Vol. 47, No. 2, pp. 136–142 (February 1994).

Roggo, B. E., et al., "3-Alkanoyl-5-Hydroxymethyl Tetronic Acid Homologues and Resistomycin: New Inhibitors of HIV-1 Protease, II. Structure Determination" *J. of Antibiotics,* Vol. 47, No. 2, pp. 143–147 (February 1994).

Lang, Marc and Roesel, Johannes, "HIV-1 Protease Inhibitors: Development, Status and Potential Role in the Treatment of AIDS," Archives of Pharmacy, Vol. 326, pp. 921–924 (1993). Undisclosed tetronic acid-type compounds thought to be possible HIV-1 protease inhibitor.

Chemical Abstracts, Vol. 98: 119144p (1983) page 20, anticoagulant activity of 3-arylalkyl-5-phenyl tetronic acids. 10 tetronic acid derivatives. Registry number of one compound is 80936-00-1, CA index name, 2(5H)- Furanone, 3-(1-(4-chlorophenyl)ethyl)-4-hydroxy-5-methyl- (9CI).

Chemical Abstracts, Vol. 90: 185907a (1979) page 575, Mass spectrometric investigation of anticoagulant 3-(1-arylpropyl) tetronic acids. Tetronic acid derivatives. Registry number of one compound, 69354-72-9, CA index name, 2(5H)- Furanone, 4-hydroxy-5-methyl-3-(1-phenylpropyl)- (9CI).

Chemical Abstracts, Vol. 90: 114925u (1979) page 28, Anticoagulant activity of 3-5-disubstituted tetronic acids. Tetronic acid derivatives. Registry number of one compound, 69354-71-8, CA index name, 2(5H)- Furanone, 3-(1-(4-chlorophenyl)propyl)-4-hydroxy-5-methyl-(9CI).

Chemical Abstracts, Vol. 55, Column 16687, paragraph f, disclosure of 3-(1-aminoethyl)-5-methyltetronic acid. Registry number 89910-36-1. CA index name, valeric acid, 2-(1-aminoethyl)-4-hydroxy-3-oxo, gamma. -lactone (6CI, 7CI).

Fell, S. C. M. et al. "Synthesis of 4Substituted Tetronic Acids: Multicolanic Acid." *J. Chem. Soc., Chem. Commun.,* Vol. 2, pp. 81–2 (1979).

Chemical Abstracts, Vol. 34, Alicyclic Compounds (1963), Column 2378, paragraph f, disclosure of ethyl and methyl benzyltetronic acid. Registry number 91910-33-7. CA index name, valeric acid, 2 ethyl-4-hydroxy-3-oxo-5-phenyl, gamma. -lactone (7CI).

Chemical Abstracts, Vol. 118: 45729r (1993) page 457, vasodilators containing terpenes, Registry number 145298-30-2, -29-9, -28-8, -27-7 CA index names, 2(5H)- Furanone, 3-(3,7-dimethyl-2,6-octadienyl)-4-hydroxy-5-(3-methyl-2-butenyl)- (9CI); 2(5H)- Furanone, 3-(3,7-dimethyl-2,6-octadienyl)-4-methoxy-5-(3-methyl-2-butenyl)- (9CI); 1,3-Pentanedione, 1-(4-(3,7-dimethyl-2,6-octadienyl)-2,5-dihydro-3-methoxy-2-(3-methyl-2-butenyl)-5oxo-2-furanyl)-4-methyl-2-(3-methyl-2-butenyl)- (9CI); 1,3-Pentanedione, 1-(4-(3,7-dimethyl-2,6-octadienyl)-2,5-dihydro- 3-hydroxy-2-(3-methyl-2-butenyl)-5-oxo-2-furanyl)-4methyl-2-(3-methyl-2-butenyl)-(9CI).

Sibi M. P. et al., "A Convenient Synthesis of 3-alkyltetronic acids from 3-acyltetronic acids." *Synthetic Communications,* Vol. 22, No. 6, pp. 809–816 (1992). Reductive deoxygenation of 3-acyltetronic acids provides 3-alkyltetronic acids in high yields. CA index names, 2(5H)-Furanone, 4-hydroxy-5-methyl-3-(2-methylpropyl)-, (S)-(9CI); 2(5H)-Furanone, 3-butyl-4-hydroxy-5-methyl, (S)-(9CI); 2(5H)-Furanone, 4-hydroxy-5-methyl-3-propyl-, (S)-(9CI); 2(5H)-Furanone, 3-ethyl-4-hydroxy-5-methyl, (S)-(9CI).

Arai K., et al. "Metabolites of *Penicillium italicum* Wehmer: Isolation and Structures of New Metabolites Including Naturally Occurring 4-ylidene-acyltetronic Acids, Italicinic Acid and Italicic Acid." *Chem Pharm. Bull.,* Vol. 37, No. 12, pp. 3229–3235 (1989). Isolation of 4 metabolites from bacteria. CA index name, 2-Furanacetic acid, 2,5-dihydro-3-hydroxy-4-(4-methyloctyl)-5-oxo- (9CI); 2-Furanacetic acid, 2,5-dihydro-3-hydroxy-4-(4-methyloctyl)-5-oxo- (9CI); Registry number 126228-72-6.

Wakabayashi, S., "Synthesis of Optically Active Litsenolide C." *The Chemical Society of Japan.* Chemistry Letters (5) (1987) pp. 875–878. CA index name, 2(5H)-Furanone, 4-hydroxy-5-methyl-3-tetradecyl- (R)- (9CI); Registry number 111722-91-9.

Buck, J. "Directed Metallations of 4-Ethylidenetetronic Acid O-Methyl Ether and its Derivatives as a Synthetic Entry to Natural 4-Oxyfuran-2-ones." *J. Chem. Soc. Perkin Trans* 1, Vol. 11, pp. 2399–2405 (1985).

Vanwagenen, B. S. "Native American Food and Medicinal Plants." *Tetrahedron*, Vol. 42, No. 4, pp. 1117–22. CA index names, 2(5H)-Furanone, 3-hexadecyl-4-hydroxy-5-methyl- (9CI); 2(5H)-Furanone, 3-tetradecyl-4-hydroxy-5-methyl- (9CI).

Chemical Abstracts, Vol. 97: 109463g (1982) Vinyl carbanions. Registry number 82495-62-3 CA index names, 2(5H)-Furanone, 3-(1-hydroxypropyl)-4-methoxy-5-(1-methylethyl)- (9CI).

Anderson J. R., "Metabolites of Higher Fungi . . ." *J. Chem. Soc., Perkin Trans.* 1, Vol. 1, pp. 215–221. CA index name, 2(5H)- Furanone, 3-ethyl-4-hydroxy-5-propyl- (9CI). CA registry number 818608-84-6.

Chemical Abstracts, Vol. 87: 184299e (1977). Synthesis of 3,5-idodecyltetronic acid by ozonolysis of 2,6-didodecyl-3,5-dihydroxy-1,4-benzoquinone. Registry number 64580-85-4 CA index name, 2(5H)-Furanone, 3,5-didodecyl-4-hydroxy- (9CI).

Damon, R. E., et al. "A general synthesis of 2-alkyltetronic acids" *Tetrahedron Letters*, Vol. 32, pp. 2749–2752. CA index names, 3-Furanacetic acid, 5-butyl-2,5-dihydro-4-hydroxy-2-oxo, methyl ester (9CI), 2(5H)-Furanone, 4-hydroxy-5-methyl-3-(2-methylpropyl)-(9CI); 2(5H)-Furanone, 3-ethyl-4-hydroxy-5-methyl-(9CI); 2(5H)-Furanone, 4-hydroxy-5-methyl-3-(2-propenyl)- (9CI);

Gudgeon, J. A., et al, "The Structures and Biosynthesis of Multicolanic, Multicolic, and Multicolosic Acis, Novel Tetronic Acid Metabolites of Penicillium Multicolor." *Bioorganic Chemistry*, Vol. 8, pp. 311–322 (1979). CA index name, 2-Furanacetic acid, 2,5-dihydro-3-hydroxy-4-(5-hydroxypentyl)-5-oxo- (9CI).

Gudgeon, J. A., et al, "Use of singly and doubly labeled carbon-13-acetate in the elucidation of the structures and biosynthesis of multicolic and multicolosic acids, new tetronic acids from Penicillium multicolor." *J. Chem. Soc., Chem. Commun.*, Vol. 16, pp. 636–8 (1974).

Sudo, R, et al, "Synthesis of Carolic Acid," *J. Org. Chem.*, Vol. 32, No. 6, pp. 1844–6. CA67(5): 21426s.

Chemical Abstracts, registry number 6232-63-9, CA index name. 2,4(3H,5H)-Furandione, 3-(2-iminoethyl)-5-methyl- (8CI, 9CI).

Chemical Abstracts, Vol. 63, Column 13064, paragraph "a," (1965), registry number 4697-28-3, CA index name, 2-Furanacetic acid, 4-heptyl-2,5-dihydro-3-hydroxy-.alpha.-(3-methyl-2-butenylidene)-5-oxo-. (9CI).

EP 0,365,329 A2, published Apr. 25, 1990, inventor, Matsumoto, Koichi; et al. Antiobiotics acitve against Anaerobic Bacteria, their production and use, and strains of Enterobacter producing the same.

EP 0,202,589 A2, published Nov. 26, 1986, inventor, Terao, Shinji; Ascorbic acid derivatives, production and use.

EP 0,480,624 A1, published Apr. 15, 1992, inventor, Treiber, Lazsio; et al., A novel dipeptide isostere inhibits HIV protease.

All the above documents are incorporated by reference herein.

3. Scientific and Historical Background

AIDS is a disease that is characterized by a severe immune deficiency primarily caused by a decreased cell-mediated immune response. Gottlieb, et al., N. Engl. J. Med., 305: 1425–1431 (1981); Masur, et al., N. Engl. J. Med., 305: 1431–1438 (1981). The immunodeficient state is characterized by a decrease in T4 lymphocytes, also known as helper T cells, a reversal of the normal T4<+>:T8<+> cell ratio, lymphopenia, and opportunistic infections often caused by *Pneumocystis carinii*. Some patients also develop lymphoma or Kaposi's sarcoma at increased incidence. The disease is usually fatal.

The virus that the majority of scientists believes causes AIDS, first identified in 1983, has been described by several names. It is the third known human T-lymphotropic virus (HTLV-III) and has the capacity to replicate within cells of the immune system and thereby lead to a profound destruction of T4<+> T-cells (or CD4<+> cells). See, e.g., Gallo, et al., Science, 224: 500–503 (1984), and Popovic, et al., Science, 224: 497–500 (1984). This retrovirus has been known as lymphadenopathy-associated virus (LAV) or AIDS-related virus (ARV) and, more recently, as human immunodeficiency virus (HIV).

Two distinct AIDS viruses, HIV-1 and HIV-2, have been described. HIV-1 is the virus originally identified in 1983 by Montagnier and co-workers at the Pasteur Institute in Paris. Montagnier, et al., Ann. de Virologie, 135 E: No. 1, 119–134 (1984), while HIV-2 was more recently isolated by Montagnier and his coworkers in 1986. Guyader, Nature, 326: 662–669 (1987). Additional distinct AIDS viruses may exist. As used herein, HIV is meant to refer to all of these viruses in a generic sense.

Retroviruses are enveloped RNA viruses. See, Hayward and Neel, Curr. Top. Microbiol. Immunol., 91: 217–276 (1981). The virus particle consists of a ribonucleoprotein core enclosed by an outer membrane envelope. Viral envelope glycoproteins protrude from the outer envelope. The viral genome consists of two identical single-stranded RNA molecules. Haseltine and Wong-Stall, Scientific American, 259: 52–62 (1988).

U.S. Pat. No. 4,724,232 claims a method of treating humans having AIDS utilizing 3-azido-3-deoxythymidine. On Mar. 20, 1987, the FDA approved the use of this compound, zidovudine (AZT), to treat AIDS patients with a recent initial episode of pneumocystis carinil pneumonia and for treatment of patients infected with the virus with an absolute CD4 lymphocyte count of less than 200/mm$^3$ in the peripheral blood. AZT is a known inhibitor of viral reverse transcriptase.

Reverse transcriptase (RT) is an enzyme unique to retroviruses that catalyzes the conversion of viral RNA into double stranded DNA. Blockage at any point during the transcription process, by AZT or any other aberrant deoxynucleoside triphosphate incapable of elongation, is postulated to have dramatic consequences relative to viral replication, although no such therapy has yet been perfected.

Another approach to AIDS therapy focuses on the principal receptor on the T4 cell that the HIV seems to prefer to bind to, the so-called CD4 molecule. This molecule, a nonpolymorphic surface glycoprotein, has been targeted as an intervention point in AIDS therapy. Fisher, et al., Nature, 331: 76–78 (1988); Hussey, et al., Nature, 331: 78–81 (1988); and Deen, et al., Nature, 331: 82–84 (1988).

The present invention concerns a different therapeutic target in AIDS, the inhibition of the viral protease (or proteinase) that is essential for processing HIV-fusion polypeptide precursors. In HIV and several other retroviruses, the proteolytic maturation of the gag (group specific antigen) and gag/pol (polymerase) fusion polypeptides (a process indispensable for generation of infective viral particles) has been shown to be mediated by a protease that is, itself, encoded by the pol region of the viral genome. Yoshinaka, et al., Proc. Nad. Acad. Sci., USA, 82: 1618–1622 (1985); Yoshinaka, et al., J. Virol., 55: 870–873 (1985); Yoshinaka, et al., J. Virol., 57: 826–832 (1986).

The protease (or proteinase) enzyme, consisting of only 99 amino acids, is among the smallest enzyme known. Nutt, et al., Proc. Natl. Acad. Sci., USA, 85: 7129–7133 (1988). Pearl and Taylor, Nature, 329: 351–354 (1987). The three-dimensional structure and mechanism of the enzyme is known. Pearl and Taylor, Nature, 329: 351–354 (1987). Active HIV protease has been expressed in bacteria (e.g., Darke, et al., J. Biol. Chem., 264: 2307–2312 (1989)) and chemically synthesized. Schneider and Kent, Cell, 54: 363–368 (1988); and Nutt, et al., Proc. Natl. Acad. Sci., USA, 85: 7129–7133 (1988). All the above documents are incorporated by reference herein.

This invention comprises novel tetronic acid type compounds that are useful for the inhibition of the HIV protease enzyme. The compounds may be useful for the treatment of a person with AIDS or AIDS related diseases. The compounds may be used in the attempt to retard the further replication of any retrovirus containing the aspartyl protease enzyme or the human retrovirus such as HIV or of treating human cell systems especially including a patient infected with a human retrovirus containing the aspartyl protease enzyme.

SUMMARY OF THE INVENTION

This invention comprises novel compounds. The compounds may be used for the treatment of AIDS. Compositions and formulations including the compounds are also described. Methods for the preparation of a medicament and methods for the treatment of AIDS using the compounds are described. Also described are the procedures for making the compounds. The compounds are represented by the structures shown in formula 1, Formula 1

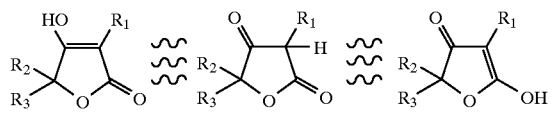

wherein 3 tautomers of the same structure are shown, wherein $R_1$ is a) —CH—($C_3$—$C_6$ cycloalkyl)$_2$,
b) diphenylmethyl,
c) diphenylethyl,
d) diphenylethenyl,
e) diphenylpropyl,
f) phenylcyclobutyl;
g) —CH($CH_2$-phenyl)$_2$,
h) -5,6,7,8,9-tetrahydro-5H-benzocycloheptenyl,
i) -1,2,3,4-tetrahydro-naphthalenyl, substituted with zero, one (1) or two (2) —O— ($C_{1-6}$ alkyl) or —$CH_3$, -continued j) 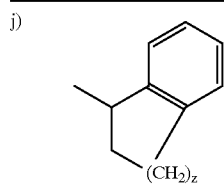

Formula 2, k) 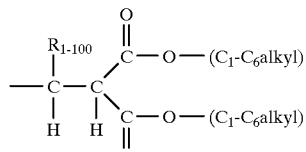

Formula 9, l) 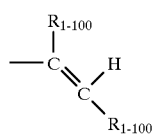

Formula 10, m) 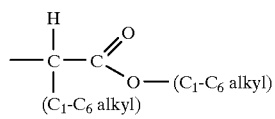

Formula 15, n) 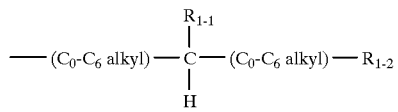

Formula R1A, o) 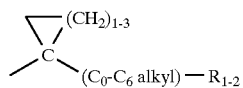

Formula R1B, or p) 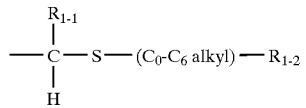

Formula R1C;

wherein $R_{1-1}$ is
a) —$C_{1-10}$ alkyl,
b) —$C_{2-10}$ alkenyl,
c) —$C_{3-7}$ cycloalkyl,
d) —($C_{1-6}$ alkyl)—($C_{3-7}$ cycloalkyl),
e) —$CH_2$—C(O)—O—((H or ($C_{1-6}$ alkyl)),
f) —($C_{0-6}$ alkyl)—$R_{1-100}$,
g) —($C_{0-6}$ alkyl)—$R_{1-500}$, or
h) —($C_{0-6}$ alkyl)—CH=CH—$R_{1-100}$;
wherein $R_{1-2}$ is
a) -halo,
b) -trifluoromethyl, c) —$C_{3-7}$ cycloalkyl,
d) —$C_{2-10}$ alkenyl,
e) —($C_{0-6}$ alkyl)—(($CH_2$)$CH_2$—O—)$_q$—($C_{1-6}$ alkyl),
f) —$R_{1-100}$,
g) —C(O)—O—($C_{0-6}$ alkyl)—$R_{1-100}$,
h) —$R_{1-500}$,
i) —C(O)—$R_{1-500}$ or
j) —O—$R_{1-500}$;
wherein $R_{1-100}$ is
  a) phenyl, substituted with zero (0) to three (3) of $RA_1$,
  b) naphthyl, substituted with zero (0) to three (3) of $RA_1$,
  c) biphenyl, substituted with zero (0) to three (3) of $RA_1$,
  d) perhalophenyl;
wherein $R_{1-500}$ is
  a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$-$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
  a) halo,
  b) —H
  c) —N-methyl-piperazino,
  d) —$C_{1-8}$ alkyl, substituted with zero (0) to three (3) halo,
  e) —$C_{2-8}$ alkenyl,
  f) —$C_{3-7}$ cycloalkyl,
  g) —($C_{0-6}$ alkyl)—$RA_{1-RA-12}$
  h) —($C_{1-6}$ alkyl)-phenyl, substituted with zero (0) to three (3) $RA_{1-RA-120}$;
  i) —($C_{0-6}$ alkyl)-$RA_{1-RA-15}$
  j) —OH,
  k) —O—($C_{1-6}$ alkyl), substituted with zero (0) to three (3) hydroxy,
  l) —($C_{1-6}$ alkyl)—O—($C_{1-6}$ alkyl), substituted with zero (0) to three (3) hydroxy,
  m) —O—($C_{2-7}$ alkenyl), substituted with zero (0) to three (3) hydroxy,
  n) —($C_{1-6}$ alkyl)—O—($C_{2-7}$ alkenyl), substituted with zero (0) to three (3) hydroxy,
  o) (o-) or (m-) —O—($C_{1-6}$ alkyl)—CH=$CH_2$,
  p) —($CH_2$—O)$_q$—$C_{1-3}$ alkyl,
  q) —O—($CH_2CH_2$—O—)$_q$—$CH_3$,
  r) —CH(O),
  s) —C(O)—($C_{1-6}$ alkyl),
  t) —C(O)—O—($C_{1-6}$ alkyl),
  u) —C(O)—N(H or $C_{1-5}$ alkyl)$_2$,
  v) —$SO_3H$,
  w) —$SO_2$—$RA_{1-RA-12}$,
  x) —($C_{0-6}$ alkyl)—$SO_2$—($C_{0-6}$ alkyl)—$RA_{1-RA-12}$,
  y) —($C_{0-6}$ alkyl)—$SO_2$—($C_{0-6}$ alkyl)—$RA_{1-RA-15}$,
  z) —CN,
  a1) —$NH_2$,
  b1) —NH—($C_{1-6}$ alkyl),
  c1) -mono or -di($C_{1-6}$ alkyl)amino,
  d1) -diethylamino,
  e1) —($C_{0-6}$ alkyl)—NH—C(NH(H or $C_{1-5}$ alkyl))=NCN,
  f1) —($C_{0-6}$ alkyl)—NH—C(NH(H or $C_{1-5}$ alkyl))=$CHNO_2$,
  g1) —($C_{0-6}$ alkyl)—NH—C(O)—O—($C_{1-6}$ alkyl)—$RA_{1-RA-12}$
  h1) —($C_{0-6}$ alkyl)—NH—C(O)—O—($C_{1-6}$ alkyl)—$RA_{1-RA-15}$,
  i1) —($C_{0-6}$ alkyl)—NH—C(O)—N($C_{1-3}$ alkyl)$_2$,
  j1) —($C_{0-6}$ alkyl)—NH—C(O)—NH—$RA_{1-RA-12}$,
  k1) —($C_{0-6}$ alkyl)—NH—$SO_2$—NH—$RA_{1-RA-12}$,
  l1) —NH—C(O)—NH—$SO_2$—$RA_{1-RA-2}$,
  m1) —($C_{0-6}$ alkyl)—NH—C($SCH_3$)=$CHNO_2$,
  n1) —($C_{0-6}$ alkyl)—NH—C($SCH_3$)=NCN),
  o1) —NH—AA—$P_1$,
  p1) —$NO_2$,
  q1) —($C_{0-6}$ alkyl)—$N_3$, $$-NH-SO_2 \atop \diagdown \diagup \atop (CH_2)_u$$

s1) —N=C—(NH—CH($C_{2-6}$ alkyl)$_2$)$_2$,
  t1) —$NR_{40}R_{41}$,
  u1) —NH—P(O)($C_{1-4}$ alkyl)—$RA_{1-RA-12}$,
  v1) —NH—P(O)($RA_{1-RA-12}$—$RA_{1-RA-12}$,
  w1) —NH—P(O)(O—$R_{11}$)—($RA_{1-RA-12}$),
  x1) —NH—C(S)—NH—$R_{42}$, or
  y1) —NH—C(S)—$CH_2$—$R_{42}$;
  z1) —($C_{1-6}$ alkyl)-$G_{1-1}$—CH=CH—$RA_{1-RA-12}$,
  a2) —($C_{0-6}$ alkyl)-$G_{1-1}$—CH=CH—$RA_{1-RA-15}$,
  b2) —($C_{0-6}$ alkyl)-$G_{1-1}$—($C_{1-10}$ alkyl), substituted with zero (0) to three (3) halo,
  c2) —($C_{0-6}$ alkyl)-$G_{1-1}$—($C_{2-5}$ alkenyl),
  d2) -$G_{1-1}$—CH(($C_{1-6}$ alkyl))—NH—C(O)—O—($C_{1-6}$ alkyl),
  e2) -$G_{1-1}$—CH(($C_{1-6}$ alkyl)—$RA_{1-RA-15}$)—NH—C(O)—O—($C_{1-6}$ alkyl),
  f2) -$G_{1-1}$—($C_{1-6}$ alkyl)—CH(NH—C(O)—O—($C_{1-6}$ alkyl)—$RA_{1-RA-12}$)—C(O)—O—($C_{1-6}$ alkyl)—$RA_{1-RA-12}$,
  g2) —($C_{0-6}$ alkyl)-$G_{1-2}$—($C_{1-12}$ alkyl),
  h2) -$G_{1-2}$—($C_{1-6}$ alkyl)-halo,
  i2) -$G_{1-2}$—($C_{1-6}$ alkyl)—$NH_2$,
  j2) -$G_{1-2}$—($C_{1-6}$ alkyl)—NH—C(O)—O—($C_{1-6}$ alkyl),
  k2) -$G_{1-2}$—($C_{1-6}$ alkyl)—CH(NH—C(O)—O—($C_{1-6}$ alkyl))—C(O)—O—($C_{1-6}$ alkyl),
  l2) -$G_{1-2}$—($C_{0-6}$ alkyl)—CH(NH—C(O)—O—($C_{1-6}$ alkyl))—($C_{1-6}$ alkyl)—$RA_{1-RA-15}$,
  m2) -$G_{1-2}$—($C_{1-6}$ alkyl)—CH($NH_2$)—C(O)—OH,
  n2) -$G_{1-2}$—($C_{1-6}$ alkyl)—C(O)—O—($C_{1-6}$ alkyl),
  o2) -$G_{1-2}$—($C_{1-6}$ alkyl)—($C_{3-6}$ cycloalkyl),
  p2) —($C_{0-6}$ alkyl)—$G_{1-2}$—($C_{0-6}$ alkyl)—$RA_{1-RA-12}$,
  q2) —(C0-6 alkyl)—$G_{1-2}$—($C_{0-6}$ alkyl)—$RA_{1-RA-15}$,
  r2) -$G_{1-2}$—($C_{0-6}$ alkyl)—O—$RA_{1-RA-12}$,
  s2) —($C_{0-6}$ alkyl)-$G_{1-2}$—($C_{0-6}$ alkyl)—O—($C_{1-6}$ alkyl),
  t2) -$G_{1-2}$—($C_{1-6}$ alkyl)—C(O)—$RA_{1-RA-15}$,
  u2) -$G_{1-2}$—($C_{1-6}$ alkyl)—C(O)—NH—($C_{1-6}$ alkyl)—$RA_{1-RA-15}$, v2) -$G_{1-2}$—($C_{1-6}$ alkyl)—S—$RA_{1-RA-15}$,
w2) —($C_{0-6}$ alkyl)-$G_{1-2}$—O—($C_{1-6}$ alkyl)—$RA_{1-RA-12}$,
x2) —($C_{0-6}$ alkyl)-$G_{1-2}$—O—($C_{1-6}$ alkyl)—$RA_{1-RA-15}$,
y2) -$G_{1-2}$—CH—$CH_2$.
z2) -$G_{1-2}$—CH═CH—$RA_{1-RA-12}$,
a3) -$G_{1-2}$—N($R_{42}$)$_2$,
b3) -$G_{1-2}$—$NH_2$,
c3) -$G_{1-2}$—($C_{1-6}$ alkyl)-phthalimido,
d3) -$G_{1-2}$-(pentafluoro)-phenyl,
e3) -$G_{1-2}$—($C_{1-6}$ alkyl)-bicyclo[2.2.1]heptane,
f3) -$G_{1-2}$—H, or
g3) -($C_{2-6}$ alkyl)—$R_{30}$;
wherein $G_{1-1}$ is
 a) —NH—C(O)—,
 b) —NH—$SO_2$—,
 c) —NH—C(O)—NH—, or
 d) —$SO_2$—NH—;
wherein $G_{1-2}$ is
 a) —NH—C(O)—,
 b) —C(O)—NH—,
 c) —NH—$SO_2$—,
 d) —$SO_2$—NH—,
 e) —NH—$SO_2$—NH—,
 f) —C(O)—O—,
 g) —O—C(O)—,
 h) —N(($C_{1-6}$ alkyl)—$RA_{1-RA-12}$)—C(O)—,
 i) —NH—C(O)—NH,
 j) —N(($C_{1-6}$ alkyl)—$RA_{1-RA-12}$)—$SO_2$—, or
 k) —N(($C_{0-6}$ alkyl)—($C_{1-6}$ alkyl))—$SO_2$—;
wherein $RA_2$ and $RA_3$ are defined independently and are the same as $RA_1$;
wherein $RA_{1-RA-12}$ is
 a) -phenyl, substituted with zero (0) to three (3) $RA_{1-RA-12-AXA}$, or
 b) -naphthyl, substituted with zero (0) to three (3) $RA_{1-RA-12-AXA}$;
wherein $RA_{1-RA-15}$ is
a 5- or 6-membered saturated or unsaturated ring containing from one (1) to four (4) heteroatoms selected from the group consisting of nitrogen, oxygen and sulfur, and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;
wherein $RA_{1-RA-120}$, $RA_{2-RA-120}$ and $RA_{3-RA-120}$, are defined independently and are
 a) —$C_1$–$C_4$ alkyl,
 b) —$C_1$–$C_3$ alkoxy,
 c) -dimethylamino,
 d) -diethylamino,
 e) —$CF_3$,
 f) —CN,
 g) -halo,
 h) —$NH_2$,
 i) —OH,
 j) —$SO_2$—$NH_2$, or
 k) —C(O)—$NH_2$;
wherein $RA_{1-RA-12-AXA}$ or $RA_{1-RA-15-AXA}$ are independent and are,
 a) —H
 b) -halo,
 c) —$NO_2$,
 d) —CN,
 e) —($C_{1-10}$ alkyl), substituted with zero (0) to three (3) halo,
 f) —($C_{0-6}$ alkyl)-phenyl, substituted with zero (0) to three (3) halo or hydroxy,
 g) —OH,
 h) —O—$C_{1-5}$ alkyl,
 i) —($C_{0-6}$ alkyl)—O—($C_{1-6}$ alkyl), substituted with zero (0) to three (3) halo or hydroxy,
 j) —($C_{0-6}$ alkyl)—O—($C_{2-7}$ alkenyl), substituted with zero (0) to three (3) halo or hydroxy,
 k) —CH(O),
 l) —C(O)—($C_{1-6}$ alkyl),
 m) —C(O)OH,
 n) —C(O)O—($C_{1-5}$ alkyl),
 o) —C(O)—N(H or $C_{1-6}$ alkyl)$_2$,
 p) —$NH_2$,
 q) —NH—($C_{1-6}$ alkyl),
 r) -mono or di —($C_{1-6}$ alkyl)amino,
 s) —NH—OH,
 t) —NH—C(O)—($C_{1-3}$ alkyl),
 u) —($C_{0-6}$ alkyl)—NH—C(O)-phenyl,
 v) —($C_{0-6}$ alkyl)—NH—$SO_2$-phenyl,
 w) —($C_{0-6}$ alkyl)—N═N-phenyl, substituted with zero (0) or one (1) —N($C_1$–$C_3$ alkyl)$_2$, or
 x) —$SO_2$-phenyl, substituted with zero (0) to three (3) $C_1$–$C_5$ alkyl;
wherein $R_2$ is
 a) —H,
 b) —$C_{1-6}$ alkyl,
 c) —($C_{1-6}$ alkyl)—$C_{3-7}$ cycloalkyl,
 d) —($C_{2-10}$ alkenyl)
 e) —($C_{1-6}$ alkyl)—$R_{2-100}$,
 f) —($C_{1-6}$ alkyl)—$R_{2-500}$,
wherein $R_{2-100}$ is independent of and defined the same as $R_{1-100}$ wherein $RA_1$ is $RA_2$;
wherein $R_{2-500}$ is independent of and defined the same as $R_{1-500}$ wherein $RA_1$ is $RA_2$;
wherein $RA_2$ is independent of and defined the same as $RA_1$;
wherein $R_3$ is
 a) —$C_{2-10}$ alkyl, substituted with zero (0) to five (5) halo,
 b) —$C_{3-7}$ cycloalkyl,
 c) —$C_{2-10}$ alkenyl,
 d) —($C_{1-6}$ alkyl)—CH═$CH_2$
 e) —($C_{0-6}$ alkyl)—C(O)—O—($C_{1-6}$ alkyl),
 f) —($C_{0-6}$ alkyl)—($CH_2CH_2$—O—)$_q$—($C_{1-6}$ alkyl),
 g) —($C_{1-6}$ alkyl)—$R_{3-4}$,
 h) —($C_{0-6}$ alkyl)—CH═CH—$R_{3-4}$,
 i) —($C_{2-10}$ alkenyl)—$R_{3-4}$,
 j) —($C_{0-6}$ alkyl)—CH($R_{3-6}$)—($C_{0-6}$ alkyl)—$R_{3-4}$,
 k) —($C_{0-6}$ alkyl)—CH($R_{3-6}$)—($C_{2-6}$ alkenyl)—$R_{3-4}$,
 l) —($C_{0-6}$ alkyl)—C(O)—N(H or —$C_{1-5}$ alkyl)—($C_{0-6}$ alkyl)—$R_{3-4}$,
 m) —($C_{1-6}$ alkyl)—N(H or —$C_{1-5}$ alkyl)—C(O)—$R_{3-4}$,
 n) —($C_{1-6}$ alkyl)—N(H or —$C_{1-5}$ alkyl)—C(O)—($C_{0-6}$ alkyl)—$R_{3-4}$,
 o) —$R_{3-100}$, except when $R_{3-100}$ is phenyl and $R_1$ is 1-phenyl-propyl,
p) —$R_{3-500}$,
q) —CH($R_{3-6}$)—CH($R_{3-6}$)—$R_{3-4}$,
r) —CH($C_{0-6}$ alkyl)—($C_{0-6}$ alkyl)—$G_{3-1}$—($C_{0-6}$ alkyl)—$RA_{3-RA-12}$, or
s) —CH($C_{0-6}$ alkyl)—($C_{0-6}$ alkyl)—$G_{3-1}$—($C_{0-6}$ alkyl)—$RA_{3-RA-15}$;
wherein $G_{3-1}$ is
  a) —NH—C(O)—,
  b) —NH—SO$_2$—,
  c) —NH—CO—NH—, or
  d) —SO$_2$—NH—;
wherein, $R_{3-4}$ is
  a) -trifluoromethyl;
  b) -halo,
  c) —($C_{1-6}$ alkyl)
  d) —$C_{3-7}$ cycloalkyl,
  e) —$C_{2-10}$ alkenyl,
  f) —($C_{0-6}$ alkyl)—(CH$_2$CH$_2$—O—)$_q$—($C_{1-6}$ alkyl),
  g) —OH,
  h) —O—($C_{1-6}$ alkyl),
  i) —O—$R_{3-500}$,
  j) —C(O)—$R_{3-500}$,
  k) —C(O)—OH,
  l) —C(O)—O—($C_{1-6}$ alkyl),
  m) —C(O)—O—($C_{0-6}$ alkyl)—$R_{3-100}$,
  n) —$R_{3-100}$, or
  o) —$R_{3-500}$;
wherein $R_{3-6}$ is
  a) —OH,
  b) —$C_{1-10}$ alkyl,
  c) —($C_{0-6}$ alkyl)—$C_3$-$C_7$ cycloalkyl,
  d) —($C_{1-6}$ alkyl)—CH=CH$_2$,
  e) —($C_{0-6}$ alkyl)—$R_{3-4}$,
  f) —($C_{1-6}$ alkyl)—$R_{3-100}$, or
  g) —($C_{1-6}$ alkyl)—$R_{3-500}$;
wherein $R_{3-9}$ is
  a) —($C_{1-6}$ alkyl),
  b) —($C_{2-7}$ alkenyl),
  c) —($C_{0-5}$ alkyl)—($C_{3-7}$ cycloalkyl),
  d) —($C_{0-6}$ alkyl)—$RA_{3-RA-12}$, or
  e) —($C_{0-6}$ alkyl)—$RA_{3-RA-15}$;
wherein $R_{3-100}$ is independent of and defined the same as $R_{1-100}$ wherein $RA_1$ is $RA_3$;
wherein $R_{3-500}$ is independent of and defined the same as $R_{1-100}$ wherein $RA_1$ is $RA_3$;
wherein $RA_3$ is independent of and defined the same as $RA_1$;
wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively,
or wherein $R_2$ and $R_3$ can be taken together to form a ring comprised of the following groups,
  a) —($C_{5-9}$ cycloalkyl),
  b) —($C_{5-9}$ cycloalkyl) substituted with one to three: —OH, =N—OH, =O, $R_{3-9}$,
  c) —($C_{1-5}$ alkyl substituted with zero to two $R_{3-9}$)—$R_{23}$—($C_{1-5}$ alkyl substituted with zero to two $R_{3-9}$)—,
  d) a 5- or 6-membered saturated ring containing one (1) or two (2) oxygen atoms, or or e) a double bond represented by the formula shown below;

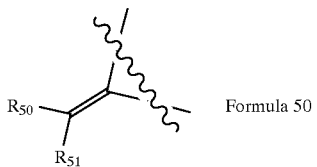

Formula 50 wherein $R_{3-9}$ is
  a) —($C_{1-6}$ alkyl),
  b) —($C_{2-7}$ alkenyl),
  c) —($C_{0-6}$ alkyl)—($C_{3-7}$ cycloalkyl),
  d) —($C_{0-6}$ alkyl)—$RA_{3-RA-12}$, or
  e) —($C_{0-6}$ alkyl)—$RA_{3-RA-15}$;
wherein $R_{11}$ is
  a) —H,
  b) —$C_1$-$C_4$ alkyl,
  c) —($RA_{3-RA-12}$), or
  d) pharmaceutically acceptable salts,
wherein $R_{23}$ is
  a) —O—,
  b) —C(O)—,
  c) —N(H)—,
  d) —N($R_{3-9}$)—,
  e) —N(C(O)—$R_{3-9}$)—, or
  f) —N(C(O)—O—$R_{3-9}$);
wherein $R_{30}$ is
  a) -morpholino,
  b) -piperidino,
  c) -piperazino,
  d) —OR$_{40}$,
  e) -halo,
  f)

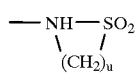

g) —NR$_{40}$R$_{41}$;
wherein $R_{40}$ and $R_{41}$ are defined independently and are,
  a) —H,
  b) —$C_1$-$C_4$ alkyl,
  c) phenyl, substituted with zero (0) to three (3) $RA_{1-RA-120}$,
wherein $R_{42}$ is
  a) —$C_1$-$C_4$ alkyl,
  b) -phenyl, substituted with zero (0) to three (3) $RA_{1-RA-120}$, or
  c) —($C_{0-6}$ alkyl)-phenyl, substituted with zero (0) to three (3) $RA_{1-RA-120}$;
wherein $RA_{2-RA-120}$ and $RA_{3-RA-120}$ are independent of and defined the same as $RA_{1-RA-120}$;
wherein $R_{50}$ and $R_{51}$ are defined independently and are
  a) —(H or $C_{1-6}$ alkyl),
  b) —($C_{0-6}$ alkyl)—$RA_{3-RA-12}$, or
  c) —($C_{0-6}$ alkyl)—$RA_{3-RA-15}$;
wherein AA is an amino acid residue,
wherein $P_1$ is hydrogen or a nitrogen protecting group, wherein m and n are independently zero (0) to five (5) inclusive, wherein p and q are independently one (1) to five (5) inclusive, wherein z is one (1) to three (3) inclusive; and pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42}$)$_2$, or —$G_{1-2}$—NH$_2$, then $G_{1-2}$ is NOT, —C(O)—NH—, —NH—SO$_2$—, —SO$_2$—NH—, —NH—SO$_2$—NH—, —C(O)—O—, —NH—C(O)—NH, —N(($C_{1-6}$ alkyl)—$RA_{1-RA-12}$)—SO$_2$—, or —N(($C_{0-6}$ alkyl)—($C_{1-6}$ alkyl))—SO$_2$—.

Additional subgroups of formula I are also disclosed, wherein $R_1$ is a)
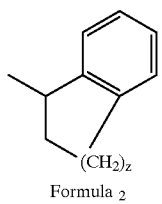
Formula 2 b)
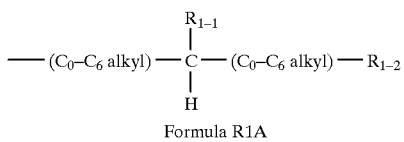
Formula R1A c)
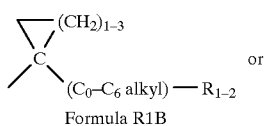
or
Formula R1B d)
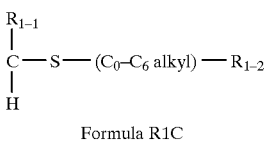
Formula R1C wherein $R_{1-1}$ is
a) —($C_{1-5}$ alkyl),
b) —($C_{2-5}$ alkenyl),
c) —($C_{3-7}$ cycloalkyl),
d) —($C_{3-5}$ cycloalkyl),
e) -cyclopropyl,
—($C_{1-5}$ alkyl)—($C_{3-7}$ cycloalkyl),
g) —$R_{1-100}$, or
h) —($C_1$–$C_5$ alkyl)—$R_{1-100}$;
wherein $R_{1-2}$ is —$R_{1-100}$, or —$R_{1-500}$;
wherein $RA_1$ is
a) —H,
b) —($C_{1-5}$ alkyl),
c) —($C_{2-5}$ alkenyl),
d) —OH,
e) —O—($C_{1-5}$ alkyl),
f) —O—($C_{2-5}$ alkenyl),
g) —C(O)OH,
h) —C(O)($C_{1-5}$ alkyl),
i) —C(O)—$RA_{1-3}$,
wherein $RA_{1-3}$ is any N-terminus substituted amino acid,
j) —C(O)—N(H)$RA_{1-1}$,
k) —CN,
l) —NH$_2$ (para or meta positions),
m) —N(H)($C_{1-5}$ alkyl) (para or meta positions),
n) —N($C_{1-5}$ alkyl)$_2$,
o) —N(H)$RA_{1-4}$,
wherein RA1-4 is any C-terminus substituted amino acid,
p) —N(H)C(O)—$RA_{1-1}$ (para or meta positions),
q) —N(H)C(O)—O—$RA_{1-1}$ (para or meta positions),
r) —N(H)(SO$_2$)—$RA_{1-2}$,
s) —N($C_{1-6}$ alkyl)(SO$_2$)—$RA_{1-2}$,
t) —N(CH$_3$)(SO$_2$)—$RA_{1-2}$,
u) —NO$_2$,
v) —PO$_3$H,
w) —SO$_3$H,
x) —SO$_2$NH$_2$,
y) —($C_{0-6}$ alkyl)—SO$_2$—$RA_{1-RA-12}$,
z) —($C_{0-6}$ alkyl)—SO$_2$—$RA_{1-RA-15}$,
a1) -halo,
b1) —$RA_{1-RA-12}$, or
c1) —$RA_{1-RA-15}$;
wherein $RA_{1-1}$ is
a) —($C_{1-5}$ alkyl),
b) —($C_{1-5}$ alkyl)—($C_{3-7}$ cycloalkyl),
c) —($C_{1-5}$ alkyl)—C(O)—O—($C_{1-5}$ alkyl),
d) —($C_{1-5}$ alkyl)—NH$_2$,
e) —($C_{1-5}$ alkyl)—N(H)C(O)—O—($C_{1-5}$ alkyl),
f) —($C_{1-5}$ alkyl)—C(H)(NH$_2$)—C(O)OH,
g) —$RA_{1-RA-12}$,
h) —$RA_{1-RA-15}$,
i) —($C_{1-5}$ alkyl)-$RA_{1-RA-12}$,
j) —($C_{1-5}$ alkyl)—$RA_{1-RA-15}$,
k) —($C_{1-5}$ alkyl)—O—$RA_{1-RA-12}$,
l) —($C_{1-5}$ alkyl)—O—$RA_{1-RA-15}$,
m) —C(O)—$RA_{1-1-3}$,
wherein $RA_{1-1-3}$ is any N-terminus amino acid,
n) —N(H)—$RA_{1-1-4}$,
wherein RA-1-1-4 is any C-terminus amino acid,
p) —($C_{1-5}$ alkyl)—$R_{1-500}$,
q) —($C_{1-5}$ alkyl)—C(O)—$R_{1-500}$, or
r) —($C_{1-5}$ alkyl)—C(O)—N(H)(($C_1$–$C_5$ alkyl)—$R_{1-500}$),
wherein $RA_{1-2}$ is
a) —($C_{1-5}$ alkyl),
b) —$RA_{1-RA-12}$,
c) —$RA_{1-RA-15}$,
d) —($C_{1-5}$ alkyl)—$RA_{1-RA-12}$,
e) —($C_{1-5}$ alkyl)—$RA_{1-RA-15}$,
f) —($C_{1-5}$ alkyl)—O—$RA_{1-RA-12}$,
g) —($C_{1-5}$ alkyl)—O—$RA_{1-RA-15}$,
wherein $RA_{1-RA-12}$ is
a) phenyl, substituted with zero (0) to three (3) $RA_{1-RA-1-AXA}$, or b) naphthyl, substituted with zero (0) to three (3) $RA_{1-RA-12-AXA}$;

wherein $RA_{1-RA-15}$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;

wherein $RA_{1-RA-12-AXA}$ or $RA_{1-RA-15-AXA}$ are are independent and are,
 a) —H,
 b) -halo,
 c) —NO$_2$,
 d) —CN,
 e) —(C$_{1-10}$ alkyl), substituted with zero (0) to three (3) halo,
 f) —(C$_{0-6}$ alkyl)-phenyl, substituted with zero (0) to three (3) hydroxy or halo,
 g) —OH,
 h) —O—C$_{1-5}$ alkyl,
 i) —(C$_{0-6}$ alkyl)—O—(C$_{1-6}$ alkyl), substituted with zero (0) to three (3) hydroxy or halo,
 j) —(C$_{0-6}$ alkyl)—O—(C$_{2-7}$ alkenyl), substituted with zero (0) to three (3) hydroxy or halo,
 k) —CH(O),
 l) —C(O)—(C$_{1-6}$ alkyl),
 m) —C(O)OH,
 n) —C(O)O—(C$_{1-5}$ alkyl),
 o) —C(O)—N(H or C$_{1-6}$ alkyl)$_2$,
 p) —NH$_2$,
 q) —NH—(C$_{1-6}$ alkyl),
 r) mono or di —(C$_{1-6}$ alkyl)amino,
 s) —NH—OH,
 t) —NH—C(O)—(C$_{1-3}$ alkyl),
 u) —(C$_{0-6}$ alkyl)—NH—C(O)-phenyl,
 v) —(C$_{0-6}$ alkyl)—NH—SO$_2$-phenyl,
 w) —(C$_{0-6}$ alkyl)—N=N-phenyl, substituted with zero (0) or one (1) —N(C$_1$–C$_3$ alkyl)$_2$, or
 x) —SO$_2$-phenyl, substituted with zero (0) to three (3) C$_1$–C$_5$ alkyl;

wherein R$_2$ is
 a) —H,
 b) —(C$_{1-5}$ alkyl),
 c) —(C$_{3-4}$ alkyl),
 d) -n-propyl
 e) —(C$_{6-10}$ alkyl),
 f) —(C$_{2-5}$ alkenyl),
 g) —(C$_{6-10}$ alkenyl),
 h) —(C$_{1-5}$ alkyl)—(C$_{3-7}$ cycloalkyl), —i) —(C$_{1-5}$ alkyl)—R$_{2-100}$,
 j) —(C$_{1-5}$ alkyl)—R$_{2-500}$;

wherein RA$_2$ and RA$_3$ are independently defined and are independent of and defined the same as RA$_1$, wherein R$_3$ is
 a) —(C$_{1-5}$ alkyl),
 b) —(C$_{6-10}$ alkyl),
 c) —(C$_{2-5}$ alkenyl),
 d) —(C$_{6-10}$ alkenyl),
 e) —(C$_{1-6}$ alkyl)—CH=CH$_2$,
 f) —(C$_{1-5}$ alkyl)—(C$_{3-7}$ cycloalkyl),
 g) —(C$_{1-5}$ alkyl)—O—(CH$_2$CH$_2$O)$_q$—CH$_3$,
 h) —(C$_{1-6}$ alkyl)—R$_{3-4}$,
 i) —(C$_{2-6}$ alkenyl)—R$_{3-4}$,
 j) —CH(R$_{3-6}$)—R$_{3-4}$,
 k) —CH(R$_{3-6}$)—(C$_{1-6}$ alkyl)—R$_{3-4}$,
 l) —CH(R$_{3-6}$)—(C$_{2-6}$ alkenyl)—R$_{3-4}$,
 m) —R$_{3-100}$,
 n) —(C$_{1-5}$ alkyl)—R$_{3-100}$,
 o) —(C$_{3-4}$ alkyl)-RAX
 p) —H or —(C$_{1-5}$ alkyl),
 q) -n propyl-RAX,
 r) -3-phenylpropyl,
 s) —R$_{3-500}$,
 t) —(C$_{1-5}$ alkyl)—R$_{3-500}$,
 u) —(C$_{3-4}$ alkyl)—R$_{3-500}$,
 v) -n propyl-R$_{3-500}$,
 w) —C(H)(OH)—R$_{3-1}$,
 x) —(C$_{1-5}$ alkyl)—C(H)(OH)—R$_{3-1}$,
 y) —C(O)—R$_{3-1}$,
 z) —(C$_{1-5}$ alkyl)—C(O)—R$_{3-1}$,
 a1) —(C$_{1-5}$ alkyl)—N(H)R$_{3-1}$,
 b1) —(C$_{1-5}$ alkyl)—N((C$_{1-5}$ alkyl)((C$_{1-5}$ alkyl)—R$_{3-1}$),
 c1) —(C$_{1-5}$ alkyl)—N(H)C(O)—R$_{3-1}$,
 d1) —C(O)—N(H)R$_{3-1}$, or
 e1) —(C$_{1-5}$ alkyl)—C(O)—N(H)R$_{3-1}$;

wherein RAX is
 phenyl,
 benzyl, or
 phenyl or benzyl, substituted with one, two, or three of the following, —(C$_{1-5}$ alkyl), -hydroxy, —O—(C$_{1-5}$ alkyl), or -halo;

wherein R$_{3-1}$ is
 a) —(C$_{1-5}$ alkyl),
 b) —(C$_{2-5}$ alkenyl),
 c) —(C$_{1-5}$ alkyl)—(C$_{3-7}$ cycloalkyl),
 d) —(C$_{1-5}$ alkyl)—R$_{3-100}$, or
 e) —(C$_{1-5}$ alkyl)—R$_{3-500}$;

where R$_{3-4}$ is
 a) —OH,
 b) —O—(C$_{1-6}$ alkyl),
 c) —C(O)—OH,
 d) —C(O)—O—(C$_{1-6}$ alkyl),
 e) —(C$_{1-6}$ alkyl),
 f) —(C$_{3-6}$ cycloalkyl),
 g) —R$_{3-100}$, or
 h) —R$_{3-500}$;

wherein R$_{3-9}$ is
 a) —(C$_{1-6}$ alkyl),
 b) —(C$_{0-6}$ alkyl)—RA$_{3-RA-12}$, or
 c) —(C$_{0-6}$ alkyl)—RA$_{3-RA-15}$;

wherein R$_{3-100}$ is independent of and defined the same as R$_{1-100}$;

wherein R$_{3-500}$ is independent of and defined the same as R$_{1-500}$;

wherein RA$_3$ is independent of and defined the same as RA$_1$;

wherein R$_2$ and R$_3$ can be taken together to form a ring comprised of the following groups,
 a) (C$_{5-9}$ cycloalkyl), b) (C$_{5-9}$ cycloalkyl) substituted with one to two —R$_{3-9}$, or
c) —(C$_{1-5}$ alkyl substituted with zero to one R$_{3-9}$)—R$_{23}$—(C$_{1-5}$ alkyl);
wherein R$_{3-9}$ is
   a) —(C$_{1-6}$ alkyl),
   b) —(C$_{0-6}$ alkyl)—RA$_{3-RA-12}$, or
   c) —(C$_{0-6}$ alkyl)—RA$_{3-RA-15}$;
or wherein R$_2$ and R$_3$ can be taken together to form a double bond represented by formula 50, shown below,

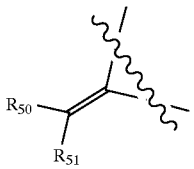

and pharmaceutical salts, including bis salts, thereof, wherein all other variables are as previously defined.
Additional subgroups are wherein R$_1$ is formula R1A.
Additional subgroups are wherein RA$_1$ is
   a) —H,
   b) —(C$_{1-5}$ alkyl),
   c) —O—(C$_{1-5}$ alkyl),
   d) —C(O)—RA$_{1-3}$,
wherein RA$_{1-3}$ is any N-terminus substituted amino acid;
   e) —C(O)—N(H)RA$_{1-1}$,
   f) —NH$_2$ (para or meta positions),
   g) —N(H)(C$_{1-5}$ alkyl) (para or meta positions),
   h) —N(C$_{1-5}$ alkyl)$_2$,
   i) —N(H)RA$_{1-4}$,
wherein RA$_{1-4}$ is any C-terminus substituted amino acid,
   j) —N(H)C(O)—RA$_{1-1}$ (para or meta positions),
   k) —N(H)(SO$_2$)—RA$_{1-2}$,
   l) —N(C$_{0-6}$ alkyl)(SO$_2$)—RA$_{1-2}$,
   m) —N(CH$_3$)(SO$_2$)—RA$_{1-2}$,
   n) —NO$_2$,
   o) —SO$_2$NH$_2$,
   p) —(C$_{1-3}$ alkyl)—SO$_2$—RA$_{1-RA-12}$,
   q) —(C$_{1-3}$ alkyl)—SO$_2$—RA$_{1-RA-15}$, or
   r) -halo;
wherein RA$_{1-1}$ is
   a) —(C$_{1-5}$ alkyl),
   b) —(C$_{1-5}$ alkyl)—C(O)—O—(C$_{1-5}$ alkyl),
   c) —(C$_{1-5}$ alkyl)—NH$_2$,
   d) —(C$_{1-5}$ alkyl)—N(H)C(O)—O—(C$_{1-5}$ alkyl),
   e) —(C$_{1-5}$ alkyl)—C((H)(NH$_2$))—C(O)OH,
   f) —RA$_{1-A-12}$,
   g) —RA$_{1-RA-15}$,
   h) —(C$_{1-5}$ alkyl)—RAX,
   i) —(C$_{1-5}$ alkyl)—O—RAX,
   j) —C(O)—RA$_{1-1-3}$,
wherein RA$_{1-1-3}$ is any N-terminus amino acid,
   k) —N(H)—RA$_{1-1-4}$, or
wherein RA$_{1-1-4}$ is any C-terminus amino acid,
   l) —R$_{1-500}$;
wherein RA$_{1-2}$ is
   a) —RAX,
   b) —(C$_{1-5}$ alkyl)—RAX,
   c) —(C$_{1-5}$ alkyl)—O—RAX,
   d) —RA$_{1-RA-12}$,
   e) —RA$_{1-RA-15}$,
   f) —(C$_1$–C$_5$ alkyl)—RA$_{1-RA-12}$,
   g) —(C$_1$–C$_5$ alkyl)—RA$_{1-RA-15}$,
   h) —(C$_1$–C$_5$ alkyl)—O—RA$_{1-RA-12}$, or
   i) —(C$_1$–C$_5$ alkyl)—O—RA$_{1-RA-15}$;
wherein RA$_2$ and RA$_3$ are defined independently and are independent of and defined the same as RA$_1$.
Additional subgroups are wherein R$_2$ is
   a) —(C$_{1-5}$ alkyl),
   b) —(C$_{3-4}$ alkyl),
   c) -n-propyl
   d) —(C$_{6-10}$ alkyl),
   e) —(C$_{2-5}$ alkenyl),
   f) —(C$_{6-10}$ alkenyl),
   g) —(C$_{1-5}$ alkyl)—(C$_{3-7}$ cycloalkyl),
   h) —(C$_{1-5}$ alkyl)—R$_{2-100}$, or
   i) —(C$_{1-5}$ alkyl)—R$_{2-500}$;
wherein R$_3$ is
   a) —(C$_{1-5}$ alkyl),
   b) —(C$_{6-10}$ alkyl),
   c) —CH$_2$—CH=CH$_2$,
   d) —(C$_{1-5}$ alkyl)—(C$_{3-7}$ cycloalkyl),
   e) —(C$_{0-5}$ alkyl)—(CH$_2$CH$_2$—O)$_q$—CH$_3$,
   f) —(C$_{1-5}$ alkyl)—R$_{3-100}$,
   g) —(C$_{3-4}$ alkyl)—RAX,
   h) -n propyl-RAX,
   i) -3-phenylpropyl,
   j) —(C$_{1-5}$ alkyl)—R$_{3-500}$,
   k) —(C$_{3-4}$ alkyl)—R$_{3-500}$,
   l) -n propyl-R$_{3-500}$,
   m) —(C$_{3-4}$ alkyl)—R$_{3-100}$,
   n) —CH$_2$—RAX,
   o) -benzyl,
   p) —(C$_{3-4}$ alkyl)—R$_{3-500}$,
   q) —CH$_2$—R$_{3-500}$,
   r) —(C$_{1-5}$ alkyl)—C(H)(OH)—R$_{3-1}$,
   s) —(C$_{1-5}$ alkyl)—N(H)R$_{3-1}$,
   t) —(C$_{1-5}$ alkyl)—N((C$_{1-5}$ alkyl)(C$_{1-5}$ alkyl)—R$_{3-1}$),
   u) —(C$_{1-5}$ alkyl)—N(H)C(O)—R$_{3-1}$,
   v) —(C$_{1-5}$ alkyl)—C(O)—N(H)—R$_{3-1}$,
   w) —(C$_{2-6}$ alkenyl)—R$_{3-4}$,
   v) —CH(R$_{3-6}$)—R$_{3-4}$,
   y) —CH(R$_{3-6}$)—(C$_{1-6}$ alkyl)—R$_{3-4}$, or
   z) —CH(R$_{3-6}$)—(C$_{1-6}$ alkenyl)—R$_{3-4}$;
wherein R$_{3-1}$ is independent of and defined the same as R$_{1-1}$;
wherein R$_{3-2}$ is independent of and defined the same as R$_{1-2}$;
wherein R$_2$ and R$_3$ can be taken together to form a ring comprised of the following groups,
   a) (C$_{5-9}$ cycloalkyl),
   b) (C$_{5-9}$ cycloalkyl) substituted with one to two R$_{3-9}$,
   c) —(C$_{1-5}$ alkyl substituted with zero to one R$_{3-9}$)—R$_{23}$—(C$_{1-5}$ alkyl).
Additional subgroups are wherein R$_{1-100}$ is phenyl, substituted with zero (0) to three (3) of RA$_1$;
wherein R$_{2-100}$ and R$_{3-100}$ are defined independently and are independent of and defined the same as R$_{1-100}$,
Additional subgroups are wherein, R$_1$ is —CH(R$_{1-1}$)—R$_{1-2}$.

Additional subgroups are wherein $R_{1-1}$ is
a) —$(C_{1-5}$ alkyl),
b) —$(C_{3-5}$ cycloalkyl), or
c) -cyclopropyl;
wherein $RA_1$ is
a) —H,
b) —N(H)C(O)—$RA_{1-1}$ (para or meta positions),
c) —N(H)(SO$_2$)—$RA_{1-2}$,
d) —N(C$_{0-6}$ alkyl)(SO$_2$)—$RA_{1-2}$,
e) —N(CH$_3$)(SO$_2$)—$RA_{1-2}$,
f) —(C$_{1-3}$ alkyl)—SO$_2$—$RA_{1-RA-12}$, or
g) —(C$_{1-3}$ alkyl)—SO$_2$—$RA_{1-RA-15}$;
wherein $RA_2$ and $RA_3$ are defined independently and are independent of and defined the same as $RA_1$;
wherein $RA_{1-1}$ is
a) —(C$_{1-5}$ alkyl), or
b) —(C$_{1-5}$ alkyl)—C(H)(NH$_2$)—C(O)OH;
wherein RAX is phenyl;
wherein $R_2$ is
a) —(C$_{1-5}$ alkyl),
b) —(C$_{3-4}$ alkyl),
c) -n-propyl,
d) —(C$_{6-10}$ alkyl),
e) —(C$_{2-5}$ alkenyl),
f) —(C$_{6-10}$ alkenyl),
g) —(C$_{1-5}$ alkyl)—(C$_{3-7}$ cycloalkyl),
h) —(C$_{1-3}$ alkyl)—RAX, or
i) -phenylmethyl;
wherein $R_3$ is
a) —(C$_{1-5}$ alkyl),
b) —(C$_{1-5}$ alkyl)—$R_{3-100}$,
c) —(C$_{3-4}$ alkyl)—RAX,
d) -n propyl-RAX,
e) -3 phenyl propyl,
f) —(C$_{1-5}$ alkyl)—$R_{3-500}$,
g) -n propyl-$R_{3-500}$,
h) —CH($R_{3-6}$)—$R_{3-4}$,
i) —CH($R_{3-6}$)—(C$_{1-6}$ alkyl)—$R_{3-4}$,
j) —CH($R_{3-6}$)—(C$_{1-6}$ alkenyl)—$R_{3-4}$,
k) —(C$_{3-4}$ alkyl)—$R_{3-100}$,
l) —CH$_2$—RAX,
m) -benzyl,
n) —(C$_{3-4}$ alkyl)—$R_{3-500}$, or
o) —CH$_2$—$R_{3-500}$;
or wherein $R_2$ and $R_3$ can be taken together to form a ring comprised of the following groups,
a) (C$_{5-9}$ cycloalkyl),
b) (C$_{5-9}$ cycloalkyl)—$R_{3-9}$, or
c) —(C$_2$ alkyl substituted with zero to one $R_{3-9}$)—$R_{23}$—(C$_2$ alkyl).
Additional subgroups are wherein —$RA_{1-RA-12}$, —$RA_{2-RA-12}$, and —$RA_{3-RA-12}$ are defined independently as phenyl, cyanophenyl, fluorophenyl, naphthyl; or phenyl or naphthyl—substituted with 1 to 3 groups of —(C$_{1-6}$ alkyl), cyano, halo, hydroxy or —(C$_{1-6}$ alkoxy);
wherein —$RA_{1-RA-15}$, —$RA_{2-RA-15}$, and —$RA_{3-RA-15}$ are defined independently as pyridinyl, cyano-pyridinyl, quinolinyl, pyrimidinyl, quinazolinyl, benzimidazolyl, imidazolyl, methyl-imidazolyl, thiazolyl or purinyl; or pyridinyl, quinolinyl, pyrimidinyl, quinazolinyl, benzimidazolyl, intidazolyl, thiazolyl, or purinyl—substituted with 1 to 3 groups of —(C$_{1-6}$ alkyl), cyano, halo, hydroxy or —(C$_{1-6}$ alkoxy);
wherein $R_2$ and $R_3$ can be taken together to form a ring comprised of the following groups,
a) (C$_6$ cycloalkyl),
b) (C$_6$ cycloalkyl)—$R_{3-9}$, or
c) —(C$_2$ alkyl substituted with zero to one $R_{3-9}$)—$R_{23}$—(C$_2$ alkyl substituted with zero to one $R_{3-9}$)—.
Additional subgroups are wherein —$RA_{1-RA-12}$, is phenyl, fluorophenyl or cyanophenyl;
wherein —$RA_{1-RA-15}$, is
1-methyl-4imidazolyl, 2-pyridinyl, 5-cyano-2-pyridinyl, 2-quinolinyl, 8-quinolinyl, 2-pyrimidinyl, 2-quinazolinyl, 2-benzimidazolyl, 2-imidazolyl, 4-thiazolyl, 6-purinyl;
wherein $R_{2-100}$ and $R_{3-100}$ are defined independently and are,
phenyl,
benzyl, or
phenyl or benzyl, substituted with one, two, or three of the following, —(C$_{1-5}$ alkyl), -hydroxy, —O—(C$_{1-5}$ alkyl), or -halo.
Additional subgroups are wherein $R_2$ is
a) —(C$_{1-5}$ alkyl),
b) —(C$_{3-4}$ alkyl),
c) -n-propyl,
d) —(C$_{6-10}$ alkyl),
e) —(C$_{2-5}$ alkenyl),
f) —(C$_{6-10}$ alkenyl),
g) —(C$_{1-5}$ alkyl)—(C$_{3-7}$ cycloalkyl),
h) —(C$_{1-3}$ alkyl)—RAX, or
i) -phenylmethyl;
wherein $R_3$ is
a) —(C$_{1-5}$ alkyl),
b) —(C$_{1-5}$ alkyl)—$R_{3-100}$,
c) —(C$_{3-4}$ alkyl)—RAX,
d) -n propyl-RAX,
e) -3 phenyl propyl,
f) —(C$_{1-5}$ alkyl)—$R_{3-500}$,
g) -n propyl-$R_{3-500}$,
h) —CH($_{3-6}$)—$R_{3-4}$,
i) —CH($R_{3-6}$)—(C$_{1-6}$ alkyl)—$R_{3-4}$,
j) —CH($R_{3-6}$)—(C$_{1-6}$ alkenyl)—R
k) —(C$_{3-4}$ alkyl)—$R_{3-100}$,
l) —CH$_2$—RAX,
m) -benzyl,
n) —(C$_{3-4}$ alkyl)—$R_{3-500}$, or
o) —CH$_2$—$R_{3-500}$;
or wherein $R_2$ and $R_3$ can be taken together to form a ring comprised of the following groups,
a) (C$_{5-9}$ cycloalkyl),
b) (C$_{5-9}$ cycloalkyl) substituted with one to two $R_{3-9}$,
c) —(C$_{1-5}$ alkyl substituted with zero to one $R_{3-9}$)—$R_{23}$—(C$_{1-5}$ alkyl).
Additional subgroups are wherein $R_{2-100}$ and $R_{3-100}$ are defined independently and are,
a) phenyl, substituted with zero (0) to three (3) $RA_{2-RA-12-AXA}$, or
b) naphthyl, substituted with zero (0) to three (3) $RA_{2-RA-12-AXA}$;
wherein $R_{2-500}$ and $R_{3-500}$ are defined independently and are, a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{2\text{-}RA\text{-}15\text{-}AXA}$;

wherein $RA_{2\text{-}RA\text{-}12\text{-}AXA}$ or $RA_{2\text{-}RA\text{-}15\text{-}AXA}$ are are defined independently and are, a) —H,
b) -halo,
c) —$NO_2$,
d) —CN,
e) —$C_{1\text{-}10}$ alkyl, substituted with zero (0) to three (3) halo,
f) —($C_{0\text{-}6}$ alkyl)-phenyl, substituted with zero (0) to three (3) hydroxy or halo,
g) —OH,
h) —O—$C_{1\text{-}5}$ alkyl,
i) —($C_{0\text{-}6}$ alkyl)—O($C_{1\text{-}6}$ alkyl), substituted with zero (0) to three (3) hydroxy or halo,
j) —($C_{0\text{-}6}$ alkyl)—O—($C_{2\text{-}7}$ alkenyl), substituted with zero (0) to three (3) hydroxy or halo,
k) —CH(O),
l) —C(O)—($C_{1\text{-}6}$ alkyl),
m) —C(O)OH,
n) —C(O)O—($C_{1\text{-}5}$ alkyl),
o) —C(O)—N(H or $C_{1\text{-}6}$ alkyl)$_2$,
p) —$NH_2$,
q) —NH—($C_{1\text{-}6}$ alkyl),
r) mono or di —($C_{1\text{-}6}$ alkyl)amino,
s) —NH—OH,
t) —NH—C(O)—($C_{1\text{-}3}$ alkyl),
u) —($C_{0\text{-}6}$ alkyl)—NH—C(O)-phenyl,
v) —($C_{0\text{-}6}$ alkyl)—NH—$SO_2$-phenyl
w) ($C_{0\text{-}6}$ alkyl)—N=N-phenyl, substituted by zero (0) or one (1) —N($C_1$–$C_3$ alkyl)$_2$, or
x) —$SO_2$-phenyl, substituted with zero (0) to three (3) $C_1$–$C_5$ alkyl;

wherein $R_2$ and $R_3$ can be taken together to form a ring comprised of the following groups, a) ($C_{5\text{-}9}$ cycloalkyl),
b) ($C_{5\text{-}9}$ cycloalkyl) substituted with one $R_{3\text{-}9}$,
c) —($C_{1\text{-}5}$ alkyl substituted with zero to one $R_{3\text{-}9}$)—$R_{23}$—($C_{1\text{-}5}$ alkyl).

Additional subgroups are wherein $R_1$ is —CH($R_{1\text{-}1}$)—$R_{1\text{-}2}$, wherein $R_{3\text{-}1}$ is
a) —($C_{1\text{-}5}$ alkyl),
b) —($C_{2\text{-}5}$ alkenyl),
c) —($C_{1\text{-}2}$ alkyl)—($C_{3\text{-}7}$ cycloalkyl),
d) —($C_{1\text{-}2}$ alkyl)—$R_{3\text{-}100}$, or
e) —($C_{1\text{-}2}$ alkyl)—$R_{3\text{-}500}$;

wherein $R_{2\text{-}100}$ and $R_{3\text{-}100}$ are defined independently and are,
phenyl,
benzyl, or
phenyl or benzyl, substituted with one, two, or three of the following, —($C_{1\text{-}5}$ alkyl), -hydroxy, —O—($C_{1\text{-}5}$ alkyl), or -halo;

or wherein $R_2$ and $R_3$ can be taken together to form a ring comprised of the following groups, a) ($C_6$ cycloalkyl),
b) ($C_6$ cycloalkyl) substituted with one $R_{3\text{-}9}$, or
c) —($C_2$ alkyl substituted with zero to one $R_{3\text{-}9}$)—$R_{23}$—($C_2$ alkyl).

A pharmaceutical composition consisting of a pharmaceutically acceptable carrier and an effective amount of a compound of formula 1. The use of a compound of formula 1 to prepare a medicament for treating AIDS and diseases caused by all variants of HIV comprising administering an effective amount of a compound of formula 1 to a patient in need thereof. A new compound described by formula 1 and all the variations suggested by the various subgroups described. A new pharmaceutical composition, substantially as herein described. A substance or composition for a new use in a method of treatment, substantially as herein described. A substance or composition for use in a method for treating AIDS or a disease caused by a variant of HIV, said substnace or composition comprising a compound of formula 1 and said method comprising administering an effective amount of said substance or composition to a patient in need thereof.

Additional Description of the Invention

1. Definitions

The compounds of this invention are identified in two ways: by descriptive names and by reference to structures having various chemical moieties. The following terms may also be used and are defined below.

OPTIONALLY SUBSTITUTED. The term "optionally substituted" shall mean a group or radical that is substituted with halogen, lower alkyl, mono- or di(lower alkyl)-substituted lower alkyl, (lower alkyl)thio, halo-substituted lower alkyl, amino-substituted lower alkyl, mono- or di(lower alkyl)-substituted amino, lower alkenyl, lower alkynyl, halogen, lower alkoxy, aryloxy, aryl(lower alkyl), hydroxy, cyano, amino, mono- and di(lower alkyl)amino, or nitro and the like.

The parenthetical term ($C_n$-$C_m$) or ($C_{n\text{-}m}$) is inclusive such that a compound of ($C_1$–$C_8$) or ($C_{n\text{-}m}$) would include compounds of 0 to 8 carbons and their isomeric forms. The term $C_0$ of would mean no carbon atom or no carbon group in that particular position.

ALKYL. The parenthetical term ($C_n$-$C_m$) is inclusive such that a compound of ($C_1$–$C_8$) would include compounds of 0 to 8 carbons and their isomeric forms. The various carbon moieties are aliphatic hydrocarbon radicals and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl and isomeric forms thereof.

LOWER ALKYL. The term "lower alkyl" refers to branched or unbranched saturated hydrocarbon radicals having from one to six carbon atoms. Representatives of such groups are methyl, ethyl, n-propyl, isopropyl, n-butyl, isobutyl, sec-butyl, t-butyl, n-pentyl, isopentyl, hexyl, and the like.

(LOWER ALKYL)THIO. The term "(lower alkyl)thio" refers to a lower alkyl group as defined above, attached to the parent molecular moiety through a sulfur atom. Typical (lower alkyl)thio groups include methylthio, ethylthio, propylthio, iso-propylthio, and the like.

ALKOXY. Alkoxy as represented by —$OR_1$ when $R_1$ is ($C_1$–$C_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy and the like.

LOWER ALKOXY. The term "lower alkoxy" denotes an alkyl group as defined above, attached to the patent molecular moiety through an oxygen atom. Representatives of such groups include methoxy, ethoxy, butyoxy, pentoxy and the like.

ALKENYL. Alkenyl refers to a radical of an aliphatic unsaturated hydrocarbon having at least one double bond and includes both branched and unbranched forms such as ethenyl, ($-CH=CH_2$), 1-methyl-1-ethenyl, 1-propenyl, ($-CH_2-CH=CH_2$), 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl and the like.

ALKYNYL. Alkynyl refers to a monovalent branched or unbranched hydrocarbon radical containing at least one carbon-carbon triple bond, for example ethynyl, propynyl, and the like.

CYCLOALKYL. ($C_3-C_{10}$)cycloalkyl refers to a radical of a saturated cyclic hydrocarbon which includes alkyl-substituted cycloalkyl, such as cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl and cyclodecyl and the like. Each of these moieties may be substituted as appropriate.

HETEROALKYL. "Heteroalkyl" refers to alkyls as described above, only where one, two or three non-adjacent carbon atoms are replaced by heteroatoms such as nitrogen, sulfur and oxygen.

ARYL. Aryl refers to a 6 to 12 carbon atom base structure, one or two fused or nonfused aromatic rings, that may be optionally substituted or substituted with one to 3 hydroxy, $C_1-C_3$ alkoxy, $C_1-C_3$ alkyl, trifluoromethyl, fluoro, chloro, or bromo groups. Examples of "aryl" are: phenyl, m-methylphenyl, p-trifluoromethylphenyl, α-naphthyl, β-naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)-tolyl, 4isopropyl-2,6-xylyl, 3-propyl-4-ethylphenyl, (2,3,4-, 2,3,6-, or 2,4,5-) trimethylphenyl, (o-, m-, or p-)fluorophenyl, (o-, m-, or p-trifluoromethyl)phenyl, 4-fluoro-2,5-xylyl, (2,4, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-,)trifluorophenyl, (o-, m-, p-)ethoxyphenyl, (4 or 5-)chloro-2-methoxy-phenyl, and 2,4-dichloro(5- or 6-)methylphenyl and the like. Each of these moieties may be substituted as appropriate.

ALKYLARYL. Alkylaryl refers to alkyl chains of one to 8 carbon atoms and isomeric forms thereof which are substituted with aryl groups of 6 to 12 carbon atoms as described above.

HEIEROCYCLICS. Examples of heterocyclics include: (2-, 3-, or 4-)pyridyl, imidazolyl, indolyl, $N^{in}$-formyl-indolyl, $N^{in}-C_2-C_5$alkyl-C(O)-indolyl, (1,2,4)-triazolyl, (2-, 4-, 5-)pyrimidinyl, (2-, 3-)thienyl, piperidinyl, pyrrolyl, pyrrolinyl, pyrrolidinyl, pyrazolyl, pyrazolinyl, pyrazolidinyl, imidazolyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, puryl, phenazyl, carbazolyl, thienyl, and benzothienyl, thienyl, indolyl, iso-quinolyl and the like. Each of these moieties may be substituted as appropriate.

HETEROARYL or HET. A heteroaryl is a 5- or 6-membered saturated or unsaturated ring containing from one (1) to four (4) heteroatoms selected from the group consisting of nitrogen, oxygen and sulfur, and including any bicyclic group in which any of the above heterocyclic rings is fused to a benzene ring, $C_3-C_8$ cycloalkyl, or another heterocycle; and if chemically feasible, the nitrogen and sulfur atoms may be in the oxidized forms; and substituted by zero (0) to three (3) substituents. Substituents attached to either Aryl or Heteroaryl ring systems are denoted with the term "RA."

Examples of heteroaryl can include pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4isoquinolyl, 2-quinazolinyl, 4-quinazolinyl, 2-quinoxalinyl, 1-phthalazinyl, 2-imidazolyl, 4imidazolyl, 3-isoxazolyl, 4-isoxazolyl, 5-isoxazolyl, 3-pyrazolyl, 4pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4triazol-1-yl, 1-tetrazolyl, 1-indolyl, 1-indazolyl, 2-isoindolyl, 1-purinyl, 3-isothiazolyl, 4isothiazolyl and 5-isothiazolyl. Each of these moieties may be substituted as appropriate.

AMINO ACIDS. Amino acid residues referred to in this application are listed below, they may also be given either three letter or single letter abbreviations, as follows:

Alanine, Ala, A; Arginine, Arg, R; Asparagine, Asn, N; Aspartic acid, Asp, D; Cystein, Cys, C; Glutarine, Gln, Q; Glutamic Acid, Glu, E; Glycine, Gly, G; Histidine, His, H; Isoleucine, Ile, I; Leucine, Leu, L; Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamine, Glx, Z; Any amino acid, Xaa, X.

All amino acids have a carboxyl group and an amino group. The amino group of the amino acid is also referred to as the "N-terminus" of the amino acid. The carboxyl group of an amino acid is also referred to as the "C-terminus" of the amino acid. The "N-terminus" of an amino acid may form a peptide bond with a carboxyl group of another compound. The carboxyl group that combines with the "N-terminus" of an amino acid may be the carboxyl group of another amino acid or it may be from another source. If several amino acids are linked into a polypeptide, then the polypeptide will have a "free" N-terminus and a "free" C-terminus.

With the compounds of this invention some of the possible moieties are described as "("compound")—C(O)—$RA_{1-3}$" and "("compound)"—N(H)$RA_{1-4}$." The groups "RA$_{1-3}$" and "RA$_{1-4}$" (and "RA$_{1-1-3}$" and "RA1-1-4") are amino acids of the type listed above. Thus it is understood that RA$_{1-3}$ would be attached to the compound via the "N-terminus" of the amino acid. RA$_{1-3}$ is thus said to be an "N-terminus" amino acid, or even "any N-terminus amino acid," referring to any of the amino acids listed above. RA$_{1-4}$ would be attached to the compoud via the "C-terminus" of the amino acid. RA$_{1-4}$ is thus said to be a "C-terminus" amino acid or even "any C-terminus amino acid," referring to any of the amino acids listed above.

It should be apparent then that, compound-C(O)—RA$_{1-3}$ would indicate, compound-C(O)—amino acid, where the N-terminus or amino terminus of the amino acid forms a peptide bond with the compound and compound-N(H)RA$_{1-4}$ would indicate, compound-N(H)-amino acid, where the C-terminus or carboxyl group of the amino acid forms a peptide bond with the compound. The former compound would have a "free" amino or N-terminus and the latter a "free" carboxy or C-terminus.

HALOGEN. The term "halo-" and "halogen" refer to substituents selected from fluoro, chloro, bromo, iodo or trifluoromethyl.

CHIRALITY. It will be apparent to those skilled in the art that compounds of this invention may contain one or more chiral centers and may exist in optically active forms including cis-trans- and/or R- and S- isomeric forms and mixtures thereof. The scope of this invention includes all of these forms, the enantiomeric or diastereomeric forms of the compounds, including optically active forms, in pure form or as mixtures of enantiomers or diastereomers including cis-/trans-isomeric forms. The therapeutic properties of the compounds may to a greater or lesser degree depend on the stereochemistry of a particular compound.

SALTS. The present invention provides for compounds of formula 1 or pharmacologically acceptable salts and/or hydrates thereof. Pharmacologically acceptable salts refers to those salts that would be readily apparent to a manufacturing pharmaceutical chemist to be equivalent to the parent compound in properties such as formulation, stability, patient acceptance and bioavailability.

The tetronic acids form base addition salts when reacted with bases of sufficient strength. The pharmaceutically acceptable salts include both inorganic and organic bases. The pharmaceutically acceptable salts may be preferred over the free acids since they produce compounds that are more water soluble and more crystalline. The preferred pharmaceutically acceptable salts include, but are not limited to, salts of the mono and divalent metals such as: calcium, lithium, magnesium, potassium, or sodium; and salts formed with organic bases, such as: hydroxide, tro-methamine (THAM), 2-amino-2-(hydroxymethyl)-1,3-propanediol, and other salts as would be apparent to one skilled in the art. Bis salts, where two equivalents of base are added, may also be made from some of the compounds of this invention. Bis salts may be constructed of the salts mentioned above, the following bis salts are frequently used, potassium, or sodium.

Some of the compounds of this invention contain basic functional groups, including amines. These compounds are made into salts when combined with appropriate organic or inorganic acids. These salts can be prepared in situ during the final isolation and purification of the compounds or by separately reacting the purified compound in its free base form with a suitable organic or inorganic acid and isolating the salt thus formed. Representative salts include the acetate, adipates, alginates, aspartates, benzoates, borate, citrate, fumarates, glucoheptonate, hydrochloride, hydrobromide, hydroiodide, lactate, lactiobionate, laurate, malate, maleate, mesylate, naphthylate, nitrate, oleate, oxalate, palmitate, phosphate, propionate, succinate, stearate, sulfate, bisulfate, benzenesulfonates, cyclohexylsulfanates, ethanesulfonates, laurylsulphonate, methanesulfonates, toluenesulfonates, sulfamate, cyclohexylsulfamate, tartrate, tosylate, valerate and other pharmaceutically acceptable counter ions. These salts are readily prepared by methods known in the art.

Additionally, the compounds of this invention may be administered in a suitable hydrated form. Representative alkali or alkaline earth salts include the sodium, potassium, calcium, and magnesium salts and the like. Those skilled in the art would know how to formulate the acids, the salts (including bis salts), and any hydrates of the compounds of this invention into appropriate pharmaceutical dosage forms.

OTHER. LAH is lithium aluminum hydride. LDA is lithium diisopropylamide. THF is tetrahydrofuran. HRMS is High Resolution Mass Spectrometry, EIMS is electron impact mass spectrometry. Et is ethyl. EtOAc is ethyl acetate. HOAc is acetic acid. Carbonyl groups are usually written "C(O)" to indicate a carbon oxygen double bond. Carboxyl is usually written "C(O)O" or "C(O)—O—."

NMR. Operating frequence is $^1$H-NMR (300.133 MHz) and $^{13}$C-NMR (75.469 MHz).

All variables are independently defined unless stated otherwise. For example, if R$_1$ and R$_2$ were both defined as being A, B, or C then R$_1$ could be A at the same time that R$_2$ was A, B or C. When a group can be substituted, usually one to three possibilities, the substitutents need not be the same groups. When a variable in a dependent claim is left undefined it takes the definition of the same variable in the preceding claim from which the dependent claim depends on.

Some variables are combined to form a single recognizable moeity. For example, the R$_2$ and R$_3$ groups may be "combined" to form a cyclic structure. In this situation a C$_6$ cycloalkyl would indicate a six member carbon skelton ring which includes one carbon from the tetronic acid ring, for example, see compound IX-3, etc. Alternatively, a heterocyclic ring composed of R$_2$ and R$_3$ would be indicated by "—C$_{1-5}$ alkyl-R$_{23}$—C$_{1-5}$ alkyl-." In this latter case, the "—C$_{1-5}$ alkyl-" groups would not include the carbon of the tetronic acid ring, thus a six member hetero ring would be written, "—C$_2$ alkyl-R$_{23}$—C$_2$ alkyl-." For example, see compound OX-1, which contains a six membered piperidine ring. Note that there does not have to be an equal number of carbon atoms on either side of the R$_{23}$ group, nor does R$_{23}$ have to be a hetero atom.

2. Administration and Compositions

In clinical practice the compounds of the present invention will normally be administered orally, rectally, or by injection, in the form of pharmaceutical preparations comprising the active ingredient either as a free acid or as a pharmaceutically acceptable non-toxic, base addition salt, such as of the types listed above in association with a pharmaceutically acceptable carrier. The use and administration to a patient to be treated in the clinic would be readily apparent to a physician or pharmacist or ordinary skill in the art.

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally (i.e., intravenously, intramuscularly, or subcutaneously), intracisternally, intravaginally, intraperitoneally, topically (as by powders, ointments, or drops), bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar-agar, calcium carbonate, potato ortapioca starch, alginic acid, certain silicates, and sodium carbonate, e) solution retarding agents such as paraffin, f) absorption accelerators such as quatemaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Ophthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally dosage levels of about 0.1 to about 200, more preferably of about 0.5 to about 150, and most preferably about 1 to about 125 mg of active compound per kilogram of body weight per day are administered orally to a mammalian patient. If desired, the effective daily dose may be divided into multiple doses for purposes of administration, e.g., two to four separate doses per day.

3. Utility of the Invention.

The compounds of formula I of the present invention inhibit retroviral proteinases, having a aspartyl protease enzyme, and thus inhibit the replication of the virus. More particularly, the compounds of the present invention are useful as novel human retroviral protease inhibitors, having a aspartyl protease enzyme. They are useful for treating human patients infected with a human retrovirus containing the aspartyl protease enzyme, such as human immunodeficiency virus (strains of HIV-1 or HIV-2) or human T-cell leukemia viruses (HTLV-I or HTV-II) which results in acquired immunodeficiency syndrome (AIDS) and/or related diseases.

The capsid and replicative enzymes (i.e. protease, reverse transcriptase, integrase) of retroviruses are translated from the viral gag and pol genes as polyproteins that are further processed by the viral protease (PR) to the mature proteins found in the viral capsid and necessary for viral functions and replication. If the PR is absent or nonfunctional, the virus cannot replicate. The retroviral PR, such as HIV-1 PR or HIV-2 PR has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses containing the aspartyl protease enzyme.

More specifically, an example of one such human retrovirus containing the aspartyl protease enzyme is the human immunodeficiency virus (HIV, also known as HTLV-III or LAV) which has been recognized as the causative agent in human acquired immunodeficiency syndrome (AIDS). HIV contains a retro viral encoded protease, HIV-I protease, that cleaves the fusion polypeptides into the functional proteins of the mature viral particle, E. P. Lillehoj, et al., J. Virology, 62: 3053 (1988); C. Debuck, et al., Proc. Natl. Acad. Sci., 84: 8903 (1987). This enzyme, HIV-I protease, has been classified as an aspartyl protease and has a demonstrated homology to other aspartyl proteases such as renin, L. H. Pearl, et al., Nature 329: 351 (1987); I. Katoh, et al., Nature 329: 654 (1987). Inhibition of HIV-I protease blocks the replication of H[V and thus is useful in the treatment of human AIDS, E. D. Clerq, J. Med. Chem. 29: 1561 (1986). Inhibitors of HIV-I protease are useful in the treatment of HIV-infected individuals who are asymptomatic or symptomatic of AIDS.

Pepstatin A, a general inhibitor of aspartyl proteases, has been disclosed as an inhibitor of HIV-I protease, S. Seelmeier, et al., Proc. Natl. Acad. Sci. USA, 85: 6612 (1986). Other substrate derived inhibitors containing reduced bond isosteres or statine at the sassile position have also been disclosed, M. L. Moore, et al., Biochem. Biophys, Res. Commun. 159: 420 (1989); S. Billich, et al., J. Biol. Chem. 263: 17905 (1988); Sandoz, D. E. 3812-576-A.

Patients to be treated would be those individuals: 1) infected with one or more strains of a human retrovirus containing the aspartyl protease enzyme as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

Thus, the compounds of the present invention are useful for treating diseases caused by retroviruses containing the aspartyl protease enzyme, such as human acquired immunodeficiency disease syndrome (AIDS).

The compounds are also useful for treating non-human animals infected with a retrovirus containing the aspartyl protease enzyme, such as cats infected with feline leukemia virus or feline immunodeficiency virus, simians infected with the simian immunodeficiency virus, goats, and any other animal that may be infected with a virus containing the aspartyl protease enzyme. Exact dosages, forms and modes of administration of the compounds of the present invention to non-human animals would be apparent to one of ordinary skill in the art, such as a veterinarian.

The compounds of formula I of the present invention are prepared as described in the Preparations and Examples below, or are prepared by methods analogous thereto, which are readily known and available to one of ordinary skill in the art of organic synthesis.

Also claimed are essential intermediates, useful in the preparation of the compounds of formula 1.

4. Measures of Activity

The HIV protease assay. Surprisingly and unexpectedly, the compounds of the present invention are effective and potent inhibitors of HIV protease. The HIV protease assay is described below.

Because the compounds of the present invention inhibit retroviral proteases, having an aspartyl protease enzyme, they are expected to inhibit the replication of the HIV virus. The compounds are thus useful for treating human patients infected with a human retrovirus containing the aspartyl protease enzyme, such as human immunodeficiency virus (strains of HIV-1 or HIV-2) or human T-cell leukemia viruses (HLV-I or HTLV-II) that results in acquired immunodeficiency syndrome (AIDS) and/or related diseases.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, that belong to the same or related viral families and that create similar physiological effects in humans as various human retroviruses containing the aspartyl protease enzyme.

Patients to be treated are those individuals: 1) infected with one or more strains of a human retrovirus containing the aspartyl protease enzyme as determined by the presence of either measurable viral antibody or antigen in the serum and 2) in the case of HIV, having either a symptomatic AIDS defining infection such as i) disseminated histoplasmosis, ii) isopsoriasis, iii) bronchial and pulmonary candidiasis including pneumocystic pneumonia, iv) non-Hodgkin's lymphoma or v) Kaposi's sarcoma. Treatment consists of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) that has been recognized as the causative agent in human acquired immunodeficiency disease syndrome (AIDS), Gallo, et al., Science, 224: 500–503 (1984). HIV contains a retro viral encoded protease, HIV-I protease, that cleaves the fusion polypeptides into the functional proteins of the mature virus particle. Lillehoj, et al., J. Virology, 62: 3053–3058 (1988); Debouck, et al., Proc. Natl. Acad. Sci., USA, 84: 8903–8906 (1987). This enzyme, HIV-I protease, has been classified as an aspartyl protease and has a demonstrated homology to other aspartyl proteases such as renin. Pearl and Taylor, Nature, 329: 351–354 (1987); Katoh, et al., Nature, 329: 654–656 (1987). Inhibition of HIV-I protease blocks the replication of HIV and thus is useful in the treatment of human AIDS. Clercq, J. Med. Chem., 29: 1561–1569 (1986). Inhibitors of HIV-I or HIV-II protease are useful in the treatment of AIDS.

IN VITRO HIV PROTEASE INHIBITORY ASSAY

The HIV protease screening assay is based on a fluorescently labeled substrate which can be resolved from nonlabeled cleavage product using avidin-polystyrene particles, 0.7–0.9 $\mu$m. The substrate is biotinylated at the amino terminal arginine and fluorescently labeled with fluorescein isothiocynate (FITC) at the carboxyl terminal lysine. This assay has been employed to detect novel, nonpeptidic inhibitors of HIV-1 protease. Substrate (20 $\mu$l of 0.2 $\mu$M), sample (10 $\mu$l of desired concentraion), and enzyme (10 $\mu$l of 0.1 $\mu$M) are added to a 96 well pandex plate. The assay is run in 0.1 M sodium acetate buffer at pH 5.5 in the presence of 1.0 M sodium chloride and 0.05% NP-40 and incubated in the dark for one hour at room temperature. Avidin coated polystyrene beads (40 $\mu$l of 0.1% (w/v)) are added and the incubation is continued in the dark for an additional half hour. The labeled cleavage product is separated from the unreacted substrate via filtration and is read on the IDEXX Screen Machine. (IDEXX Corporation—Portland, Me.) The data are analyzed by appropriate computer algorithms to ascertain percent inhibition values.

The Activity Table showing the results of the HIV Protease Inhibitory Assay appears below in TABLE 1. The table has three columns, the left column provides the code number of the compound for easy cross reference to structure tables and detailed procedures, the middle column provides the concentration of test compound and the column on the right provides the percent inhibition.

Determination of $K_i$ values utilizes the same materials and equipment employed for percent inhibition studies. Two-fold serial dilutions are made for a given inhibitor from 2, 3 or 4 starting concentrations with a total of 24, 36 or 48 individual inhibitor concentrations. These dilutions are performed utilizing the BioMek robotics system. The assay consists of 10 $\mu$L of 40 nM HIV-1 protease, 10 $\mu$L of the various inhibitor concentrations, and 20 $\mu$L of 200 $\mu$M substrate (40 $\mu$L total). The reaction is allowed to proceed for 90 min at room temperature, terminated with 40 $\mu$L of avidin beads and processed (supra vide). An inhibitor with a known $K_i$ is run in parallel to verify the validity of the assay. The data is processed utilizing a computer program employing a nonlinear least square analysis of the data to generate the $K_i$ values.

The % inhibition values and, in some instances, $IC_{50}$ values or $K_i$ values, of representative compounds of the present invention are listed in Tables II and IV below.

Several compounds of the present invention, such as IX-14, IX-17 and IX-24 were tested in known human cell lines, such as human T-cell lines, e.g., MT4 and H9, which were infected with HIV-1$_{IIIB}$, and were found to inhibit retroviral replication.

Preferred Compounds.

The following compounds of the present invention are preferred: IX-15, IX-16, IX-17, IX-18, IX-21, IX-24, IX-28, IX-35, IX-37, IX-45. The most preferred compounds of the present invention are IX-14, IX-22, IX-42.

Compounds of the Invention.

The compounds of this invention are the compounds described under the section titled, "Summary of the Invention," formulas I–VI and all associated moieties.

Preparation of the Compounds.

The compounds of the present invention are prepared as described in the Charts, Preparations and Examples below, or are prepared by methods analogous thereto, which are readily known and available to one of ordinary skill in the art of organic synthesis.

The descriptions below refer to the various CHARTS which show figures and formula that represent various compounds. The structures, or formula, are provided to facilitate an understanding of the description of the invention. The structures in the CHARTS provide general descriptions of reaction schemes and are not intended to limit the procedures to describe only those compounds shown. The aromatic structures in the figures may have a double zero placed within the aromatic ring to emphasize the fact that the structure is not only benzene but any suitable aromatic group, including obvious substitutions, such as those provided in the definition section for aryl, heteroaryl and the like. This is true for any aromatic ring shown not just rings with double zeros in them.

In addition to the preparations and procedures below many of the side chains to the basic tetronic acid "core" structure will be apparent to one ordinarily skilled in the art. Tetronic acid is the trivial name for 5H-Furan-2-one,4-hydroxy. Additional side chains are disclosed in WO 94/11361, published May 26, 1994, (International Application Number PCT/U.S.93/10645) and WO 94/18188, published Aug. 18, 1994, (International Application Number PCT/U.S.94/00938), incorporated by reference herein. Reference to those documents may be necessary for a complete description of how to make some of the compounds described in this invention.

CHART A

Chart A describes the alkylation of commercially available tetronic acid (A-1) with benzylic or tertiary alcohols (A-2) and alkyl halides (A-3) in the presence of Lewis acids to provide the 3-substituted tetronic acids of general formul A-4. Tetronic acid has also been shown to react with tertiary alcohols in the presence of sulfuric acid to provide the alkylated derivatives (Zimmer, H.; Amer, A.; Pham, C. V.; Schmidt, D. G. J. Org. Chem. 1988, 53, 3368.).

Compounds of formula A-4 in which $R_1$ contains a heteroaroaryl group can be prepared in a manner analagous to that described for the preparation of the heteroaryl containing compounds in Chart II, example 195, of WO 94/11361 and Charts FF-UU, examples 379–394, of WO/94/18188, published Aug. 18, 1994.

WO 94/11361, published May 26, 1994, (International Application Number PCT/U.S.93/10645, filed Nov. 9, 1993) and WO 94/18188, published Aug. 18, 1994, (International Application Number PCT/US94/00938, filed Feb. 3, 1994, incorporated by reference herein.

PREPARATIONS AND EXAMPLES OF CHART A

Preparation AP-1

(See Chart A, figure "A-4": $R_1$ is cyclopropylphenylmethyl.) Intermediate AP-1. 2(5H)-Furanone, 3-(cyclopropylphenylmethyl)-4-hydroxy-.

1.2 gm of tetronic acid (A-1) is dissolved in 75 ml of sieve-dried dioxane followed by the addition of 1.71 ml (18 mmol) of a-cyclopropylbenzyl alcohol ("A-2" where $R_1$ is cyclopropylphenylmethyl) and 7.2 ml (59 mmol) of $BF_3$-$Et_2O$. The reaction is stirred for 24 hours at room temperature under a nitrogen atmosphere. During the course of the reaction the solution gradually darkens. The reaction is quenched by the addition of 10 ml of water, and the solvent is removed under reduced pressure. The residue is dissolved in 1N NaOH and extracted three times with $CH_2Cl_2$. The aqueous phase is made acidic with 1N HCl and repeatedly extracted with large volumes of $CH_2Cl_2$. The $CH_2Cl_2$ is removed under reduced pressure, and the solid residue is crystalized from $EtOHl/H_2O$ to yield 1.138 gm (41% yield) of a white solid. The crystals are dried for two days under vacuum.

Physical properties as follows:
$^1$H-NMR($CDCl_3$)δ0.20–0.25(m,1H), 0.48–0.50(m,1H), 0.55–0.65(m,2H), 1.30–1.40(m,1H), 3.24(d,1H), 4,55(d, 2H), 7.26–7.41(m,5H).

Anal: (calc. for $C_{14}H_{14}O_3 \cdot 0.2H_2O$) C,H,N. MP=175° C.

Preparation AP-2

(See Chart A, figure "A-4": $R_1$ is 1-phenylpropyl.) Intermediate AP-2.

Using the procedure described in Preparation AP-1 starting with α-ethyl benzyl alcohol (Chart A, figure "A-2" where $R_1$ is I-phenylpropyl), intermediate AP-2 is produced.

CHART B

Chart B describes the reaction of tetronic acids of general formula A-4 with readily available primary alkyl halides (B-1) in the presence of butyl lithium as base provides the 5-substituted derivatives of general formula B-3. In addition to the monoalkylated product (B-3), variable amounts of the bis-alkylated product (B-4) may be produced. Use of LDA as base leads to improved yields of B-4. For the efficient reaction with secondary halides, NaI is used as a catalyst. Chart B also describes the reaction of A-4 with non-enolizable aldehydes (such as cinnamaldehyde) to form the 5-substituted tetronic acids of general formula B-5.

PREPARATIONS AND EXAMPLES OF CHART B

Preparation BP-1 and Example BX-1

(See Chart B, figure 3": $R_1$ is cyclopropylphenylmethyl and $R_2$ is phenylmethyl.) 5H-Furan-2-one, 5-benzyl-3-cyclopropylphenylmethyl-4-hydroxy.

139 mg of title product of Preparation AP-1 and 25 ml of dry THF is cooled to –20° C. 1 ml of 1.6M n-BuLi is added, and the solution, containing partially precipitated dianion, is stirred at –20° C. for 30 minutes. 72 μl of commercially available benzyl bromide (Chart B, figure "B-1" where $R_2$ is phenylmethyl) is added, and the solution is stirred at –20° C. for 30 minutes, warmed slowly to room temperature and quenched by the addition of 2.0 ml of $H_2O$. Most of the solvent is removed under reduced pressure. The basic aqueous residue is extracted 3 times with $CH_2Cl_2$. The aqueous layer is made acidic with 1N HCl and extracted 3 times with $CH_2Cl_2$. The organic layer is dried over $MgSO_4$, and the product is purified by flash chromatography using 2% HOAc/28% EtOAc/70% hexane as eluant to yield 89 mg of the title product. Crystals are obtained by crystallization from $CH_2Cl_2$/hexane.

Physical characteristics are as follows:
$^1$H-NMR($CDCl_3$)δ0.20–0.25(m,2H), 0.48–0.52(m,1H), 0.59–0.65(m,1H), 1.45(m,1H), 2.95–3.06(m,2H), 3.23–3.33 (m,1H), 4.89–4.96(m,1H), 7.08–7.34(m,10H). EIMS m/z 320 (M).

Following procedures analogous to those described above and using starting materials and reagents readily known and available to one of ordinary skill in the art of organic synthesis, the following additional compounds of the present invention are prepared:

Example BX-2

(See Chart B, figure "B-3" where $R_1$ is cyclopropylphenylethyl and $R_2$ is 2-phenylethyl.) 2(5H)-Furanone, 3-(cyclopropylphenylmethyl)-4-hydroxy-5-(2-phenylethyl).

Physical characteristics are as follows:
$^1$H-NMR($CD_3OD$) δ0.20–0.23(m,2H), 0.53–0.61(m,2H), 1.72–1.86(m,2H), 2.20–2.29(m,1H), 2.61 –2.70(m,2H), 2.88–2.92(dd,1H), 4.74–4.77(m,1 H), 7.12–7.42(m,10H. EIMS m/z 334 (M).

Example BX-3

(See Chart B, figure "B-3" where $R_1$ is cyclopropylphenylmethyl and $R_2$ is 3-phenylpropyl.) 2(5H)-Furanone, 3-(cyclopropylphenylmethyl)-4-hydroxy-5-(3-phenylpropyl).

Physical characteristics are as follows:
$^1$H-NMR($CD_3OD$) δ0.20(m,2H), 0.50(m,1H), 0.59(m, 1H), 1.65(m,4H), 1.98(m,1H), 2.61(m,2H), 2.83(m,1H), 4.77(d,1H) 7.13–7.39(m,10H). EIMS m/z 348 (M).

Example BX-4

(See Chart B, figure "B-3" where $R_1$ is cyclopropylphenylmethyl and $R_2$ is propyl.) 2(5H)-Furanone, 3-(cyclopropylphenylmethyl)-4-hydroxy-5-propyl.

Physical characteristics are as follows:
$^1$H-NMR($CD_3OD$) δ0.15–0.25(m,2H), 0.50–0.63(m,2H), 0.92–0.98(m,3H), 1.40–1.42(m,2H), 1.57–1.59(m,1H), 1.74 (m,1H), 1.91–1.98(m,1H), 2.85–2.88(dd,1H), 4.74–4.77(m, 1H), 7.12–7.40(m,5H). EIMS m/z 272 (M).

Example BX-5

(See Chart B, figure "B-3" where $R_1$ is cyclopropylmethyl and $R_2$ is 3-cyclohexylpropyl.) B2(5H)-Furanone, 5-(2-cyclohexylethyl)-3-(cyclopropylphenylmethyl)-4-hydroxy.

Physical characteristics are as follows:
$^1$H-NMR($CD_3OD$)δ0.18–0.23(m,2H), 0.53–0.60(m,2H), 0.81–0.92(m,2H), 1.10–1.22(m,7H), 1.53–1.80(m,8H), 1.91–2.05(m,1H), 2.84–2.87(m,1H), 4.75(m,1H), 7.15–7.40 (m,5H). EIMS m/z 340 (M).

Example BX-6

(See Chart B, figure "B-3" where $R_1$ is cyclopropylphenylmethyl and $R_2$ is 3-phenyl-2-propenyl.) 2(5H)-Furanone, 3-(cyclopropylphenylmethyl)-4-hydroxy-5-(3-phenyl-2-propenyl)-.

Physical characteristics are as follows:
$^1$H-NMR(300 mHz $CDCl_3$) δ0.16–0.22(m, 1H), 0.23–0.62(m,3H), 1.19–1.41(m,1H), 2.52–2.60(m,1H), 2.70–2.90(m,1H), 3.15–3.25(m,1H), 4.69–4.87(m,1H), 5.92–6.10(m,1H), 6.42–6.50(m,1H), 7.08–7.39(m,10H). EIMS m/z 346 (M).

Example BX-7

(See Chart B, figure "B-5" where $R_1$ is cyclopropylphenylmethyl and $Z_1$ is 2-phenylvinyl.) 2(5H)-Furanone, 3-(cyclopropylphenylmethyl)-4-hydroxy-5-(1-hydroxy-3-phenyl-2-propenyl)-.

Using the procedure described in Example BP-1, starting with the title compound of Preparation AP-1 and commercially available trans cinnamaldehyde (Chart B, figure "B-2" where $Z_1$ is 2-phenylvinyl), title compound is produced.
Physical characteristics are as follows:
$^1$H-NMR(300 mHz CDCl$_3$) δ0.18(m,2H), 0.52(m,2H), 2.83(m,1H), 4.99(m,1H), 5.47(m,1H), 5.81(m,1H), 6.69(m, 1H), 7.12(m,10H). HRMS calculated for $C_{23}H_{22}O_4$: 362.1518, found 362.1528.

Procedure BP-2 and Example BX-8

(See Chart B, figure "B-5" where $R_1$ is cyclopropylphenylmethyl and $Z_1$ is 2-phenylethyl). 2(5H)-Furanone, 3-(cyclopropylphenylmethyl)-4-hydroxy-5-(1-hydroxy-3-phenylpropyl)-.

31 mg of the title compound from Example BX-7, 55 mg of 10% Pd/C and 10 ml of EtOH are placed in a Parr bottle and shaken for two hours at 15 psi of hydrogen pressure. The reaction mixture is filtered through celite, and the solvent is removed to yield the title compound.
Physical characteristics are as follows:
$^1$H-NMR(CDCl$_3$) δ0.0(m,2H), 0.30(m,1H), 0.41(m,1H), 1.50(m,3H), 2.64(m,2H), 3.72(m,1H), 4.53(m,1H), 6.98(m, 8H), 7.21(m,2H). HRMS calculated for $C_{23}H_{24}O_4$: 364.1674, found 364.1665.

Example BX-9

(See Chart B, figure "B-4" where $R_1$ is 1-phenylpropyl and $R_2$ is phenylmethyl.)
Physical characteristics are as follows:
$^1$H-NMR(CDCl$_3$) δ0.65–0.9(m,3H), 1.79–2.08(m,2H), 2.90–2.97(m,1H), 3.19–3.22(m,1H), 3.47–3.51(m,1H), 4.82–4.87(m,1H), 7.20–7.24(m,10H). 75 mHz $^{13}$C-NMR (CDCl$_3$) 12, 25, 30, 37, 42, 79, 110, 126, 127.1, 127.7, 128.3, 128.5, 130, 134, 143, 174, 177. HRMS calculated for $C_{20}H_{20}O_3$: 308.1412, found 308.1422.

Example BX-10

(Chart B, "B-3" where $R_2$ is 1-methylethyl and $R_1$ is cyclopropylphenylnethyl).
Physical characteristics are as follows: $^1$H NMR (CDCl$_3$) δ10.45 (br s, 1H), 7.39-7.09 (m, 5H), 4.53-4.51 (m, 1H), 3.02-2.97 (m, 1H), 2.24-2.20 (m, 1H), 1.66-1.64 (m, 1H), 1.03-0.99 (m, 3H), 0.73-0.69 (m, 3H), 0.61-0.46 (m, 2H), 0.21-0.19 (m, 2H) ppm; HRMS (EI) Calcd for $C_{17}H_{20}O_3$: 272.1412. Found: 272.1410.

Example BX-11

(Chart B, "B-3" where $R_2$ is butyl and $R_1$ is cyclopropylphenylmethyl)
Physical characteristics are as follows: $^1$H NMR (CDCl$_3$) δ7.38-7.15 (m, 5H), 4.67-4.63 (m, 1H), 3.02-2.99 (m, 1H), 1.99-1.88 (m, 1H), 1.67-1.52 (m, 2H), 1.35-1.21 (m, 4H), 0.88-0.85 (m, 3H), 0.63-0.49 (m, 2H), 0.25-0.18 (m, 2H) ppm; MS (EI) m/z 286; HRMS EI) Calcd for $C_{18}H_{22}O_3$: 286.1569. Found: 286.1559.

Example BX-12

(Chart B, "B-4" where $R_2$ and $R_3$ are propyl and $R_1$ is cyclopropylphenylmethyl)
The title compound was isolated as the minor product from the reaction of AP-1 with propyl bromide.
Physical characteristics are as follows: $^1$H NMR (CDCl$_3$) δ7.38-7.15 (m, 5H), 3.05 (d, J=9.8 Hz, 1H), 1.69 (t, J=7.9 Hz, 4H), 1.61-1.52 (m, 1H), 1.27-1.06 (m, 4H), 0.91-0.79 (m, 6H), 0.63-0.47 (m, 2H), 0.26-0.18 (m, 2H) ppm; $^{13}$C MNR (CDCl$_3$) δ176.47, 175.56, 142.22, 128.50, 127.66, 126.47, 105.42, 86.62, 43.71, 37.89, 16.62, 13.96, 13.75, 6.43, 4.19 ppm; HRMS (EI) calcd for $C_{20}H_{26}O_3$: 314.1882. Found: 314.1876.

Example BX-13

(Chart B, "B-4" where $R_2$ and $R_3$ are 1-methylethyl and $R_1$ is cyclopropylphenylmethyl)
Physical characteristics are as follows: mp 189.6–190.2° C.; $^1$H NMR (CDCl$_3$) δ7.45-7.16 (m, 5H), 3.00 (d, J=8.6, 1H), 2.30-2.24 (m, 2H), 1.72-1.63 (m, 1H), 0.97-0.90 (m, 12H), 0.74-0.65 (m, 1H), 0.58-0.49 (m, 1H), 0.32-0.18 (m, 2H) ppm; MS (EI) m/z 314; HRMS (EI) Calcd for $C_{20}H_{26}O_3$: 314.1882. Found: 314.1881.

Example BX-14

(Chart B, "B-4" where $R_2$ and $R_3$ are ethyl and $R_1$ is cyclopropylphenylmethyl)
The title compound was prepared from the reaction of AP-1 and bromoethane as described for example BX-1 using LDA as base to promote the formation of the otherwise minor product "B-4".
Physical characteristics are as follows: mp 131.4–133.4° C.; $^1$H NMR (CDCl$_3$) δ9.83 (br s, 1H), 7.38-7.14 (m, 5H), 3.05 (d, J=9.9 Hz, 1H), 1.79-1.72 (m, 4H), 1.64-1.52 (m, 1H), 0.75-0.69 (m, 6H), 0.63-0.45 (m, 2H), 0.22-0.20 (m, 2H) ppm; MS (EI) m/z 286; HRMS (EI) Calcd for $C_{18}H_{22}O_3$: 286.1569. Found: 286.1556.

Example BX-15

(Chart B, "B-4" where $R_2$ and $R_3$ are butyl and $R_1$ is cyclopropylphenylmethyl)
The title compound was prepared using the modification described in example BX-14.
Physical characteristics are as follows: mp 97.5–98.7° C.; $^1$H NMR (CDCl$_3$) δ9.59 (br s, 1H), 7.38-7.12 (m, 5H), 3.07 (d, J=9.7 Hz, 1H), 1.75-1.70 (m, 4H), 1.61-1.50 (m, 1H), 1.26-1.02 (m, 8H), 0.85-0.79 (m, 6H), 0.68-0.46 (m, 2H), 0.26-0.19 (m, 2H) ppm; MS (EI) m/z 342; HRMS (EI) Calcd for $C_{22}H_{30}O_3$: 342.2195. Found: 342.2190.

Example BX-16

(Chart B, "B-4" where $R_2$ is 2-phenylethyl and $R_1$ is 1-phenylpropyl)
Physical characteristics are as follows: $^1$H NMR (CDCl$_3$) δ7.39-7.03 (m, 10H), 4.66-4.61 (m, 1H), 3.67 (q, J=6.2 Hz, 1H), 2,73-2.52 (m, 2H), 2.25-1.84 (m, 4H), 0.91 (t, J=7.3 Hz, 3H) ppm.; $^{13}$C NMR (CDCl$_3$) δ176.89, 176.53, 128.55, 128.43, 127.78, 126.60, 126.16, 103.96, 41.65, 33.42, 30.53, 25.38, 12.72 ppm; HRMS (EI) calcd for $C_{21}H_{23}O_3$: 323.1647. Found: 323.74.

CHART C

Chart C describes a method for forming 5-mono and 5-disubstituted tetronic acids of general formula C-5

(Wititak, D. T.; Tehim, A. K. *J. Org Chem.* 1987, 52, 2324.). Condensation of the lithium anion of commercially available ethyl propriolate (C-2) with an aldehyde or ketone (C-1) affords the hydroxy ester of general formula (C-3). Cyclization to the methyl tetronate (C-4) with sodium methoxide and subsequent deprotection with hydrobromic acid affords the desired tetronic acid of general formula C-5. These synthetic intermediates are further elaborated as described in Charts I and K.

PREPARATIONS AND EXAMPLES OF CHART C

Preparation CP-1

(See Chart C, figure "C-3" where $R_2$ is 2-phenylethyl and $R_3$ is methyl.) Intermediate CP-1.

Using the general procedure described by Midland, M. M., et al (J. Org. Chem. 1980, 45, 28–29) 981 mg of commercially available ethyl propiolate (C-2) and 20 ml of dry THF are cooled to −78° C. 6.25 ml of 1.6M n-BuLi are added dropwise, and the solution is stirred for 10 minutes at −78° C. 1.48 gm of commercially available benzyl acetone (C-1) are added, and the solution is stirred at −78° C. for 20 minutes. The cooling bath is removed, and the reaction is quenched by the addition of saturated $NH_4Cl$ and glacial acetic acid. Ether is added, and the organic layer is washed with saturated $NaH_2CO_3$ 3 times and dried over $MgSO_4$. After removal of solvent the residue is distilled in a Kugelrohr apparatus. The fraction boiling at 190–210° C. pot temperature at 2 mm pressure contains 1.06 grams of the title product.
Physical characteristics are as follows:
$^1$H-NMR(CDCl$_3$) δ1.32(t,3H), 1.59(s,3H), 2.01–2.07(m, 2H), 2.77–2.89(m,2H), 4.17–4.29(m,2H), 7.17–7.32(m,5H).

Preparation CP-2

(See Chart C, figure "C-3" where $R_2$ and $R_3$ together form a cyclopentyl ring.) Intermediate CP-2.

Using the procedure described in Preparation CP-1, starting with cyclopentanone (C-1), the title compound is synthesized. It is purified by distillation in a Kugelrohr apparatus at 5 mm pressure (160–180° C. degrees).
Physical characteristics are as follows:
$^1$H-NMR(300 mHz CDCl$_3$) δ1.28–1.33(t,3H), 1.74–1.91 (m,4H), 1.95–2.07(m,4H), 4.20–4.28(q,2H).

Preparation CP-3

(See Chart C, figure "C-3" where $R_2$ and $R_3$ together form a cyclooctyl ring.) Intermediate CP-3.

Using the procedure described in Preparation CP-2, starting with cyclooctanone (Chart C, figure "C-1"), title compound is synthesized. It is purified by flash chromatography on silica gel using 20% EtOAc/hexane as eluant.
Physical characteristics are as follows:
$^1$H-NMR(CDCl$_3$) δ1.28–1.34(t,3H), 1.45–1.66(M,10H), 1.92–2.05(m,4H), 4.20–4.28(q,2H).

Preparation CP4

(See Chart C, figure "C-4" where $R_2$ and $R_3$ form a cyclooctyl ring.) Intermediate CP-4.

Using the general procedure described by Witiak, D. T. and Tehim, A. K. (J. Org. Chem. 1987, 52, 2324–2327) 1.88 gm of the title product of Preparation CP-3, intermediate CP-3, are dissolved in 8.0 ml of 3A sieve-dried MeOH. 14 ml of NaOMe (25% by weight in MeOH) are added dropwise. The dark orange solution is stirred under argon for 6 hours. 10 ml of ice cold water are added. The resulting precipitate is filtered. Most of the solvent is removed from the filtrate, and the residue is treated with 0.1N HCl. This solution is extracted with $CH_2Cl_2$ 3 times. The organic layer is dried over $MgSO_4$. The product is purified by flash chromatography using 30% EtOAc/hexane to yield 670 mg of the title product after recrystallization from $CH_2Cl_2$. The precipitate from the reaction is recrystallized from $CH_2Cl_2$/hexane to yield an additional 462 mg of title compound.
Physical characteristics are as follows:
MP=53–54° C.
$^1$H-NMR(CDCl$_3$) δ1.42–1.85(m,10H), 1.88–1.92(m,4H), 3.87(s,3H), 4.91(s,1H). EIMS m/z 210 (M).

Preparation CP-5

(See Chart C, figure "C-4" where $R_2$ and $R_3$ form a cyclopentyl ring.) Refer to Chart C. Intermediate CP-5.

Using the procedure described in Preparation CP-4, starting with the title compound from Preparation CP-2, intermediate CP-2, the cyclization reaction is performed to produce the title compound.
Physical characteristics are as follows:
MP=60° C.
$^1$H-NMR(300 mHz CDCl$_3$) δ1.77–2.09(m,8H), 3.92(s, 3H), 5.04(s,1H). EIMS m/z 168 (M).

Preparation CP-6

(See Chart C, figure "C-4" where $R_2$ is 2-phenylethyl and $R_3$ is methyl.) Intermediate CP-6.

Using the procedure described in Preparation CP-4, starting with the title compound from Preparation CP-1, intermediate CP-1, the cyclization reaction is performed to produce the title compound.
Physical characteristics are as follows:
$^1$H-NMR(CDCl$_3$) δ1.50(s,3H), 2.02–2.15(m,2H), 2.38–2.49(m,1H), 2.63–2.67(m,1H), 3.80(s,3H), 5.01(s,1H), 7.14–7.29(m,5H). EIMS m/z 232 (M).

Preparation CP-7

(See Chart C, figure "C-5" where $R_2$ and $R_3$ form a cyclopentyl ring.) Intermediate CP-7.

550 mg of title compound of Preparation CP-5, intermediate CP-5, (Chart C, figure "C-4") is stirred with 10 ml of 48% HBr for 19 hours under Argon. 10 ml of cold $H_2O$ are added and the precipitate is removed. The precipitate is recrystallized from $CH_2Cl_2$/hexane to yield 220 mg of the title product. An additional 120 mg of title product is obtained from the filtrate after flash chromatography using 48% EtOAc50% hexane2% HOAc as eluant.
Physical characteristics are as follows:
MP—softens from 145–150° with melting at 150–153° C.
$^1$H-NMR(CDCl$_3$) δ1.81–2.10, 3.24, (4.96-minor amount of enol form). EIMS m/z 154 (M).

Preparation CP-8

(See Chart C, figure "C-5" where $R_2$ is 2-phenylethyl and $R_3$ is methyl.) Intermediate CP-8.

Starting with the title compound from Preparation CP-6, intermediate CP-6, (Chart C, FIG. "C-4"), the procedure described in Preparation CP-7 is used to form the title product, with the modification that the reaction is warmed to 45° C.
Physical characteristics are as follows:
$^1$H-NMR(300 mHz CDCl$_3$) δ1.51(t,3H), 2.12–2.26(m, 2H), 2.50–2.61(m,1H), 2.71–2.82(m,1H), 2.88–2.95(d,1H), 3.13–3.21(d,1H), 7.14–7.31(m,5H). EIMS m/z 218 (M).

Preparation CP-9

(See Chart C, figure "C-5" where $R_2$ and $R_3$ form a cyclooctyl ring.) Intermediate CP-9.

Starting with the title compound from Preparation CP-4, intermediate CP-4, (Chart C, figure "C-4"), the procedure described in Preparation CP-7 is used to form the title product.

Physical characteristics are as follows:
MP=170° C.
$^1$H-NMR(CDCl$_3$) δ1.49–1.73(m, 10H), 1.94–1.98(m, 4H), 3.24(s,2H), 4.85(minor amount of enol form). EIMS m/z 196 (M).

CHART D

Chart D describes the preparation of 5,5-disubstituted tetronic acids of general formula D-2 by alkylation of the previously described monosubstituted derivatives (B-3) with alkyl halides (D-1) in the presence of LDA as base. For the efficient reaction of secondary alkyl halides, NaI is used as a catalyst.

PREPARATIONS AND EXAMPLES OF CHART D

Preparation DP-1 and Example DX-1

(See Chart D, figure "D-3" where $R_2$ is 3-phenylpropyl, $R_3$ is propyl and $R_1$ is cyclopropylphenylmethyl.)

138 mg of the title compound of Example BX-3 (Chart D, "B3" where $R_2$ is 3-phenylpropyl and $R_1$ is cyclopropylphenylmethyl) and 10 ml of dry THF are cooled to −78° C. 416 ul of lithium diisopropylamide (2.0 M in heptane\THF\ethyl benzene) are added, and the yellow solution is stirred for 10 min at −78° C. 46 μl of commercial propylbromide (D-1) is added, and the solution is stirred for 30 minutes at −78° C. The reaction is allowed to slowly warm to −5° C., and then quenched by the addition of 5 ml of H$_2$O. After removal of most of the solvent, the basic aqueous solution is washed twice with CH$_2$Cl$_2$, acidified with 1N HCl and washed 3 times with CH$_2$Cl$_2$. The CH$_2$Cl$_2$ layer is dried over MgSO$_4$. After removal of the solvent, flash chromatography of the crude residue using 75% hexane\23%EtOAc\2%HOAc as eluant yields 46 mg of the title product and 49 mg of unreacted starting material. Yield may be improved by generating the anion and alkylating at −20° C. to −10° C. instead of −78° C.

Physical characteristics are as follows:
$^1$H-NMR(CDCl$_3$) δ0.20–0.30(m,1H), 0.40–0.51(m,1H), 0.53–0.68(m,2H), 0.88(t,3H), 1.25–1.35(m,2H), 1.52–1.80 (m,7H), 2.52–2.62(m,2H), 3.30–3.41(m,1H), 7.14–7.40(m, 10). EIMS m/z 390 (M).

Following procedures analogous to those described above and using starting materials and reagents readily known and available to one of ordinary skill in the art of organic synthesis, the following additional compounds of the present invention are prepared:

Example DX-2

(See Chart D, figure "D-2" where $R_2$ is phenylmethyl, $R_3$ is methyl and $R_1$ is cyclopropylphenylmethyl).
Physical characteristics are as follows:
$^1$H-NMR(CDCl$_3$) δ0.14(m,2H), 0.33(m,1H), 0.57(m,1H), 1.28(m,1H), 1.57(m,3H), 2.80(m,1H), 3.06(m,2H), 7.00(m, 2H), 7.34(m,8H). HRMS calculated for C$_{22}$H$_{22}$O$_3$: 334.1569, found 334.1577.

Example DX-3

(See Chart D, figure "D-2" where $R_2$ is phenylmethyl, $R_3$ is ethyl and $R_1$ is cyclopropylphenylmethyl).
Physical characteristics are as follows:
$^1$H-NMR(CD$_3$OD) δ0.19(m,4H), 0.75(m,3H), 1.32(m, 1H), 1.86(m,2H), 2.58(m,1H), 3.00(m,2H), 6.72(m,1H), 7.04(m,9H). HRMS calculated for C$_{23}$H$_{24}$O$_3$: 348.1725, found 348.1721.

Example DX-4

(Chart D, "D-2" where $R_2$ is propyl, $R_3$ is phenylmethyl and $R_1$ is cyclopropylphenylmethyl).
Physical characteristics are as follows: mp 154.4–155.3° C.; $^1$H NMR (CDCl$_3$) δ7.34-7.15 (m, 10H), 6.76-6.72 (m, 1H), 3.18-3.01 (m, 2H), 2.94-2.88 (m, 1H), 1.90-1.73 (m, 2H), 1.43-1.06 (m, 3H), 0.96-0.88 (m, 3H), (0.71-0.62 (m), 0.62-0.56 (m), 0.46-0.38 (m), 0.30-0.07 (m) 4H] ppm; MS (EI) m/z 362; HRMS (EI) Calcd for C$_{24}$H$_{26}$O$_3$: 362.1882. Found: 362.1878.

Example DX-5

(Chart D, "D-2" where $R_2$ and $R_3$ are phenylmethyl and $R_1$ is cyclopropylphenylmethyl).
Physical characteristics are as follows: mp 249.3–249.4° C.; $^1$H NMR (CDCl$_3$) δ7.30-7.18 (m, 13H), 6.67-6.64 (m, 2H), 5.90 (s, 1H), 3.24 (d, J=13.9 Hz, 2H), 3.12-3.04 (m, 2H), 2.73 (d, J=8.7 Hz, 1H), 1.23-1.18 (m, 1H), [0.62-0.53 (m), 0.43-0.35 (m), 0.21-0.12 (m), 0.06-0.01 (m) 4H] ppm; MS (EI) m/z 410; HRMS (EI) Calcd for C$_{28}$H$_{26}$O$_3$: 410.1882. Found: 410.1880.

Example DX-6

(Chart D, "D-2" where $R_2$ is 3-pyridinylmethyl, $R_3$ is propyl and $R_1$ is cyclopropylphenylmethyl).
Physical characteristics are as follows: mp 151.4–153.1° C.; $^1$H NMR (CDCl$_3$) δ8.40-8.35 (m, 1H), 7.91-7.82 (m, 1H), 7.45-7.04 (m, 5H), 6.80-6.75 (m, 1H), 6.58-6.49 (m, 1H), 3.01-2.54 (m, 3H), 1.97-1.87 (m, 2H), 1.53-1.26 (m, 3H), 1.05-0.89 (m, 3H), 0.61-0.52 (m, 1H), 0.44-0.24 (m, 1H), 0.21-0.04 (m, 2H) ppm; MS (EI) m/z 363; HRMS (EI) Calcd for C$_{23}$H$_{25}$NO$_3$: 363.1834. Found: 363.1829.

Example DX-7

(Chart D, "D-2" where $R_2$ is ethyl, $R_3$ is 2-phenylethyl and $R_1$ is cyclopropylphenylmethyl).
Physical characteristics are as follows: $^1$H NMR (CDCl$_3$) δ7.45-7.10 (m, 10H), 6.40 (br s, 1H), 3.42-3.37 (m, 1H), 2.65-2.34 (m, 2H), 2.14-1.70 (m, 3H), 1.36-1.21 (m, 2H), 0.88-0.78 (m, 3H), 0.68-0.65 (m, 2H), 0.54-0.47 (m, 1H), 0.30-0.23 (m, 1H) ppm; MS (EI) m/z 362; HRMS (EI) Calcd for C$_{24}$H$_{26}$O$_3$: 362.1882. Found: 362.1896.

Example DX-8

(Chart D, "D-2" where $R_2$ is propyl, $R_3$ is 2-phenylethyl and $R_1$ is cyclopropylphenylmethyl).
Physical characteristics are as follows: $^1$H NMR (CDCl$_3$) δ7.45-7.09 (m, 10H), 3.33-3.28 (m, 1H), 2.57-2.37 (m, 2H), 2.08-1.97 (m, 1H), [1.80-1.70 (m), 1.38-0.98 (m), 0.90-0.84 (m), 9H], 0.66-0.63 (m, 2H), 0.49-0.43 (m, 1H), 0.30-0.24 (m, 1H) ppm; MS (EI) m/z 376; HRMS (EI) Calcd for C$_{25}$H$_{28}$O$_3$: 376.2038. Found: 376.2027.

Example DX-9

(Chart D, "D-2" where $R_2$ and $R_3$ are 2-phenylethyl and $R_1$ is cyclopropylphenylmethyl).
Physical characteristics are as follows: $^1$H NMR (CDCl$_3$) δ7.47-7.09 (m, 15H), 3.38 (d, J=8.7 Hz, 1H), 2.66-2.40 (m, 4H), 2.13-2.00 (m, 4H), 1.38-1.35 (m, 1H), 0.68-0.66 (m, 2H), 0.50-0.48 (m, 1H), 0.30-0.29 (m, 1H) ppm; MS (EI) m/z 438; HRMS (EI) Calcd for $C_{30}H_{30}O_3$: 438.2195. Found: 438.2198.

Example DX-10

(Chart D, "D-2" where $R_2$ is methyl, $R_3$ is 3-phenylpropyl and $R_1$ is cyclopropylphenylmethyl).

Physical characteristics are as follows: $^1$H NMR (CDCl$_3$) δ7.38-7.13 (m, 10H), [6.24 (s), 6.14 (s), 1H], 3.41-3.37 (m, 1H), 2.64-2.56 (m, 2H), 1.88-1.25 (m, 8H), 0.68-0.62 (m, 2H), 0.53-0.48 (m, 1H), 0.30-0.23 (m, 1H) ppm; MS (EI) m/z 362; HRMS (EI) Calcd for $C_{24}H_{26}O_3$: 362.1882. Found: 362.1888.

Example DX-11

(Chart D, "D-2" where $R_2$ is ethyl, $R_3$ is 3-phenylpropyl and $R_1$ is cyclopropylphenylmethyl).

Physical characteristics are as follows: $^1$H NMR (CDCl$_3$) δ7.44-7.08 (m, 10H), [6.40 (s), 6.34 (s) 1H] 3.36 (overlapping d, J=8.0 Hz, 1H), 2.61-2.55 (m, 2H), 1.84-1.59 (m, 6H), 1.32-1.25 (m, 1H), 0.89-0.74 (m, 3H), 0.64-0.63 (m, 2H), 0.47-0.45 (m, 1H), 0.26-0.24 (m, 1H) ppm; MS (EI) m/z 376; HRMS (EI) Calcd for $C_{25}H_{28}O_3$: 376.2038. Found: 376.2032.

Example DX-12

(Chart D, "D-2" where $R_2$ is butyl, $R_3$ is 3-phenylpropyl and $R_1$ is cyclopropylphenylmethyl).

Physical characteristics are as follows: $^1$H NMR (CDCl$_3$) δ7.40-7.10 (m, 10H), [6.37 (s), 6.31 (s) 1H], 3.38-3.34 (m, 1H), 2.62-2.52 (m, 2H), 1.81-1.58 (m, 6H), 1.30-1.20 (m, 4H), 1.18-0.98 (m, 1H), 0.87-0.85 (m, 3H), 0.69-0.60 (m, 2H), 0.48-0.41 (m, 1H), 0.26-0.20 (m, 1H) ppm; MS (EI) m/z 404; HRMS (EI) Calcd for $C_{27}H_{32}O_3$: 404.2351. Found: 404.2345.

Example DX-13

(Chart D, "D-2" where $R_2$ and $R_3$ are 3-phenylpropyl and $R_1$ is cyclopropylphenylmethyl).

Physical characteristics are as follows: $^1$H NMR (CDCl$_3$) δ7.38-7.08 (m, 15H), 6.32 (s, 1H), 3.34 (d, J=8.4 Hz, 1H), 2.59-2.53 (m, 4H), 1.85-1.26 (m, 9H), 0.63-0.60 (m, 2H), 0.47-0.43 (m, 1H), 0.27-0.21 (m, 1H) ppm; MS (EI) m/z 466; HRMS (EI) Calcd for $C_{32}H_{34}O_3$: 466.2508. Found: 466.2516.

Example DX-14

(Chart D, "D-2" where $R_2$ is cyclopropylmethyl, $R_3$ is 3-phenylpropyl and $R_1$ is cyclopropylphenylmethyl).

Physical characteristics are as follows: $^1$H NMR (CDCl$_3$) δ7.43-7.08 (m, 10H), 3.27 (d, J=8.9, 1H), 2.58-2.51 (m, 2H), 1.87-1.25 (m, 8H), [0.62-0.59 (m), 0.43-0.32 (m), 0.25-0.24 (m), 0.06-0.04 (m) 8H] ppm; MS (EI) m/z 402; HRMS (EI) Calcd for $C_{27}H_{30}O_3$: 402.2195. Found: 402.2210.

Example DX-15

(Chart D, "D-2" where $R_2$ is phenylmethyl, $R_3$ is 3-phenylpropyl and $R_1$ is cyclopropylphenylmethyl).

Physical characteristics are as follows: mp 135.1–136.6° C.; $^1$H NMR (CDCl$_3$) δ7.30-7.11 (m, 14H), 6.73-6.72 (m, 1H), [6.26 (s), 6.11 (s) 1H], 3.17-2.99 (m, 2H), 2.93-2.87 (m, 1H), 2.65-2.56 (m, 2H), 1.96-1.80 (m, 2H), 1.78-1.40 (m, 2H), [1.28-1.24 (m), 1.11-1.08 (m), 0.90-0.87 (m), 0.77-0.73 (m), 0.60-0.54 (m), 0.48-0.41 (m), 0.38-0.33 (m), 0.29-0.24 (m), 0.20-0.14 (m), 0.10-0.02 (m) 5H] ppm; MS (EI) m/z 438; HRMS (EI) Calcd for $C_{30}H_{30}O_3$: 438.2195. Found: 438.2192.

Example DX-16

(Chart D, "D-2" where $R_2$ is 2-propenyl, $R_3$ is 3-phenylpropyl and $R_1$ is cyclopropylphenylmethyl).

Physical characteristics are as follows: $^1$H NMR (CDCl$_3$) δ9.95 (br s, 1H), 7.33-7.01 (m, 10H), 5.59-5.43 (m, 1H), 5.03-4.97 (m, 2H), 3.05-3.00 (m, 1H), 2.52-2.41 (m, 4H), 1.80-1.75 (m, 2H), 1.54-1.46 (m, 3H), 0.58-0.39 (m, 2H), 0.16-0.15 (m, 2H) ppm; MS (EI) m/z 388; HRMS (EI) Calcd for $C_{26}H_{28}O_3$: 388.2038. Found: 388.2033.

Example DX-17

(Chart D, "D-2" where $R_2$ is 1-methylethyl, $R_3$ is 3-phenylpropyl and $R_1$ is cyclopropylphenylmethyl).

Physical characteristics are as follows: $^1$H NMR (CDCl$_3$) δ7.35-7.01 (m, 10H), 3.10-3.05 (m, 1H), 2.52-2.45 (m, 2H), 2.04-1.88 (m, 2H), 1.76-1.72 (m, 1H), 1.51-1.38 (m, 3H), 0.93-0.90 (m, 3H), 0.78-0.76 (m, 3H), 0.60-0.50 (m, 1H), 0.49-0.39 (m, 1H), 0.24-0.14 (m, 2H) ppm; MS (EI) m/z 390; HRMS (EI) Calcd for $C_{26}H_{30}O_3$: 390.2195. Found: 390.2209.

Example DX-18

(Chart D, "D-2" where $R_2$ is 2-phenylethyl, $R_3$ is 3-phenylpropyl and $R_1$ is cyclopropylphenylmethyl).

Physical characteristics are as follows: $^1$H NMR (CDCl$_3$) δ[9.58 (br s), 9.47 (br s), 1H], 7.28-6.90 (m, 15H), 3.04 (d, J=9.7, 1H), 2.45-2.28 (m, 4H), 1.98-1.88 (m, 2H), 1.73-1.65 (m, 2H), 1.47-1.36 (m, 3H), 0.50-0.34 (m, 2H), 0.18-0.08 (m, 2H) ppm; MS (EI) m/z 452; HRMS (EI) Calcd for $C_{31}H_{32}O_3$: 452.2351. Found: 452.2353.

Example DX-19

(Chart D, "D-2" where $R_2$ is 1-methylpropyl, $R_3$ is 3-phenylpropyl and $R_1$ is cyclopropylphenylmethyl).

Physical characteristics are as follows: $^1$H NMR (CDCl$_3$) δ[9.61 (br s), 9.35 (br s) 1H], 7.35-7.00 (m, 10H), 3.09-3.03 (m, 1H), 2.49-2.42 (m, 2H), 1.94-1.88 (m, 1H), 1.78-1.70 (m, 2H), 1.57-1.33 (m, 4H), 1.11-0.98 (m, 1H), 0.91-0.75 (m, 6H), 0.59-0.39 (m, 2H), 0.20-0.12 (m, 2H) ppm; MS (EI) m/z 404; HRMS (EI) Calcd for $C_{27}H_{32}O_3$: 404.2351. Found: 404.2344.

Example DX-20

(Chart D, "D-2" where $R_2$ is 3-phenylpropyl, $R_3$ is 2-methylpropyl and $R_1$ is cyclopropylphenylmethyl)

Physical characteristics are as follows: $^1$H NMR (CDCl$_3$) δ[9.90 (br s), 9.67 (br s) 1H], 7.36-7.00 (m, 10H), 3.07-3.02 (m, 1H), 2.47-2.34 (m, 2H), 1.79-1.43 (m, 8H), 0.88-0.77 (m, 6H), 0.59-0.41 (m, 2H), 0.22-0.15 (m, 2H) ppm; MS (EI) m/z 404; HRMS (EI) Calcd for $C_{27}H_{32}O_3$: 404.2351. Found: 404.2348.

CHART E

CHART E describes a literature procedure for general methodology for synthesizing 3-substituted tetronic acids. Damon, R. E., Luo, T. and Schlessinger, R. H. Tet. Let. 1976, 32, 2749–2752.

CHART F

CHART F describes the aldol condensation of benzylic aldehydes of the formula F-1 with tetronic acid analogs to form a dimer, F-2, which can be reduced using cyanoborohydride to form analogs of the formula F-3. Specific examples of side chains of this type are found in application Ser. No. 08/090,876, filed Jul. 13, 1993 (pyrones). (Begley, M. J., Clemo, N. G. and Pattenden, G. J. Chem. Soc. Perkin Trans.I 1985, 2393–2397) Alternatively, under acid conditions, aldol condensation of substituted benyzlic aldehydes of formula F-1 with tetronic acid analogs form 3-aryl methylene derivatives of formula F-6, which can be further elaborated by reaction with Grignard reagents of formula F-7 to form tetronic acid analogs of formula F-8 (Zimmer, H., Hillstrom, W. W., Schmidt, J. C., Seemuth, P. D. and Vogeli, R. J. Org. Chem. 1978 43, 1541–1544) and (Amer, A., Ho, D., Rumpel, K., Schenkel, R. I. and Zimmer, H. J. Org. Chem. 1991, 56, 5210–5213). Alkylation at the 5-positioni of the tetronic acid (as described for the example BX-3) provides analogs of formula F-9.

PREPARATIONS AND EXAMPLES OF CHART F

Example FX-1

(See Chart F, "F-9" where $R_2$ is 3-phenylpropyl and $Z_1$ is phenylmethyl.) 2(5H)-Furanone, 3-(1,2-diphenylethyl)-4-hydroxy-5-(3-phenylpropyl)-.

Alkylation of 250 mg of 3-(1',2'-diphenylethyl)-4-hydroxy-2(5H)-furanone (Chart F, figure "F-8") prepared by the procedure of Amer, A. et al. (J. Org. Chem. 1991, 56, 5210) with 708 mg of 1-bromo-3-phenylpropane (Chart F, figure "F-4") in the presence of 2.5 equivalents of lithium diisopropylamide provided 126 mg of the tide compound as a colorless powder.

Physical characteristics are as follows:
$^1$H-NMR(CDCl$_3$) δ1.38–1.82 (m,4H), 2.50–2.55(m,2H), 3.22–3.59(m, 2H), 4.02–4.07(m, 1H), 4.48–4.51(m,1H), 7.02–7.48(m, 15H). $^{13}$C-NMR(75mHZ CDCl$_3$) δ, 25.25, 30.88, 35.11, 48.37, 41.29, 77.48, 103.08, 125.64, 125.76, 126.21, 126.27, 127.57, 127.90, 127.94, 128.11, 128.19, 128.21, 128.33, 128.68, 140.29, 141.50, 143.25, 174.76, 174.89. HRMS calculated for $C_{27}H_{26}O_3$: 398.1882, found 398.1875.

Following procedures analogous to those described above and using starting materials and reagents readily known and available to one of ordinary skill in the art of organic synthesis, the following additional compounds of the present invention are prepared:

Example FX-2

(Chart F, "F-9" where $R_2$ is 3-phenylpropyl and $Z_1$ is phenyl)

Physical characteristics are as follows: $^1$H NMR (CDCl$_3$) δ7.36-7.12 (m, 15H), 5.18 (s, 1H), 4.67 (m, 1H), 2.62 (t, J=7.4 Hz, 2H), 1.96–1.61 (m, 4H) ppm; $^{13}$C NMR (CDCl$_3$) δ174.00, 173.07, 141.25, 139.82, 128.92, 128.23, 128.16, 128.10, 127.24, 127.20, 125.72, 103.50, 77.30, 45.26, 35.06, 30.95, 25.57 ppm; HRMS (EI) calcd for $C_{26}H_{24}O_3$: 384.1725. Found: 384.1726.

Example FX-3

(See Chart F, figure "F-9" where $R_2$ is 3-phenylpropyl and $Z_1$ is vinyl.)

Physical characteristics are as follows: $^1$H-NMR(300 mHz CDCl3) δ1.68(m,3H), 1.96(m,1H), 2.60(m,2H), 4.51 (d, J=5.5Hz, 1H), 4.66(m,1H), 5.08(d, J=17.2Hz, 1H), 5.26 (d, 10.1 Hz, 1H), 6.29(m,1H), 7.19(m,10H). $^{13}$C-NMR(75 mHz CDCl$_3$) δ25.67, 31.02, 35.21, 43.02, 77.80, 102.53, 117.40, 125.85, 127.17, 127.75, 128.29, 128.88, 136.91, 129.68, 141.54, 173.99, 174.91. HRMS calculated for $C_{22}H_{22}O_3$: 334.1596, found 334.1577.

Example FX-4

(See Chart F, figure "F-9" where $R_2$ is 3-phenylpropyl and $Z_1$ is 1-methylethyl.)

Physical characteristics are as follows:
$^1$H-NMR(300 mHz CDCl$_3$) δ0.74(d, J=6.5Hz, 3H), 0.96 (d, J=6.5Hz, 3H), 1.61(m,3H), 1.92(m,1H), 2.60(m,2H), 2.73(m,1H), 3.22(m,1H), 4.59(m,1H), 7.20(m,10H). $^{13}$C-NMR(75 mHz CDCl$_3$) δ21.42, 25.15, 28.86, 29.22, 30.93, 35.08, 48.40, 77.41, 104.36, 125.66, 126.03, 128.15, 141.49, 143.52, 174.33, 175.03. HRMS calculated for $C_{23}H_{26}O_3$: 350.1882, found 350.1889.

Example FX-5

(See Chart F, figure "F-9" where $R_2$ is 3-phenylpropyl and $Z_1$ is 1,1-dimethylethyl.)

Physical characteristics are as follows:
$^1$H-NMR(300 mHz CDCl$_3$) δ1.00(s,9H), 1.67(m,3H), 1.97(m,1H), 2.60(q, J=7.8Hz, 2H), 3.62(s,1H), 4.62(m,1H), 7.20(m,8H), 7.56(d, J=7.8Hz, 2H). $^{13}$C-NMR(75 mHz CDCl$_3$) δ25.30, 25.52, 28.77, 28.78, 30.98, 31.13, 34.96, 35.05, 51.75, 52.13, 77.02, 103.34, 103.59, 125.58, 125.94, 127.34, 128.08, 128.13, 130.13, 141.40, 141.52, 174.60, 175.11, 175.88, 176.23. NMR complicated by the presence of diastereomers. HRMS calculated for $C_{24}H_{28}O_3$: 364.2038, found 364.2036.

CHART G

CHART G describes a method for preparing Sa-substituted tetronic acid analogs of formula G-8. Protection of 3-substituted tetronic acids (A-4) as their methyl ethers is accomplished using a modification of the literature procedure (Gill, M.; Kiefel, M. J.; Lally, D. A.; Ten, A. Aust. J. Chem. 1990, 43, 1497) to provide intermediates of general structure G-1. Aldol reaction of the anion generated from G-1 with an appropriate aldehyde (general structure G-2) provides the hydroxy analogs of formula G-3. A two step dehydration (Kametani, T.; Katoh, T.; Tsubuki, M.; Honda, T. J. Am. Chem. Soc. 1986, 108, 7055.) provides the alkene derivatives (G-4) [for the aldol reaction/dehydration of methyl tetronate ("G-1", where $R_1$ is proton) see Pelter, A.; Al-Bayati, R. I. H.; Ayoub, M. J.; Lewis, W.; Pardasani, P.; Hansel, R. J. Chem. Soc. Perkin Trans. I 1987, 717] which react with either organocuprates (G-5) (For general reviews of organocuprate conjugate additions see: Lipshutz, B. H.; Sengupta, S. Org. Reactions 1992, 41, 138. Lipshutz, B. H. Synthesis, 1987, 325. Taylor, R. J. K. Synthesis 1985, 364. Posner, B. H. Org. Reactions 1972, 19, 1.) or organoaluminum reagents (G-6) (Westermann, J.; Nickisch, K. Angew. Chem. Int. Ed. Engl. 1993, 32, 1368.) in a conjugate manner to provide the 5α-substituted analogs of formula G-7. Demethylation with LiBr (Campbell, A. C.; Maidment, M. S.; Pick, J. H.; Stevenson, D. F. J. Chem. Soc. Perkin Trans. I 1985, 1567.) provides the target compounds of formula G-8.

Preparation GP-1

(Chart G, "G-1" where $R_1$ is cyclopropylmethylphenyl).

To a solution of AP-1 (20 g, 86.9 mmol) in anhydrous THF (750 ml) at ambient temperature was added cesium carbonate (39.6 g, 122 mmol). After 30 min, dimethyl sulfate (13.87 g, 110 mmol) was added and the mixture stirred for 48 h. Removal of the volatiles in vacuo provided a residue which was partitioned between chloroform and water. The organic layer was washed with water and brine, dried ($Na_2SO_4$), filtered and concentrated in vacuo. Flash chromatography of the residue using methylene chloride as eluent afforded the title compound (16.4 g, 77%) as a crystalline solid: mp 65.3–65.8° C.; $^1$H NMR ($CDCl_3$) δ7.42-7.16 (m, 5H), 4.71 (s, 2H), 3.85 (s, 3H), 2.86 (d, J=10.5 Hz, 1H), 1.82-1.69 (m, 1H), 0.62-0.51 (m, 2H), 0.25-0.17 (m, 2H) ppm; $^{13}$C NMR ($CDCl_3$) δ173.87, 172.58, 142.94, 128.26, 127.69, 126.39, 107.28, 64.50, 57.31, 45.24, 13.63, 5.64, 4.89 ppm; EIMS m/z 244 (M$^+$); Anal calcd for $C_{15}H_{16}O_3$: C, 73.75; H, 6.60. Found: C, 73.69; H, 6.63.

Preparation GP-2

(Chart G, "G-3" where $R_1$ is cyclopropylmethylphenyl and $Z_2$ is 2-phenylethyl).

To a cooled (–78° C.) solution of GP-1 (4.27 g, 17.5 mmol) in anhydrous THF (300 ml) was added n-butyllithium (13.6 mL of a 1.6 M solution in hexanes, 21.76 mmol) dropwise over a period of 10 min. After an additional 10 min, hydrocinnamaldehyde ("G-2" where $Z_2$ is 2-phenylethyl, 3.37 mL, 24.3 mmol) was added dropwise maintaining the internal reaction temperature below –77° C. After 20 min, the reaction mixture was quenched with acetic acid (100 mL of a 20% solution in hexane), partially concentrated in vacuo, diluted with ethyl acetate and washed with brine. The organic layer was dried ($MgSO_4$), filtered, and concentrated in vacuo to afford a residue that was purified by flash chromatography using hexane/2-propanol (2–15%) as eluent. Recrystallization from ethyl acetate/hexane provided GP-2 (4.13 g, 62%) as a crystalline solid; mp 115.5–117.5° C.; $^1$H NMR ($CDCl_3$) δ7.42-7.12 (m, 10H), 4.87 (d, J=3.6 Hz, 1H), 3.94-3.85 (m, 1H), 3.77 (s, 3H), 3.09 (dd, J=10.2 Hz, 4.7 Hz, 1H), 2.92-2.65 (m, 2H), 2.10 (d, J=8.3 Hz, 1H), 1.87-1.62 (m, 3H), 0.75-0.65 (m, 2H), 0.42-0.20 (m, 2H) ppm; EIMS m/z 378 (M+).

Preparation GP-3

(Chart G, "G-4" where $R_1$ is cyclopropylmethylphenyl and $Z_2$ is 2-phenylethyl).

To a solution of GP-2 (1.84 g, 4.87 mmol), triethylamine (2.03 mL, 14.6 mmol), and 4-dimethylaminopyridine (178 mg, 1.46 mmol) in methylene chloride (50 mL) at ambient temperature was added trifluoroacetic anhydride (2.06 mL, 14.6 mmol) over a period of 15 min. After 3 hours, the reaction mixture was poured into water and extracted with methylene chloride. The combined organic extracts were washed with brine, dried ($MgSO_4$), filtered, concentrated in vacuo and used without further purification.

The trifluoroacetate prepared above was dissolved in benzene (75 mL) and 1,8-diazabicyclo[5.4.0]undec-7-ene (873 μL, 5.84 mmol) was added. The solution was heated to reflux for 1 h, then stirred overnight at ambient temperature. The volatiles were removed in vacuo and the residue dissolved in ethyl acetate. The organic layer was washed with 0.25 N HCl, and brine, dried ($MgSO_4$), filtered and concentrated in vacuo. Flash chromatography of the residue using hexane/ethyl acetate (2–5%) as eluent afforded the title compound (1.22 g, 70%) as an oil: $^1$H NMR ($CDCl_3$) δ7.44-7.18 (m, 10H), 5.39 (t, J=7.6 Hz, 1H), 3.85, (s, 3H), 3.16 (d, J=10.2 Hz, 1H), 2.81-2.62 (m, 4H), 1.78-1.69 (m, 1H), 0.79-0.55 (m 2H), 0.34-0.24 (m, 2H) ppm; $^{13}$C NMR ($CDCl_3$) δ169.28, 161.94, 143.63, 142.46, 140.72, 128.32, 127.41, 126.44, 125.97, 110.36, 109.42, 60.44, 45.27, 34.93, 27.27, 14.35, 6.35, 4.43 ppm; EIMS m/z 360 (M$^+$).

Preparation GP-4A and GP-4B (Chart G, "G-7" where $R_1$ is cyclopropylmethylphenyl, $Z_2$ is 2-phenylethyl and $Z_3$ is butyl) by the reaction of "G-4" with a Grignard reagent (G-5).

To a flame dried 25 mL 2-neck flask was added CuCN (56 mg, 0.63 mmol). The flask was flushed and evacuated with argon 4 times and left under an atmosphere of argon. Anhydrous ethyl ether (2 mL) was added and the suspension cooled to –78° C. n-Butyllithium (790 μL of a 1.6 M solution in hexanes, 1.27 mmol) was added dropwise and mixture allowed to warm to –20° C. at which point dissolution was complete. The solution was recooled to –78° C. and a solution of GP-3 (152 mg, 0.42 mmol) in anhydrous ethyl ether (4 mL) was added. The reaction mixture was warmed to 0–5° C., stirred for 45 min then quenched by the addition of a 10% $NH_4OH$, saturated $NH_4Cl$ solution (5 mL). The mixture was diluted with ethyl acetate and the organic layer washed with 0.25 N HCl and brine, dried ($MgSO_4$), filtered and evaporated in vacuo. The residue was purified by flash chromatography using hexane/ethyl acetate (1–2%) as eluant which allowed the partial separation of the mixture of stereoisomers into a faster eluting component GP4A (36 mg, 20%), a slower eluting component GP-4B (44 mg, 25%) both as oils as well as 30 mg (17%) of fractions contain both components.

GP-4A: $^1$H NMR ($CDCl_3$) δ7.42-7.39 (m, 2H), 7.28-7.16 (m, 6H), 7.07-6.99 (m, 2H), [4.89 (s) and 4.88 (s), 1H], [3.66 (s) and 3.65 (s), 3H], 3.04 (d, J=10.3 Hz, 1H), 2.69-2.44 (m, 2H), 1.78-1.71 (m, 2H), 1.57-1.25 (overlapping m's, 8H), 0.93-0.89 (m, 3H), 0.69-0.51 (m, 2H), 0.28-0.19 (m, 2H) ppm; $^{13}$C NMR ($CDCl_3$) δ173.71, 173.23, 143.10, 141.83, 128.35, 127.57, 127.48, 126.38, 125.85, 109.167, 78.18, 58.77, 45.21, 38.44, 33.22, 30.78, 30.55, 29.40, 28.80, 14.12, 6.33, 4.61 ppm.

GP-4B: $^1$H NMR ($CDCl_3$) δ7.44-7.39 (m, 2H), 7.30-7.02 (m, 8H), [4.93 (s) and 4.92 (s), 1H], [3.73 (s) and 3.69 (s), 3H], [3.06 (d, J=10.3) and 3.04 (d, J=10.3 Hz), 1H], 2.85-2.61 (m, 2H), 1.89-1.69 (overlapping m's, 4H), 1.25-1.14 (overlapping m's, 6H), 0.86-0.78 (m, 3H), 0.71-0.52 (m, 2H), 0.31-0.20 (m, 2H) ppm; $^{13}$C NMR ($CDCl_3$) δ173.75, 173.35, 143.02, 141.81, 128.47, 128.32, 127.45, 126.40, 125.98, 109.30, 78.16, 58.95, 45.33, 45.11, 38.72, 33.24, 32.35, 29.69, 26.83, 22.86, 14.30, 14.05, 13.84, 6.37, 4.50 ppm; EIMS m/z 418 (M$^+$).

Preparation of GP-5A and GP-5B (Chart G, "G-7" where $R_1$ is cyclopropylmethylphenyl, $Z_2$ is 2-phenylethyl and $Z_3$ is ethyl) by the reaction of G-4 with an organoaluminum reagent (G-6).

To a mixture of GP-3 (240 mg, 0.67 mmol) and copper(I) bromide-dimethyl sulfide complex (14 mg, 0.07 mmol) in THF (4 mL) at –78° C. was added triethylaluminum ("G-6" where $Z_3$ is ethyl, 1.2 mL of a 1.0 M solution in hexanes, 1.2 mmoL). After warming to ambient temperature the mixture was stirred overnight then quenched by the addition of a 10% $NH_4OH$, saturated $NH_4Cl$ solution (5 mL). The mixture was diluted with ethyl acetate and the organic layer washed with 0.25 N HCl and brine, dried ($MgSO_4$), filtered and evaporated in vacuo. The residue was purified by flash chromatography using hexane/ethyl acetate (5%) as eluant which allowed the partial separation of the mixture of stereoisomers into a faster eluting component GP-SA (45 mg, 19%), a slower eluting component GP-5B (60 mg, 25%) both as oils as well as 35 mg (15%) of fractions contain both components.

GP-SA: $^1$H NMR (CDCl$_3$) δ7.43-7.17 (m, 10H), 4.93-4.92 (m, 1H), [3.75 (s) and 3.70 (s), 3H], 3.08-3.03 (m, 1H), 2.84-2.64 (m, 2H), 1.88-1.68 (m, 4H), 1.29-1.19 (m, 2H), 0.89-0.82 (m, 3H), 0.70-0.54 (m, 2H), 0.31-0.19 (m, 2H) ppm; $^{13}$C NMR (CDCl$_3$) δ173.37, 173.27, 142.95, 141.63, 128.47, 127.47, 126.34, 125.97, 109.09, 78.13, 58.99, 45.38, 45.11, 40.48, 33.23, 31.84, 20.10, 14.33, 14.17, 11.93, 6.38, 4.48 ppm.

GP-5B: $^1$H NMR (CDCl$_3$) δ7.42-7.39 (m, 2H), 7.29-7.15 (m, 6H), 7.07-6.99 (m, 2H), 4.92-4.90 (m, 1H), [3.67 (s) and 3.65 (s), 3H], 3.05 (d, J=10.3 Hz, 1H), 2.72-2.41 (m, 2H), 1.75-1.44 (m, 6H), 1.04-0.94 (m, 3H), 0.69-0.51 (m, 2H), 0.28-0.19 (m, 2H) ppm; $^{13}$C NMR (CDCl$_3$) δ173.69, 173.22, 143.10, 141.81, 128.61, 127.55, 126.39, 125.97, 109.15, 78.12, 58.84, 45.27, 40.36, 39.99, 33.20, 28.52, 23.96, 23.73, 14.25, 14.12, 11.93, 6.33, 4.60 ppm; EIMS m/z 390 (M$^+$).

Preparation GP-6 and Example GX-1

(Chart G, "G-8" where R$_1$ is cyclopropylmethylphenyl, Z$_2$ is butyl and Z$_3$ is 2-phenylethyl).

To a solution of GP-4A (36 mg, 0.09 mmol) in anhydrous DMF (15 mL) was added LiBr (13 mg, 0.15 mmol). After heating the mixture at reflux for 1 h, the volatiles were removed in vacuo and the residue partitioned between ethyl acetate and 0.25 N HCl. The organic layer was washed with brine, dried (MgSO$_4$), filtered and concentrated. Purification of the residue by flash chromatography using hexane/ethyl acetate (25%) as eluent provided the title compound (12 mg, 34%) as an oil: $^1$H NMR (CDCl$_3$) δ7.41-7.05 (m, 10H), [4.80 (d, J=2.4 Hz) and 4.76 (d, J=2.4 Hz), 1H], 3.28-3.17 (m, 1H), 2.75-2.46 (m, 2H), 1.95-1.83 (m, 1H), 1.76-1.23 (overlapping m's, 9H), 0.89-0.86 (overlapping t's, 3H), 0.63-0.56 (m, 2H), 0.40-0.20 (m, 2H) ppm; $^{13}$C NMR (CDCl$_3$) δ174.37, 173.37, 142.01, 141.21, 129.24, 128.90, 128.24, 127.11, 125.81, 106.04, 79.21, 43.57, 38.60, 33.55, 33.34, 30.29, 30.12, 29.24, 22.80, 14.02, 13.76, 13.61, 4.77, 4.59, 4.35 ppm; HRMS (EI) calcd for C$_{27}$H$_{32}$O$_3$: 404.2351. Found: 404.2339;

Following procedures analogous to those described above and using starting materials and reagents readily known and available to one of ordinary skill in the art of organic synthesis, the following additional compounds of the present invention are prepared:

Example GX-2

(Chart G, "G-8" where R$_1$ is cyclopropylmethylphenyl, Z$_2$ is butyl and Z$_3$ is 2-phenylethyl).

Physical characteristics are as follows: $^1$H NMR (CDCl$_3$) δ7.42-7.15 (m, 10H), [6.43 (br s) and 6.38 (br s), 1H] [4.86 (m) and 4.71 (m), 1H], 3.38-3.40 (m, 1H), 2.82-2.61 (m, 2H), 1.87-1.73 (m, 2H), 1.62-1.48 (m, 1H), 1.41-1.12 (m, 7H), 0.85 (t, J=6.8 Hz, 3H), 0.71-0.62 (m, 2H), 0.55-0.45 (m, 1H), 0.28-0.14 (m 1H) ppm; $^{13}$C NMR (CDCl$_3$) δ173.67, 172.62, 141.89, 140.79, 129.16, 128.41, 127.78, 127.38, 125.89, 106.12, 78.91, 43.37, 38.73, 33.59, 32.21, 29.71, 29.40, 27.09, 22.88, 13.91, 13.65, 4.32, 4.18 ppm.

Example GX-3

(Chart G, "G-8" where R$_1$ is cyclopropylmethylphenyl, Z$_2$ is methyl and Z$_3$ is 2-phenylethyl).

Physical characteristics are as follows: $^1$H NMR (CDCl$_3$) δ7.41-7.08 (m, 10H), 4.64-4.60 (m, 1H), 3.28-3.20 (m, 1H), 2.67-2.45 (m, 2H), 2.11-1.91 (m, 1H), 1.63-1.25 (m, 4H), 1.08-1.01 (m, 3H), 0.90-0.76 (m, 1H), 0.68-0.55 (m, 2H), 0.41-0.39 (m, 1H), 0.24-0.19 (m, 1H) ppm; $^{13}$C NMR (CDCl$_3$) δ174.30, 172.74, 141.80, 141.02, 128.95, 128.68, 128.34, 128.23, 127.74, 127.18, 125.87, 106.09, 81.43, 43.44, 34.19, 33.27, 31.09, 29.71, 15.57, 13.72, 4.65, 4.34 ppm; HRMS (EI) calcd for C$_{24}$H$_{26}$O$_3$: 362.1882. Found: 362.1894.

Example GX-4

(Chart G, "G-8" where R$_1$ is cyclopropylmethylphenyl, Z$_2$ is phenyl and Z$_3$ is 2-phenylethyl).

Following the general procedure described for the synthesis of GX-1 and using phenyl lithium (prepared from commercially available bromobenzene and lithium metal) to prepare the requisite organocuprate, the title compound was isolated as an amorphous solid: $^1$H NMR (CDCl$_3$) δ7.31-6.64 (m, 16H), 4.87-4.79 (m, 1H), 3.13-3.11 (m, 1H), 2.93-2.87 (m, 1H), 2.57-2.01 (m, 4H), [1.25-1.11 (m) and 0.93-0.84 (m), 1H], 0.52-0.41 (m, 2H), 0.22-(–)0.07 (m, 2H) ppm; $^{13}$C NMR (CDCl$_3$) δ174.30, 174.12, 172.41, 141.47, 141.43, 140.13, 136.78, 129.43, 129.08, 129.01, 128.89, 128.64, 127.98, 126.86, 125.95, 105.99, 79.88, 46.08, 45.91, 43.05, 34.09, 33.83, 33.56, 13.68, 13.31, 4.72, 4.54, 3.99 ppm; HRMS (EI) calcd for C$_{29}$H$_{28}$O$_3$: 424.2038. Found: 424.2019.

Example GX-5

(Chart G, "G-8" where R$_1$ is cyclopropylmethylphenyl, Z$_2$ is butyl and Z$_3$ is ethyl).

Physical characteristics are as follows: $^1$H NMR (CDCl$_3$) δ7.39 (d, J=7.1 Hz, 2H), 7.29-7.17 (m, 3H), 4.77-4.74 (m, 1H), 3.07 (d, J=9.7 Hz, 1H), 1.77 (br, 1H), 1.61-1.40 (m, 3H), 1.28-1.12 (m, 5H), 0.93-0.80 (m, 6H), 0.61-0.55 (m, 2H), 0.29-0.20 (m,2H) ppm; $^{13}$C NMR (CDCl$_3$) δ175.96, 175.04, 142.04, 128.48, 127.73, 127.67, 126.64, 105.54, 79.64, 43.98, 40.65, 29.58, 26.62, 23.71, 22.91, 13.91, 13.65, 11.63, 5.31, 4.43 ppm; HRMS (EI) calcd for C$_{21}$H$_{28}$O$_3$: 328.2038. Found: 328.2030.

Example GX6

(Chart G, "G-8" where R$_1$ is cyclopropylmethylphenyl, Z$_2$ is phenyl and Z$_3$ is ethyl).

Physical characteristics are as follows: mp 185–186° C.; $^1$H NMR (CDCl$_3$) δ7.37–6.75 (m, 10H), 4.81-4.79 (m, 1H), 3.00-2.94 (m, 1H), 2.60-2.55 (m, 1H), 1.92-1.80 (m, 2H), 1.28-1.24 (m,1H), 0.81 (t, J=7.3 Hz, 3H), 0.48-0.36 (m, 1H), 0.20-0.02 (m,3H) ppm; $^{13}$C NMR (CDCl$_3$) δ175.11, 173.55, 173.33, 141.96, 136.96, 128.57, 127.89, 127.85, 127.74, 127.02, 126.81, 126.65, 105.05, 79.45, 48.077, 43.05, 25.31, 13.47, 13.12, 11.94, 5.75, 5.40, 3.40 ppm; HRMS (EI) calcd for C$_{23}$H$_{24}$O$_3$: 348.1725. Found: 348.1729.

Example GX-7

(Chart G, "G-8" where R$_1$ is cyclopropylmethylphenyl, Z$_2$ is phenyl and Z$_3$ is propyl).

Physical characteristics are as follows: mp 164–165° C.; $^1$H NMR (CDCl$_3$) δ7.347.10 (m, 10H), 6.61-6.59 (m, 1H), 6.38 (s, 1H), 4.92-4.82 (m, 1H), 3.12 -3.05 (m, 1H), 2.99 (t, J=8.5 Hz, 1H), 2.04-1.84 (m, 2H), 1.32-1.23 (m, 3H), 0.90 (t, J=7.2 Hz, 3H), 0.72-0.10 (m, 4H) ppm; $^3$C MNR (CDCl$_3$) δ171.91, 171.85, 140.71, 139.62, 137.41, 137.25, 129.17, 128.87, 128.65, 128.50, 128.13, 127.94, 127.66, 127.49, 105.93, 79.43, 46.39, 46.23, 42.80, 34.48, 34.09, 20.59, 13.74, 13.53, 13.16, 4.16, 4.03 ppm; HRMS (EI) calcd for C$_{24}$H$_{26}$O$_3$: 362.1882. Found: 362.1900.

Example GX-8

(Chart G, "G-8" where $R_1$ is cyclopropylmethylphenyl, $Z_2$ and $Z_3$ are propyl).

The title example was prepared using tripropyl aluminum as the reagent of general formula G-6.

Physical characteristics are as follows: $^1$H NMR (CDCl$_3$) δ7.42-7.15 (m, 5H), 4.84-4.72 (m, 1H), 3.16-3.12 (m, 1H), 1.93-1.64 (m, 1H), 1.60-1.00 (m, 6H), 1.00-0.52 (m, 10H), 0.40-0.13 (m, 2H) ppm; $^{13}$C NMR (CDCl$_3$) δ175.2, 174.0, 141.8, 128.7, 128.4, 128.1, 127.8, 126.8, 126.5, 105.9, 79.7, 43.8, 33.1, 29.7, 26.9, 20.6, 20.3, 14.3, 13.7, 5.1, 4.4 ppm; HRMS (EI) calcd for $C_{21}H_{28}O_3$: 329.2117. Found: 329.2118.

CHART H

CHART H describes a method for preparing Sa-substituted tetronic acid analogs of general formulas H-5 and H-7. Wadsworth-Emmons Wittig chemistry using commercially available phosphonate esters (H-1) and commercially available or readily synthesized aldehydes (H-2) provides unsaturated esters of the general formula H-3. Reaction of these esters with the anion generated from G-1 in a Michael fashion affords the desired Sa-substituted analogs of the formula H-4. The ester functionality is readily modified as demonstrated by its selective reduction with lithium borohydride (Ireland, R. E.; Thompson, W. J. *J. Org. Chem.* 1979, 44, 3041.) to provide the alcohol of formula H-6. Demethylation of the protected tetronates with LiBr provides the target compounds of formula H-5 and H-7 respectively.

Preparation HP-1

(Chart H "H-3" where $Z_4$ is 2-phenylethyl).

To a cooled (-78° C.) solution of methyl diethylphosphonoacetate ("H-1", 1.48 g, 7.07 mmol) in anhydrous THF (5 mL) was added potassium tert-butoxide (6.71 mL of a 1 M solution in THF, 6.71 mmol). After 30 min, hydrocinnamaldehyde ("H-2" where $Z_4$ is 2-phenylethyl, 980 μL, 7.07 mmol) was added slowly and the mixture allowed to warm gradually to ambient temperature. After stirring for 48 h, the reaction was quenched by the addition of water (20 mL) and ethyl acetate. The organic layer was washed with water and brine, dried (MgSO$_4$), filtered and concentrated in vacuo. Flash chromatography of the residue using hexane/ethyl acetate (10%) as eluent afforded the tide compound (1.17 g, 87%) as an oil: $^1$H NMR (CDCl$_3$) δ7.31-7.16 (m, 5H), 7.01 (dt, J=15.7 Hz, 6.8 Hz, 1H), 5.84 (dt, J=15.7, 1.5 Hz, 1H), 3.72 (s, 3H), 2.77 (t, J=8.15 Hz, 2H), 2.51 (m, 2H) ppm.

Preparation HP-2

(Chart H "H-4" where $R_1$ is cyclopropylphenylmethyl and $Z_4$ is 2-phenylethyl).

To a cooled (-78° C.) solution of GP-1 (1.1 g, 4.52 mmol) in anhydrous THF (20 ml) was added n-butyllithium (0.42 μL of a 1.6 M solution in hexanes, 0.67 mmol) dropwise over a period of 5 min. After an additional 15 min, a solution of HP-1 (0.78 g, 4.1 mmol) in anhydrous THF (10 mL) was added dropwise maintaining the internal reaction temperature below -70° C. The reaction mixture was stirred for 4 h maintaining the temperature between -60 and -70° C. then quenched by transferring the reaction mixture via cannula into a stirred solution of saturated NH$_4$Cl. After diluting with ethyl acetate, the organic layer washed with 0.25 N HCl, brine, dried (MgSO$_4$), filtered, and concentrated in vacuo. The resulting residue was purified by flash chromatography using hexanelethyl acetate (15–20%) as eluent to provide the title compound (770 mg, 43%) as a solid; $^1$H NMR (CDCl$_3$) δ7.20-7.17 (m, 2H), 7.07-6.95 (m, 6H), [4.85 (s), 4.84 (s), 1H], 3.53 (s, 3H), 3.49 (s, 3H), 2.76 (d, J=10.3 Hz, 1H), 2.51-2.18 (m, 5H), 1.58-1.16 (m, 3H), 0.47-0.27 (m, 2H), 0.74-(-)0.01 (m, 2H) ppm; $^{13}$C NMR (CDCl$_3$) δ173.03, 172.71, 142.74, 140.84, 128.25, 128.15, 127.52, 126.22, 125.91, 109.69, 77.55, 58.75, 51.66, 45.02, 35.45, 34.88, 32.68, 27.55, 13.67, 5.92, 4.73 ppm; EIMS m/z 434 (M$^+$).

Example HX-1

(Chart H "H-5" where $R_1$ is cyclopropylphenylmethyl and $Z_4$ is 2-phenylethyl).

Following the general procedure described in preparation GP-6, the title compound was isolated as an oil: $^1$H NMR (CDCl$_3$) δ7.39 (d, J=6.8 Hz, 2H), 7.28-7.05 (m, 6H), 7.03 (d, J=6.7 Hz, 2H), [4.75 (s), 4.74 (s), 1H], 3.68 (s, 3H), 3.01 (d, J=9.9 Hz, 1H), 2.67-2.34 (m, 5H), 1.73-1.58 (m, 2H), 1.47-1.37 (m, 1H), 0.60-0.50 (m, 2H), 0.27-0.18 (m, 2H) ppm; $^{13}$C NMR (CDCl$_3$) δ174.31, 172.67, 142.16, 141.07, 128.95, 128.43, 128.15, 126.55, 125.97, 106.19, 78.86, 52.19, 44.30, 36.14, 34.93, 29.25, 14.10, 6.04, 5.21 ppm; HRMS (EI) calcd for $C_{26}H_{28}O_5$: 420.1937. Found: 420.1952.

Preparation HP-3

(Chart H "H-6" where $R_1$ is cyclopropylphenylmethyl and $Z_4$ is 2-phenylethyl).

To a solution of HP-2 (200 mg, 0.46 mmol) in anhydrous THF (5 mL) at ambient temperature was added lithium borohydride (800 μL of a 2.0 M solution in THF, 1.6 mmol). After 3 h, the solution was cooled to 0–5° C. and the reaction quenched by the slow addition of acetic acid (2 mL). The mixture was diluted with ethyl acetate and the organic layer washed with 0.25 N HCl, brine, dried (MgSO$_4$), filtered, and concentrated in vacuo. The resulting residue was purified by flash chromatography using methylene chloride/methanol (1–2%) as eluent to provide the tide compound (770 mg, 43%) as a solid; $^1$H NMR (CDCl$_3$) δ7.39 (d, J=7.1 Hz, 2H), 7.27-7.03 (m, 6H), 7.00 (d, J=6.7 Hz, 2H), [5.01 (s), 4.97 (s), 1H], 3.78-3.66 (m, 2H), 3.66 (s, 3H), 3.00 (d, J=10.4 Hz, 1H), 2.68-2.41 (m, 2H), 2.15-2.03 (m, 1H), 1.89-1.68 (m, 4H), 1.52-1.42 (m, 2H), 0.70-0.47 (m, 2H), 0.30-0.18 (m, 2H) ppm; $^{13}$C NMR (CDCl$_3$) δ73.68, 173.29, 142.95, 141.55, 128.45, 127.64, 126.79, 125.86, 109.17, 80.49, 60.43, 58.97, 45.28, 37.64, 35.07, 34.96, 33.52, 28.43, 14.04, 6.17, 4.79 ppm; EIMS m/z 406 (M$^+$).

Example HX-2

(Chart H "H-7" where $R_1$ is cyclopropylphenylmethyl and $Z_4$ is 2-phenylethyl).

Physical characteristics are as follows: $^1$H NMR (CDCl$_3$) δ7.43-7.10 (m, 10H), [4.73 (s), 4.71 (s), 1H], 3.90-3.81 (m, 2H), [3.03 (d, J=8.4 Hz), 2.96 (d, J=9.9 Hz), 1H], 2.64-2.55 (m, 2H), 2.26-1.71 (m, 4H), 1.66-1.50 (m, 2H), 0.92-0.51 (m, 2H), 0.31-0.21 (m, 2H) ppm; $^{13}$C NMR (CDCl$_3$) δ174.56, 173.98, 142.81, 141.50, 128.86, 128.42, 127.37, 126.46, 125.99, 105.59, 99.61, 79.82, 78.55, 58.95, 57.75, 44.65, 39.08, 33.85, 30.22, 29.71, 13.93, 5.46, 4.65 ppm; HRMS (EI) calcd for $C_{25}H_{28}O_4$: 392.1987. Found: 392.1980.

CHART I

CHART I describes a method for preparing tetronic acid derivatives of the general formula I-5 (related to general formula K-2 where X of general formula I-5 is equal to proton). This method is an improvement over the method described in Chart K when 5,5-disubstituted tetronic acids (figure "C-5" where $R_2$ and $R_3$ do not equal proton) are used.

Aldol condensation of tetronic acid derivatives of general formula C-5 with an aromatic aldehyde (I-1) in the presence of an appropriate Lewis acid such as aluminum chloride or boron trifluoride provides the intermediate of general formula 1–2 which may be used directly in the subsequent step without purification. Conjugate addition with either a Grignard reagent (I-3) or trialkylaluminum reagent (I-4) in the presence of copper bromide provides the tetronic acid derivatives of general formula I-5 and variable yields of the bis-addition product I-10. In the cases where X is a nitro group, transfer hydrogenation of I-5 provides the amine of general formula I-6, a versatile synthetic intermediate which may be reacted with a commercially available or readily prepared sulfonyl chloride (I-7) to prepare sulfonamides of general structure I-8. For the synthesis of sulfonyl chlorides see: Roblin, R. O.; Clapp, J. W. *J. Amer. Chem. Soc.* 1950, 72, 4890; Gilbert, E. E. in *Sulfonation and Related Reactions* Olah, G. A., Ed. John Wiley and Sons, New York; 1965; Pala, G. Ed. Sci. 1958, 13, 461; Close, W. J.; Swett, L. R.; Brady, L. E.; Short, J. H.; Vemsten, M. *J. Amer. Chem. Soc.* 1960, 82, 1132; Langler, R. F. *Can. J. Chem.* 1976, 54, 498; Park, Y. J.; Shin, H. H.; Kin, Y. H. *Chem. Lett.* 1992, 1483; Kim D.; Ko, Y. K.; Kim, S. H. *Synthesis*, 1992, 1203. The amine I-6 may also be reacted with chloroformates to prepare carbamates of general formula I-9.

In addition to being an intermediate in the preparation of sulfonamides and carbanates, amine I-6 can be condensed with carboxylic acids to prepare various amides. For the preparation of various amides please refer to two documents: WO 94/11361, published May 26, 1994, (International Application Number PCT/U.S.93/100645, filed Nov. 9, 1993) and WO 94/18188, published Aug. 18, 1994, (International Application Number PCT/U.S.93/00938), filed Feb. 3, 1994), incorporated by reference herein. For the preparation of an amide of β-alanine see WO 94/11361, Chart M, formula M-6. Preparation of another amide of β-alanine, is in WO 94/18188, published Aug. 18, 1994, Chart N, formula N-2, see also, this same document, Chart R, formula R-6. For the preparation of an amide of 3-(1-indolyl)-proprionic acid of formula N-5 see WO 94/11361, Chart N. Also see WO 94/11361 for the preparation of other amides such as N-Boc-protected amino acids, Samino acids and aryl carboxylic acids in Charts N and P, and examples 197–212 and 214–215. The amine I-6 can also be reacted with an isocyanate to form a urea, see WO 94/18188, Chart S, preparation of examples 223 and 224, or with a thioisocyanate to form a compound of general formula V-2, same document, Chart V, preparation of examples 366 and 367.

Amine I-6 may also be readily converted into a sulfonylurea by reaction with an appropriate sulfonyl chloride WO 94/18188, Chart DDD, examples 397–399.

Preparation IP-1

(Chart I, "I-2" where $R_2$ and $R_3$ are propyl and X is 3-nitro).

To a solution of "C-5" ($R_2$ and $R_3$ are propyl, prepared according to the preparations provided in Chart C from 4-heptanone as starting ketone "C-1") (2.65 g, 14.39 mmol) in anhydrous THF (100 mL) was added 3-nitrobenzaldehyde (I-1 where X is nitro) (2.37 g, 15.7 mmol) followed by aluminum chloride (3.84 g, 28.8 mmol) and the resulting solution stirred at room temperature for 18h. The reaction mixture was slurried with sodium carbonate decahydrate ( 8.23 g, 28.8 mmol) followed by anhydrous sodium carbonate (3.05 g, 28.8 mmol) for 10 min and then filtered through a pad of celite. The filtrate was concentrated in vacuo and the resulting yellow oil was partially dissolved in 100 mL of ethyl acetate under a nitrogen atmosphere. The mixture was filtered through a pad of celite and concentrated in vacuo afforded the title compound (5.96 g, 130%) as a yellow viscous oil which was used without further purification: $^1$H NMR (CDCl$_3$) δ8.55 (m, 2H), 8.03-7.88 (m, 1H), 7.80-7.69 (m, 2H), 1.98-1.76 (m, 4H), 1.55-1.10 (m, 4H), 1.00-0.80 (m, 6H) ppm.

Preparation IP-2 and Example IX-1

(Chart I, "I-5" where $R_2$ and $R_3$ are propyl, $Z_5$ is cyclopropyl, and X is 3-nitro) by the reaction of general structure I-2 with a Grignard reagent (I-3).

To a stirred mixture of IP-1 (4.56 g, 14.39 mmol) and copper(I) bromide dimethylsulfide complex (296 mg, 1.44 mmol) in anhydrous THF (100 mL) at –78° C. was added cyclopropylmagnesium bromide (58 mL of a 0.5M solution in THF prepared by the reaction of magnesium metal with cyclopropyl bromide, 29 mmol). After 2 h –78° C. the reaction was judged incomplete and additional cyclopropylmagnesium bromide (43 mL of 0.5M solution in THF, 21.5 mmol) was added. The reaction mixture was quenched after an additional 10 minutes at –78° C. with 5% glacial acetic acid in hexanes (40 mL) and allowed to warm to room temperature. The quenched reaction mixture was partitioned between ethyl acetate and 1.0N HCl. The organic layer was separated, washed with brine, dried over anhydrous sodium sulfate, and concentrated in vacuo. Purification by flash chromatography eluting with hexanelethyl acetate (50%) afforded the title compound (3.2 g, 62%) as an amorphous solid: $^1$H NMR (CDCl$_3$) δ10.52 (br, 1H), 8.17 (s, 1H), 8.03 (d, J=8.1 Hz, 1H), 7.69 (d, J=7.7 Hz, 1H), 7.40 (t, J=8.0 Hz, 1H), 3.08 (d, J=10.0 Hz, 1H), 1.71-1.55 (m, 5H), 1.17-1.09 (m, 4H), 0.84-0.77 (m, 6H), 0.70-0.44 (m, 2H), 0.27-0.08 (m, 2H) ppm; $^{13}$C NMR (CDCl$_3$) δ177.87, 176.02, 148.15, 144.76, 133.85, 128.98, 122.51, 121.39, 104.18, 87.60, 43.37, 37.74, 16.07, 15.97, 13.88, 13.35, 6.04, 4.15 ppm; HRMS (EI) calcd for $C_{20}H_{25}NO_5$: 359.1733. Found: 359.1729.

Preparation IP-3 and Example IX-2

(Chart I, "I-5" where $R_2$ and $R_3$ are propyl, $Z_5$ is ethyl, and X is 3-nitro) by the reaction of general structure I-2 with a trialkylaluminum reagent (I-4).

To a solution of IP-1 (171 mg, 0.54 mmol) in anhydrous THF (5 mL) was added copper(I) bromide dimethylsulfide complex (11 mg, 0.054 mmol) followed by triethylaluminum (1.35 ml of a 1.0M solution in hexanes solution, 1.35 mmol) and the resulting mixture stirred at room temperature for 1 h. The reaction mixture was partitioned between crushed ice in 1.ON HCl and ethyl acetate. The organic layer was separated washed with brine, dried over anhydrous sodium sulfate, and concentrated in vacuo. Purification by chromatography eluting with hexane/ethyl acetate (50%) afforded the title compound (116 mg, 62%) as an amorphous solid: $^1$H NMR (CDCl$_3$) δ8.21 (s, 1H), 8.03 (d, J=8.1 Hz, 1H), 7.69 (d, J=7.6 Hz, 1H), 7.40 (t, J=7.9 Hz, 1H), 3.82 (t, J=6.6 Hz, 1H), 2.21-2.16 (m, 1H), 2.02-1.93 (m, 1H), 1,89-1.65 (m, 4H), 1.23-0.68 (m, 13H) ppm; $^{13}$C NMR (CDCl$_3$) δ179.40, 176.50, 148.18, 145.86, 134.09, 129.05, 122.63, 121.36, 103.05, 87.58, 40.80, 37.88, 37.73, 25.06, 16.13, 13.88, 13.84, 12.61 ppm; HRMS (EI) calcd for $C_{19}H_{25}NO_5$: 347.1733. Found: 347.1737.

Following procedures analogous to those described above and using starting materials and reagents readily known and available to one of ordinary skill in the art of organic synthesis, the following additional compounds of the present invention are prepared:

Example IX-3

(Chart I, "I-5" where $R_2$ and $R_3$ are cyclohexyl, $Z_5$ is cyclopropyl and X is proton).

Physical characteristics are as follows: $^1$H NMR (CDCl$_3$) δ7.42-7.22 (m, 5H), 3.06 (d, J=9.4 Hz, 1H), 1.96-1.46 (m, 10 H), 1.38-1.15 (m, 1H), 0.64-0.56 (m, 2H), 0.30-0.19 (m, 2H) ppm; $^{13}$C NMR (CDCl$_3$) δ177.63, 173.29, 141.95, 128.33, 128.12, 127.36, 126.28, 125.67, 102.40, 81.86, 43.23, 32.56, 24.15, 21.49, 13.57, 5.56, 3.85 ppm; HRMS (EI) calcd for $C_{19}H_{22}O_3$: 298.1569. Found: 298.1565.

Example IX-4

(Chart I, "I-5" where $R_2$ and $R_3$ together represent a 2-(2-phenylethyl)cyclohexyl ring, $Z_5$ is cyclopropyl and X is proton).

The title compound and Example IX-5 are prepared according to the procedures provided in Charts L, C, and I. The required starting ketone LP-3 (Chart L, "L-2" where $Z_7$ is 2-phenylethyl) is reacted as described in Chart C to provide a mixture of diastereomers "C-3" (Chart C where $R_2$ and $R_3$ form a 2-(2-phenylethyl)cyclohexyl ring) which are partially seperated by flash chromatography into two mixtures of isomers of unassigned stereochemistry. These two mixtures are then transformed independently according to Charts C and I to provide the title compound and Example IX-5.

Physical characteristics of IX-4 are as follows: $^1$H NMR (CDCl$_3$) δ7.41-6.98 (m, 10H), 2.99-2.93 (m, 1H), 2.81-2.32 (m, 2H), 2.02-1.68 (m, 10H), 1.32-1.22 (m, 2H), 0.71-0.01 (m, 4H) ppm; $^{13}$C NMR (CDCl$_3$) δ179.70, 179.43, 144.00, 143.47, 130.53, 129.39, 129.26, 128.68, 127.27, 127.17, 126.87, 126.76, 105.81, 104.32, 86.13, 44.71, 44.46, 37.24, 37.01, 34.62, 31.51, 28.56, 26.04, 23.52, 17.84, 14.33, 7.35, 7.09, 4.90 ppm; HRMS (EI) calcd for $C_{27}H_{30}O_3$: 402.2195. Found: 402.2201.

Example IX-5

(Chart I, "I-5" where $R_2$ and $R_3$ together represent a 2-(2-phenylethyl)cyclohexyl ring, $Z_5$ is cyclopropyl and X is proton).

Physical characteristics are as follows: $^1$H NMR (CDCl$_3$) δ7.37-6.92 (m, 10H), 3.12-3.03 (m, 1H), 2.62-2.37 (m, 2H), 1.82-1.36 (m, 10H), 1.27-1.15 (m, 2H), 0.57-0.44 (m, 2H), 0.27-0.14 (m, 2H) ppm; $^{13}$C NMR (CDCl$_3$) δ177.62, 175.03, 142.08, 128.53, 128.22, 127.67, 126.62, 125.67, 104.45, 43.78, 43.46, 39.72, 34.45, 33.22, 30.75, 27.37, 27.16, 25.18, 21.83, 14.15, 13.78, 13.59, 5.48, 5.11, 4.28 ppm.

Example IX-6

(Chart I, "I-5" where $R_2$ and $R_3$ together represent a 2-(phenylmethyl)cyclohexyl ring, $Z_5$ is cyclopropyl and X is proton).

The title compound and Example IX-7 were prepared as described for the preparation of IX-4 starting from commercially available 2-benzylcyclohexanone.

Physical characteristics are as follows: $^1$H NMR (CDCl$_3$) δ7.48-7.06 (m, 10H), 2.99 (d, J=10.1 Hz, 1H), 2.72-2.60 (m, 1H), 2.23-1.45 (m, 9H), 1.41-1.06 (m 2H), 0.72-0.48 (m, 2H), 0.35-0.22 (m, 2H) ppm; $^{13}$C NMR (CDCl$_3$) δ176.49, 174.03, 142.58, 139.80, 129.01, 128.51, 128.00, 127.40, 126.06, 125.67, 104.22, 84.48, 43.98, 41.92, 35.12, 34.48, 26.33, 25.01, 21.74, 13.78, 5.78, 3.92 ppm.

Example IX-7

(Chart I, "I-5" where $R_2$ and $R_3$ together represent a 2-(phenylmethyl)cyclohexyl ring, $Z_5$ is cyclopropyl and X is proton).

Physical characteristics are as follows: $^1$H NMR (CDCl$_3$) δ7.47-7.12 (m, 10H), 3.14-3.10 (m, 1H), 2.95-2.75 (m, 1H), 2.10-1.22 (m, 10H), 0.78-0.55 (m, 2H), 0.41-0.32 (m, 2H) ppm; $^{13}$C NMR (CDCl$_3$) δ77.14, 173.13, 141.68, 139.83, 129.04, 128.39, 128.07, 127.36, 126.48, 104.67, 84.64, 46.15, 43.07, 36.28, 35.36, 26.29, 24.44, 22.59, 13.65, 5.63, 3.78 ppm.

Example IX-8

(Chart I, "I-5" where $R_2$ and $R_3$ are cycloheptyl, $Z_5$ is cyclopropyl and X is proton).

Physical characteristics are as follows: $^1$H NMR (CDCl$_3$) δ7.72-7.16 (m, 5H), 2.92 (d, J=9.9 Hz, 1H), 2.05-1.55 (m, 13H), 0.68-0.48 (m, 2H), 0.27-0.17 (m, 2H) ppm; $^{13}$C NMR (CDCl$_3$) δ179.57, 174.33, 142.57, 127.91, 127.27, 125.91, 101.12, 85.32, 43.39, 36.36, 28.29, 22.27, 13.44, 5.55, 3.86 ppm; HRMS (EI) calcd for $C_{20}H_{24}O_3$: 312.1725. Found: 312.1717.

Example IX-9

(Chart I, "I-5" where $R_2$ is ethyl, $R_3$ is phenylmethyl, $Z_5$ is 1-methylethyl and X is proton).

Physical characteristics are as follows: $^1$H NMR (CDCl$_3$) δ7.32-7.01 (m, 10H), 3.24-3.09 (m, 3H), 2.63-2.54 (m, 1H), 2.07-1.88 (m, 2H), [0.94 (t, J=7.3 Hz), 0.82-0.67 (m), 0.48 (d, J=6.5 Hz), 9H] ppm; $^{13}$C NMR (CDCl$_3$) δ173.51, 143.22, 142.88, 134.25, 133.73, 129.73, 129.38, 127.73, 127.60, 126.45, 125.51, 106.19, 85.15, 47.91, 41.69, 41.30, 29.32, 28.87, 28.16, 21.17, 20.59, 6.89, 6.57 ppm; HRMS (EI) calcd for $C_{23}H_{26}O_3$: 350.1882. Found: 350.1874.

Example IX-10

(Chart I, "I-5" where $R_2$ is ethyl, $R_3$ is phenylmethyl, $Z_5$ is ethyl and X is proton).

Physical characteristics are as follows: $^1$H NMR (CDCl$_3$) δ7.27-7.04 (m, 10H), 3.51-3.44 (m, 1H), 3.13-3.02 (m, 2H), 2.04-1.62 (m, 4H), [0.96-0.74 (m), 0.68 (t, J=7.3 Hz), 0.62 (t, J=7.3 Hz) 6H] ppm; $^{13}$C NMR (CDCl$_3$) δ175.18, 175.06, 142.46, 142.29, 134.37, 130.46, 128.78, 128.13, 127.57, 126.99, 126.37, 105.93, 86.64, 41.76, 41.55, 41.14, 41.01, 28.90, 28.70, 25.14, 24.95, 12.31, 12.19, 7.31 ppm; HRMS (EI) calcd for $C_{22}H_{24}O_3$: 336.1725. Found: 336.1736.

Preparation IP-4 and Example IX-11

(Chart I "I-6" where $R_2$ and $R_3$ are propyl and $Z_5$ is cyclopropyl).

To a solution of IP-2 (3.2 g, 8.9 mmol) in methanol (250 mL) at room temperature was added ammonium formate (11.23 g, 178 mmol) followed by 10% palladium on carbon (842 mg). The resulting mixture was stirred for 18 h, filtered through a pad of celite and the filtrate concentrated in vacuo. The resulting residue was partitioned between water and ethyl acetate and the organic layer separated. The aqueous layer was acidified with 1.0N HCl to a pH of 6 and reextracted with ethyl acetate. The combined organic extracts were washed with brine, dried over anhydrous sodium sulfate, and concentrated in vacuo affording the title compound (2.83 g, 97%) as an amorphous brown solid which was used without further purification: $^1$H NMR (CDCl$_3$) δ7.11 (t, J=7.7 Hz, 1H), 6.85-6.77 (m, 2H), 6.58-6.50 (m, 1H), 5.05 (br, 1H), 3.11 (d, J=9.0 Hz, 1H), 1.72-1.61 (m, 4H), 1.36-1.12 (m, 5H), 0.88-0.83 (m, 6H), 0.67-0.57 (m, 2H), 0.44-0.10 (m, 2H) ppm; $^{13}$C NMR (CDCl$_3$) δ175.62, 174.39, 146.28, 143.15, 129.84, 118.00, 114.77, 114.14, 105.13, 85.82, 43.28, 38.11, 37.97, 16.01, 14.04, 13.74, 4.81, 4.20 ppm; HRMS (EI) calcd for C$_{20}$H$_{27}$NO$_3$: 329.1991. Found: 329.1987.

Preparation IP-5 and Example IX-12

The hydrochloride salt of Example IX-11 (Chart I, "I-6" where R$_2$ and R$_3$ are propyl and Z$_5$ is cyclopropyl).

The amine IP-4 (60 mg, 0.18 mmol) was dissolved in methanol saturated with anhydrous hydrochloric acid (5 mL) at and the resulting solution stirred at room temperature for 1 h. The reaction mixture was concentrated in vacuo and the resulting white residue triturated in diethyl ether, filtered and dried in vacuo affording the title compound (28 mg, 43%) as an off-white solid: $^1$H NMR (CDCl$_3$) δ7.53-7.48 (m, 2H), 7.37 (t, J=7.8 Hz, 1H), 7.22 (d, J=7.5 Hz, 1H), 3.37-3.36 (m, 1H), 3.04 (d, J=10.2 Hz, 1H), 1.83-1.65 (m, 5H), 1.31-1.10 (m, 4H), 0.93-0.84 (m, 6H), 0.69-0.56 (m, 2H), 0.30-0.22 (m, 2H) ppm; $^{13}$C NMR (CDCl$_3$) δ176.18, 174.44, 145.62, 129.55, 129.40, 128.12, 121.88, 120.17, 103.88, 85.77, 43.61, 37.76, 37.58, 15.60, 13.52, 13.48, 13.21, 5.46, 3.99 ppm; HRMS (EI) calcd for C$_{20}$H$_{27}$NO$_3$: 329.1991. Found: 329.1988.

Following procedures analogous to those described above and using starting materials and reagents readily known and available to one of ordinary skill in the art of organic synthesis, the following additional compounds of the present invention are prepared:

Example IX-13

(Chart I, "I-6" where R$_2$ and R$_3$ are propyl and Z$_5$ is ethyl)

Physical characteristics are as follows: $^1$H NMR (CDCl$_3$) δ7.09 (t, J=7.6 Hz, 1H), 6.79 (d, J=7.4 Hz, 1H), 6.70 (s,1H), 6.55 (d, J=7.5 Hz, 1H), 5.34 (br,2H), 3.56 (t, J=7.7 Hz, 1H), 2.19-2.12 (m,1H), 1.89-1.69 (m,5H), 1.12-0.82 (m, 13H) ppm; $^{13}$C NMR (CDCl$_3$) δ176.27, 175.04, 146.39, 143.86, 129.79, 117.87, 114.91, 113.92, 104.43, 85.98, 41.55, 38.09, 37.90, 25.30, 16.04, 14.19, 13.99, 12.53 ppm; HRMS (EI) calcd for C$_{19}$H$_{27}$NO$_3$: 317.1991. Found: 317.1981.

Preparation IP-6 and Example IX-14

(Chart I, "I-8" where R$_2$ and R$_3$ are propyl, Z$_5$ is cyclopropyl and Z$_6$ is 4-cyanophenyl).

To a solution of IP-4 (130 mg, 0.39 mmol) in anhydrous methylene chloride (10 mL) was added 4-cyanobenzene sulphonylchloride (83 mg, 0.41 mmol) and pyridine (60 µL, 0.78 mmol). The reaction mixture was stirred at room temperature for 18 h and then partitioned between methylene chloride and 1.0N HCl. The organic layer was separated, washed with brine, dried over anhydrous sodium sulfate, and concentrated in vacuo. Purification by chromatography eluting with methylene chloride/methanol (5%) afforded the title compound (103 mg, 53%) as an amorphous solid: $^1$H NMR (CDCl$_3$) δ7.84 (d, J=8.6 Hz, 2H), 7.69 (d, J=8.6 Hz, 2H), 7.32 (s, 1H), 7.21 (s, 1H), 7.15-7.07 (m, 2H), 6.87-6.85 m, 1H), 3.06 (d, J=9.3 Hz, 1H), 1.84-1.58 (m, 4H), 1.44-1.02 (m,5H), 0.93-0.81 (m, 6H), 0.63-0.48 (m, 2H), 0.30-0.09 (m, 2H) ppm; $^{13}$C NMR (CDCl$_3$) δ175.97, 174.52, 144.29, 143.25, 135.67, 132.40, 128.82, 127.56, 124.81, 120.93, 119.47, 117.04, 116.74, 104.42, 85.80, 43.65, 37.71, 37.58, 15.67, 13.95, 5.56, 3.94 ppm; HRMS calcd for C$_{27}$H$_{30}$N$_2$O$_5$S: 494.1875. Found: 494.1880.

Example IX-15

(Chart I, "I-8" where R$_2$ and R$_3$ are propyl, Z$_5$ is cyclopropyl and Z$_6$ is phenyl).

Physical characteristics are as follows: $^1$H NMR (CDCl$_3$) δ7.82-7.74 (m, 2H), 7.48-7.43 (m, 2H), 7.34 (t, J=7.8 Hz, 2H), 7.25 (s, 1H), 7.07-7.02 (m, 2H), 6.89-6.88 (m, 1H), 2.95 (d, J=9.6 Hz, 1H), 1.82-1.57 (m, 4H), 1.50-1.38 (m, 1H), 1.28-0.98 (m, 4H), 0.87-0.70 (m, 6H), 0.56-0.36 (m, 2H), 0.21-0.00 (m, 2H) ppm; $^{13}$C NMR (CDCl$_3$) δ176.44, 175.20, 143.92, 138.77, 136.44, 132.97, 129.21, 128.98, 127.24, 124.86, 120.98, 119.74, 86.58, 43.58, 37.89, 15.95, 13.97, 13.59, 5.49, 4.22 ppm; HRMS calcd for C$_{26}$H$_{31}$NO$_5$S: 469.1923 Found: 469.1917.

Example IX-16

(Chart I, "I-8" where R$_2$ and R$_3$ are propyl, Z$_5$ is cyclopropyl and Z$_6$ is 4-flourophenyl).

Physical characteristics are as follows: $^1$H NMR (CDCl$_3$) δ7.78-7.73 (m, 2H), 7.56 (s, 1H), 7.08-6.98 (m, 4H), 6.88-6.86 (m, 1H), 2.95 (d, J=9.5 Hz, 1H), 1.86-1.53 (m, 4H), 1.53-1.38 (m, 1H), 1.24-0.98 (m, 4H), 0.86-0.67 (m, 6H), 0.56-0.35 (m, 2H), 0.23-0.00 (m, 2H) ppm; $^{13}$C NMR (CDCl$_3$) δ176.69, 175.34, 166.74, 163.35, 143.98, 136.15, 134.63, 130.04, 129.91, 129.11, 124.88, 120.87, 119.63, 116.21, 115.91, 104.62, 86.64, 43.49, 37.74, 15.83, 13.81, 13.77, 13.43, 5.42, 4.12 ppm; HRMS calcd for C$_{26}$H$_{30}$FN$_1$O$_5$S: 487.1829. Found: 487.1820.

Example IX-17

(Chart I, "I-8" where R$_2$ and R$_3$ are propyl, Z$_5$ is cyclopropyl and Z$_6$ is 1-methyl-4-imidazolyl).

Physical characteristics are as follows: $^1$H NMR (CDCl$_3$) δ7.44 (s, 1H), 7.40 (s, 1H), 7.26 (s, 1H), 7.19-7.07 (m, 2H), 6.94-6.92 (m, 1H), 3.66 (s, 3H), 2.86 (d, J=10.1 Hz, 1H), 1.80-1.58 (m, 5H), 1.31-1.13 (m, 4H), 0.91-0.83 (m, 6H), 0.81-0.49 (m, 2H), 0.23-0.13 (m, 2H) ppm; $^{13}$C NMR (CDCl$_3$) δ175.52, 174.21, 143.96, 138.90, 138.13, 136.53, 128.58, 125.30, 124.03, 120.12, 119.01, 104.57, 85.55, 43.76, 38.00, 37.74, 33.84, 15.85, 15.80, 13.81, 13.58, 5.87, 3.89 ppm.

Example IX-18

(Chart I, "I-8" where R$_2$ and R$_3$ are propyl, Z$_5$ is cyclopropyl and Z$_6$ is 8-quinolinyl).

Physical characteristics are as follows: $^1$H NMR (CDCl$_3$) δ9.09-9.08 (m, 1H), 8.30 (br, 1H), 8.24 (t, J=6.6 Hz, 2H), 7.95 (d, J=7.4 Hz, 1H), 7.56-7.44 (m, 2H), 7.14 (s, 1H), 6.95-6.80 (m, 3H), 2.85 (d, J=9.5 Hz, 1H), 1.77-1.50 (m, 4H), 1.35-0.93 (m, 11H), 0.83-0.69 (m, 6H), 0.47-0.21 (m, 2H), 0.15-(–)0.2 (m, 2H) ppm; $^{13}$C NMR (CDCl$_3$) δ176.38, 174.72, 151.41, 143.64, 142.98, 137.19, 136.85, 134.89, 133.77, 131.82, 129.03, 128.72, 125.63, 125.12, 122.44, 121.46, 120.22, 86.21, 43.27, 37.78, 15.92, 13.98, 13.56, 5.11, 4.02 ppm.

Example IX-19

(Chart I, "I-8" where R$_2$ and R$_3$ are propyl, Z$_5$ is cyclopropyl and Z$_6$ is 1-naphthyl).

Physical characteristics are as follows: $^1$H NMR (CDCl$_3$) δ8.70 (d, J=8.3 Hz, 1H), 8.19 (d, J=7.3 Hz, 1H), 7.92 (d, J=8.2 Hz, 1H), 7.83 (d, J=7.4 Hz, 1H), 7.69 (s, 1H), 7.54-7.45 (m, 2H), 7.34 (t, J=7.9 Hz, 1H), 7.19 (s, 1H), 7.06-6.72 (m,3H), 2.87 (d, J=9.6 Hz, 1H), 1.80-1.50 (m, 4H), 1.42-0.96 (m, 5H), 0.86-0.66 (m, 6H), 0.47-0.27 (m, 2H), 0.15-(-)0.2 (m, 2H) ppm; $^{13}$C NMR (CDCl$_3$) δ176.42, 175.19, 143.69, 136.41, 134.60, 134.06, 133.86, 130.41, 129.03, 128.53, 128.09, 126.88, 124.63, 124.24, 124.01, 120.65, 119.42, 104.79, 86.54, 43.42, 37.73, 15.92, 13.93, 13.49, 5.32, 4.10 ppm.

Example IX-20

(Chart I, "I-8" where R$_2$ and R$_3$ are propyl, Z$_5$ is ethyl and Z$_6$ is phenyl).

Physical characteristics are as follows: $^1$H NMR (CDCl$_3$) δ7.77 (d, J=7.8 Hz, 2H), 7.52-7.27 (m, 4H), 7.23 (s, 1H), 7.12-7.03 (m, 2H), 6.91 (d, J=7.6 Hz, 1H), 3.58 (t, J=7.6 Hz, 1H), 2.19-1.97 (m, 1H), 1.90-1.59 (m, 5H), 1.31-0.68 (m, 13H) ppm. $^{13}$C NMR (CDCl$_3$) δ177.24, 175.39, 144.84, 138.68, 136.50, 132.99, 129.35, 128.97, 127.28, 124.95, 121.01, 119.64, 104.22, 86.45, 41.17, 37.79, 25.20, 16.01, 13.94, 12.55 ppm; HRMS (EI) calcd for C$_{25}$H$_{31}$NO$_5$S: 457.1923. Found: 457.1931.

Example IX-21

(Chart I, "I-8" where R$_2$ and R$_3$ are propyl, Z$_5$ is 2-methylpropyl and Z$_6$ is 4-cyanophenyl).

Physical characteristics are as follows: $^1$H NMR (CDCl$_3$) δ7.88-7.85 (m, 2H), 7.71-7.68 (m, 2H), 7.16-7.07 (m, 3H), 6.92 (d, J=7.5 Hz, 1H), 3.72 t, J=7.7 Hz, 1H), 2.08-1.94 (m, 1H), 1.72-1.59 (m, 4H), 1.36-0.74 (m, 18H) ppm; $^{13}$C NMR (CDCl$_3$) δ176.27, 174.44, 145.43, 143.14, 135.63, 132.32, 128.92, 127.56, 124.88, 120.91, 119.35, 116.98, 115.77, 103.70, 85.48, 40.89, 37.74, 37.52, 36.75, 25.64, 22.42, 21.64, 15.58, 15.52, 13.64 ppm; HRMS calcd for C$_{28}$H$_{34}$N$_2$O$_5$S: 510.2188. Found: 510.2171.

Example IX-22

(Chart I, "I-8" where R$_2$ and R$_3$ are propyl, Z$_5$ is 2-methylpropyl and Z$_6$ is 1-methyl-4imidazolyl).

Physical characteristics are as follows: $^1$H NMR (CDCl$_3$) δ7.45 (d, J=8.4 Hz, 2H), 7.19-7.15 (m, 2H), 7.07 (t, J=7.8 Hz, 1H), 6.94 (d, J=8.1 Hz, 1H), 3.78-3.73 (m, 1H), 3.66 (s, 3H), 2.14-2.05 (m, 1H), 1.72-1.54 (m, 5H), 1.44-1.40 (m, 1H), 1.26-0.74 (m, 17H) ppm; $^{13}$C NMR (CDCl$_3$) δ176.22, 174.14, 145.23, 138.73, 138.08, 136.22, 128.75, 125.09, 123.97, 119.98, 118.66, 103.38, 85.16, 41.09, 37.92, 37.59, 36.72, 33.76, 25.70, 22.68, 21.51, 15.61, 13.69 ppm; HRMS calcd for C$_{25}$H$_{35}$N$_3$O$_5$S: 489.2297. Found: 489.2287.

Example IX-23

(Chart I, "I-8" where R$_2$ and R$_3$ are propyl, Z$_5$ is 1-methylethyl and Z$_6$ is 4-cyanophenyl).

Physical characteristics are as follows: $^1$H NMR (CDCl$_3$) δ7.86 (d, J=8.4 Hz, 2H), 7.69 (d, J=8.3 Hz, 2H), 7.31-6.95 (m, 4H), 3.10 (d, J=1 1.2 Hz, 1H), 2.62-2.56 (m, 1H), 1.75-1.57 (m, 4H), 1.13-0.56 (m, 16H) ppm; $^{13}$C NMR (CDCl$_3$) δ176.59, 174.77, 145.26, 143.25, 135.80, 132.56, 129.17, 127.85, 125.60, 121.57, 119.92, 117.22, 115.97, 104.38, 85.82, 48.10, 38.10, 37.80, 28.68, 21.63, 21.28, 16.01, 15.69, 13.87 ppm.

Example IX-24

(Chart I, "I-8" where R$_2$ and R$_3$ are propyl, Z$_5$ is 1-methylethyl and Z$_6$ is 1-methyl-4-imidazolyl).

Physical characteristics are as follows: $^1$H NMR (CDCl$_3$) δ7.48 (s, 1H), 7.39 (s, 1H), 7.25 (d, J=7.8 Hz, 1H), 7.12-7.07 (m, 2H), 6.97 (d, J=6.9 Hz, 1H), 3.66 (s, 3H), 3.08 (d, J=11.2 Hz, 1H), 2.71-2.65 (m, 1H), 1.73-1.57 (m, 4H), 1.26-0.59 (m, 16H) ppm; $^{13}$C NMR (CDCl$_3$) δ176.30, 174.38, 145.08, 139.02, 136.23, 129.11, 125.43, 124.65, 121.15, 119.38, 104.31, 85.40, 48.23, 38.32, 37.93, 34.00, 28.77, 21.81, 21.31, 16.05, 15.75, 13.96, 13.88 ppm.

Example IX-25

(Chart I, "I-8" where R$_2$ and R$_3$ are propyl, Z$_5$ is 1,1-dimethylethyl and Z$_6$ is 4-cyanophenyl).

Physical characteristics are as follows: $^1$H NMR (CDCl$_3$) δ7.86 (d, J=8.5 Hz, 2H), 7.69 (d, J=8.5 Hz, 2H), 7.33-7.02 (m, 4H), 3.73 (br, 1H), 3.48 (s, 1H), 1.76-1.61 (m, 4H), 1.26-1.02 (m, 4H), 0.86-0.76 (m, 15H) ppm; $^{13}$C NMR (CDCl$_3$) δ177.43, 175.39, 143.33, 143.04, 136.17, 132.42, 128.24, 127.71, 123.79, 120.22, 117.12, 116.79, 103.62, 85.38, 51.29, 37.95, 37.77, 36.03, 28.68, 15.90, 15.76, 13.72 ppm.

Example IX-26

(Chart I, "I-8" where R$_2$ and R$_3$ are propyl, Z$_5$ is 1,1-dimethylethyl and Z$_6$ is 1-methyl-4-imidazolyl).

Physical characteristics are as follows: $^1$H NMR (CDCl$_3$) δ7.49 (s, 1H), 7.39 (s, 1H), 7.36-7.29 (m, 2H), 7.09 (t, J=7.6 Hz, 1H), 6.99 (d, J=7.6 Hz, 1H), 3.66 (s, 3H), 3.50 (s, 1H), 1.78-1.63 (m, 4H), 1.24-0.79 (m, 19H) ppm; $^{13}$C NMR (CDCl$_3$) δ177.06, 176.30, 142.71, 138.77, 138.05, 135.54, 127.81, 126.78, 125.02, 122.72, 119.32, 103.36, 85.94, 51.29, 37.84, 37.66, 34.77, 33.57, 28.56, 15.67, 13.54 ppm.

Example IX-27

(Chart I, "I-8" where R$_2$ is phenylmethyl, R$_3$ is propyl, Z$_5$ is 1-methylethyl and Z$_6$ is phenyl).

Physical characteristics are as follows: $^1$H NMR (CDCl$_3$) δ8.4 (br s, 1H), 7.79-7.75 (m, 2H), 7.51-7.48 (m, 1H), 7.43-7.38 (m, 2H), 7.11-6.91 (m, 9H), 3.08-2.96 (m, 3H), 2.46-2.30 (m, 1H), 1.85-1.82 (m, 2H), 1.30-0.90 (m, 2H), 0.87-0.75 (m, 3H), [0.61 (d, J=6.5 Hz), 0.51-0.47 (m) and 0.42 (d, J=6.5 Hz) 6H] ppm; $^{13}$C NMR (CDCl$_3$) δ175.5, 174.9, 144.8, 144.6, 138.6, 136.1, 134.2, 133.7, 133.0, 130.1, 129.8, 129.3, 129.0, 128.2, 127.8, 127.3, 126.9, 126.2, 121.3, 119.5, 105.9, 86.2, 47.8, 42.0, 37.8, 28.9, 21.3, 20.9, 16.3, 14.2, 14.0 ppm; MS (EI) m/z 519; HRMS (EI) calcd for C$_{30}$H$_{33}$NO$_5$S: 519.2079 Found: 519.2082.

Example IX-28

(Chart I, "I-8" where R$_2$ is phenylmethyl, R$_3$ is propyl, Z$_5$ is 1-methylethyl and Z$_6$ is 4-cyanophenyl).

Physical characteristics are as follows: $^1$H NMR (CDCl$_3$) δ7.84-7.80 (m, 2H), 7.68-7.64 (m, 2H), 7.13-6.74 (m, 9H), 3.09-2.83 (m, 3H), 2.33-2.27 (m, 1H), 1.85-1.71 (m, 2H), 1.30-0.80 (m, 2H), [0.88 (t, J=7.3 Hz), 0.72 (m), 0.40 (d, J=6.6 Hz) and 0.21 (d, J=6.5 Hz) 9H] ppm; $^{13}$C NMR (CDCl$_3$) δ174.9, 174.8, 173.9, 173.8, 145.1, 144.7, 143.4, 143.3, 135.7, 134.3. 133.6, 132.5, 130.0, 129.5, 129.2, 128.9, 128.0, 127.8, 127.5, 126.9, 126.8, 125.6, 125.5, 121.5, 121.4, 119.9, 117.2, 116.0, 116.0, 105.5, 105.4, 85.4, 47.8, 42.2, 41.7, 38.3, 37.7, 28.7, 28.5, 21.3, 21.2, 21.1, 21.0, 20.7, 16.2, 15.8, 14.0, 13.9, 13.8 ppm; MS (EI) m/z 544; HRMS (EI) calcd for C$_{31}$H$_{32}$N$_2$O$_5$S: 544.2032. Found: 544.2031.

Example IX-29

(Chart I, "I-8" where R$_2$ is phenylmethyl, R$_3$ is propyl, Z$_5$ is 1-methylethyl and Z$_6$ is 4-flourophenyl).

Physical characteristics are as follows: $^1$H NMR (CDCl$_3$) δ7.75-7.69 (m, 2H), 7.15-6.80 (m, 11H), 3.10-2.84 (m, 3H), 2.38-2.34 (m, 1H), 1.82-1.72 (m, 2H), [1.20-1.0 (m), 0.87 (t, J=7.3 Hz), 0.72 (t, J=7.3 Hz), 0.45-0.42 (m) and 0.23 (d, J=6.5 Hz) 11H] ppm; $^{13}$C NMR (CDCl$_3$) δ174.8, 173.7, 163.2, 144.8, 144.4, 135.8, 134.1, 133.4, 129.8, 129.7, 129.9, 129.3, 128.9, 128.8, 127.8, 127.3, 126.6, 124.9, 121.2, 119.4, 115.9, 115.6, 105.3, 85.2, 47.7, 42.0, 41.5, 38.1, 37.5, 28.5, 28.3, 21.1, 21.0, 20.5, 16.0, 15.6, 13.7, 13.6 ppm; MS (EI) m/z 537.

Example IX-30

(Chart I, "I-8" where R$_2$ is phenylmethyl, R$_3$ is propyl, Z$_5$ is 1-methylethyl and Z$_6$ is 1-methyl-4-imidazolyl).

Physical characteristics are as follows: $^1$H NMR (CDCl$_3$) δ7.46 (d, J=7.6 Hz, 1H), 7.37 (d, J=9.8 Hz, 1H), 7.11-5.69, (m, 9H), 3.64-3.59, (m, 3H), 3.07-2.82 (m, 3H), 2.45-2.40 (m, 1H), 1.81-1.73 (m, 2H), [1.30-1.05 (m), 0.88 (t, J=7.4 Hz), 0.75-0.71 (m), 0.51-0.44 (m) and 0.27 (d, J=6.4 Hz) 11H] ppm; $^{13}$C NMR (CDCl$_3$) δ174.6, 173.6, 144.8, 144.5, 139.0, 136.1, 135.9, 134.5, 133.8, 130.0, 129.5, 129.3, 129.1, 128.0, 127.5, 126.8, 126.6, 125.4, 124.6, 124.4, 121.1, 119.3, 116.7, 105.4, 85.1, 85.0, 48.0, 42.3, 41.6, 38.4, 37.9, 33.9, 28.6, 21.5, 21.2, 20.9, 16.2, 15.9, 14.0, 13.8 ppm; MS (EI) m/z 523; HRMS (EI) calcd for C$_{28}$H$_{33}$N$_3$O$_5$S: 523.2141. Found: 523.2151.

Example IX-31

(Chart I, "I-8" where R$_2$ is phenylmethyl, R$_3$ is propyl, Z$_5$ is 1-methylethyl and Z$_6$ is 8-quinolinyl).

Physical characteristics are as follows: $^1$H NMR (CDCl$_3$) δ9.13 (m, 1H), 8.31-8.22, (m, 2H), 7.97-7.94, (d, J=8.3 Hz, 1H), 7.59-7.55 (m, 1H), 7.50-7.44 (m, 1H), 7.05-6.72 (m, 9H), 3.02-2.96 (m, 2H), 2.85-2.79 (m, 1H), 2.13-2.09 (m, 1H), 1.80-1.73 (m, 2H), 1.26-0.86 (m, 1H), [0.77 (t, J=7.1 Hz), 0.66 (t, J=7.1 Hz), 0.55 (d, J=6.4 Hz), 0.29 (d, J=6.4 Hz) and 0.14 (d, J=6.4 Hz) 10H] ppm; $^{13}$C NMR (CDCl$_3$) δ175.2, 174.5, 151.6, 144.5, 143.0, 137.0, 136.4, 136.3, 134.6, 134.1, 133.8, 133.7, 132.0, 130.0, 129.7, 129.0, 128.7, 128.0, 127.7, 126.8, 125.5, 122.5, 121.8, 121.6, 119.6, 105.6, 86.0, 85.9, 47.7, 41.9, 41.6, 38.1, 37.7, 28.8, 28.7, 21.3, 21.0, 20.9, 16.2, 16.0, 14.0, 13.9 ppm; MS (EI) m/z 570.

Preparation IP-7 and Example IX-32

(Chart I, "I-9" where R$_2$ and R$_3$ are propyl and Z$_5$ is cyclopropyl).

To a solution of sodium bicarbonate (38 mg, 0.45 mmol) in THF/water (1:1) (2 mL) at room temperature was added IP-4 (100 mg, 0.30 mmol) followed by benzyl chloroformate (64 μL, 0.45 mmol) and the resulting solution stiffed at room temperature for 3 h. The reaction mixture was partitioned between methylene chloride and saturated sodium bicarbonate. The organic layer was separated, washed with brine, dried over anhydrous sodium sulfate, and concentrated in vacuo. Purification by chromatography eluting with hexane/ethyl acetate (50%) afforded the tide compound (57 mg, 41%) as an amorphous solid: $^1$H NMR (CDCl$_3$) δ7.43 (s, 1H), 7.37-7.16 (m, 7H), 7.04 (d, J=7.5 Hz, 1H), 6.86 (s, 1H), 5.15 (s,2H), 3.09 (d, J=9.4 Hz, 1H), 1.76-1.64 (m, 4H), 1.47-1.44 (m, 1H), 1.20-1.13 (m, 4H), 0.83 (t, J=7.1 Hz, 6H), 0.64-0.50 (m, 2H), 0.28-0.16 (m, 2H) ppm; $^{13}$C NMR (CDCl$_3$) δ175.81, 174.61, 153.48, 143.10, 137.77, 135.85, 129.12, 128.50, 128.25, 128.11, 122.97, 118.07, 117.14, 104.93, 86.10, 66.94, 43.43, 37.92, 37.81, 16.52, 15.90, 13.89, 13.62, 5.15, 4.05 ppm.

Example IX-33

(Chart I, "I-5" where R$_2$ and R$_3$ together represent a 2-(ethyl)cyclohexyl ring, Z$_5$ is cyclopropyl and X is proton).

The title compound and example IX-34 were prepared as described for the preparation of IX-4 starting from 2-ethylcyclohexanone which was prepared as described in Chart L.

Physical characteristics are as follows: $^1$H NMR (CDCl$_3$) δ7.40-7.17 (m, 5H), 3.12-3.08 (overlapping d, J=9.48 Hz, 1H), 1.84-1.50 (m, 8H), 1.25-1.21 (m, 3H), 1.00-0.94 (m, 1H), 0.79 (t, J=7.3 Hz, 3H), 0.59-0.52(m, 2H), 0.32-0.17 (m, 2H) ppm; $^{13}$C NMR (CDCl$_3$) δ178.09 and 178.00, 175.38 and 175.33, 142.25 and 142.13, 128.44, 127.72, 126.54, 104.11, 85.72, 43.72 and 43.57, 41.60, 34.58, 29.69, 26.55 and 26.51, 25.22, 21.89, 21.67, 13.90 and 13.77, 11.62, 5.29 and 5.22, 4.26 ppm.

Example IX-34

(Chart I, "I-5" where R$_2$ and R$_3$ together represent a 2-(ethyl)cyclohexyl ring, Z$_5$ is cyclopropyl and X is proton).

Physical characteristics are as follows: $^1$H NMR (CDCl$_3$) δ7.41-7.20 (m, 5H), 3.26-3.22 (overlapping d, J=8.9 Hz, 1H), 1.85-1.57 (m, 8H), 1.50-1.37 (m, 3H), 1.27-1.22 (m, 1H), 0.92-0.81 overlapping t, 3H), 0.62-0.54 (m, 2H), 0.67-0.30 (m, 1H), 0.22-0.17 (m, 1H) ppm; $^{13}$C NMR (CDCl$_3$) δ177.68, 174.02, 141.39 and 141.25, 128.71, 127.87, 127.74, 126.91, 104.77, 85.09, 45.27, 42.85, 35.93 and 35.75, 26.36, 24.80 and 24.66, 22.37, 21.62 and 21.05, 13.67, 11.89, 4.89, 4.12 ppm.

Example IX-35

(Chart I, "I-8" where R$_2$ and R$_3$ are propyl, Z$_5$ is cyclopropyl and Z$_6$ is 5-cyano-2-pyridinyl).

Physical characteristics are as follows: $^1$H NMR (CDCl$_3$) δ8.90 (s, 1H), 8.09-7.98 (m, 2H), 7.69 (s, 1H), 7.31-6.97 (m, 4H), 3.05 (d, J=9.2 Hz, 1H), 2.04-1.87 (m, 1H), 1.82-1.63 (m, 5H), 1.39-1.08 (m, 6H), 0.88-0.83 (m, 7H), 0.57 (d, J=7.7 Hz, 2H), 0.24-0.16 (m, 2H) ppm; $^{13}$C NMR (CDCl$_3$) δ175.7, 174.2, 159.0, 152.4, 143.6, 141.9, 135.5, 129.6, 125.7, 123.0, 121.7, 120.7, 115.1, 113.1, 104.8, 86.2, 43.5, 38.0, 16.1, 14.0, 13.7, 5.3, 4.2 ppm; MS (EI) m/z 495.

Example IX-36

(Chart I, "I-8" where R$_2$ and R$_3$ are propyl, Z$_5$ is cyclopropyl and Z$_6$ is 2-imidazolyl).

Physical characteristics are as follows: $^1$H NMR (CDCl$_3$\CD$_3$OD) δ7.36-6.85 (m, 7H), 3.90-3.39 (m, 2H), 2.77-2.74 (d, J=10.3 Hz, 1H), 1.84-1.56 (m, 5H), 1.33-1.24 (m, 2H), 1.17-1.01 (m, 2H), 0.94-0.89 (m, 3H), 0.69-0.62 (m,1H), 0.55-0.48 (m,1H), 0.24-0.22 (m, 2H) ppm; $^{13}$C NMR (CDCl$_3$—CD$_3$OD) δ170.1, 165.1, 141.7, 137.9, 135.8, 129.1, 124.7, 123.1, 120.7, 120.4, 87.5, 45.2, 37.6, 37.2, 20.9, 15.9, 15.8, 14.0, 13.7, 13.2, 6.3, 3.9 ppm; MS (EI) m/z 459.

Example IX-37

(Chart I, "I-8" where R$_2$ and R$_3$ are propyl, Z$_5$ is cyclopropyl and Z$_6$ is 1-methyl-2-imidazolyl).

Physical characteristics are as follows: $^1$H NMR (CDCl$_3$/CD$_3$OD) δ7.33-6.91 (m, 6H), 3.63 (s, 3H), 2.85-2.82 (d, J=5.7, 1H), 1.75-1.64 m, 5H), 1.29-1.05 (m, 5H), 0.94-0.81 (m, 6H), 0.57-0.51 (m, 2H), 0.17-0.15 (m, 2H) ppm; $^{13}$C NMR (CDCl$_3$/CD$_3$OD) δ144.7, 142.1, 135.1, 129.1, 128.0, 125.6, 125.4, 122.0, 120.8, 104.3, 85.6, 44.1, 38.2, 32.0, 35.1, 15.9, 14.0, 13.8, 5.9, 4.3 ppm; MS (EI) m/z 473.

Preparation IP-8 and Example IX-38

(Chart I, "I-8" where $R_2$ and $R_3$ are propyl, $Z_5$ is cyclopropyl and $Z_6$ is 2-quinolinyl).

The following preparation is a modification of the procedure reported by Roblin, R. O., Clapp, J. W. *J. Amer. Chem. Soc.* 1950, 72, 4890 for preparing heterocyclic sulfonyl chlorides.

To a solution of 2-quinolinethiol (387 mg, 2.4 mmol) was added 1 N HCl (20 mL) causing cloudiness. The mixture was cooled (0–5° C.) and chlorine gas was bubbled through the mixture for 10 minutes. Additional 1 N HCl was added (20 mL) and the solid collected by filtration. The solid was washed with ice cold water and dried briefly in vacuo. The resulting sulfonyl chloride was used without further purification or characterization.

Physical characteristics are as follows: $^1$H NMR (CDCl$_3$/CD$_3$OD) δ8.4 (d, J=8.6, 1H), 8.2 (d, J=8.5, 1H), 7.9-7.8 (m, 3H), 7.7-7.6 (m, 1H), 7.3 (s, 1H), 7.1-7.0 (m, 3H), 2.8 (d, J=10.2, 1H), 1.7-1.5 (m, 5H), 1.3-1.1 (m, 4H), 0.9-0.8 (m, 6H), 0.5-0.4 (m, 2H), 0.1-0.05 (m, 2H) ppm; $^{13}$C NMR (CDCl$_3$) δ175.1, 173.9, 155.8, 146.9, 143.3, 138.9, 136.4, 131.3, 129.6, 129.5, 129.2, 129.0, 127.9, 125.4, 121.6, 120.8, 118.6, 104.8, 85.8, 60.5, 43.2, 37.9, 21.1, 15.9, 14.2, 14.0, 13.6, 4.8, 4.0, ppm.

Example IX-39

(Chart I, "I-8" where $R_2$ and $R_3$ are propyl, $Z_5$ is benzyl and $Z_6$ is 4-cyanophenyl).

Physical characteristics are as follows: $^1$H NMR (CDCl$_3$) δ7.84 (d, J=8.5 Hz, 2H), 7.68 (d, J=8.6 Hz, 2H), 7.28-7.09 (m, 8H), 6.90 (d, J=7.9 Hz, 1H), 4.07-4.01 (m, 1H), 3.52-3.44 (m, 1H), 3.12-3.05 (m, 1H), 1.62-1.45 (m, 4H), 1.10-0.65 (m, 9H), 0.56-0.38 (m, 1H) ppm; $^{13}$C NMR (CDCl$_3$) δ176.9, 174.4, 145.4, 143.6, 139.9, 136.1, 132.8, 129.6, 128.9, 128.3, 127.9, 126.1, 125.2, 121.3, 119.7, 117.2, 116.3, 103.4, 85.9, 40.9, 38.2, 37.6, 15.8, 15.5, 13.9 ppm; HRMS (EI) calcd for C$_{31}$H$_{32}$N$_2$O$_5$S: 544.2032. Found: 544.2028.

Example IX-40

(Chart I, "I-8" where $R_2$ and $R_3$ are propyl, $Z_5$ is benzyl and $Z_6$ is 1-methyl-4-imidazolyl).

Physical characteristics are as follows: $^1$H NMR (CDCl$_3$) δ7.44 (s, 2H), 7.31 (s, 1H), 7.22-6.97 (m, 8H), 4.13-4.07 (m, 1H), 3.61-3.43 (m, 4H), 3.08-3.01 (m, 1H), 1.60-1.43 (m, 4H), 1.13-0.95 (m, 1H), 0.91-0.62 (m, 8H), 0.52-0.31 (m, 1H) ppm; $^{13}$C NMR (CDCl$_3$) δ177.4, 174.6, 144.9, 140.2, 139.2, 138.3, 136.8, 129.2, 128.9, 128.2, 125.9, 125.5, 124.1, 120.2, 119.2, 102.7, 85.8, 49.0, 40.8, 38.3, 37.6, 34.1, 15.8, 13.9 ppm; HRMS (EI) calcd for C$_{28}$H$_{33}$N$_3$O$_5$S: 523.2141. Found: 523.2152.

Example IX-41

(Chart I, "I-8" where $R_2$ and $R_3$ are propyl, $Z_5$ is cyclopentyl and $Z_6$ is 4-cyanophenyl).

Physical characteristics are as follows: $^1$H NMR (CDCl$_3$) δ7.86 (d, J=8.5 Hz, 2H), 7.70 (d, J=8.6 Hz, 2H), 7.17-6.95 (m, 4H), 4.07 (br, 1H), 3.24 (d, J=11.5 Hz, 1H), 2.85-2.76 (m, 1H), 1.77-1.45 (m, 10H), 1.29-0.95 (m, 6H), 0.83 (t, J=7.2 Hz, 3H), 0.74 (t, J=7.3 Hz, 3H) ppm; $^{13}$C NMR (CDCl$_3$) δ176.2, 174.8, 145.6, 143.3, 135.7, 132.5, 129.0, 127.8, 125.5, 121.6, 119.9, 117.2, 115.8, 104.7, 95.7, 85.7, 46.9, 41.0, 38.0, 37.7, 31.9, 31.7, 25.2, 15.9, 15.7, 13.8 ppm; HRMS (FAB) calcd for C$_{29}$H$_{35}$N$_2$O$_5$S: 523.2267. Found: 523.2278.

Example IX-42

(Chart I, "I-8" where $R_2$ and $R_3$ are propyl, $Z_5$ is cyclopentyl and $Z_6$ is 1-methyl-4-imidazolyl).

Physical characteristics are as follows: $^1$H NMR (CDCl$_3$) δ7.49 (s, 1H), 7.42 (s, 1H), 7.23-7.16 (m, 2H), 7.08 (t, J=7.7 Hz, 1H), 6.97-6.95 (m, 1H), 3.66 (s, 3H), 3.27 (d, J=1 1.5 Hz,1H), 2.94-2.85 (m, 1H), 1.80-1.45 (m, 10H), 1.38-1.24 (m, 1H), 1.20-1.00 (m, 4H), 0.99-0.88 (m, 2H), 0.83 (t, J=7.4 Hz, 3H), 0.74 (t, J=7.3 Hz, 3H) ppm; $^{13}$C NMR (CDCl$_3$) δ175.9, 174.4, 145.2, 138.9, 138.0, 136.1, 128.7, 125.3, 124.4, 120.6, 119.0, 104.6, 85.3, 45.9, 41.0, 38.0, 37.7, 33.8, 31.7, 25.1, 15.8, 15.6, 13.7 ppm; HRMS (FAB) calcd for C$_{26}$H$_{36}$N$_3$O$_5$S: 502.2376. Found: 502.2361.

Example IX-43

(Chart I, "I-8" where $R_2$ and $R_3$ are benzyl, $Z_5$ is cyclopropyl and $Z_6$ is 4-cyanophenyl).

Physical characteristics are as follows: $^1$H NMR (CDCl$_3$) δ7.79 (d, J=6.9 Hz, 2H), 7.64 (d, J=6.7 Hz, 2H), 7.24-7.10 (m, 10H), 6.86-6.77 (m, 3H), 6.04 (d, J=7.1 Hz, 1H), 3.77 (br, 1H), 3.19-3.13 (m, 4H), 2.37 (d, J=10.0 Hz, 1H), 1.01-0.98 (m, 1H), 0.36-0.23 (m, 1H), −0.02-(−)0.20 ppm; $^{13}$C NMR (CDCl$_3$) δ173.5, 143.7, 143.6, 135.5, 134.3, 132.6, 130.1, 128.9, 128.2, 128.0, 127.7, 126.9, 124.6, 120.7, 119.3, 117.3, 115.9, 106.2, 85.6, 43.1, 42.1, 41.9, 13.2, 5.7, 3.5 ppm; HRMS (FAB) calcd for C$_{35}$H$_{31}$N$_2$O$_5$S: 591.1954. Found: 591.1946.

Example IX-44

(Chart I, "I-8" where $R_2$ and $R_3$ are benzyl, $Z_5$ is cyclopropyl and $Z_6$ is 4-fluorophenyl).

Physical characteristics are as follows: $^1$H NMR (CDCl$_3$) δ7.73-7.67 (m, 2H), 7.21-7.12 (m, 10H), 7.05 (t, J=8.5 Hz, 1H), 6.03 (d, J=6.3 Hz, 1H), 4.00 (br, 1H), 3.23-3.13 (m, 4H), 2.36 (d, J=10.1 Hz, 1H), 1.07-0.93 (m, 1H), 0.35-0.26 (m, 1H), −0.04-(−)0.18 (m, 2H) ppm; $^{13}$C NMR (CDCl$_3$) δ173.3, 166.4, 163.0, 143.3, 135.7, 135.0, 134.1, 129.8, 129.6, 129.4, 128.6, 127.9, 126.6, 124.0, 120.2, 118.8, 115.9, 115.6, 106.0, 85.3, 42.9, 41.8, 41.7, 13.0, 5.5, 3.2 ppm; HRMS (FAB) calcd for C$_{34}$H$_{31}$NO$_5$S: 584.1907. Found: 584.1897.

Example IX-45

(Chart I, "I-8" where $R_2$ and $R_3$ are benzyl, $Z_5$ is cyclopropyl and $Z_6$ is 1-methyl-4-imidazolyl).

Physical characteristics are as follows: $^1$H NMR (CDCl$_3$) δ7.36-7.07 (m, 13H), 6.98-6.75 (m, 2H), 6.11-6.03 (m, 1H), 3.40 (s, 3H), 2.48-2.38 (m, 1H), 1.08-1.05 (m, 1H), 0.37-0.29 (m, 1H), −0.05-(−)0.12 (m, 2H) ppm; $^{13}$C NMR (CDCl$_3$) δ173.7, 173.2, 144.1, 143.1, 142.9, 138.7, 138.0, 135.8, 135.6, 134.2, 129.8, 128.8, 128.5, 127.8, 126.6, 124.9, 124.1, 123.8, 123.6, 119.8, 119.0, 118.4, 117.8, 117.5, 115.6, 106.1, 105.9, 85.3, 43.0, 41.8, 33.6, 13.1, 5.6, 3.2 ppm.

Example IX-46

(Chart I, "I-8" where $R_2$ and $R_3$ are benzyl, $Z_5$ is cyclopropyl and $Z_6$ is 8-quinolinyl).

Physical characteristics are as follows: 1H NMR (CDCl$_3$) δ9.08 (d, J=4.2 Hz, 1H), 8.25 (d, J=7.4 Hz, 2H), 7.98 (d, J=8.3 Hz, 1H), 7.60-7.48 (m, 2H), 7.18-7.07 (m, 11H), 6.73-6.65 (m, 3H), 5.90 (br, 1H), 3.51 (br, 1H), 3.20-3.08 (m, 4H), 2.23 (d, J=10.1 Hz, 1H), 0.93-0.77 (m, 1H), 0.16-0.04 (m, 1H), −0.13-(−)0.30 (m, 2H) ppm; $^{13}$C NMR (CDCl$_3$) δ172.9, 151.0, 143.0, 142.7, 136.8, 135.6, 134.6, 134.1, 133.4, 131.4, 129.8, 128.4, 127.8, 126.5, 125.2, 124.2, 122.1, 120.7, 119.2, 105.6, 85.0, 42.7, 41.8, 41.6, 13.7, 13.0, 5.3, 2.9 ppm; HRMS (FAB) calcd for C$_{37}$H$_{33}$N$_2$O$_5$S: 617.2110. Found: 617.2120.

Example IX-47

(Chart I, "I-8" where R$_2$ and R$_3$ are propyl, Z$_5$ is phenyl and Z$_6$ is 4-cyanophenyl).

Physical characteristics are as follows: $^1$H NMR (CDCl$_3$) δ7.74 (d, J=8.6 Hz, 2H), 7.61-7.55 (m, 3H), 7.32-7.27 (m, 3H), 7.15 (t, J=7.8 Hz, 1H), 7.06-6.88 (m, 5H), 5.13 (s, 1H), 1.75-1.62 (m, 4H), 1.28-1.06 (m, 4H), 0.88-0.81 (m, 6H) ppm; $^{13}$C NMR (CDCl$_3$) δ176.9, 173.8, 142.9, 142.2, 139.9, 136.3, 132.7, 129.8, 129.2, 128.3, 127.9, 127.7, 126.0, 125.4, 122.0, 120.7, 117.3, 116.4, 103.3, 86.5, 45.1, 38.1, 37.9, 16.3, 16.1, 14.1 ppm; EIMS m/z 530.

Example IX-48

(Chart I, "I-8" where R$_2$ and R$_3$ are propyl, Z$_5$ is phenyl and Z$_6$ is 1-methyl-4-imidazolyl).

Physical characteristics are as follows: $^1$H NMR (Acetone-d$_6$) δ7.54 (d, J=12.7 Hz, 2H), 7.29-7.07 (m, 8H), 6.93-6.90 (m, 1H), 5.61 (s, 1H), 3.71 (s, 3H), 3.30 (br, 1H), 1.80-1.74 (m, 4H), 1.29-1.10 (m, 4H), 0.87-0.80 (m, 6H) ppm; $^{13}$C NMR (Acetone-d$_6$) δ176.9, 173.2, 143.9, 142.9, 140.3, 139.7, 139.1, 129.8, 129.3, 128.8, 127.1, 126.4, 125.0, 121.0, 118.9, 105.1, 85.7, 45.4, 39.0, 34.1, 16.9, 14.3 ppm; EIMS m/z 509.

Example IX-49

(Chart I, derived from I-10, the product of bis-addition where R$_2$ and R$_3$ are propyl and Z$_5$ is cyclopentyl. This nitro compound was then subjected to the same synthetic sequence as I-5 to prepare the sulfonamide where Z$_6$ is 4-cyano-phenyl).

Physical characteristics are as follows: $^1$H NMR (CDCl$_3$) δ7.81 (d, J=8.6 Hz, 2H), 7.70 (d, J=8.5 Hz, 2H), 7.35 (s, 1H), 7.26 (d, J=6.4 Hz, 1H), 7.09 (d, J=8.2 Hz, 1H), 6.99 (s, 1H), 3.39 (d, J=11.3 Hz, 1H), 2.85-2.67 (m, 1H), 1.89-0.73 (m, 30H) ppm; EIMS m/z 590.

Example IX-50

(Chart I, "I-8" where R$_2$ and R$_3$ are propyl, Z$_5$ is cyclopropyl and Z$_6$ is 1-phenyl-5-tetrazolyl).

Physical characteristics are as follows: $^1$H NMR (CDCl$_3$) δ7.58-7.38 (m, 6H), 7.32-7.12 (m, 4H), 3.05 (d, J=9.5 Hz, 1H), 1.85-1.60 (m, 4H), 1.53-1.39 (m, 1H), 1.31-1.03 (m, 4H), 0.93-0.75 (m, 6H), 0.65-0.44 (m, 2H), 0.27-0.07 (m, 2H) ppm; $^{13}$C NMR (CDCl$_3$) δ176.8, 174.9, 154.2, 144.2, 134.1, 132.9, 131.3, 129.5, 127.0, 125.5, 123.6, 122.3, 104.3, 86.5, 43.5, 38.0, 29.7, 16.0, 14.0, 13.6, 5.5, 4.2 ppm; EIMS m/z 537.

Example IX-51

(Chart I, "I-8" where R$_2$ and R$_3$ are propyl, Z$_5$ is cyclopropyl and Z$_6$ is 2-benzimidazolyl).

Physical characteristics are as follows: $^1$H NMR (CDCl$_3$/CD$_3$OD) δ7.48-6.7 (m, 8H), 2.75 (d, J=10.1, 1H), 19.1-1.40 (m, 6H), 1.16-0.89 (m, 5H), 0.75-0.59 (m, 7H), 0.33-0.30 (m, 2H), 0.16-0.12 (m, 2H) ppm; HRMS (EI) Calcd for C$_{27}$H$_{31}$N$_3$O$_5$S: 509.1984. Found: 509.1979.

Example IX-52

(Chart I, "I-8" where R$_2$ and R$_3$ are propyl, Z$_5$ is cyclopropyl and Z$_6$ is 2-pyridinyl).

Physical characteristics are as follows: $^1$H NMR (CDCl$_3$) δ8.85 (s, 1H), 8.62 (d, J=4.3, 1H), 7.86 (d, J=7.8, 1H), 7.77-7.72 (m, 1H), 7.40-7.28 (m, 2H), 7.04 (s, 3H), 2.91 (d, J=9.6, 1H), 1.69 (bs, 4H), 1.47(bs, 1H), 1.23-1.03 (m, 5H), 0.83-0.76 (m, 7H), 0.45-0.43 (d, J=7.1, 2H), 0.13 (s, 1H), 0.05 (S, 1H) ppm; $^{13}$C NMR (CDCl$_3$) δ176.6, 175.2, 155.8, 149.9, 144.0, 138.3, 136.1, 129.1, 127.2, 125.0, 123.4, 121.5, 120.3, 104.8, 85.5, 60.6, 43.6, 37.9, 37.8, 21.1, 16.0, 14.2, 14.0, 13.6, 5.7, 4.2 ppm; EIMS m/z 470.

Example IX-53

(Chart I, "I-8" where R$_2$ and R$_3$ are propyl, Z$_5$ is 1,1-dimethylethyl and Z$_6$ is 1-methyl-4-imidazolyl).

Physical characteristics are as follows: $^1$H NMR (CD$_3$CN) δ8.13 (br, 1H), 7.50 (s, 1H), 7.44 (s, 1H), 7.08-6.96 (m, 13H), 6.82 (br, 1H), 3.64 (s, 3H), 3.29 (s, 1H), 3.24-3.03 (m, 4H), 0.43 (s, 9H) ppm; $^{13}$C NMR (CD$_3$OD) δ176.4, 175.1, 143.7, 141.0, 139.9, 137.7, 135.6, 135.5, 131.2, 131.0, 128.9, 128.0, 127.8, 127.5, 127.0, 123.8, 119.8, 106.6, 86.7, 52.8, 43.1, 42.9, 35.8, 34.2, 29.2 ppm; EIMS m/z 585.

Example IX-54

(Chart I, "I-8" where R$_2$ and R$_3$ are propyl, Z$_5$ is 1,1-dimethylethyl and Z$_6$ is 4-cyanophenyl).

Physical characteristics are as follows: $^1$H NMR (CDCl$_3$) δ7.81 (d, J=8.5 Hz, 2H), 7.63 (d, J=8.5 Hz, 2H), 7.14-6.81 (m, 14H), 4.28 (br, 1H), 3.17-3.07 (m, 4H), 3.01 (s, 1H), 0.34 (s, 9H) ppm; $^{13}$C NMR (CDCl$_3$) δ175.1, 174.7, 143.3, 142.3, 134.9, 133.9, 133.5, 132.4, 130.0, 129.8, 129.5, 128.0, 127.8, 127.7, 127.5, 126.8, 124.3, 123.5, 119.9, 117.1, 115.7, 105.5, 85.4, 50.8, 41.9, 41.5, 34.4, 28.0 ppm; EIMS m/z 606.

Example IX-55

(Chart I, "I-8" where R$_2$ and R$_3$ are propyl, Z$_5$ is cyclopropyl and Z$_6$ is 2-pyrimidinyl).

Physical characteristics are as follows: $^1$H NMR (CDCl$_3$—CD$_3$OD) δ8.89 (d, J=4.8 Hz, 2H), 7.53 (t, J=7.9 Hz, 1H), 7.30 (s, 1H), 7.15-7.08 (m, 3H), 2.82 (d, J=10.2 Hz, 1H), 1.76-1.69 (m, 5H), 1.38-1.02 (m, 4H), 0.91-0.82 (m, 7H), 0.60-0.51 (m, 2H), 0.19-0.15 (m, 2H) ppm; $^{13}$C NMR (CDCl$_3$—CD$_3$OD) δ175.7, 174.5, 164.8, 158.4, 144.1, 135.9, 128.7, 124.4, 123.2, 121.0, 119.5, 104.6, 85.6, 43.9, 37.9, 37.7, 29.4, 22.4, 15.8, 13.7, 13.7, 13.4, 7.2, 5.8, 3.9 ppm; EIMS m/z 471.

Example IX-56

(Chart I, "I-8" where R$_2$ and R$_3$ are propyl, Z$_5$ is proton and Z$_6$ is 4-cyanophenyl).

Reduction of aldol product of general structure I-2 (where R$_2$ and R$_3$ are propyl and Z$_5$ is 3-nitro) provides the amine of general structure I-6 (where R$_2$ and R$_3$ are propyl and Z$_5$ is proton) which further reacts with 4-cyanobenzene sulfonyl chloride to provide the title compound.

Physical characteristics are as follows: 1H NMR (CDCl$_3$) δ7.81 (d, J=8.5 Hz, 2H), 7.68 (d, J=8.7 Hz, 2H), 7.18 (s, 10H), 6.84-6.76 (m, 2H), 6.53 (s, 1H), 5.86 (d, J=6.7 Hz, 1H), 4.25 (br, 2H), 3.16 (s, 4H), 2.98 (s, 2H) ppm; $^{13}$C NMR (CDCl$_3$) δ175.4, 174.5, 143.5, 139.7, 135.5, 134.2, 132.5, 129.9, 129.0, 127.8, 127.4, 126.7, 124.1, 121.1, 118.5, 117.1, 115.7, 100.9, 85.9, 41.7, 25.8 ppm; EIMS m/z 550.

Example IX-57

(Chart I, "I-8" where R$_2$ and R$_3$ are propyl, Z$_5$ is cyclopropyl and Z$_6$ is 1-phenyl-5-tetrazolyl).

Physical characteristics are as follows: $^1$H NMR (CDCl$_3$) δ7.31-7.02 (m, 4H), 4.26 (br, 2H), 4.02 (s, 3H), 2.87 (d, J=10.2 Hz, 1H), 1.80-1.55 (m, 5H), 1.30-1.11 (m, 4H), 0.91-0.84 (m, 6H), 0.66-0.49 (m, 2H), 0.21-0.16 (m, 2H) ppm; $^{13}$C NMR (CDCl$_3$) δ176.4, 174.6, 154.1, 144.9, 134.1, 129.1, 126.4, 123.1, 121.7, 104.3, 85.9, 43.8, 37.9, 35.8, 15.9, 13.9, 13.3, 5.9, 4.1 ppm.

Example IX-58

(Chart I, "I-5" where R$_2$ and R$_3$ form a 9-fluorenylmethyloxycarbonyl substituted 6-membered azaspirocyclic ring, Z$_5$ is cyclopropyl and X is proton).

The title compound was prepared using the product of preparation PP-3 as the starting tetronic acid intermediate of general structure C-5 (Chart I).

Physical characteristics are as follows: 1H NMR (CDCl$_3$) δ7.73 (d, J=7.5 Hz, 2H), 7.50 (d, J=7.4 Hz, 2H), 7.39-7.16 (m, 9H), 4.39-4.02 (overlapping m's, 5H), 3.13-3.06 (m, 3H), 2.03-1.88 (m, 2H), 1.57-1.43 (m, 3H), 0.63-0.53 (m, 2H), 0.28-0.17 (m, 2H); $^{13}$C NMR (CDCl$_3$) δ176.31, 172.93, 155.19, 143.71, 141.68, 141.29, 128.56, 127.78, 127.59, 127.06, 126.76, 124.81, 120.04, 103.68, 79.95, 67.59, 60.57, 47.20, 43.52, 40.09, 32.34, 14.13, 13.67, 5.47, 4.38; Anal calcd for C$_{33}$H$_{31}$NO$_5$.0.2 H$_2$O: C,H,N.

Following procedures described herein and using starting materials and reagents readily known and available to one of ordinary skill in the art of organic synthesis, the following additional compounds of the present invention are prepared:

"I-8" where R$_2$ and R$_3$ are propyl, Z$_5$ is cyclopropyl and Z$_6$ are 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl the heteroaromatics, 2-Pyridinesulfonamide, N-[3-(cyclopropyl(2,5-dihydro4-hydroxy-2-oxo-5,5-dipropyl-3-furanyl)methyl)phenyl)-, 5-cyano-2-pyridinesulfonamide, N-(3-(cyclopropyl(2,5-dihydro-4-hydroxy-2-oxo-5,5-dipropyl-3-furanyl)methyl)phenyl)-, 2-Quinolinesulfonamide, N-(3-(cyclopropyl(2,5-dihydro-4-hydroxy-2-oxo-5,5-dipropyl-3-furanyl)methyl)phenyl)-, 2-Pyrimidinesulfonamide, N-(3-(cyclopropyl(2,5-dihydro-4-hydroxy-2-oxo-5,5-dipropyl-3-furanyl)methyl)phenyl)-, 2-Quinazolinesulfonamide, N-(3-(cyclopropyl(2,5-dihydro-4-hydroxy-2-oxo-5,5-dipropyl-3-furanyl)methyl)phenyl)-, 1H-Benzimidazole-2-sulfonamide, N-(3-(cyclopropyl(2,5-dihydro-4-hydroxy-2-oxo-5,5-dipropyl-3-furanyl)methyl)phenyl)-, 1H-Imidazole-2-sulfonamide, N-(3-(cyclopropyl(2,5-dihydro-4-hydroxy-2-oxo-5,5-dipropyl-3-furanyl)methyl)phenyl)-, 4-Thiazolesulfonamide, N-(3-(cyclopropyl(2,5-dihydro-4-hydroxy-2-oxo-5,5-dipropyl-3-furanyl)methyl)phenyl)-, 7H-Purine-6-sulfonamide, N-(3-(cyclopropyl(2,5-dihydro-4-hydroxy-2-oxo-5,5-dipropyl-3-furanyl)methyl)phenyl)-, "I-8" where R$_2$ and R$_3$ are phenylmethyl, Z$_5$ is cyclopropyl and Z$_6$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, Benzenesulfonamide, N-(3-(cyclopropyl-(5,5-dibenzyl-4-hydroxy-2-oxo-2,5-dihydro-3-furanyl)methyl)phenyl)-, Benzenesulfonamide, 4-cyano-N-(3-(cyclopropyl-(5,5-dibenzyl-4-hydroxy-2-oxo-2,5-dihydro-3-furanyl)methyl)phenyl)-, 1H-Imidazole-4-sulfonamide, N-(3-(cyclopropyl-(5,5-dibenzyl-4-hydroxy-2-oxo-2,5-dihydro-3-furanyl)methyl)phenyl)-1-methyl-, 2-Pyridinesulfonamide, N-(3-(cyclopropyl-(5,5-dibenzyl-4-hydroxy-2-oxo-2,5-dihydro-3-furanyl)methyl)phenyl)-, 5-cyano-2-pyridinesulfonamide, N-(3-(cyclopropyl-(5,5-dibenzyl-4-hydroxy-2-oxo-2,5-dihydro-3-furanyl)methyl)phenyl)-, 2-Quinolinesulfonamide, N-(3-(cyclopropyl-(5,5-dibenzyl-4-hydroxy-2-oxo-2,5-dihydro-3-furanyl)methyl)phenyl)-, 2-Pyrimidinesulfonamide, N-(3-(cyclopropyl-(5,5-dibenzyl-4-hydroxy-2-oxo-2,5-dihydro-3-furanyl)methyl)phenyl)-, 2-Quinazolinesulfonamide, N-(3-(cyclopropyl-(5,5-dibenzyl-4-hydroxy-2-oxo-2,5-dihydro-3-furanyl)methyl)phenyl)-, 1H-Benzimidazole-2-sulfonamide, N-(3-(cyclopropyl-(5,5-dibenzyl-4-hydroxy-2-oxo-2,5-dihydro-3-furanyl)methyl)phenyl)-, 1H-Imidazole-2-sulfonamide, N-(3-(cyclopropyl-(5,5-dibenzyl-4-hydroxy-2-oxo-2,5-dihydro-3-furanyl)methyl)phenyl)-, 4-Thiazolesulfonamide, N-(3-(cyclopropyl-(5,5-dibenzyl-4-hydroxy-2-oxo-2,5-dihydro-3-furanyl)methyl)phenyl)-, 7H-Purine-6-sulfonamide, N-(3-(cyclopropyl-(5,5-dibenzyl-4-hydroxy-2-oxo-2,5-dihydro-3-furanyl)methyl)phenyl)-, "I-8" where R$_2$ and R$_3$ are propyl, Z$_5$ is 1,1-dimethylethyl and Z$_6$ are phenyl, 4-cyanophenyl, 1-methyl-4-imidazolyl, 2-pyridinyl, 5-cyano-2-pyridinyl, $^2$quinolinyl, 2-pyrimidinyl, 2quinazolinyl, 2-benzimidazolyl, 2-imidazolyl, 4-thiazolyl, 6-purinyl, Benzenesulfonamide, N-(3-(1-(hydroxy-2-oxo-5,5-dipropyl-2,5-dihydro-3-furanyl)-2,2-dimethyl-propyl)-phenyl)-, Benzenesulfonamide, 4-cyano-N-(3-(1-(4-hydroxy-2-oxo-5,5-dipropyl-2,5-dihydro-3-furanyl)-2,2-dimethyl-propyl)-phenyl)-, 1H-Imidazole-4-sulfonamide, N-(3-(1-(4-hydroxy-2-oxo-5,5-dipropyl-2,5-dihydro-3-furanyl)-2,2-methyl-propyl)-phenyl)-1-methyl-, 2-Pyridinesulfonamide, N-(3-(1-(4-hydroxy-2-oxo-5,5-dipropyl-2,5-dihydro-3-furanyl)-2,2-dimethyl-propyl)-phenyl)-, 5-cyano-2-pyridinesulfonamide, N-(3-(1-(4-hydroxy-2-oxo-5,5-dipropyl-2,5-dihydro-3-furanyl)-2,2-dimethyl-propyl)-phenyl)-, 2-Quinolinesulfonamide, N-(3-(1-(4-hydroxy-2-oxo-5,5-dipropyl-2,5-dihydro-3-furanyl)-2,2-dimethyl-propyl)-phenyl)-, 2-Pyrimidinesulfonamide, N-(3-(1-(4-hydroxy-2-oxo-5,5-dipropyl-2,5-dihydro-3-furanyl)- 2,2-dimethyl-propyl)-phenyl)-, 2-Quinazolinesulfonamide, N-(3-(1-(4-hydroxy-2-oxo-5,5-dipropyl-2,5-dihydro-3-furanyl)-2,2-dimethyl-propyl)-phenyl)-, 1H-Benzimidazole-2-sulfonamide, N-(3-(1-(4-hydroxy-2-oxo-5,5-dipropyl-2,5-dihydro-3-furanyl)-2,2-dimethyl-propyl)-phenyl)-, 1H-Imidazole-2-sulfonamide, N-(3-(1-(4-hydroxy-2-oxo-5,5-dipropyl-2,5-dihydro-3-furanyl)-2,2-dimethyl-propyl)-phenyl)-, 4-Thiazolesulfonamide, N-(3-(1-(4-hydroxy-2-oxo-5,5-dipropyl-2,5-dihydro-3-furanyl)-2,2-dimethyl-propyl)-phenyl)-, 7H-Purine-6-sulfonamide, N-(3-(1-(4-hydroxy-2-oxo-5,5-dipropyl-2,5-dihydro-3-furanyl)-2,2-dimethyl-propyl)-phenyl)-, "I-8" where $R_2$ and $R_3$ are phenylmethyl, $Z_5$ is 1,1-dimethylethyl and $Z_6$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, Benzenesulfonamide, N-3-(1-(5,5-dibenzyl-4-hydroxy-2-oxo-2,5-dihydro-3-furanyl)-2,2-dimethyl-propyl)-phenyl)-, Benzenesulfonamide, 4-cyano-N-3-(1-(5,5-dibenzyl-4-hydroxy-2-oxo-2,5-dihydro-3-furanyl)-2,2-dimethyl-propyl)-phenyl)-, 1H-Imidazole-4-sulfonamide, N-3-(1-(5,5-dibenzyl-4-hydroxy-2-oxo-2,5-dihydro-3-furanyl)-2,2-dimethyl-propyl)-phenyl)-1-methyl-, 2-Pyridinesulfonamide, N-3-(1-(5,5-dibenzyl-4-hydroxy-2-oxo-2,5-dihydro-3-furanyl)-2,2-dimethyl-propyl)-phenyl)-, 5-cyano-2-pyridinesulfonamide, N-3-(1-(5,5-dibenzylhydroxy-2-oxo-2,5-dihydro-3-furanyl)-2,2-dimethyl-propyl)-phenyl)-, 2-Quinolinesulfonamide, N-3-(1-(5,5-dibenzyl-4-hydroxy-2-oxo-2,5-dihydro-3-furanyl)-2,2-dimethyl-propyl)-phenyl)-, 2-Pyrimidinesulfonamide, N-3-(1-(5,5-dibenzyl-4-hydroxy-2-oxo-2,5-dihydro-3-furanyl)-2,2-dimethyl-propyl)-phenyl)-, 2-Quinazolinesulfonamide, N-3-(1-(5,5-dibenzyl-4-hydroxy-2-oxo-2,5-dihydro-3-furanyl)-2,2-dimethyl-propyl)-phenyl)-, 1H-Benzimidazole-2-sulfonamide, N-3-(1-(5,5-dibenzyl-4-hydroxy-2-oxo-2,5-dihydro-3-furanyl)-2,2-dimethyl-propyl)-phenyl)-, 1H-Imidazole-2-sulfonamide, N-3-(1-(5,5-dibenzyl-4-hydroxy-2-oxo-2,5-dihydro-3-furanyl)-2,2-dimethyl-propyl)-phenyl)-, 4-Thiazolesulfonamide, N-3-(1-(5,5-dibenzyl-4-hydroxy-2-oxo-2,5-dihydro-3-furanyl)-2,2-dimethyl-propyl)-phenyl)-, 7H-Purine-6-sulfonamide, N-3-(1-(5,5-dibenzyl-4-hydroxy-2-oxo-2,5-dihydro-3-furanyl)-2,2-dimethyl-propyl)-phenyl)-.

CHART J

Chart J describes the synthesis of tetronic acids of general formula J-1 by way of demethylation of the alkene derivative of general formula G-4.

Example JX-1

(Chart J "J-1 " where $R_1$ is cyclopropylphenylmethyl and $Z_2$ is 2-phenylethyl).

Following the general procedure described in preparation GP-6 the title compound was isolated as an oil: $^1$H NMR (CDCl$_3$) δ7.42-7.18 (m, 10H), 5.39 (t, J=7.6 Hz, 1H), 3.42 (d, J=8.7 Hz, 1H), 2.78-2.74 (m, 2H), 2.69-2.62 (m, 2H), 1.40-1.31 (m, 1H), 0.69-0.61 (m, 2H), 0.54-0.49 (m, 1h), 0.26-0.23 (M, 1H) ppm; $^{13}$C NMR (CDCl$_3$) δ169.28, 160.71, 143.20, 140.82, 140.36, 129.17, 128.45, 127.86, 127.51, 126.15, 109.15, 106.33, 43.59, 34.99, 27.27, 13.88, 4.56, 4.37, ppm; HRMS (EI) calcd for $C_{23}H_{22}O_3$: 346.1569. Found: 346.1563.

Example JX-2

(Chart J "J-11" where $R_1$ is cyclopropylphenylmethyl and $Z_2$ is phenyl).

Physical characteristics are as follows: mp 166–7° C.; $^1$H NMR (CDCl$_3$) δ7.72 (d, J=7.4 Hz, 2H), 7.46 (d, J=7.3 Hz, 2H), 7.37-7.21 (m, 6H), 6.31 (s, 1H), 3.27 (d, J=9.3 Hz, 1H), 1.65-1.61 (m, 1H), 0.68-0.60 (m, 2H), 0.41-0.27 (m,2H) ppm; $^{13}$C NMR (CDCl$_3$) δ169.91, 162.81, 142.46, 141.23, 132.60, 130.13, 128.43, 127.57, 126.63, 107.03, 105.49, 43.82, 13.70, 4.96, 4.34 ppm; HRMS (EI) calcd for $C_{21}H_{18}O_3$: 318.1256. Found: 318.1249.

Example JX-3

(Chart J "J-1" where $R_1$ is cyclopropylphenylmethyl and $Z_2$ is ethyl).

Physical characteristics are as follows: $^1$H NMR (CDCl$_3$) δ7.42 (d, J=7.2 Hz, 2H), 7.33-7.20 (m, 2H), 5.51 (t, J=7.8 Hz, 1H), 3.19 (d, J=9.5 Hz, 1H), 2.31 (quintet, J=7.6 Hz, 2H), 1.59-1.49 (m, 1H), 1.05 (t, J=7.6 Hz, 3H), 0.64-0.55 (m, 2H), 0.38-0.20 (m, 2H) ppm; $^{13}$C NMR (CDCl$_3$) δ170.52, 161.58, 142.77, 141.38, 128.73, 127.80, 126.98, 112.75, 106.39, 43.97, 19.22, 13.82, 13.48, 5.07, 4.60 ppm; HRMS (EI) calcd for $C_{17}H_{18}O_3$: 270.1256. Found: 270.1247.

Example JX-4

(Chart J "J-1" where $R_1$ is cyclopropylphenylmethyl and $Z_2$ is propyl)

Physical characteristics are as follows: $^1$H NMR (CDCl$_3$) δ7.43-7.23 (m, 5H), 5.47 (t, J=7.9 Hz, 1H), 3.25 (d, J=9.2 Hz, 1H), 2.26 (q, J=7.5 Hz, 2H), 1.53-1.41 (m, 3H), 0.93 (t, J=7.3 Hz, 3H), 0.69-0.59 (m, 2H), 0.44-0.41 (m, 1H), 0.26-0.23 (m, 1H) ppm; $^{13}$C NMR (CDCl$_3$) δ170.25, 161.31, 143.12, 141.27, 128.94, 127.86, 127.21, 110.69, 106.44, 43.85, 27.65, 22.25, 13.90, 13.79, 4.78, 4.60 ppm; HRMS (EI) calcd for $C_{18}H_{20}O_3$: 284.1412. Found: 284.1419.

CHART K

Chart K describes the reaction of tetronic acids of general formula C-5 with benzylic or tertiary alcohols (K-1) in the presence of Lewis acids to afford 3-substituted analogs of general structure K-2.

Preparation KP-1 and Example KX-1

(See Chart K, figure "K-2" where $R_2$ and $R_3$ form a cyclopentyl ring and $R_1$ is cyclopropylphenylmethyl.) 1-Oxaspiro<4.4>non-3-en-2-one,-3-(cyclopropylphenylmethyl)-4-hydroxy-.

The procedure described in Preparation AP-1 is followed. 78 mg of the title compound from Preparation CP-7 (Chart C, figure "C-5") are dissolved in 5 ml of 4A molecular sieve-dried dioxane. 144 mg of α-cyclopropylbenzyl alcohol (K-1) and 0.4 ml of BF$_3$-Et$_2$O are added. The reaction is stirred for 24 hours at room temperature under argon. The reaction is quenched by the addition of 1 ml of water, and the solvent is removed under reduced pressure. The residue is treated with H$_2$0 and extracted three times with CH$_2$Cl$_2$. The aqueous phase is made acidic with 1N HCl and extracted 3 times with CH$_2$Cl$_2$, which is dried over MgSO$_4$. The CH$_2$Cl$_2$ is removed under reduced pressure, and the desired product is obtained by flash chromatography using 28% EtOAc\70%hexane\2% HOAc as eluant. The title product is further purified by recrystallization from EtOAc\hexane to yield 30 mg of a white solid.

Physical characteristics are as follows:

$^1$H-NMR(CDCl$_3$) δ0.15–0.30(m,1H), 0.31–0.40(m,1H), 0.53–0.78(m,2H), 1.23–1.44(m,1H), 1.58–2.04(m,8H), 3.40–3.42(m,1H), 7.25–7.40(m,5H). EIMS m/z 284 (M).

Following procedures described herein and using starting materials and reagents readily known and available to one of ordinary skill in the art of organic synthesis, the following additional compounds of the present invention are prepared:

Example KX-2

(See Chart K, "K-2" where $R_2$ and $R_3$ form a cyclooctyl ring and $R_1$ is cyclopropylphenylmethyl.) 1-Oxaspiro<4.7>dodec-3-en-2-one, 3-(cyclopropylphenylmethyl)-4-hydroxy-.

Physical characteristics are as follows:

$^1$H-NMR(CDCl$_3$) δ0.15–0.38(m,2H), 0.50–0.78(m,2H), 1.33–1.98(m,15H), 3.39–3.49(m,1H), 7.26–7.40(m,5H). EIMS m/z 326 (M).

Example KX-3

(See Chart K, "K-2" where $R_2$ is 2-phenylethyl and $R_3$ is methyl.) 2(5H)-Furanone, 3-cyclopropylphenylmethyl)-4-hydroxy-5-methyl-5-(2-phenylethyl)-.

Physical characteristics are as follows:

$^1$H-NMR(CD$_3$OD) δ0.19–0.22(m,2H), 0.55–0.65(m,2H), 1.48–1.50(t,2H), 1.72–1.81(m,1H), 2.06–2.10(m,2H), 2.28–2.53(m,2H), 2.92(d,1H), 7.07–7.45(m,10H). HRMS calculated for C$_{23}$H$_{24}$O$_3$: 349.1804, found 349.1816.

CHART L

CHART L describes a method of preparation of α-functionalized ketones. Condensation of a ketone L-1 with N,N-dimethylhydrazine affords the N,N-dimethylhydrazone L-2. Metallation with butyl lithium or LDA and reaction with an appropriate electrophile such as an alkyl bromide affords the a-substituted hydrazone which after hydrolysis affords the requisite ketone.

Preparation LP-1

(Chart L "L-2").

The title compound was prepared by a modification of the literature procedure (Corey, E. J.; Enders, D. Chem. Ber. 1978, 111, 1337).

To a mixture of cyclohexanone (L-1, 10.0 g, 0.1 mol) and 4-toluenesulfonic acid (40 mg, 0.21 mmol) in anhydrous benzene (250 ml) was added 1,1-dimethylhydrazine (18.03 g, 0.3 mol). After heating at reflux with azeotropic removal of water for 16 h, the mixture was concentrated in vacuo. Vacuum distillation afforded the title compound (10.46 g, 75%) as an oil; $^1$H NMR (CDCl$_3$) δ2.53-2.49 (m, 2H), 2.44 (s, 6H), 2.26-2.22 (m, 2H), 1.70-1.63 (m, 6H) ppm.

Preparation LP-2

(Chart L "L-3" where $Z_7$ is 2-phenylethyl).

To a solution of LDA (20 mL of a 1.5 M solution of the mono tetrahydrofuran complex in cyclohexane, 30 mmol) in anhydrous THF (20 mL) at −78° C. was slowly added a solution of the N,N-dimethylhydrazone L-2 (3.5 g, 25.0 mmol) in anhydrous THF (20 mL). After stirring at −78° C. for 5 min and at 0–5° C. for 30 min, (2-bromoethyl)benzene (13.8 g, 75 mmol) and tetrabutylammonium iodide (920 mg, 2.5 mmol) were added. The reaction mixture was stirred an additional hour at 0–5° C. then at ambient temperature for 16 h. The mixture was made acidic (pH ca. 3) with 1N HCl and stirred for 1 h at ambient temperature to effect hydrolysis of the hydrazone. The mixture was diluted with ethyl acetate and the organic layer washed with 0.25 N HCl and brine, dried (MgSO$_4$), filtered, and concentrated in vacuo. Flash chromatography of the residue with hexanelethyl acetate (2%) as eluant afforded the title compound (4.04 g, 80%) as an oil; $^1$H NMR (CDCl$_3$) δ7.30-7.24 (m, 2H), 7.18-7.13 (m, 3H), 2.62 (t, J=7.9 Hz, 2H), 2.37-2.01 (m, 6H), 1.85-1.84 (m, 1H), 1.67-1.38 (m, 4H) ppm; EIMS m/Z 202 (M$^+$).

CHART M

Chart M describes the preparation of N-methylsulfonamides of general structure M-3. Reductive alkylation of amine (I-6) with formaldehyde in the presence of hydrogen and palladium on carbon as catalyst provides the N-methyl analog of structure M-1. Reaction with a sulfonyl chloride (M-2) as described in preparation IP-6 provides the target compounds of general structure M-3. Following procedures analogous to those described above and using starting materials and reagents readily known and available to one of ordinary skill in the art of organic synthesis, the following additional compounds of the present invention are prepared:

M-3 where $R_2$ and $R_3$ are propyl, $Z_5$ is cyclopropyl and $Z_8$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, N-(3-(Cyclopropyl-(4-hydroxy-2-oxo-5,5-dipropyl-2,5-dihydro-3-furanyl)-methyl)-phenyl)-N-methyl-benzenesulfonamide, 4-Cyano-N-(3-(cyclopropyl-(4-hydroxy-2-oxo-5,5-propyl-2,5-dihydro-3-furanyl)-methyl)-phenyl)-N-methyl-benzenesulfonamide, 1-Methyl-1H-imidazole-4-sulfonic acid (3-(cyclopropyl-(4-hydroxy-2-oxo-5,5-tripropyl-2,5-dihydro-3-furanyl)-methyl)-phenyl)-methyl-amide, Pyridine-2-sulfonic acid (3-(cyclopropyl-(4-hydroxy-2-oxo-5,5-dipropyl-2,5-dihydro-3-furanyl)-methyl)-phenyl)-methyl-amide, 5-Cyano-pyridine-2-sulfonic acid (3-(cyclopropyl-(4-hydroxy-2-oxo-5,5-dipropyl-2,5-dihydro-3-furanyl)-methyl)-phenyl)-methyl-amide, Quinoline-2-sulfonic acid (3-(cyclopropyl-(4-hydroxy-2-oxo-5,5-dipropyl-2,5-dihydro-3-furanyl)-methyl)-phenyl)-methyl-amide, Pyrimidine-2-sulfonic acid (3-(cyclopropyl-(4-hydroxy-2-oxo-5,5-dipropyl-2,5-dihydro3-furanyl)-methyl)-phenyl)-methyl-amide, Quinazoline-2-sulfonic acid (3-(cyclopropyl-(4-hydroxy-2-oxo-5,5-dipropyl-2,5-dihydro-3-furanyl)-methyl)-phenyl)-methyl-amide, 1H-Benzimidazole-2-sulfonic acid (3-(cyclopropyl-(4-hydroxy-2-oxo-5,5-dipropyl-2,5-dihydro-3-furanyl)-methyl)-phenyl)-methyl-amide, 1H-Imidazole-2-sulfonic acid (3-(cyclopropyl-(4-hydroxy-2-oxo-5,5-dipropyl-2,5-dihydro-3-furanyl)-methyl)-phenyl)-methyl-amide, Thiazole-4-sulfonic acid (3-(cyclopropyl-(4-hydroxy-2-oxo-5,5-dipropyl-2,5-dihydro-3-furanyl)-methyl)-phenyl)-methyl-amide, 7H-Purine-6-sulfonic acid (3-(cyclopropyl-(4-hydroxy-2-oxo-5,5-propyl-2,5-dihydro-3-furanyl)-methyl)-phenyl)-methyl-amide, M-3 where R$_2$ and R$_3$ are propyl, Z$_5$ is 1,1 dimethylethyl and Z$_8$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, N-(3-(1-(4-hydroxy-2-oxo-5,5-dipropyl-2,5-dihydro-3-furanyl)-2,2-dimethyl-propyl)-phenyl)-N-methyl-benzenesulfonamide, 4-Cyano-N-(3-( 1 -(hydroxy-2-oxo-5,5-dipropyl-2,5-dihydro-3-furanyl)-2,2-methyl-propyl)-phenyl)-N-methyl-benzenesulfonamide, 1-Methyl-1H-imidazole-4-sulfonic acid (3-(1-(4-hydroxy-2-oxo-5,5-dipropyl-2,5-dihydro-3-furanyl)-2,2-dimethyl-propyl)-phenyl)-methyl-amide, Pyridine-2-sulfonic acid (3-(1-(4-hydroxy-2-oxo-5,5-dipropyl-2,5-dihydro-3-furanyl)-2,2-dimethyl-propyl)-phenyl)-methyl-amide, 5-Cyano-pyridine-2-sulfonic acid (3-(1-(4-hydroxy-2-oxo-5,5-dipropyl-2,5-dihydro-3-furanyl)-2,2-dimethyl-propyl)-phenyl)-methyl-amide, Quinoline-2-sulfonic acid (3-(1-(4-hydroxy-2-oxo-5,5-dipropyl-2,5-dihydro-3-furanyl)-2,2-dimethyl-propyl)-phenyl)-methyl-amide, Pyrimidine-2-sulfonic acid (3-(1-(4-hydroxy-2-oxo-5,5-dipropyl-2,5-dihydro-3-furanyl)-2,2-dimethyl-propyl)-phenyl)-methyl-amide, Quinazoline-2-sulfonic acid (3-(1-(4-hydroxy-2-oxo-5,5-dipropyl-2,5-dihydro-3-furanyl)-2,2-dimethyl-propyl)-phenyl)-methyl-amide, 1H-Benzimidazole-2-sulfonic acid (3-(1-(4-hydroxy-2-oxo-5,5-dipropyl-2,5-dihydro-3-furanyl)-2,2-dimethyl-propyl)-phenyl)-methyl-amide, 1H-Imidazole-2-sulfonic acid (3-(1-(4-hydroxy-2-oxo-5, 5-dipropyl-2,5-dihydro-3-furanyl)-2,2-dimethyl-propyl)-phenyl)-methyl-amide, Thiazole-4-sulfonic acid (3-(1-(4-hydroxy-2-oxo-5,5-dipropyl-2,5-dihydro-3-furanyl)-2,2-dimethyl-propyl)-phenyl)-methyl-amide, 7H-Purine-6-sulfonic acid (3-(1-(4-hydroxy-2-oxo-5,5-dipropyl-2,5-dihydro-3-furanyl)-2,2-dimethyl-propyl)-phenyl)-methyl-amide, M-3 where R$_2$ and R$_3$ are propyl, Z$_5$ is cyclopropyl and Z$_8$ are phenyl, 4-cyanophenyl, 1-methyl-4-imidazolyl, 2-pyridinyl, 5-cyano-2-pyridinyl, $^2$quinolinyl, 2-pyrimidinyl, 2-quinazolinyl, 2-benzimidazolyl, 2-imidazolyl, 4-thiazolyl, 6-purinyl, N-(3-(Cyclopropyl-(5,5-dibenzyl-4-hydroxy-2-oxo-2,5-dihydro-3-furanyl)-methyl)-phenyl)-N-methyl-benzenesulfonamide, 4-Cyano-N-(3-(cyclopropyl-(5,5-dibenzyl-4-hydroxy-2-oxo-2,5-dihydro-3-furanyl)-methyl)-phenyl)-N-methyl-benzenesulfonamide, 1-Methyl-1H-imidazole-4-sulfonic acid (3-(cyclopropyl-(5,5-dibenzyl-4-hydroxy-2-oxo-2,5-dihydro-3-furanyl)-methyl)-phenyl)-methyl-amide, Pyridine-2-sulfonic acid (3-(cyclopropyl-(5,5-dibenzyl-4-hydroxy-2-oxo-2,5-dihydro-3-furanyl)-methyl)-phenyl)-methyl-amide, 5-Cyano-pyridine-2-sulfonic acid (3-(cyclopropyl-(5,5-dibenzyl-4-hydroxy-2-oxo-2,5-dihydro-3-furanyl)-methyl)-phenyl)-methyl-amide, Quinoline-2-sulfonic acid (3-(cyclopropyl-(5,5-dibenzyl-4-hydroxy-2-oxo-2,5-dihydro-3-furanyl)-methyl)-phenyl)-methyl-amide, Pyrimidine-2-sulfonic acid (3-(cyclopropyl-(5,5-dibenzyl-4-hydroxy-2-oxo-2,5-dihydro-3-furanyl)-methyl)-phenyl)-methyl-amide, Quinazoline-2-sulfonic acid (3-(cyclopropyl-(5,5-dibenzyl-4-hydroxy-2-oxo-2,5-dihydro-3-furanyl)-methyl)-phenyl)-methyl-amide, 1H-Benzimidazole-2-sulfonic acid (3-(cyclopropyl-(5,5-dibenzyl-4-hydroxy-2-oxo-2,5-dihydro-3-furanyl)-methyl)-phenyl)-methyl-amide, 1H-Imidazole-2-sulfonic acid (3-(cyclopropyl-(5,5-dibenzyl-4-hydroxy-2-oxo-2,5-dihydro-3-furanyl)-methyl)-phenyl)-methyl-amide, Thiazole-4-sulfonic acid (3-(cyclopropyl-(5,5-benzyl-4-hydroxy-2-oxo-2,5-dihydro-3-furanyl)-methyl)-phenyl)-methyl-amide, 7H-Purine-6-sulfonic acid (3-(cyclopropyl-(5,5-dibenzyl-4-hydroxy-2-oxo-2,5-dihydro-3-furanyl)-methyl)-phenyl)-methyl-amide, M-3 where R$_2$ and R$_3$ are phenylmethyl, Z$_5$ is 1,1-dimethylethyl and Z$_8$ are phenyl, 4-cyanophenyl, 1-methyl-4-imidazolyl, 2-pyridinyl, 5-cyano-2-pyridinyl, $^2$quinolinyl, 2-pyrimidinyl, 2-quinazolinyl, 2-benzimidazolyl, 2-imidazolyl, 4-thiazolyl, 6-purinyl, N-(3-(1-(5,5-dibenzyl-4-hydroxy-2-oxo-2,5-dihydro-3-furanyl)-2,2-diethyl-propyl)-phenyl)-N-methyl-benzenesulfonamide, 4-Cyano-N-(3-(1-(5,5-dibenzyl-4-hydroxy-2-oxo-2,5-dihydro-3-furanyl)-2,2-diethyl-propyl)-phenyl)-N-methyl-benzenesulfonamide, 1-Methyl-1H-imidazole-4-sulfonic acid (3-(1-(5,5-benzyl-4-hydroxy-2-oxo-2,5-dihydro-3-furanyl)-2,2-dimethyl-propyl)-phenyl)-methyl-amide, Pyridine-2-sulfonic acid (3-(1-(5,5-dibenzyl-4-hydroxy-2-oxo-2,5-dihydro-3-furanyl)-2,2-dimethyl-propyl)-phenyl)-methyl-amide, 5-Cyano-pyridine-2-sulfonic acid (3-(1-(5,5-dibenzyl-4-hydroxy-2-oxo-2,5-dihydro-3-furanyl)-2,2-dimethyl-propyl)-phenyl)-methyl-amide, Quinoline-2-sulfonic acid (3-(1-(5,5-dibenzyl-4-hydroxy-2-oxo-2,5-dihydro-3-furanyl)- 2,2-dimethyl-propyl)-phenyl)-methyl-amide, Pyrimidine-2-sulfonic acid (3-(1-(5,5-dibenzyl-4-hydroxy-2-oxo-2,5-dihydro-3-furanyl)-2,2-dimethyl-propyl)-phenyl)-methyl-amide, Quinazoline-2-sulfonic acid (3-(1-(5,5-dibenzyl-4-hydroxy-2-oxo-2,5-dihydro-3-furanyl)-2,2-dimethyl-propyl)-phenyl)-methyl-amide, 1H-Benzimidazole-2-sulfonic acid (3-(1-(5,5-dibenzyl-4-hydroxy-2-oxo-2,5-dihydro-3-furanyl)-2,2-methyl-propyl)-phenyl)-methyl-amide, 1H-Imidazole-2-sulfonic acid (3-(1-(5,5-dibenzyl-4-hydroxy-2-oxo-2,5-dihydro-3-furanyl)-2,2-dimethyl-propyl)-phenyl)-methyl-amide, Thiazole-4-sulfonic acid (3-(1-(5,5-dibenzyl-4-hydroxy-2-oxo-2,5-dihydro-3-furanyl)-2,2-dimethyl-propyl)-phenyl)-methyl-amide, 7H-Purine-6-sulfonic acid (3-(1-(5,5-dibenzyl-4-hydroxy-2-oxo-2,5-dihydro-3-furanyl)-2,2-dimethyl-propyl)-phenyl)-methyl-amide.

CHART N

Chart N describes the synthesis of sulfones of the general structure N-10. Aldehyde N-1 (Baillargeon, V. P.; Stelle, J.

K. J. Am. Chem. Soc. 1983, 105, 7175) is protected as its tert-butyldiphenylsilyl ether (N-2) under standard conditions (Hanessian, S.; Lavallee, P. Can. J. Chem. 1975, 53, 2975). Aldol condensation with the tetronic acid C-5 and subsequent conjugate addition with the Grignard reagent N-4 by the general procedures provided by preparations IP-1 and IP-2 provides the tetronic acid of general formula N-5. Removal of the silyl ether under standard conditions and conversion to the bromide provides the halide N-7. Displacement of the halide with a thiol (N-8) provides analogs of general structure N-9. Oxidation of the sulfide with oxone or other suitable oxidants affords the requisite sulfones of structure N-10.

Following procedures described herein and using starting materials and reagents readily known and available to one of ordinary skill in the art of organic synthesis, the following additional compounds of the present invention are prepared:

N-10 where $R_2$ and $R_3$ are propyl, $Z_9$ is cyclopropyl and $Z_{10}$ are phenyl, 4-cyanophenyl, 1-methyl-4-imidazolyl, 2-pyridinyl, 5-cyano-2-pyridinyl, 2quinolinyl, 2-pyrimidinyl, 2-quinazolinyl, 2-benzimidazolyl, 2-imidazolyl, 4-thiazolyl, 6-purinyl, 3-((3-Benzenesulfonylmethyl-phenyl)-cyclopropyl-methyl)-4-hydroxy-5,5-dipropyl-5H-furan-2-one, 4-(3-(Cyclopropyl-(4-hydroxy-2-oxo-5,5-dipropyl-2,5-dihydro-furan-3-yl)-methyl)-phenylmethanesulfonyl)-benzonitrile, 3-(Cyclopropyl-(3-(1-methyl-1H-imidazole-4-sulfonylmethyl)-phenyl)-methyl)4-hydroxy- 5,5-dipropyl-5H-furan-2-one, 3-(Cyclopropyl-(3-(pyridine-2-sulfonylmethyl)-phenyl)-methyl)-4-hydroxy-5,5-dipropyl-5H-furan-2-one, 6-(3-(Cyclopropyl-(4-hydroxy-2-oxo-5,5-dipropyl-2,5-dihydro-furan-3-yl)-methyl)-phenylmethanesulfonyl)-nicotinonitrile, 3-(Cyclopropyl-(3-(quinoline-2-sulfonylmethyl)-phenyl)-methyl)-4-hydroxy-5,5-dipropyl-5H-furan-2-one, 3-(Cyclopropyl-(3-(pyrimidine-2-sulfonylmethyl)-phenyl)-methyl)-4-hydroxy-5,5-dipropyl-5H-furan-2-one, 3-(Cyclopropyl-(3-(quinazoline-2-sulfonylmethyl)-phenyl)-methyl)-4-hydroxy-5,5-dipropyl-5H-furan-2-one, 3-((3-(1H-Benzimidazole-2-sulfonyhnethyl)-phenyl)-cyclopropyl-methyl)-4-hydroxy-5,5-dipropyl-5H-furan-2-one, 3-(Cyclopropyl-(3-(1H-inidazole-2-sulfonylmethyl)-phenyl)-methyl)-4-hydroxy-5,5-dipropyl-5H-furan-2-one, 3-(Cyclopropyl-(3-(thiazole-4-sulfonylmethyl)-phenyl)-methyl)-4-hydroxy-5,5-dipropyl-5H-furan-2-one, 3-(Cyclopropyl-(3-(7H-purine-6-sulfonylmethyl)-phenyl)-methyl)-4-hydroxy-5,5-dipropyl-5H-furan-2-one, N-10 where $R_2$ and $R_3$ are propyl, $Z_9$ is 1,1-dimethylethyl and $Z_{10}$ are phenyl, 4-cyanophenyl, 1-methyl-4-imidazolyl, 2-pyridinyl, 5-cyano-2-pyridinyl, 2-quiolinyl, 2-pyrimidinyl, 2quinazolinyl, 2-benzimidazolyl, 2-imidazolyl, 4-thiazolyl, 6-purinyl, 3-(1-(3-Benzenesulfonylmethyl-phenyl)-2,2-dimethyl-propyl)-4-hydroxy-5,5-dipropyl-5H-furan-2-one, 4-(3-(1-(4Hydroxy-2-oxo-5,5-dipropyl-2,5-dihydro-furan-3-yl)-2,2-dimethyl-propyl)-phenylmethanesulfonyl)-benzonitrile, 3-(2,2-Dimethyl-1-(3-(1-methyl-1H-imidazole-4-sulfonylmethyl)-phenyl-propyl)4-hydroxy-5,5-dipropyl-5H-furan-2-one, 3-(2,2-Dimethyl-1-(3-(pyridine-2-sulfonylmethyl)-phenyl)-propyl)-4-hydroxy-5,5-dipropyl-5H-furan-2-one, 6-(3-(1-(4-Hydroxy-2-oxo-5,5-dipropyl-2,5-dihydro-furan-3-yl)-2,2-dimethyl-propyl)-phenylmethanesulfonyl)-nicotinonitrile, 3-(2,2-Dimethyl-1-(3-(quinoline-2-sulfonylmethyl)-phenyl)-propyl)-4-hydroxy-5,5-dipropyl-5H-furan-2-one, 3-(2,2-Dimethyl-1-(3-(pyrimidine-2-sulfonylmethyl)-phenyl)-propyl)-4-hydroxy-5,5-dipropyl-5H-furan-2-one, 3-(2,2-Dimethyl-1 -(3-(quinazoline-2-sulfonylmethyl)-phenyl)-propyl)-4-hydroxy-5,5-dipropyl-5H-furan-2-one, 3-(1-(3-(1H-Benzimidazole-2-sulfonylmethyl)-phenyl)-2,2-dimethyl-propyl)-4-hydroxy-5,5-dipropyl-5H-furan-2-one, 4-Hydroxy-3-(1-(3-(1H-imidazole-2-sulfonylmethyl)-phenyl)-2,2-dimethyl-propyl)-5,5-dipropyl-5H-furan-2-one, 3-(2,2-Dimethyl-1-(3-(thiazole-4-sulfonylmethyl)-phenyl)-propyl)-4-hydroxy-5,5-dipropyl-5H-furan-2-one, 3-(2,2-Dimethyl-1-(3-(7H-purine-6-sulfonylmethyl)-phenyl)-propyl)-4-hydroxy-5,5-dipropyl-5H-furan-2-one, N-10 where $R_2$ and $R_3$ are phenylmethyl, $Z_9$ is cyclopropyl and $Z_{10}$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, 3-((3-Benzenesulfonylmethyl-phenyl)-cyclopropyl-methyl)-5,5-dibenzyl-4-hydroxy-5H-furan-2-one, 4-(3-(Cyclopropyl-(5,5-dibenzyl-4-hydroxy-2-oxo-2,5-dihydro-furan-3-yl)-methyl)-phenylmethanesulfonyl)-benzonitrile, 5,5-Dibenzyl-3-(cyclopropyl-(3-(1-methyl-1H-imidazole-4-sulfonylmethyl)-phenyl)-methyl)-4-hydroxy-5H-furan-2-one, 5,5-Dibenzyl-3-(cyclopropyl-(3-(pyridine-2-sulfonylmethyl)-phenyl)-methyl)-4-hydroxy-5H-furan-2-one, 6-(3-(Cyclopropyl-(5,5-dibenzyl-4-hydroxy-2-oxo-2,5-dihydro-furan-3-yl)-methyl)-phenylmethanesulfonyl)-nicotinonitrile, 5,5-Dibenzyl-3-(cyclopropyl-(3-(quinoline-2-sulfonylmethyl)-phenyl)-methyl)4-hydroxy-5H-furan-2-one, 5,5-Dibenzyl-3-(cyclopropyl-(3-(pyrimidine-2-sulfonylmethyl)-phenyl)-methyl)4-hydroxy-5H-furan-2-one, 5,5-Dibenzyl-3-(cyclopropyl-(3-(quinazole-2-sulfonylmethyl)-phenyl)-methyl)-4-hydroxy-5H-furan-2-one, 3-((3-(1H-Benzimidazole-2-sulfonylmethyl)-phenyl)-cyclopropyl-methyl)-5,5-dibenzyl-4-hydroxy-5H-furan-2-one, 5,5-Dibenzyl-3-(cyclopropyl-(3-(1H-imidazole-2-sulfonylmethyl)-phenyl)-methyl)4-hydroxy- 5H-furan-2-one, 5,5-Dibenzyl-3-(cyclopropyl-(3-(thiazole-4-sulfonylmethyl)-phenyl)-methyl)-4-hydroxy-5H-furan-2-one, 5,5-Dibenzyl-3-(cyclopropyl-(3-(7H-purine-6-sulfonylmethyl)-phenyl)-methyl)-4-hydroxy-5H-furan-2-one, N-10 where $R_2$ and $R_3$ are phenylmethyl, $Z_9$ is 1,1-dimethylethyl and $Z_{10}$ are phenyl, 4-cyanophenyl, 1-methyl-4-imidazolyl, 2-pyridinyl, 5-cyano-2-pyridinyl, 2-quinolinyl, 2-pyrimidinyl, 2-quinazolinyl, 2-benzimidazolyl, 2-imidazolyl, 4-thiazolyl, 6-purinyl, 3-(1-(3-Benzenesulfonylmethyl-phenyl)-2,2-dimethyl-propyl)-5,5-dibenzyl-4-hydroxy-5H-furan-2-one, 4(3-(1-(5,5-Dibenzyl-4-hydroxy-2-oxo-2,5-dihydro-furan-3-yl)-2,2-dimethyl-propyl)-phenylmethanesulfonyl)-benzonitrile, 5,5-Dibenzyl-3-(2,2-dimethyl-1-(3-(1-methyl-1H-imidazole-4-sulfonylmethyl)-phenyl)-propyl)-4-hydroxy-5H-furan-2-one, 5,5-Dibenzyl-3-(2,2-dimethyl-1-(3-(pyridine-2-sulfonylmethyl)-phenyl)-propyl)-4-hydroxy-5H-furan-2-one, 6-(3-(1-(5,5-Dibenzyl-4-hydroxy-2-oxo-2,5-dihydro-furan-3-yl)-2,2-dimethyl-propyl)-phenylmethanesulfonyl)-nicotinonitrile, 5,5-Dibenzyl-3-(2,2-dimethyl-1-(3-(quinoline-2-sulfonylmethyl)-phenyl)-propyl)-4-hydroxy-5H-furan-2-one, 5,5-Dibenzyl-3-(2,2-dimethyl-1-(3-(pyrimidine-2-sulfonylmethyl)-phenyl)-propyl)-4-hydroxy-5H-furan-2-one, 5,5-Dibenzyl-3-(2,2-dimethyl-1-(3-(quinazoline-2-sulfonylmethyl)-phenyl)-propyl)-4-hydroxy-5H-furan-2-one, 3-(1-(3-(1H-Benzimidazole-2-sulfonylmethyl)-phenyl)-2,2-dimethyl-propyl)-5,5-dibenzyl-4-hydroxy-5H-furan-2-one, 5,5-Dibenzyl-4-hydroxy-3-(1-(3-(1H-imidazole-2-sulfonylmethyl)-phenyl)-2,2-dimethyl-propyl)-5H-furan-2-one, 5,5-Dibenzyl-3-(2,2-dimethyl-1-(3-(thiazole-4-sulfonylmethyl)-phenyl)-propyl)-4-hydroxy-5H-furan-2-one, 5,5-Dibenzyl-3-(2,2-dimethyl-1-(3-(7H-purine-6-sulfonylmethyl)-phenyl)-propyl)-4-hydroxy-5H-furan-2-one.

CHART O

Chart O describes a method for preparing aza-spirocyclic tetronic acids of general formula O-6 and O-8. Reaction of the anion of tetronic acids of general formula A-4 with N,N-bis(2-chloroethyl)-tert-butyl carbamate (O-1, Evans, B. E.; Leighton, J. L.; Rittle, K. E.; Gilbert, K. F.; Lundell, G. F.; Gould, N. P.; Hobbs, D. W.; DiPardo, R. M., Veber, D. F.; Pettibone, D. J.; Clineschmidt, B. V.; Anderson, P. S.; Freidinger, R. M. *J. Med. Chem.* 1992, 35, 3919) provides the monoalkylated product of formula O-2. This intermediate further reacts with bases such as LDA at low temperature to provide the cycloadduct of general formula O-3. Removal of the tert-butoxycarbonyl protecting group with acid will provide the amine O-4 which may be alkylated with an alkyl halide such as O-5 or alkylated with an aldehyde of general structure O-7 under reductive conditions to provide tetronic acids of general structures O-6 and O-8, respectively.

PREPARATIONS AND EXAMPLES OF CHART O

Preparation OP-1

(Chart O, "O-2" where $R_1$ is cyclopropylmethylphenyl).

To a cooled solution (−10° C.) of AP-1 (500 mg, 2.2 mmol) in anhydrous THF (10 ml) was added LDA (3.2 mL of a 1.5 M solution of the mono tetrahydrofuran complex in cyclohexane, 4.8 mmol). After stirring at −10° C. for 25 minutes, a solution of O-1 (1.58 g, 6.6 mmol) in THF (5 mL) was added slowly followed by tetrabutylammonium iodide (81 mg, 0.22 mmol). The mixture was stirred for 4 hours at 0–5° C., made slightly acidic with aqueous ammonium chloride and diluted with ethyl acetate. The organic layer was separated, washed with 0.25 N HCl and brine, dried (MgSO$_4$), filtered and concentrated in vacuo. The residue was purified by flash chromatography using methylene chloride/methanol (1%) as eluant to afford the title compound (361 mg, 38%) as an oil. $^1$H NMR (CDCl$_3$/CD$_3$OD) δ7.47-7.22 (m, 5H), 4.59-4.57 (m, 1H), 4.01-3.93 (m, 1H), 3.68-3.60 (m, 3H), 3.52-3.51 (m, 1H), 3.20-3.14 (m, 1H), 2.94-2.86 (m, 1H), 2.43-2.38 (m, 1H), 1.83-1.52 (m, 2H), 1.49 (s, 9H), 0.61-0.55 (m, 2H), 0.27-0.20 (m, 2H); $^{13}$C NMR (CDCl$_3$) δ175.08, 173.84, 157.49, 143.40, 128.45, 128.24, 126.44, 104.45, 83.18, 73.96, 49.47, 46.09, 44.95, 41.38, 33.96, 28.27, 13.93, 5.52, 4.37; EIMS m/z 435 (M$^+$).

Preparation OP-2 and Example OX-1

(Chart O, "O-3" where $R_1$ is cyclopropylmethylphenyl).

To a cooled (−78° C.) solution of OP-1 (40 mg, 0.09 mmol) in anhydrous THF (10 mL) was added LDA (153 µL of a 1.5 M solution of the mono tetrahydrofuran complex in cyclohexane, 0.23 mmol). The solution was stirred at −78° C. for 3 hours and quenched with a solution of 10% acetic acid in hexane (1 mL). The reaction mixture was allowed to warm to room temperature and partitioned between ethyl acetate and 0.25 N HCl. The organic layer was separated, washed with 0.25 N HCl and brine, dried (MgSO$_4$), filtered and concentrated in vacuo. The residue was purified by flash chromatography using methylene chloride/methanol (0–1%) as eluant to afford the title compound (5 mg, 14%) as an oil. $^1$H NMR (CDCl$_3$) δ7.36-7.15 (m, 5H), 4.07-3.99 (m, 2H), 3.09-3.02 (m, 3H), 2.04-1.95 (m, 2H), 1.65-1.59 (m, 1H), 1.57-1.37 (m, 11H), 0.63-0.48 (m, 2H), 0.24-0.16 (m, 2H); $^{13}$C NMR (CDCl$_3$) δ177.01, 173.58, 154.87, 142.08, 128.77, 128.40, 126.55, 103.59, 80.45, 80.39, 65.87, 39.68, 33.09, 28.41, 15.19, 13.68, 6.48, 4.38; EIMS m/z 399 (M$^+$).

Preparation OP-3 and Example OX-2

(Chart O, "O-4" where $R_1$ is cyclopropylphenylmethyl).

To a cooled (0–5° C.) solution of 70% aqueous trifluoroacetic acid (1 mL) was added OX-1 (12 mg, 0.03 mmol). After 90 minutes at 0–5° C., the solution was diluted with water (3 mL) and 4-toluenesulfonic acid (5.7 mg, 0.03 mmol) was added. Volatiles were removed in vacuo and the residue washed with ethyl ether to provide the title compound (11 mg, 78%) as a hygroscopic powder.

Physical characteristics are as follows: $^1$H NMR (CD$_3$OD) δ7.52 (d, J=8.2 Hz, 1H), 7.23 (d, J=7.3 Hz, 1H), 7.10-6.96 (m, 5H), 3.31-3.29 (m, 2H), 3.13-3.07 (m, 2H), 2.78 (d, J=10.2 Hz, 1H), 2.24-2.09 (m, 3H), 2.18 (s, 3H), 1.66-1.54 (m, 3H), 0.51-0.33 (m, 2H), 0.11-(−)0.01 (m, 2H); $^{13}$C NMR (CDCl$_3$) δ175.77, 172.57, 142.85, 141.65, 140.19, 129.37, 128.31, 127.71, 126.42, 125.67, 104.37, 77.46, 44.65, 41.09, 29.71, 29.17, 21.36, 13.75, 5.71, 4.72; EIMS m/z 299.

CHART P

Chart P describes another method of preparing aza-spirocyclic tetronic acids. Condensation of the lithium anion of commercially available ethyl propriolate (C-2) with commercially available or readily prepared (Baty, J. D.; Jones, G.; Moore, C. *J. Chem. Soc.* (C) 1967, 2645; Stork, G.; Mcelvain, S. M. *J. Amer. Chem. Soc.* 1946, 68, 1053) substituted piperidones of general structure P-1 provides the hydroxy ester of general formula P-2. Sodium methoxide cyclization provides the intermediate P-3 which is subsequently deprotected to provide the aza-spirocyclic tetronic acid of general structure P-4. The 3-position would then be introduced according to chart I by substituting general structure P-4 for intermediate C-5.

Preparation PP-1

(Chart P, "P-2" where $Z_{13}$ is proton and $Z_{14}$ is carbethoxy)

To a cooled (−78° C.) solution of ethyl propriolate (608 mg, 6.2 mmol) in anhydrous THF (15 mL) was slowly added butyllithium (3.8 mL of a 1.6 M solution in hexanes, 6.1 mmol). After stirring the solution for 10 minutes at −78° C., 1-carbethoxy-4-piperidone (1.03 g, 6.0 mmol) was added. The solution was stirred for 3 h at −78° C. and quenched by the addition of a 10% solution of acetic acid in hexane (2 mL). The solution was partially concentrated in vacuo and partitioned between ethyl acetate and 0.25 N aqueous HCl. The organic layer was separated and washed with brine, dried (MgSO$_4$), filtered and concentrated in vacuo. Flash chromatography of the residue using hexane/ethyl acetate (5–40%) as eluent afforded the product (1.5 g, 90%) as an oil: $^1$H NMR (CDCl$_3$) δ4.32 (s, 1H), 4.23 (q, J=7.1 Hz, 2H), 4.12 (q, J=7.1 Hz, 2H), 3.76–3.72 (m, 2H), 3.47–3.38 (m, 2H), 1.99–1.93 (m, 2H), 1.83–1.77 (m, 2H), 1.32 (t, J=7.1 Hz, 3H), 1.26 (t, J=7.1 Hz, 3H); $^{13}$C NMR (CDCl$_3$) δ155.33, 153.26, 88.86, 75.99, 65.86, 62.03, 61.50, 40.10, 37.68, 13.98, 13.44; EIMS m/z 269.

Preparation PP-2. (Chart P, "P-3" where $Z_{13}$ is proton and $Z_{14}$ is carbmethoxy)

To a 25 wt % solution of sodium methoxide in methanol (20 mL) at ambient temperature was added the product of preparation PP-1 (1.5 g, 5.6 mmol). After 24 h the mixture was cooled (0–5° C.), quenched by the addition of water (10 mL) and partitioned between ethyl acetate and 0.25 N aqueous HCl. The organic layer was separated, washed with brine, dried (MgSO$_4$), filtered and concentrated in vacuo. Flash chromatography of the residue using methylene chloride/methanol (0–2%) as eluent afforded the product (840 mg, 62%) as an oil: $^1$H NMR (CDCl$_3$) δ5.06 (s, 1H), 4.18–4.10 (m, 2H), 3.91 (s, 3H), 3.68 (s, 3H), 3.30–3.19 (m, 2H), 2.06–1.91 (m, 2H), 1.61–1.56 (m, 2H); $^{13}$C NMR (CDCl$_3$) δ184.39, 170.88, 155.40, 87.30, 81.25, 59.42, 52.41, 39.64, 32.21; EIMS m/z 241.

Preparation PP-3. (Chart P, "P-4" where $Z_{13}$ is proton and $Z_{14}$ is 9-fluorenylmethyloxycarbonyl)

The product of PP-2 (840 mg, 3.5 mmol) was heated at 45° C. in 48% aqueous hydrobromic acid (20 mL) for 48 h. Volatiles were removed in vacuo and the crude hydrobromide salt was dissolved in 50% aqueous dioxane (10 mL) and the pH adjusted to neutral with Na$_2$CO$_3$ (ca. 1 g). The solution was cooled (0–5° C.) and 9-fluorenylmethyl chloroformate (854 mg, 3.3 mmol) was added followed by Na$_2$CO$_3$ (318 mg, 3 mmol). The solution was allowed to warm to ambient temperature and stirring continued overnight. The aqueous solution was made acidic with 1N aqueous HCl and extracted with ethyl acetate. The organic layer was washed with 0.25 N aqueous HCl, brine, dried (MgSO$_4$), filtered and concentrated in vacuo. Flash chromatography of the residue using methylene chloride/methanol (0–5%) as eluent afforded the product (900 mg, 66%) as an oil: $^1$H NMR (CDCl$_3$) δ7.73 (d, J=7.4 Hz, 2H), 7.53 (d, J=7.4 Hz, 2H), 7.41–7.26 (m, 4H), 5.00 (s, 1H), 4.44 (d, J=6.4 Hz, 2H), 4.25–3.98 (overlapping m's, 3H), 3.28–3.06 (m, 2H), 2.02–1.82 (m, 2H), 1.59–1.53 (m, 2H); $^{13}$C NMR (CDCl$_3$) δ184.69, 174.73, 155.34, 146.58, 141.29, 127.82, 127.09, 124.76, 120.06, 88.00, 82.39, 67.67, 47.17, 40.12, 32.05.

DESCRIPTION BY INCORPORATION BY REFERENCE

The compounds of this invention may be prepared according to the procedures described in the CHARTS, by reference to general procedures, by reference to the examples provided and by using variations of procedures that would be obvious to one of ordinary skill in the art. In addition to these procedures additional compounds may be prepared by one ordinarily skilled in the art using obvious variations and adaptations from compounds described in the following two documents: WO 94/11361, published May 26, 1994 (International Application Number PCT/US93/10645, filed Nov. 8, 1993) and WO 94/18188, published Aug. 18, 1994 (International Application Number PCT/US94/00938, filed Feb. 3, 1994) and all priority cases found therein.

CHARTS

The CHARTS referred to above appear below. The CHARTS are followed by a Tables of Names and Structures. The structures in the CHARTS provide general descriptions of reaction schemes and are not intended to limit the procedures to describe only those compounds shown. The aromatic structures in the figures have a double zero placed within the aromatic ring to emphasize the fact that the structure is not only benzene but any suitable aromatic group, including obvious substitutions, such as those provided in the definition section for aryl, heteroaryl and the like. The structures in the Table of Structures are made with typical two dimensional chemical figures.

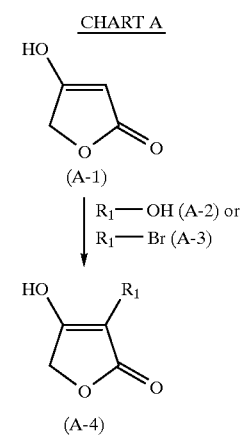

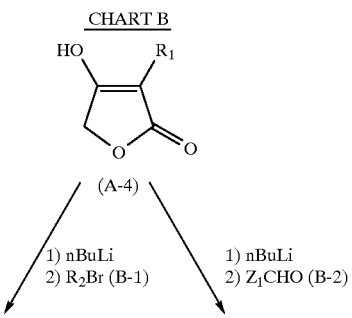

-continued
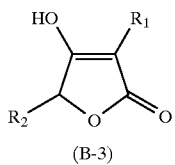
(B-3)
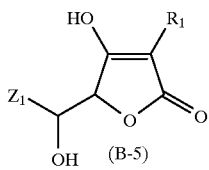
(B-5)
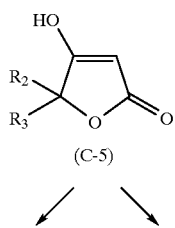
(C-5)
See Chart I   See Chart K
+
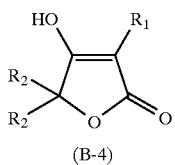
(B-4)
CHART C
H—≡—CO₂CH₂CH₃
(C-2)
1) nBuLi
2) $R_2R_3C=O$
(C-1)
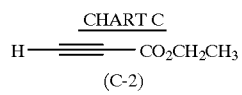
(C-3)
NaOCH₃
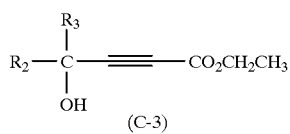
(C-4)
HBr
CHART D
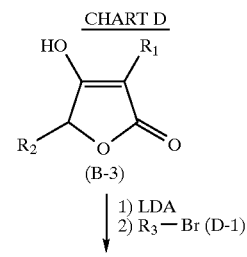
(B-3)
1) LDA
2) $R_3$—Br (D-1)
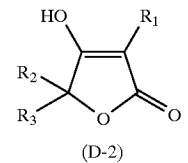
(D-2)

CHART E
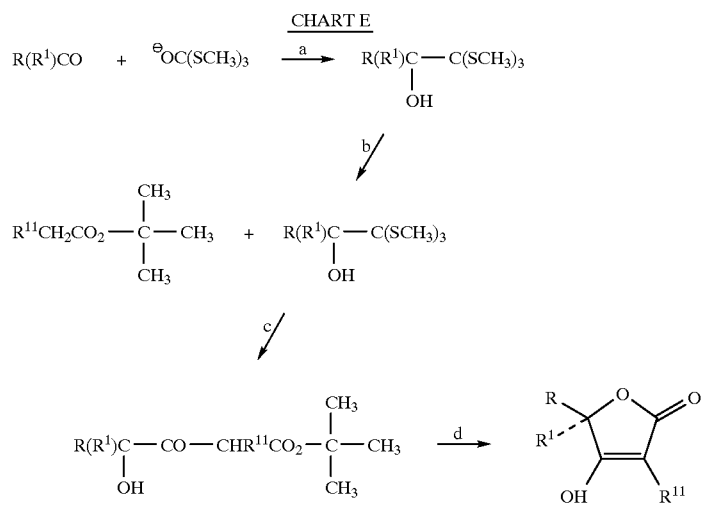
CHART F
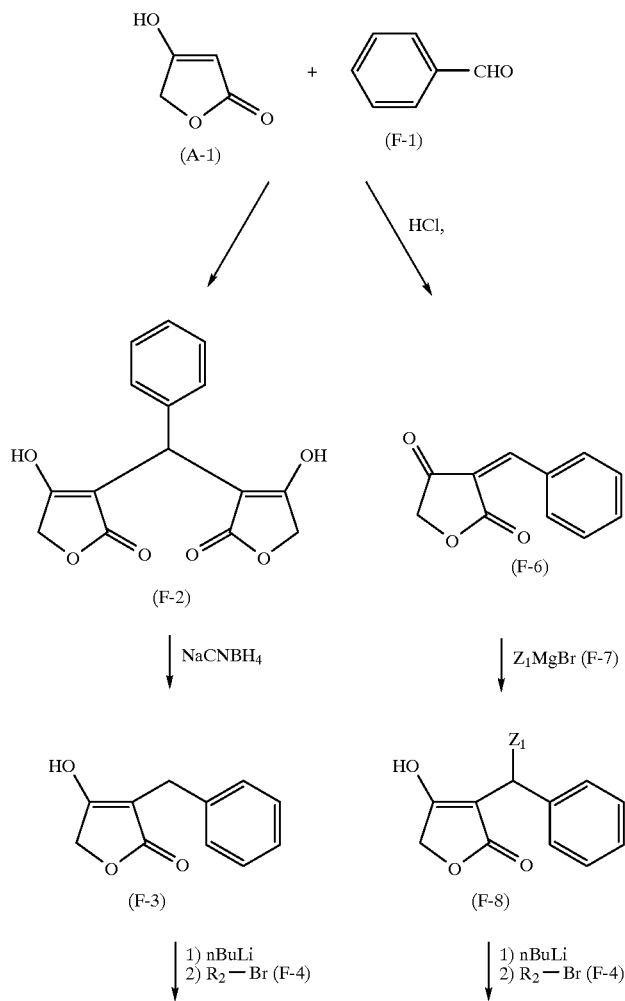

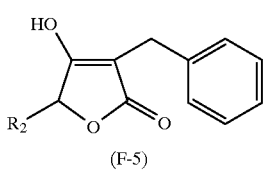
(F-5)
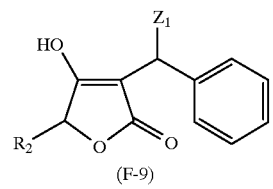
(F-9)
CHART G
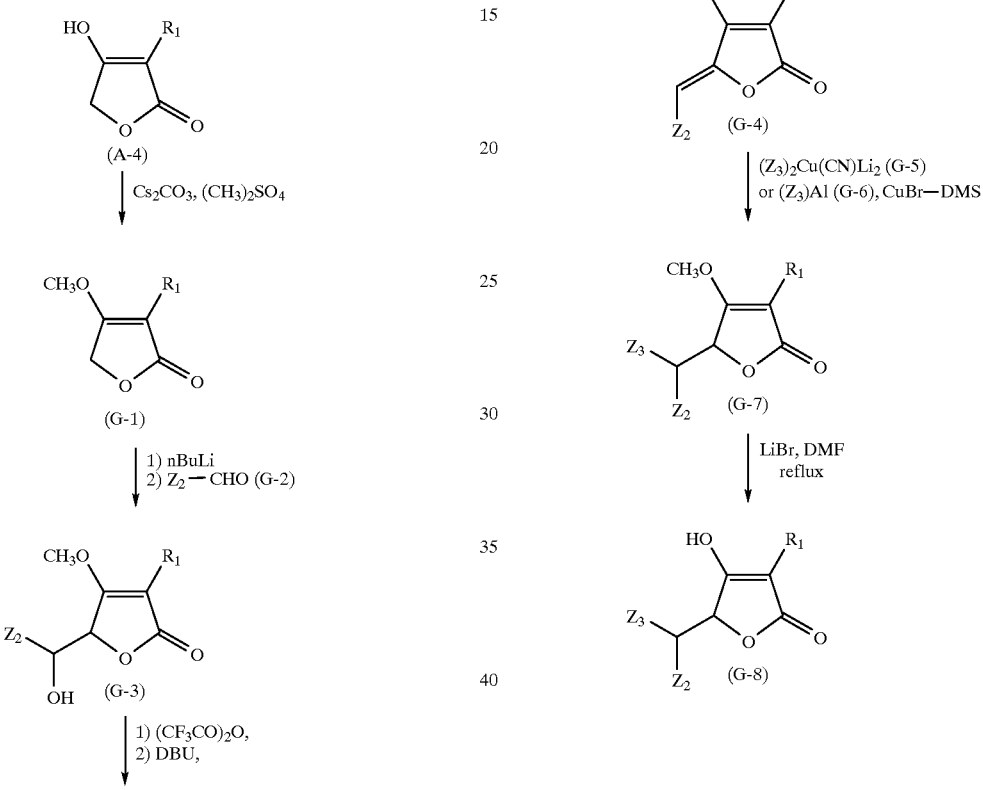
CHART H
(H-1)
1) nBuLi
2) Z₄CHO (H-2)
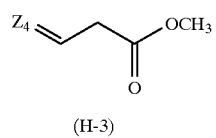
(H-3)
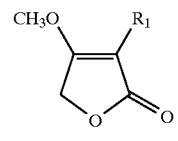
(G-1)
nBuLi -continued
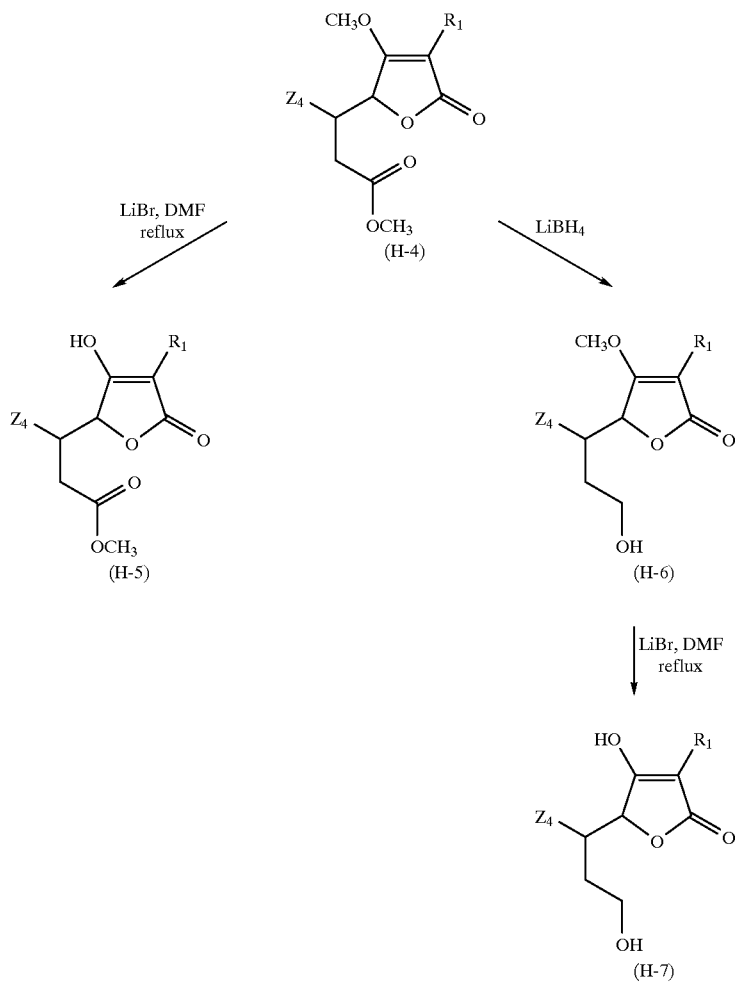
CHART I
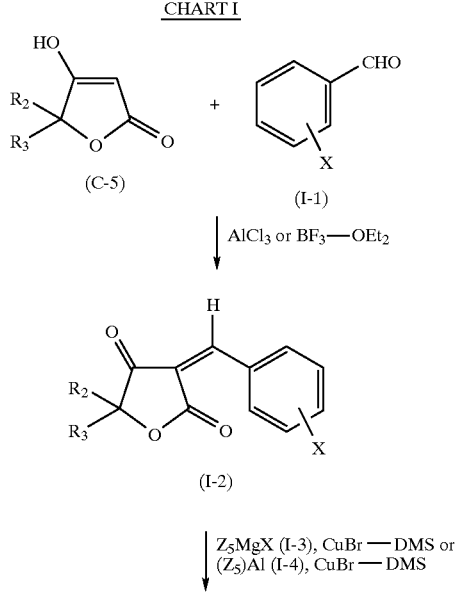

-continued
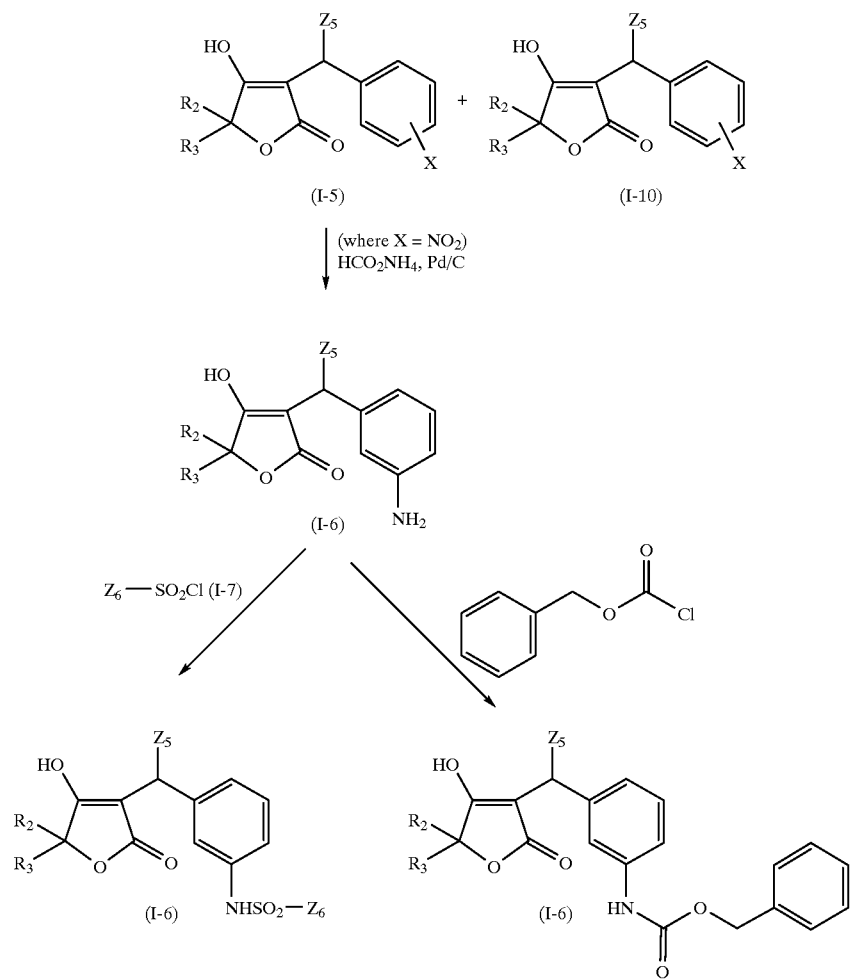
CHART J
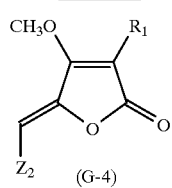
(G-4)
↓ LiBr, DMF reflux
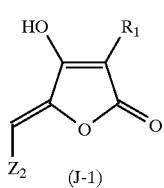
(J-1)
Chart K
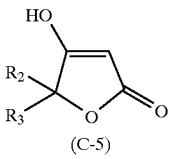
(C-5)
↓ BF$_3$—OEt$_2$, R$_1$—OH (K-1)
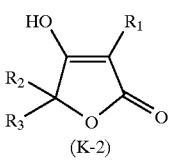
(K-2)

CHART L

CHART M

CHART N

91
-continued
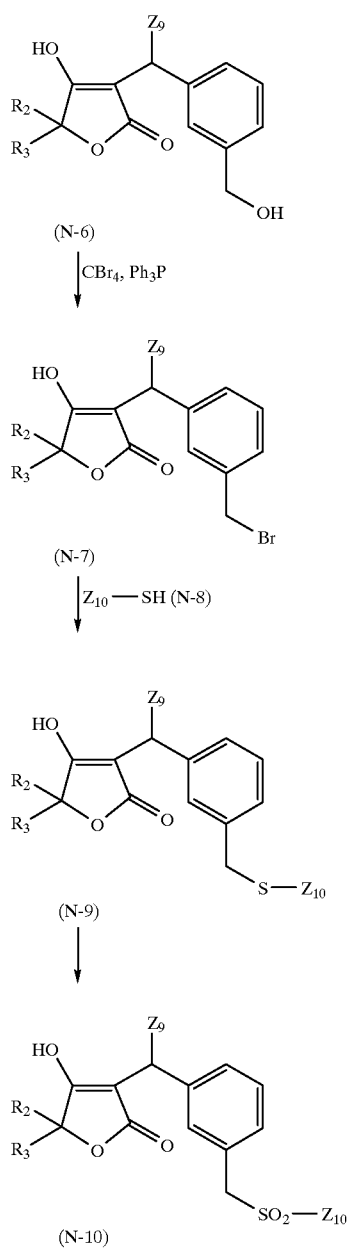
CHART O
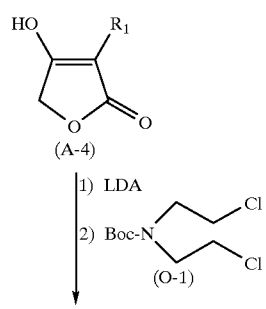
92
-continued
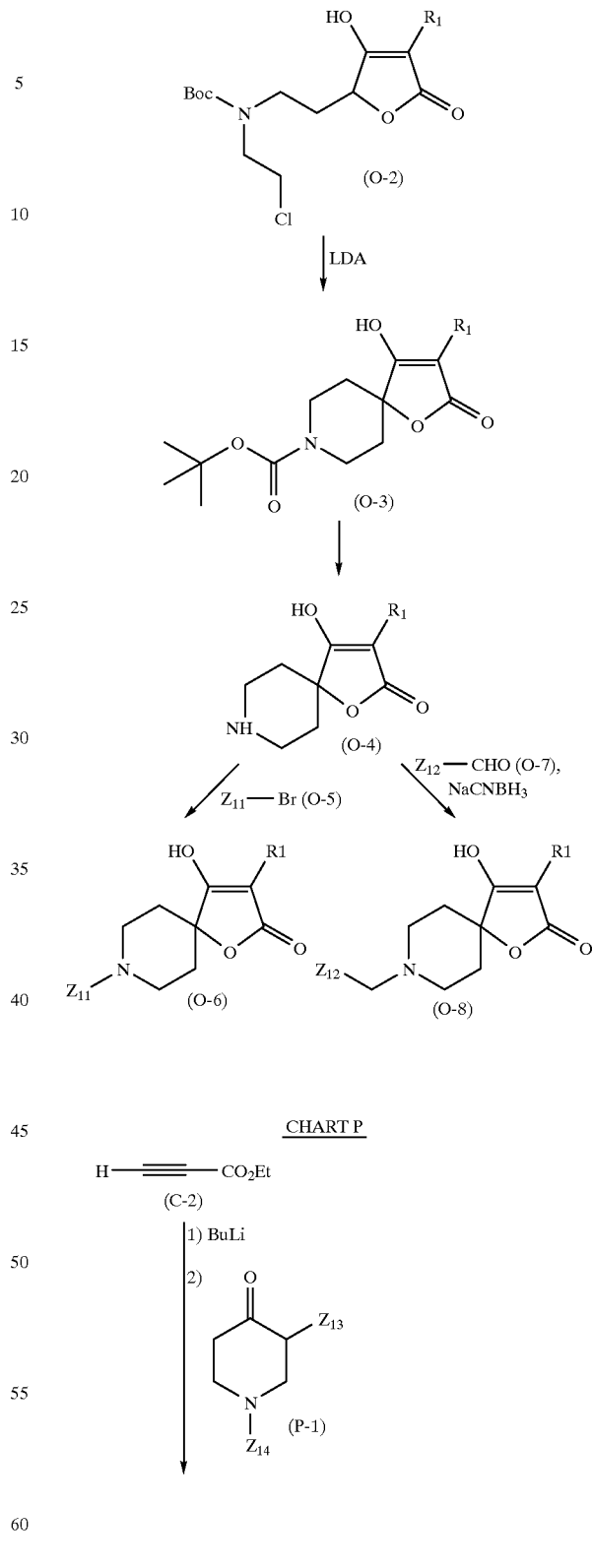

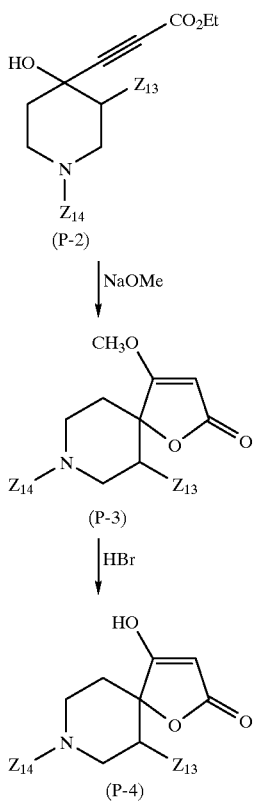

TABLE I

| | Names of Compounds |
|---|---|
| AP-1 | 2(5H)-Furanone, 3-(cyclopropylphenylmethyl)-4-hydroxy-, |
| BX-1 | 5H-Furan-2-one, 5-benzyl-3-cyclopropylphenylmethyl-4-hydroxy-, |
| BX-2 | 2(5H)-Furanone, 3(cyclopropylphenylmethyl)-4-hydroxy-5-(2-phenylethyl)-, |
| BX-3 | 2(5H)-Furanone, 3-(cyclopropylphenylmethyl)-4-hydroxy-5-(3-phenylpropyl)-, |
| BX-4 | 2(5H)-Furanone, 3-(cyclopropylphenylmethyl)-4-hydroxy-5-propyl-, |
| BX-5 | 2(5H)-Furanone, 5-(2-cyclohexylethyl)-3-(cyclopropylphenylmethyl)-4-hydroxy-, |
| BX-6 | 2(5H)-Furanone, 3-(cyclopropylphenylmethyl)-4-hydroxy-5-(3-phenyl-2-propenyl)-, |
| BX-7 | 2(5H)-Furanone, 3-(cyclopropylphenylmethyl)-4-hydroxy-5-(1-hydroxy-3--phenyl-2-propenyl)-, |
| BX-8 | 2(5H)-Furanone, 3-(cyclopropylphenylmethyl)-4-hydroxy-5-(1-hydroxy-3--phenylpropyl)-, |
| BX-9 | 2(5H)-Furanone, 4-hydroxy-5-(phenylmethyl)-3-(1-phenylpropyl)-, |
| BX-10 | 2(5H)-Furanone, 3-(cyclopropylphenylmethyl)-4-hydroxy-5-(1-methylethyl)-, |
| BX-11 | 2(5H)-Furanone, 5-butyl-3-(cyclopropylphenylmethyl)-4-hydroxy-, |
| BX-12 | 2(5H)-Furanone, 3-(cyclopropylphenylmethyl)-4-hydroxy-5,5-dipropyl-, |
| BX-13 | 2(5H)-Furanone, 3-(cyclopropylphenylmethyl)-4-hydroxy-5,5-bis(1-methylethyl)-, |
| BX-14 | 2(5H)-Furanone, 3-(cyclopropylphenymethyl)-5,5-diethyl-4-hydroxy-, |
| BX-15 | 2(5H)-Furanone, 5,5-dibutyl-3-(cyclopropylphenylmethyl)-4-hydroxy-, |
| BX-16 | 2(5H)-Furanone, 4-hydroxy-5-(2-phenylethyl)-3-(1-phenylpropyl)-, |
| CX-1 | 1-Oxaspiro[4.4]non-3-en-2-one, 3-(cyclopropylphenylmethyl)-4-hydroxy-, |
| CX-2 | 1-Oxaspiro[4.7]dodec-3-en-2-one, 3-(cyclopropylphenylmethyl)-4-hydroxy-, |
| CX-3 | 2(5H)-Furanone, 3-(cyclopropylphenylmethyl)-4-hydroxy-5-methyl-5-(2--phenylethyl)-, |
| DX-1 | 2(5H)-Furanone, 3-(cyclopropylphenylmethyl)-4-hydroxy-5-(3-phenyl-propyl)-5-propyl-, |
| DX-2 | 2(5H)-Furanone, 3-(cyclopropylphenylmethyl)-4-hydroxy-5-methyl-5-(phenyl-methyl)-, |
| DX-3 | 2(5H)-Furanone, 3-(cyclopropylphenylmethyl)-5-ethyl-4-hydroxy-5-(phenyl-methyl)-, |
| DX-4 | 2(5H)-Furanone, 3-(cyclopropylphenylmethyl)-4-hydroxy-5-(phenyl-methyl)-5-propyl-, |
| DX-5 | 2(5H)-Furanone, 3-(cyclopropylphenylmethyl)-4-hydroxy-5,5-bis(phenylmethyl)-, |
| DX-6 | 2(5H)-Furanone, 3-(cyclopropylphenylmethyl)-4-hydroxy-5-propyl-5-(3--pyridinylmethyl)-, |
| DX-7 | 2(5H)-Furanone, 3-(cyclopropylphenylmethyl)-5-ethyl-4-hydroxy-5-(2-phenyl-ethyl)-, |
| DX-8 | 2(5H)-Furanone, 3-(cyclopropylphenylmethyl)-4-hydroxy-5-(2-phenyl-ethyl)-5-propyl-, |
| DX-9 | 2(5H)-Furanone, 3-(cyclopropylphenylmethyl)-4-hydroxy-5,5-bis(2-phenylethyl)-, |
| DX-10 | 2(5H)-Furanone, 3-(cyclopropylphenylmethyl)-4-hydroxy-5-methyl-5-(3-phenyl-propyl)-, |
| DX-11 | 2(5H)-Furanone, 3-(cyclopropylphenylmethyl)-5-ethyl-4-hydroxy-5-(3-phenyl-propyl)-, |
| DX-12 | 2(5H)-Furanone, 5-butyl-3-(cyclopropylphenylmethyl)-4-hydroxy-5-(3-phenyl-propyl)-, |
| DX-13 | 2(5H)-Furanone, 3-(cyclopropylphenylmethyl)-4-hydroxy-5,5-bis(3-phenyl-propyl)-, |
| DX-14 | 2(5H)-Furanone, 5-(cyclopropylmethyl)-3-cyclopropylphen4ylmethyl)-4-hydroxy-5-(3-pheny-propyl)-, |
| DX-15 | 2(5H)-Furanone, 3-(cyclopropylphenylmethyl)-4-hydroxy-5-(phenylmethyl)-5-(3--phenylpropyl)-, |
| DX-16 | 2(5H)-Furanone, 3-(cyclopropylphenylmethyl)-4-hydroxy-5-(3-phenyl-propyl)-5-(2-propenyl)-, |
| DX-17 | 2(5H)-Furanone, 3-(cyclopropylphenylmethyl)-4-hydroxy-5-(1-methylethyl)-5-(3--phenylpropyl)-, |
| DX-18 | 2(5H)-Furanone, 3-(cyclopropylphenylmethyl)-4-hydroxy-5-(2-phenyl-ethyl)-5-(3-phenylpropyl)-, |
| DX-19 | 2(5H)-Furanone, 3-(cyclopropylphenylmethyl)-4-hydroxy-5-(1-methylpropyl)--5-(3-phenylpropyl)-, |
| DX-20 | 2(5H)-Furanone, 3-(cyclopropylphenylmethy)-4-hydroxy-5-(2-methylpropyl)-5--(3-phenylpropyl)-, |
| FX-1 | 2(5H)-Furanone, 3-(1,2-diphenylethyl)-4-hydroxy-5-(3-phenylpropyl)-, |
| FX-2 | 2(5H)-Furanone, 3-(diphenylmethyl)-4-hydroxy-5-(3-phenylpropyl)-, |
| FX-3 | 2(5H)-Furanone, 4-hydroxy-3-(1-phenyl-2-propenyl)-5-(3-phenylpropyl)-, |
| FX-4 | 2(5H)-Furanone, 4-hydroxy-3-(2-methyl-1-phenylpropyl)-5-(3-phenylpropyl)-, |
| FX-5 | 2(5H)-Furanone, 3-(2,2-dimethyl-1-phenylpropyl)-4-hydroxy-5-(3-phenyl-propyl)-, |
| GX-1 | 2(5H)-Furanone, 3-(cyclopropylphenylmethyl)-4-hydroxy-5-(1-(2-phenyl-ethyl)pentyl)-, |
| GX-2 | 2(5H)-Furanone, 3-(cyclopropylphenylmethyl)-4-hydroxy-5-(1-(2-phenyl-ethyl)pentyl)-, |
| GX-3 | 2(5H)-Furanone, 3-(cyclopropylphenylmethyl)-4-hydroxy-5-(1-methyl-3-phenyl-propyl)-, |
| GX-4 | 2(5H)-Furanone,3-(cyclopropylphenylmethyl)-5-(1,3-diphenylpropyl)-4-hydroxy-, |
| GX-5 | 2(5H)-Furanone, 3-(cyclopropylphenylmethyl)-5-(1-ethylpentyl)-4-hydroxy-, |
| GX-6 | 2(5H)-Furanone, 3-(cyclopropylphenylmethyl)-4-hydroxy-5-(1-phenylpropyl)-, |
| GX-7 | 2(5H)-Furanone, 3-(cyclopropylphenylmethyl)-4-hydroxy-5-(1-phenylbutyl)-. |
| GX-8 | 2(5H)-Furanone, 3-(cyclopropylphenylmethyl)-5-(1-ethylpropyl)-4-hydroxy-, |
| HX-1 | 2-Furanpropanoic acid, 4-(cyclopropylphenyl-methyl)-2,5-dihydro-3-hydroxy-5-oxo-.beta.-(2-phenylethyl)-, methyl ester, |
| HX-2 | 2(5H)-Furanone, 3-(cyclopropylphenylmethyl)-4-hydroxy-5-(1-(2-hydroxyethyl)--3-phenylpropyl)-, |
| IX-1 | 2(5H)-Furanone, 3-(cyclopropyl(3-nitrophenyl)methyl)-4-hydroxy-5,5-dipropyl-, |
| IX-2 | 2(5H)-Furanone, 4-hydroxy-3-(1-(3-nitrophenyl) |

TABLE I-continued

Names of Compounds

| | |
|---|---|
| | propyl)-5,5-dipropyl-, |
| IX-3 | 1-Oxaspiro[4.5]dec-3-en-2-one, 3-(cyclopropyl-phenylmethyl)-4-hydroxy-, |
| IX-4 | 1-Oxaspiro[4.5]dec-3-en-2-one, 3-(cyclo-propylphenylmethyl)-5-hydroxy--6-(2-phenylethyl)- |
| IX-5 | 1-Oxaspiro[4.5]dec-3-en-2-one, 3-(cyclo-propylphenylmethyl)-4-hydroxy--6-(2-phenylethyl)- |
| IX-6 | 1-Oxaspiro[4.5]dec-3-en-2-one, 3-(cyclo-propylphenylmethyl)-4-hydroxy--6-(2-phenylethyl)-, |
| IX-7 | 1-Oxaspiro[4.5]dec-3-en-2-one, 3-(cyclo-propylphenylmethyl)4-hydroxy-6--(2-phenylmethyl)-, |
| IX-8 | 1-Oxaspiro[4.6]undec-3-en-2-one, 3-(cyclo-propylphenylmethyl)-4-hydroxy-, |
| IX-9 | 2(5H)-Furanone, 5-ethyl-4-hydroxy-3-(2-methy1-1-phenylpropyl)-5-(phenyl-methyl)-, |
| IX-10 | 2(5H)-Furanone, 5-ethyl-4-hydroxy-5-(phenyl-methyl)-3-(1-phenylpropyl)-, |
| IX-11 | 2(5H)-Furanone, 3-((3-aminophenyl)cyclopropylmethyl)-4-hydroxy-5,5-dipropyl-, |
| IX-12 | 2(5H)-Furanone, 3-((3-aminophenyl)cyclopropylmethyl)-4-hydroxy-5,5-dipropyl-hydrochloride, |
| IX-13 | 2(5H)-Furanone, 3-(1-(3-aminophenyl)propyl)-4-hydroxy-4-hydroxy-5,5-dipropyl-, |
| IX-14 | Benzenesulfonamide, 4-cynano-N-3-(cyclopropyl(2,5-dihydro-4-hydroxy--2-oxo-5,5-dipropyl-3-furanyl)methyl)phenyl)-, |
| IX-15 | Benzenesulfonamide, N-(3-(cyclopropyl(1,5-dihydro-4-hydroxy-2-oxo--5,5-dipropyl-3-furanyl)methyl)phenyl)-, |
| IX-16 | Benzenesulfonamide, N-(3-(cyclopropyl 2,5-dihydro-4-hydroxy-2-oxo--5,5-dipropyl-3-furanyl)methyl)phenyl)-4-fluoro-, |
| IX-17 | 1H-Imidazole-4-sulfonamide, N-(3-cyclopropyl(2,5-dihydro-4-hydroxy-2-oxo--5,5-dipropyl-3-furanyl)methyl)phenyl)-1-methyl-, |
| IX-18 | 8-Quinolinesulfonamide, N-(3-cyclopropyl(2,5-dihydro-4-hydroxy-2-oxo--5,5-dipropyl-3-furanyl)methyl)phenyl)-, |
| IX-19 | 1-Naphthalenesulfonamide, N-(3-cyclopropyl(2,5-dihydro-4-hydroxy-2-oxo--5,5-dipropyl-3-furanyl)methyl)phenyl)-, |
| IX-20 | Benzenesulfonamide, N-(3-(1-(2,5-dihydro-4-hydroxy-2-oxo--5,5-dipropyl-3-furanyl)propyl)phenyl)-, |
| IX-21 | Benzenesulfonamide, 4-Cyano-N-(3-(1-(4-hydroxy-2-oxo-5,5-dipropyl-2,5-dihydro-furan-3-yl)-3-methyl-butyl)-phenyl)- |
| IX-22 | 1H-Imidazole-4-sulfonamide, N-(3-(1-(4-hydroxy-2-oxo-5,5-dipropyl-2,5-dihydro-furan-3-yl-3-methyl-butyl)-phenyl)-1-methyl-, |
| IX-23 | Benzenesulfonamide, 4-Cyano-N-(3-(1-(4-hydroxy-2-oxo-5,5-dipropyl-2,5-dihydro-furan-3-yl)-2-methyl-propyl)-phenyl)-, |
| IX-24 | 1H-Imidazole-4-sulfonamide, N-(3-(1-(4-hydroxy-2-oxo-5,5-dipropyl-2,5-dihydro-furan-3-yl)-2-methyl-propyl)-phenyl)-1-methyl-, |
| IX-25 | Benzenesulfonamide, 4-Cyano-N-(3-(1-(4-hydroxy-2-oxo-5,5-dipropyl-2,5-dihydro-furan-3-yl)-2,2-dimethyl-propyl)-phenyl)-, |
| IX-26 | 1H-Imidazole-4-sulfonamide, N-(3-(1-(4-hydroxy-2-oxo-5,5-dipropyl-2,5-dihydro-furan-3-yl)-2,2-dimethyl-propyl)-phenyl)-1-methyl-, |
| IX-27 | Benzenesulfonamide, N-(3-(1-(2,5-dihydro-4-hydroxy-2-oxo-5--(phenylmethyl)-5-propyl-3-furanyl)-2-methylpropyl)phenyl)-, |
| IX-28 | Benzenesulfonamide, 4-cyano-N-(3-(1-(2,5-dihydro-4-hydroxy-2-oxo-5--phenylmethyl)-5-propyl-3-furanyl)-2-methylpropyl)phenyl)-, |
| IX-29 | Benzenesulfonamide, N-(3-(1-(2,5-dihydro-4-hydroxy-2-oxo-5-(phenylmethyl)-5-propyl-3-furanyl)-2-methylpropyl)phenyl)-4-fluoro-, |
| IX-30 | 1H-Imidazole-4-sulfonamide, N-(3-(1-(2,5-dihydro-4-hydroxy-2-oxo-5-(phenyl-methyl-5-propyl-3-furanyl)-2-methylpropyl)phenyl)-1-methyl-, |
| IX-31 | 8-Quinolinesulfonamide, N-(3-(1-(2,5-dihydro-4-hydroxy-2-oxo-5-phenyl-methyl)-5-propyl-3-furanyl)-2-methyl-propyl)phenyl)-, |
| IX-32 | Carbamic acid, (3-(cyclopropyl(2,5-dihydro-4-hydroxy-2-oxo--5,5-dipropyl-3-furanyl)methyl)phenyl)-, phenylmethyl ester, |
| IX-33 | 1-Oxaspiro[4.5]dec-3-en-2-one, 3-(cyclopropylphenylmethyl)-4-hydroxy-6-ethyl-, |
| IX-34 | 1-Oxaspiro[4.5]dec-3-en-2-one, 3-(cyclopropylphenylmethyl)-4-hydroxy-6-ethyl-, |
| IX-35 | 5-cyano-2-pyridinesulfonamide, N-(3-(cyclopropyl(2,5-dihydro-4-hydroxy-2-oxo-5,5-dipropyl-3-furanyl)methyl)phenyl)-, |
| IX-36 | 1H-Imidazole-2-sulfonamide, N-(3-cyclproyl(2,5-dihydro-4-hydroxy-2-oxo-5,5-dipropyl-3-furanyl)methyl)phenyl)-, |
| IX-37 | 1-Methyl-1H-imidazole-2-sulfonamide, N-(3-(cyclopropyl(2,5-dihydro-4-hydroxy-2-oxo-5,5-dipropyl-3-furanyl)methyl)phenyl)-, |
| IX-38 | 2-Quinolinesulfonamide, N-3-(cyclopropyl(2,5-dihydro-4-hydroxy-2-oxo-5,5-dipropyl-3-furanyl)methyl)phenyl)-, |
| IX-39 | Benzenesulfonamide, 4-cyano-N-(3-(1-(4-hydroxy-2-oxo-5,5-dipropyl--2,5-dihydro-furan-3-yl)-2-phenyl-ethyl)-phenyl)-, |
| IX-40 | 1H-Imidazole-4-sulfonamide, N-(3-(1-(4-hydroxy-2-oxo-5,5-dipropyl-2,5-dihyro-furan-3-yl)-2-phenyl-ethyl)-(phenyl)-1-methyl-, |
| IX-41 | Benzenesulfonamide, 4-cyano-N-(3-cyclopentyl(2,5-dihydro-4-hydroxy-2-oxo-5,5-dipropyl-3-furanyl)methyl)phenyl)-, |
| IX-42 | 1H-Imidazole-4-sulfonamide, N-(3-(cyclopentyl(2,5-dihydro-4-hydroxy-2-oxo-5,5-dipropyl-3-furanyl)methyl)phenyl)-1-methyl-, |
| IX-43 | Benzenesulfonamide, 4-cyano-N-(3-(cyclopropyl-(5,5-dihydro-4-hydroxy-2-oxo-2,5-dihydro-3-furanyl)methyl)phenyl)-, |
| IX-44 | Benzenesulfonamide, N-(3-cyclopropyl-(5,5-dibenzyl-4-hydroxy-2-oxo-2,5-dihydro-3-furanyl)methyl)pheny1)fluoro-, |
| IX-45 | 1H-Imidazole-4-sulfonamide, N-(3-(cyclopropyl-(5,5-dibenzyl-4-hydroxy-2-oxo-2,5-dihydro-3-furanyl)methyl)phenyl)-1-methyl-, |
| IX-46 | 8 Quinolinesulfonamide, N-(3-(cyclopropyl-(5,5-dibenzyl-4-hydroxy-2-oxo-2,5-dihydro-3-furanyl)methyl)phenyl)- |
| IX-47 | Benzenesulfonamide, 4-cyano-N-(3-((5,5-dipropyl-4-hydroxy-2-oxo-2,5-dihydro-3-furanyl)-phenyl-methyl)phenyl)-, |
| IX-48 | 1H-Imidazole-4-sulfonamide, N-(3-((5,5-dipropyl-4-hydroxy-2-oxo-2,5-dihydro-3 furanyl)-phenyl-methyl)phenyl)-1-methyl-, |
| IX-49 | Benzenesulfonamide, 4-cyano 3-cyclpentyl-N-(3-(cyclopentyl(2,5-dihydro-4-hydroxy-2-oxo-5,5-dipropyl-3-furanyl)methyl)phenyl)-, |
| IX-50 | 1H-Tetrazole-5-sulfonamide, N(3-(cyclopropyl-(4-hydroxy-2-oxo-5,5-dipropyl-2,5-dihydro-furan-3-yl)-methyl)-phenyl-1-, phenyl-, |
| IX-51 | 1H-Benzoimidazole-2-sulfonamide, N-(3-(cyclopropyl-4-hydroxy-2-oxo-5,5-dipropyl-2,5-dihydro-furan-3-yl)-methyl)-phenyl)-, |
| IX-52 | 2-Pyridinesulfonamide, N-(3-(cyclopropyl-(4-hydroxy-2-oxo-5,5-dipropyl-2,5-dihydro-furan-3-yl)-methyl)-phenyl)-, |
| IX-53 | 1H-Imidazole-4-sulfonamide, N-(3-(1-(4-hydroxy-2-oxo-5,5-dipropyl-2,5-dihydro-2,5-dihydro-furan-3-yl)-2,2-dimethyl- |

TABLE I-continued

Names of Compounds

|  |  |
|---|---|
|  | propyl)-phenyl)-1-methyl-, |
| IX-54 | Benzenesulfonamide, 4-Cyano-N-(3-(1-(4-hydroxy-2-oxo-5,5-dipropyl-2,5-dihydro-furan-3-yl)-2,2-dimethyl-propyl)-phenyl)-, |
| IX-55 | 2-Pyrimidinesulfonamide, N-(3-(cyclopropyl-(4-hydroxy-2-oxo-5,5-dipropyl-2,5 dihydro-furan-3-yl)-methyl)-phenyl)-, |
| IX-56 | Benzenesulfonamide, 4-Cyano-N-(3-(4-hydroxy-2-oxo-5,5-dipropyl-2,5-dihydro-furan-3-ylmethyl)-phenyl)- |
| IX-57 | 1H-Tetrazole-5-sulfonamide, N-(3-(cyclopropyl-(4-hydroxy-2-oxo-5,5-dipropyl-2,5-dihydro-furan-3-yl)-methyl-)-phenyl)-1-methyl-, |
| IX-58 | 3-(Cyclopropyl-phenyl-methyl)-4-hydroxy-2-oxo-1-oxa-8-aza-spiro[4.5]dec-3-ene-8-carboxylic acid 9H-fluoren-9-ylmethyl ester, |
| JX-1 | 3-(Cyclopropyl-phenyl-methyl)-4-hydroxy-5-(3-phenyl-propyl-idene)-5H-furan-2-one, |
| JX-2 | 5-Benzylidene-3-(cyclopropyl-phenyl-methyl)-4-hydroxy-5H-furan-2-one, |
| JX-3 | 3-(Cyclopropyl-phenyl-methyl)-4-hydroxy-5-propylidene-5H-furan-2-one, |
| JX-4 | 5-Butylidene-3-(cyclopropyl-phenyl-methyl)-4-hydroxy-5H-furan-2-one, |
| OX-1 | 3-(Cyclopropyl-phenyl-methyl)-4-hydroxy-2-oXo-1-oca-8-aza-spiro[4.5]dec-3-ene-8-carboxylic acid tert-butyl ester, |
| OX-2 | 3-(Cyclopropyl-phenyl-methy1)-4-hydroxy--1-oXa-8-aza-spiro[4.5]dec-3-en-2-one. |

TABLE 11

Table of Structures

| Code Name | Structure |
|---|---|
| AP-1 | 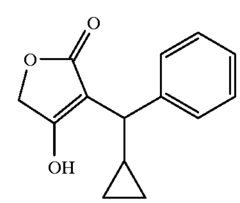 |
| AP-2 | 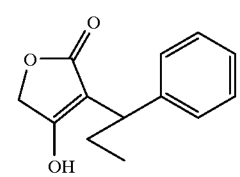 |
| BX-1 | 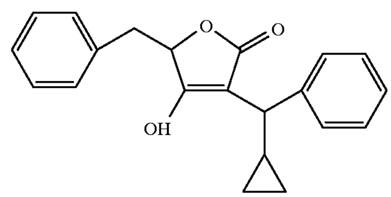 |

TABLE 11-continued
Table of Structures
| Code Name | Structure |
|---|---|
| BX-2 | 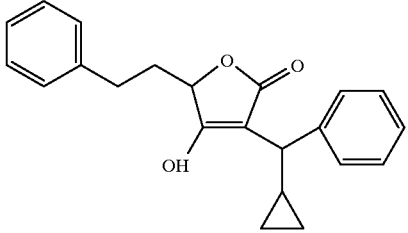 |
| BX-3 | 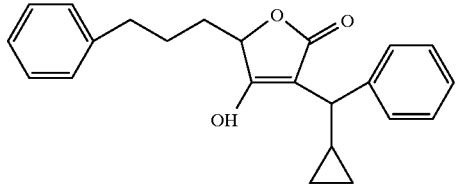 |
| BX-4 | 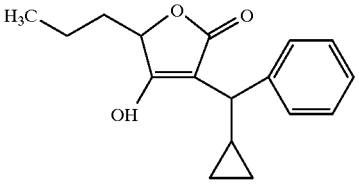 |
| BX-5 | 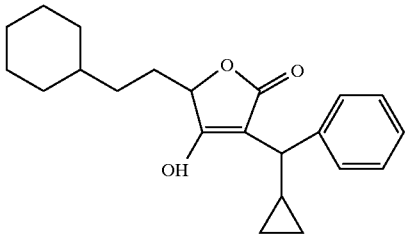 |
| BX-6 | 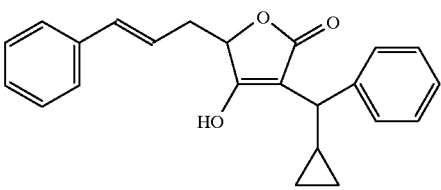 |
| BX-7 | 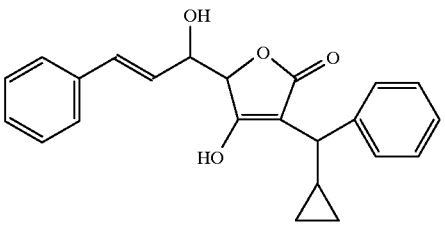 |

TABLE 11-continued
Table of Structures
| Code Name | Structure |
|---|---|
| BX-8 | 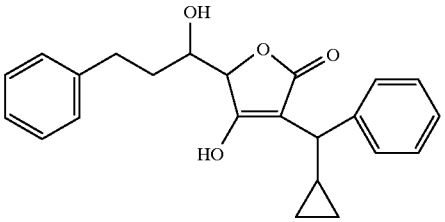 |
| BX-9 | 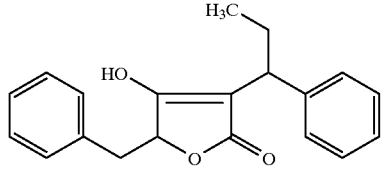 |
| BX-10 | 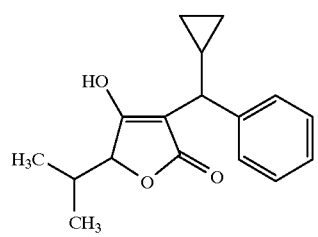 |
| BX-11 | 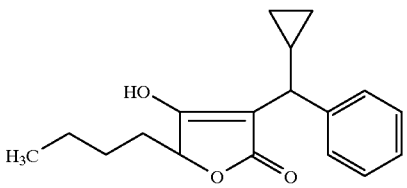 |
| BX-12 | 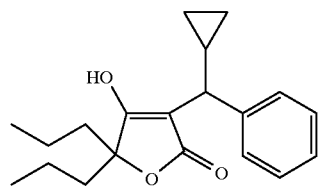 |
| BX-13 | 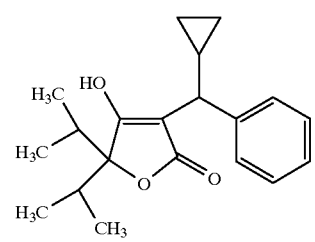 |

TABLE 11-continued
Table of Structures
| Code Name | Structure |
|---|---|
| BX-14 | 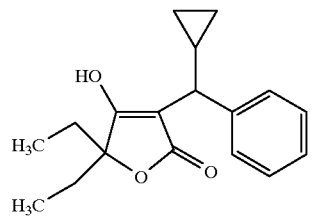 |
| BX-15 | 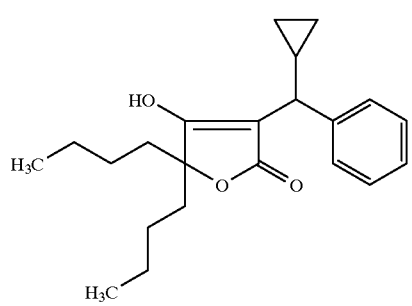 |
| BX-16 | 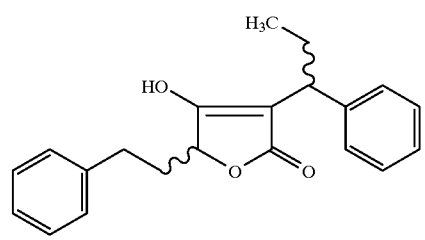 |
| CX-1 | 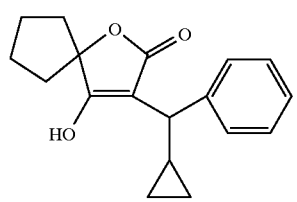 |
| CX-2 | 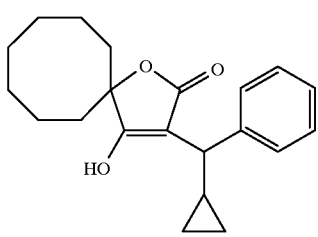 |
| CX-3 | 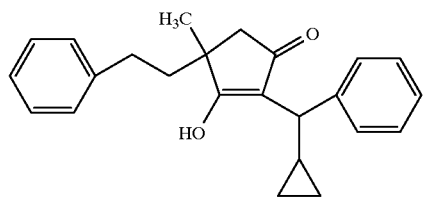 |

TABLE 11-continued
Table of Structures
| Code Name | Structure |
|---|---|
| DX-1 | 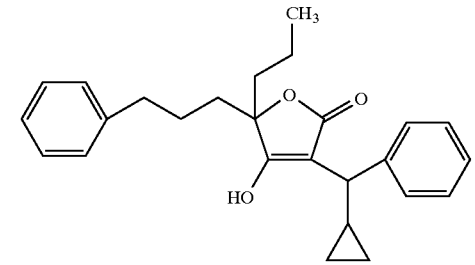 |
| DX-2 | 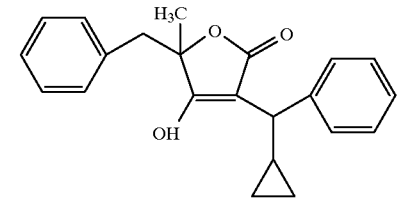 |
| DX-3 | 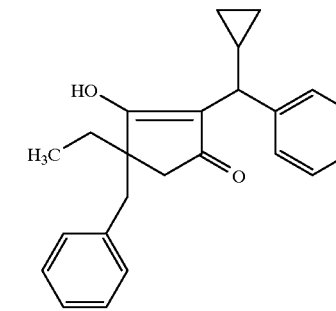 |
| DX-4 | 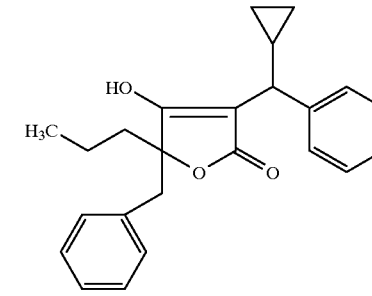 |
| DX-5 | 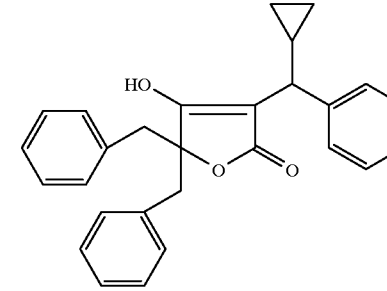 |

TABLE 11-continued
Table of Structures
| Code Name | Structure |
|---|---|
| DX-6 | 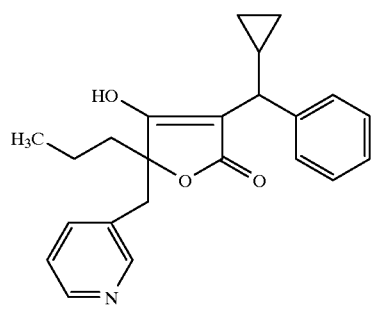 |
| DX-7 | 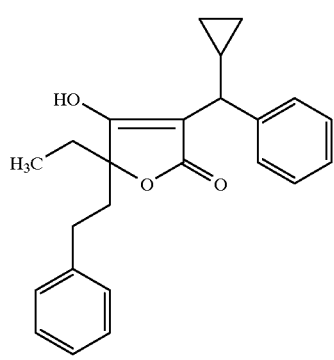 |
| DX-8 | 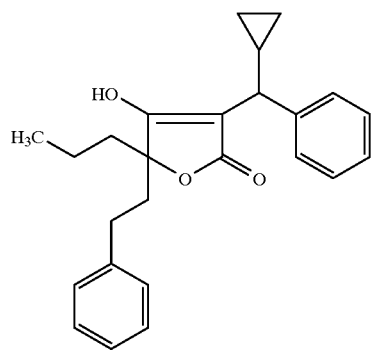 |
| DX-9 | 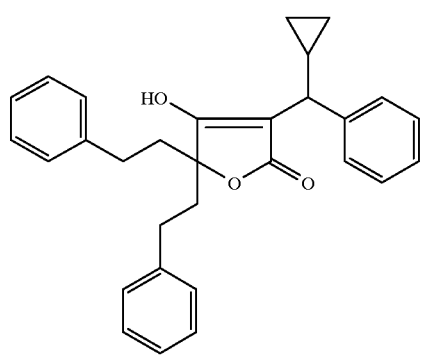 |

TABLE 11-continued
Table of Structures
| Code Name | Structure |
|---|---|
| DX-10 | 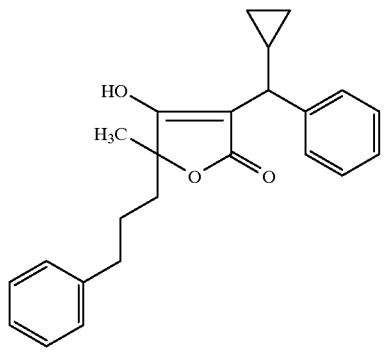 |
| DX-11 | 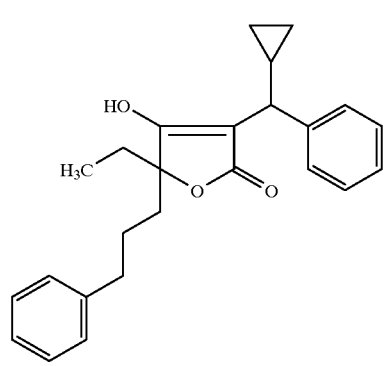 |
| DX-12 | 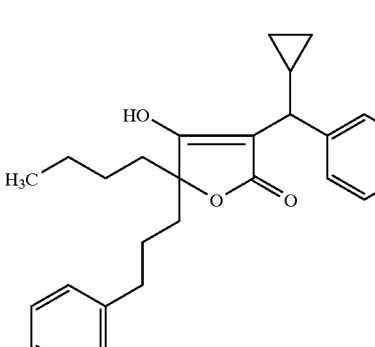 |
| DX-13 | 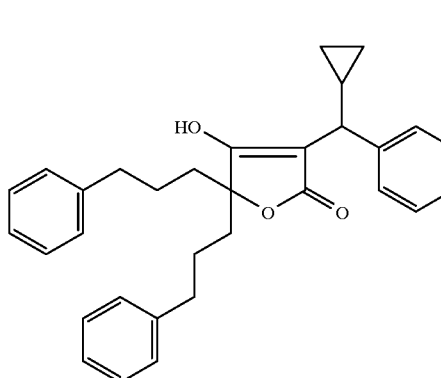 |

TABLE 11-continued
Table of Structures
| Code Name | Structure |
|---|---|
| DX-14 | 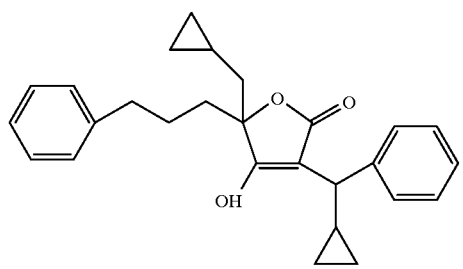 |
| DX-15 | 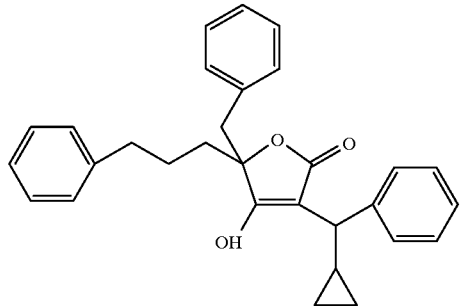 |
| DX-16 | 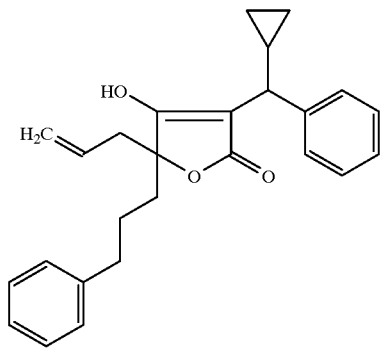 |
| DX-17 | 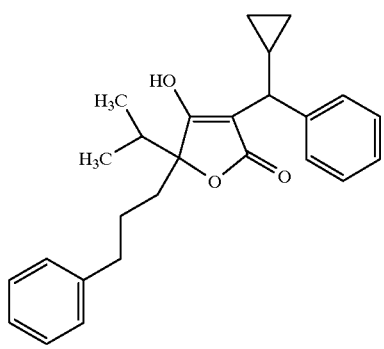 |

TABLE 11-continued
Table of Structures
| Code Name | Structure |
|---|---|
| DX-18 | 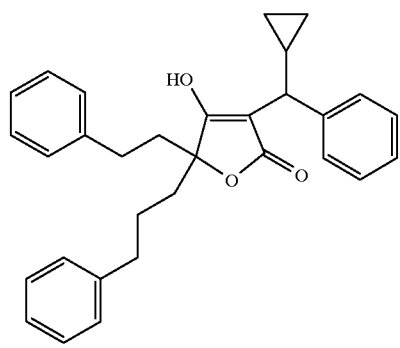 |
| DX-19 | 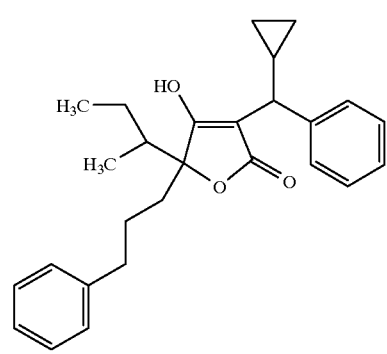 |
| DX-20 | 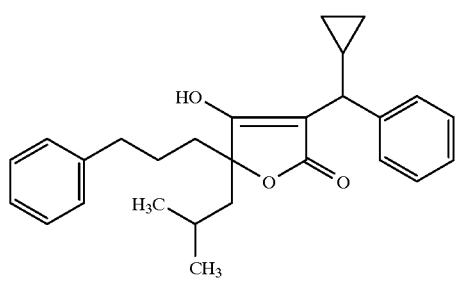 |
| FX-1 | 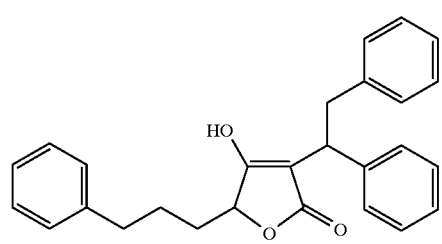 |
| FX-2 | 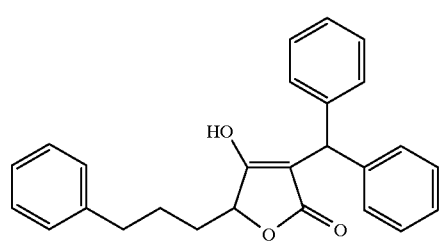 |

TABLE 11-continued

Table of Structures

| Code Name | Structure |
|---|---|
| FX-3 | (structure) |
| FX-4 | (structure) |
| FX-5 | (structure) |
| GX-1 | (structure) earlier eluting isomers |
| GX-2 | (structure) later eluting isomers |
| GX-3 | (structure) |

TABLE 11-continued

Table of Structures

| Code Name | Structure |
|---|---|
| GX-4 | |
| HX-1 | |
| HX-2 | |
| IX-1 | |
| IX-2 | |

TABLE 11-continued
Table of Structures
| Code Name | Structure |
|---|---|
| IX-3 | 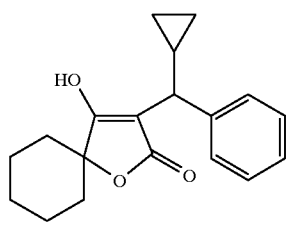 |
| IX-4 | 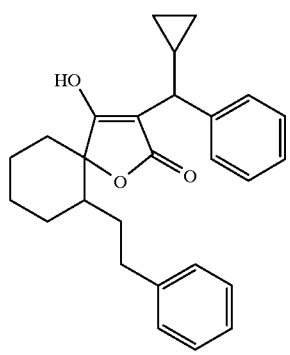<br>slower eluting |
| IX-5 | 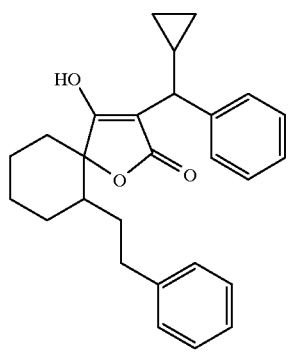<br>faster eluting |
| IX-6 | 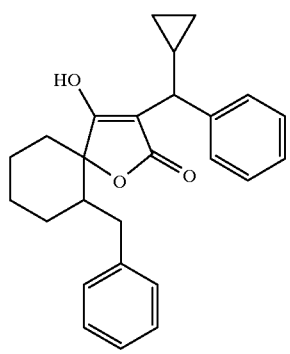<br>faster eluting |

TABLE 11-continued
Table of Structures
| Code Name | Structure |
|---|---|
| IX-7 | 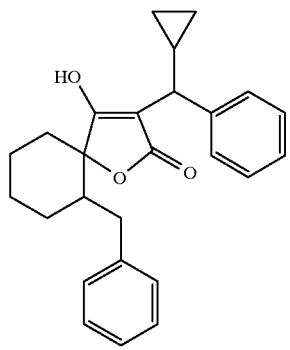<br>slower eluting |
| IX-8 | 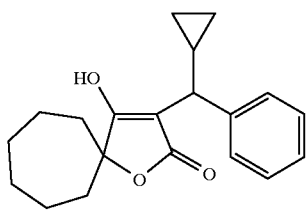 |
| IX-9 | 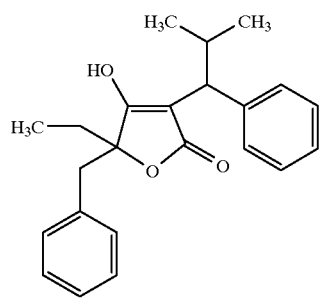 |
| IX-10 | 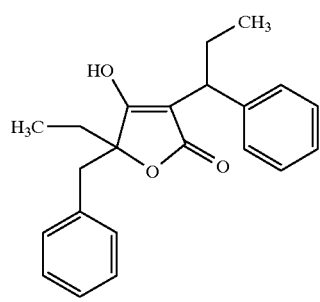 |
| IX-11 | 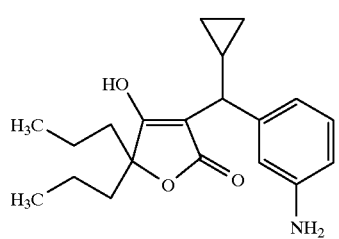 |

TABLE 11-continued

Table of Structures

| Code Name | Structure |
|---|---|
| IX-12 | 3-[cyclopropyl(4-hydroxy-5,5-dipropyl-2-oxo-2,5-dihydrofuran-3-yl)methyl]aniline · HCl |
| IX-13 | 3-[1-(4-hydroxy-5,5-dipropyl-2-oxo-2,5-dihydrofuran-3-yl)propyl]aniline |
| IX-14 | N-{3-[cyclopropyl(4-hydroxy-5,5-dipropyl-2-oxo-2,5-dihydrofuran-3-yl)methyl]phenyl}-4-cyanobenzenesulfonamide |
| IX-15 | N-{3-[cyclopropyl(4-hydroxy-5,5-dipropyl-2-oxo-2,5-dihydrofuran-3-yl)methyl]phenyl}benzenesulfonamide |
| IX-16 | N-{3-[cyclopropyl(4-hydroxy-5,5-dipropyl-2-oxo-2,5-dihydrofuran-3-yl)methyl]phenyl}-4-fluorobenzenesulfonamide |

TABLE 11-continued

Table of Structures

| Code Name | Structure |
|---|---|
| IX-17 | 4-hydroxy-5,5-dipropyl-3-[cyclopropyl(3-((1-methylimidazol-4-yl)sulfonylamino)phenyl)methyl]furan-2(5H)-one |
| IX-18 | 4-hydroxy-5,5-dipropyl-3-[cyclopropyl(3-(quinolin-8-ylsulfonylamino)phenyl)methyl]furan-2(5H)-one |
| IX-19 | 4-hydroxy-5,5-dipropyl-3-[cyclopropyl(3-(naphthalen-1-ylsulfonylamino)phenyl)methyl]furan-2(5H)-one |
| IX-20 | 4-hydroxy-5,5-dipropyl-3-[1-(3-(phenylsulfonylamino)phenyl)propyl]furan-2(5H)-one |
| IX-21 | 4-hydroxy-5,5-dipropyl-3-[1-(3-((4-cyanophenyl)sulfonylamino)phenyl)-3-methylbutyl]furan-2(5H)-one |

TABLE 11-continued

Table of Structures

| Code Name | Structure |
|---|---|
| IX-22 | 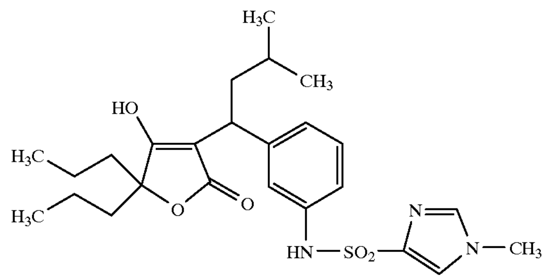 |
| IX-23 | 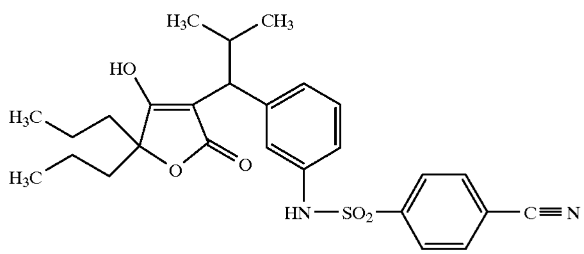 |
| IX-24 | 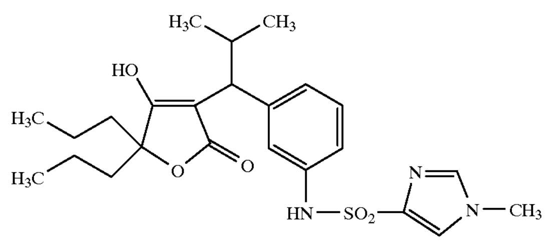 |
| IX-25 | 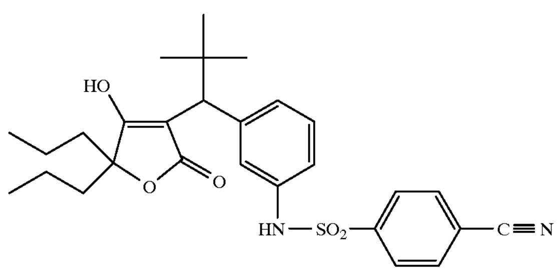 |
| IX-26 | 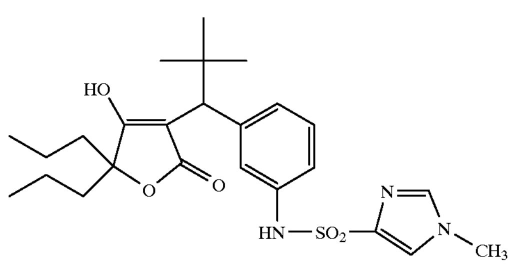 |

TABLE 11-continued
Table of Structures
| Code Name | Structure |
|---|---|
| IX-27 | 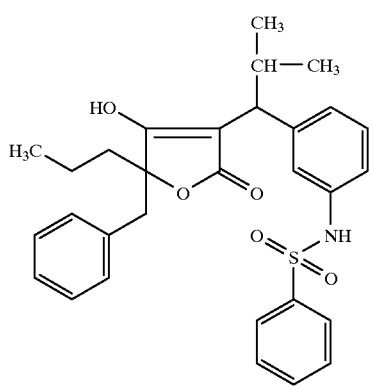 |
| IX-28 | 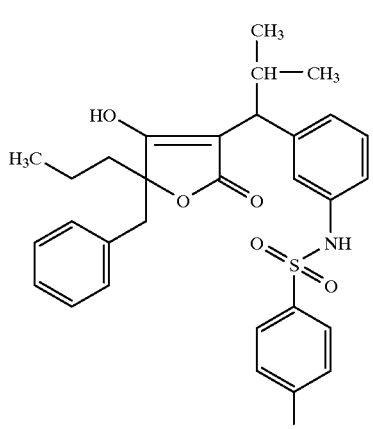 |
| IX-29 | 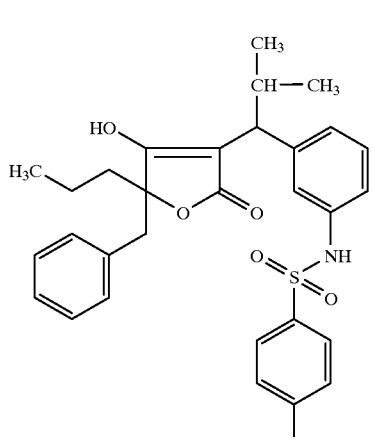 |

TABLE 11-continued

Table of Structures

| Code Name | Structure |
|---|---|
| IX-30 | 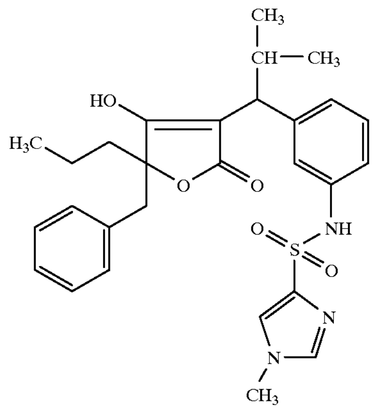 |
| IX-31 | 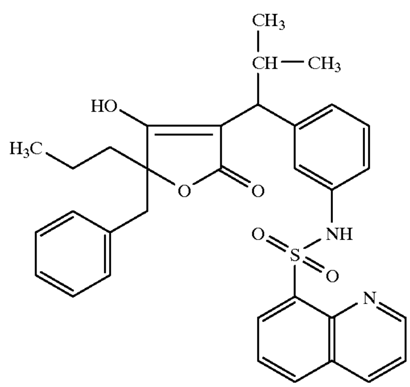 |
| IX-32 | 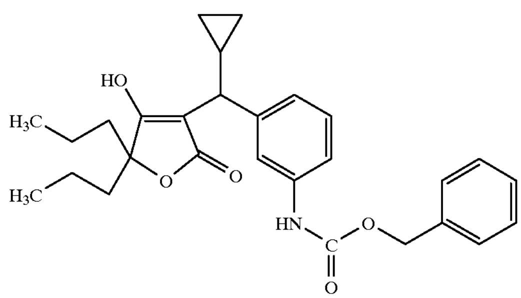 |
| IX-33 | faster eluting |

TABLE 11-continued
Table of Structures
| Code Name | Structure |
|---|---|
| IX-34 | 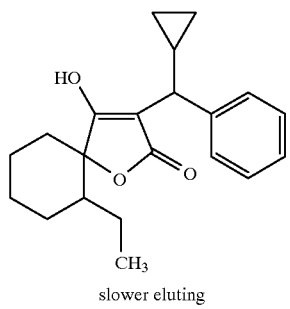<br>slower eluting |
| IX-35 | 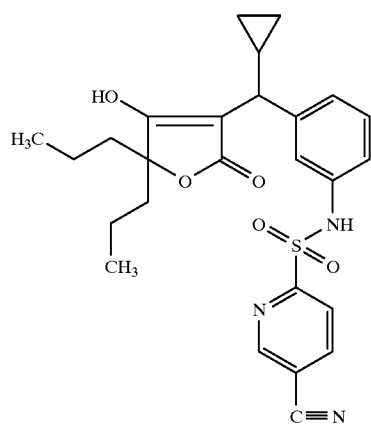 |
| IX-36 | 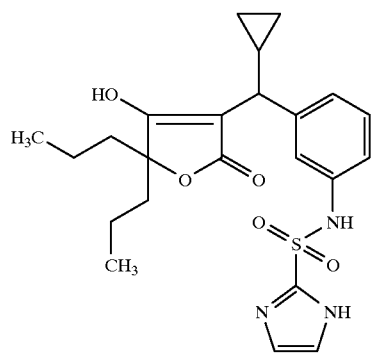 |
| IX-37 | 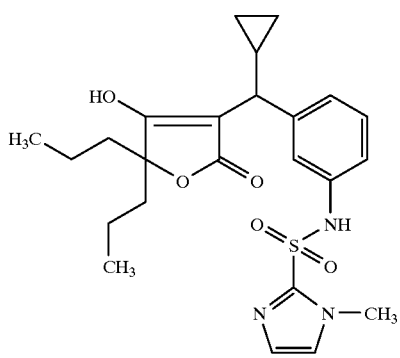 |

TABLE 11-continued

Table of Structures

| Code Name | Structure |
|---|---|
| IX-38 | 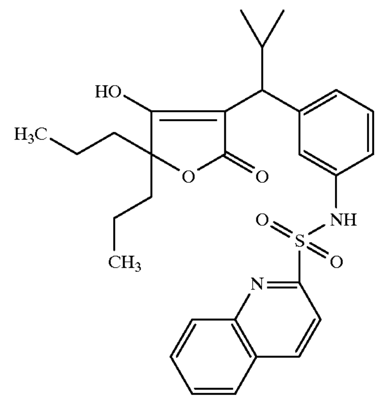 |
| IX-39 | 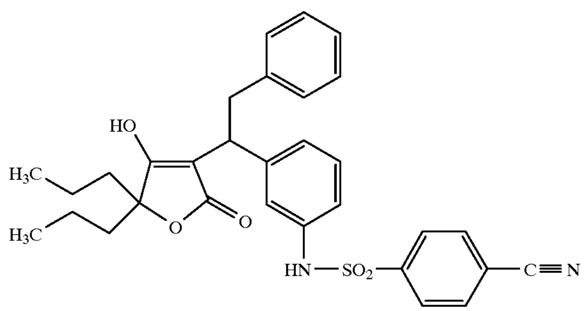 |
| IX-40 | 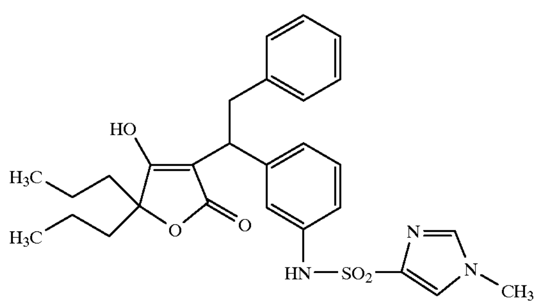 |
| IX-41 | 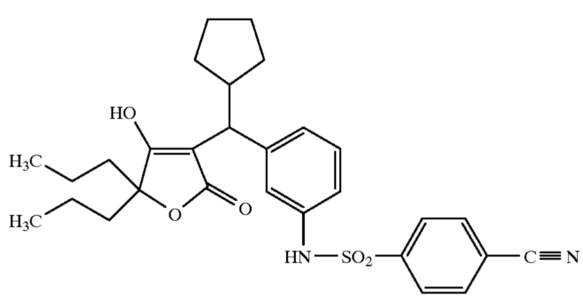 |

TABLE 11-continued

Table of Structures

| Code Name | Structure |
|---|---|
| IX-42 | 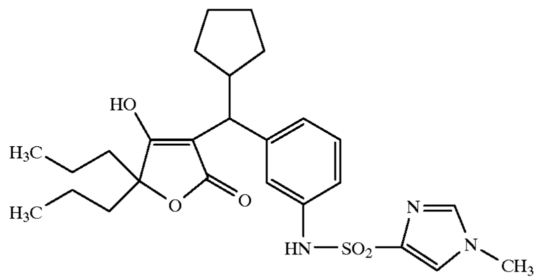 |
| IX-43 | 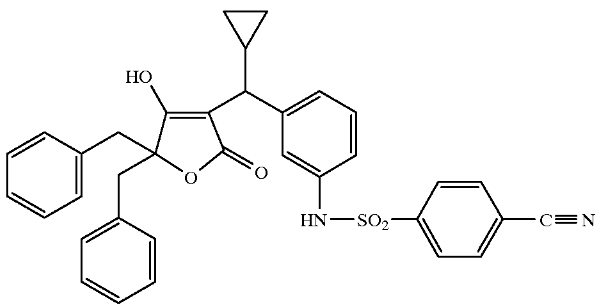 |
| IX-44 | 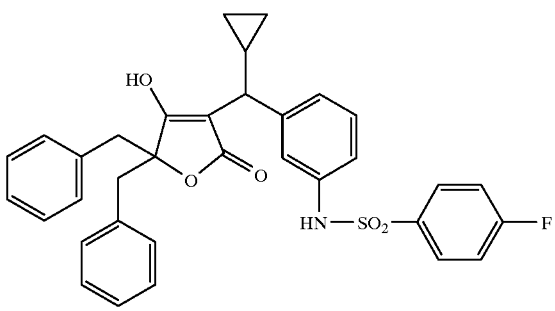 |
| IX-45 | 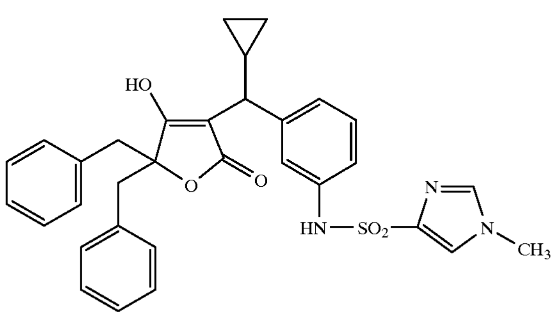 |

TABLE 11-continued
| Table of Structures | |
| --- | --- |
| Code Name | Structure |
| IX-46 | 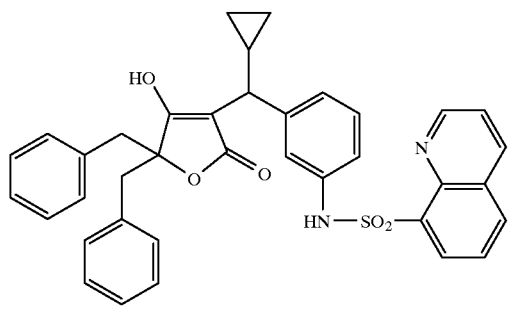 |
| IX-47 | 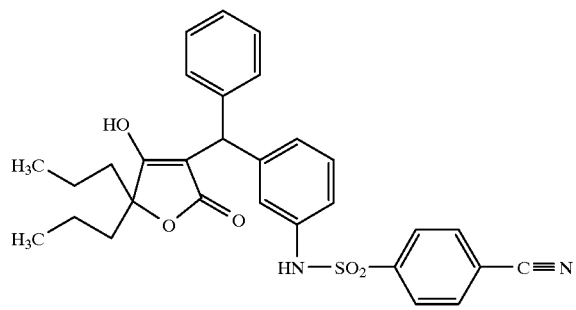 |
| IX-48 | 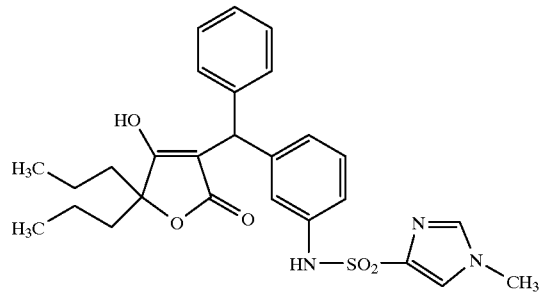 |
| IX-49 | 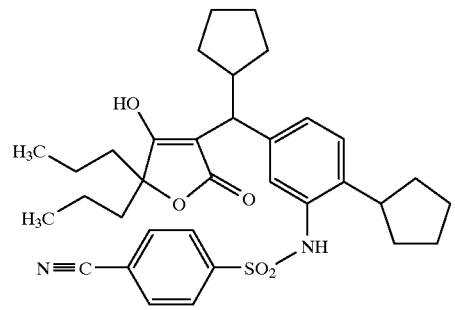 |

TABLE 11-continued

Table of Structures

| Code Name | Structure |
|---|---|
| IX-50 | 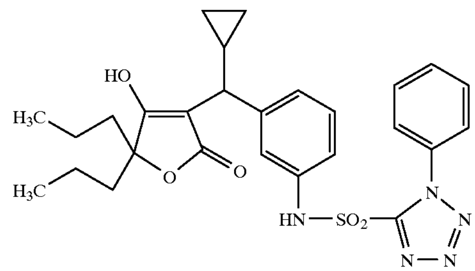 |
| IX-51 | 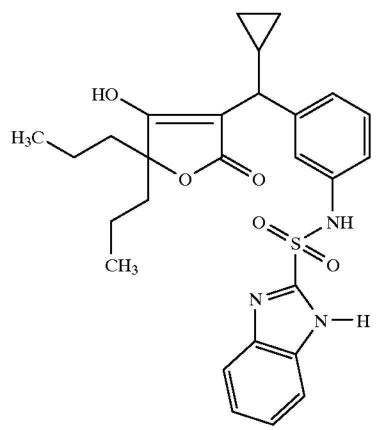 |
| IX-52 | 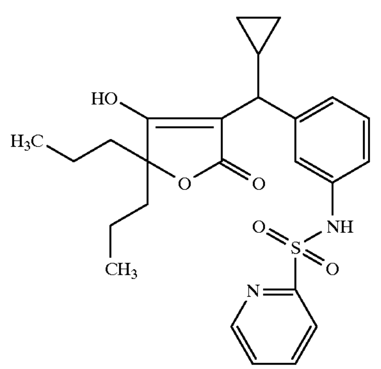 |
| IX-53 | 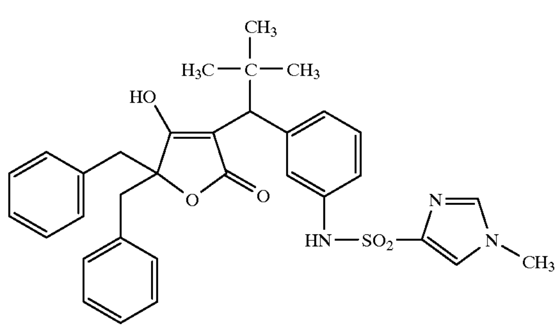 |

TABLE 11-continued

Table of Structures

| Code Name | Structure |
|---|---|
| IX-54 | 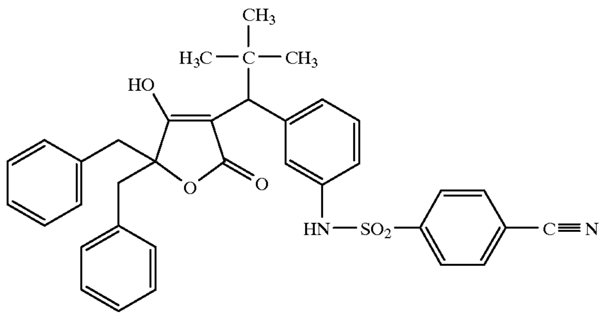 |
| IX-55 | 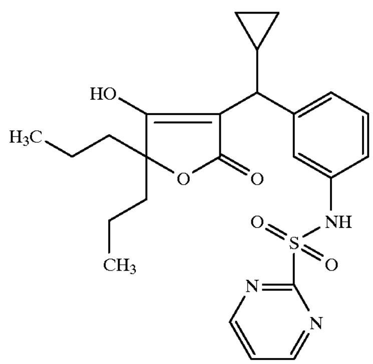 |
| IX-56 | 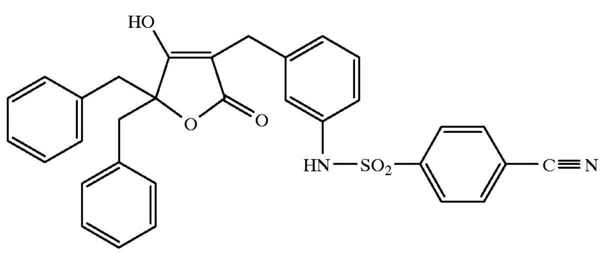 |
| IX-57 | 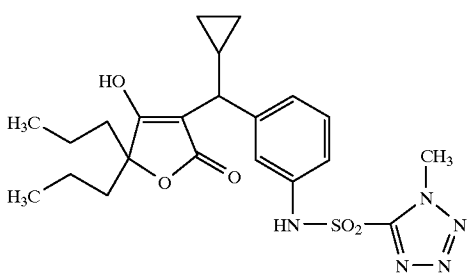 |
| IX-58 | 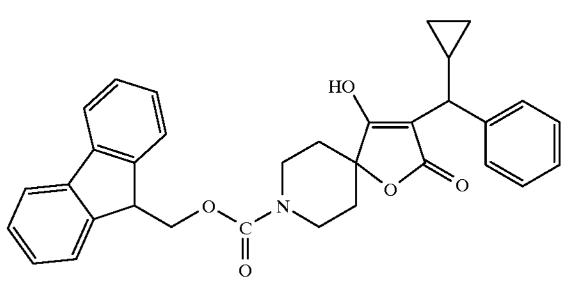 |

TABLE 11-continued
Table of Structures
| Code Name | Structure |
|---|---|
| JX-1 | 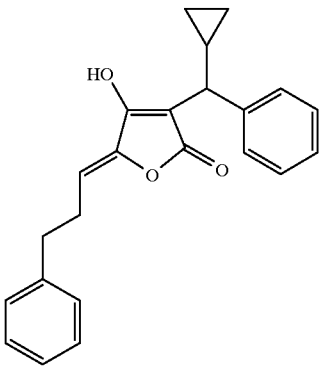 |
| JX-2 | 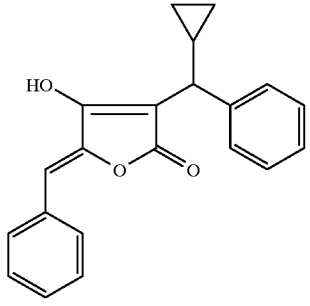 |
| JX-3 | 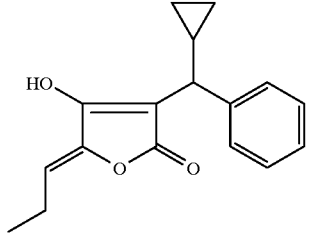 |
| JX-4 | 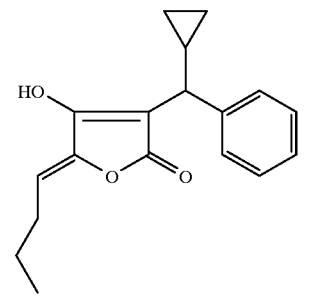 |

TABLE 11-continued

Table of Structures

| Code Name | Structure |
|---|---|
| OX-1 | (structure) |
| OX-2 | (structure) |

TABLE III

ACTIVITY TABLE

HIV Protease Inhibitory Assay

| Code Number | HIV-1 Dose ($\mu$M) | HIV-1 Protease % Inhibition |
|---|---|---|
| BX-1 | 1.0 | 18.66 |
|  | 10.0 | 80.07 |
|  | 100.0 | 90.51 |
| BX-2 | 1.0 | 47.16 |
|  | 10.0 | 80.95 |
|  | 100.0 | 81.44 |
| BX-3 | 1.0 | 46 |
|  | 10.0 | 90.6 |
|  | 100.0 | 93.2 |
| BX-4 | 1.0 | <10 |
|  | 10.0 | 61.13 |
|  | 100.0 | 83.27 |
| BX-5 | 1.0 | 12.62 |
|  | 10.0 | 61.23 |
|  | 100.0 | 71.49 |
| BX-6 | 3.3 | 65.66 |
|  | 10.0 | 77.17 |
|  | 30.0 | 82.09 |
| BX-7 | 3.3 | <10 |
|  | 10.0 | 17.97 |
|  | 30.0 | 40.04 |
| BX-8 | 3.3 | 50.98 |
|  | 10.0 | 73.32 |
|  | 30.0 | 78.21 |
| BX-9 | 3.3 | 50.11 |
|  | 10.0 | 75.07 |
|  | 30.0 | 86.12 |
| BX-10 | 3.3 | 40.49 |
|  | 10.0 | 74.62 |
|  | 30.0 | 98.63 |
| BX-11 | 3.3 | 45.08 |
|  | 10.0 | 78.31 |
|  | 30.0 | 93.41 |
| BX-12 | 3.3 | 109.78 |
|  | 10.0 | 112.16 |
|  | 30.0 | 95.32 |
| BX-13 | 1.1 | 94.07 |
|  | 3.3 | 104.43 |
|  | 10.0 | 108.23 |
| BX-14 | 3.3 | 92.69 |
|  | 10.0 | 94.02 |
|  | 30.0 | 98.98 |
| BX-15 | 3.3 | 114.85 |
|  | 10.0 | 117.58 |
|  | 30.0 | 122.16 |
| BX-16 | 3.3 | 41.37 |
|  | 10.0 | 71.38 |
|  | 30.0 | 80.31 |
| CX-1 | 3.7 | 109.08 |
|  | 11.0 | 114.55 |
|  | 100.0 | 108.81 |
| CX-2 | 1.1 | 96.01 |
|  | 10.0 | 104.36 |
|  | 30.0 | 110.45 |
| CX-3 | 3.3 | 98.08 |
|  | 10.0 | 111.46 |
|  | 30.0 | 117.53 |
| DX-1 | 3.3 | 108.03 |
|  | 10.0 | 105.54 |
|  | 30.0 | 105.1 |
| DX-2 | 3.3 | 94.54 |
|  | 10.0 | 98.19 |
|  | 30.0 | 103.82 |
| DX-3 | 3.3 | 95.54 |
|  | 10.0 | 103.41 |
|  | 30.0 | 105.07 |
| DX-4 | 3.3 | 124.98 |
|  | 10.0 | 128.42 |
|  | 30.0 | 115.68 |
| DX-5 | 3.3 | 102.74 |
|  | 10.0 | 116.22 |
|  | 30.0 | 102.98 |

TABLE III-continued

ACTIVITY TABLE

HIV Protease Inhibitory Assay

| Code Number | HIV-1 Dose ($\mu M$) | HIV-1 Protease % Inhibition |
|---|---|---|
| DX-6 | 3.3 | 102.89 |
| | 10.0 | 102.32 |
| | 30.0 | 104.09 |
| DX-7 | 3.3 | 107.54 |
| | 10.0 | 112.09 |
| | 30.0 | 103.38 |
| DX-8 | 3.3 | 114.04 |
| | 10.0 | 108.55 |
| | 30.0 | 103.24 |
| DX-9 | 3.3 | 86.67 |
| | 10.0 | 104.26 |
| | 30.0 | 99.81 |
| DX-10 | 3.3 | 112.17 |
| | 10.0 | 103.87 |
| | 30.0 | 91.46 |
| DX-11 | 3.3 | 101.03 |
| | 10.0 | 111.3 |
| | 30.0 | 105.05 |
| DX-12 | 3.3 | 116.17 |
| | 10.0 | 128.6 |
| | 30.0 | 123.12 |
| DX-13 | 3.3 | 84.98 |
| | 10.0 | 101.66 |
| | 30.0 | 105.79 |
| DX-14 | 0.123 | 89.15 |
| | 0.370 | 103.96 |
| | — | — |
| DX-15 | 3.3 | 107.93 |
| | 10.0 | 116.39 |
| | 30.0 | 114.11 |
| DX-16 | 3.3 | 114.11 |
| | 10.0 | 115.43 |
| | 30.0 | 117.51 |
| DX-17 | 3.3 | 103.21 |
| | 10.0 | 97.61 |
| | 30.0 | 96.03 |
| DX-18 | 3.3 | 113.19 |
| | 10.0 | 113.78 |
| | 30.0 | 101.12 |
| DX-19 | 0.37 | 100.5 |
| | 1.10 | 102.97 |
| | 3.30 | 100 |
| DX-20 | 0.12 | 29.24 |
| | 0.37 | 71.49 |
| | 1.10 | 90.28 |
| FX-1 | 3.3 | 15.47 |
| | 10.0 | 35.36 |
| | 30.0 | 50.65 |
| FX-2 | 3.3 | 41.47 |
| | 10.0 | 69 |
| | 30.0 | 77.34 |
| FX-3 | 3.3 | 38.62 |
| | 10.0 | 66.34 |
| | 30.0 | 68.6 |
| FX-4 | 3.3 | 56.64 |
| | 10.0 | 84.37 |
| | 30.0 | 96.51 |
| FX-5 | 3.3 | 61.88 |
| | 10.0 | 84.37 |
| | 30.0 | 84.34 |
| GX-1 | 3.3 | 74.58 |
| | 10.0 | 89.19 |
| | 30.0 | 74.04 |
| GX-2 | 3.3 | 70.88 |
| | 10.0 | 88.33 |
| | 30.0 | 74.86 |
| GX-3 | 3.3 | 67.25 |
| | 10.0 | 84.66 |
| | 30.0 | 87.43 |
| GX-4 | 3.3 | 93.6 |
| | 10.0 | 107.78 |
| | 30.0 | 103.25 |
| GX-5 | 3.3 | 94.04 |
| | 10.0 | 94.12 |
| | 30.0 | 99.18 |
| GX-6 | 3.3 | 91.89 |
| | 10.0 | 99.68 |
| | 30.0 | 103 |
| GX-7 | 3.3 | 92.66 |
| | 10.0 | 103.06 |
| | 30.0 | 102.34 |
| GX-8 | 3.3 | 85.87 |
| | 10.0 | 104.02 |
| | 30.0 | 84.29 |
| HX-1 | 1.1 | 37.62 |
| | 3.3 | 62.11 |
| | 10.0 | 90.94 |
| HX-2 | 0.1 | <10 |
| | 0.3 | 13.48 |
| | — | — |
| IX-1 | 3.3 | 108.04 |
| | 10.0 | 120.77 |
| | 30.0 | 121.54 |
| IX-2 | 3.3 | 102.33 |
| | 10.0 | 113.49 |
| | 30.0 | 102.01 |
| IX-3 | 3.3 | 102.12 |
| | 10.0 | 114.3 |
| | 30.0 | 102.52 |
| IX-4 | 3.3 | 56.89 |
| | 10.0 | 78.08 |
| | 30.0 | 85.95 |
| IX-5 | 3.3 | 91.93 |
| | 10.0 | 95.68 |
| | 30.0 | 92.9 |
| IX-6 | 3.3 | 101.19 |
| | 10.0 | 103.68 |
| | 30.0 | 104.57 |
| IX-7 | 3.3 | 102.85 |
| | 10.0 | 99.7 |
| | 30.0 | 95.76 |
| IX-8 | 3.3 | 103.9 |
| | 10.0 | 108.24 |
| | 30.0 | 103.53 |
| IX-9 | 3.3 | 103.05 |
| | 10.0 | 109.42 |
| | 30.0 | 108.32 |
| IX-10 | 3.3 | 97.26 |
| | 10.0 | 104.93 |
| | 30.0 | 100.99 |
| IX-11 | 3.3 | 108.06 |
| | 10.0 | 108.04 |
| | 30.0 | 114.05 |
| IX-12 | 3.3 | 117.79 |
| | 10.0 | 119.69 |
| | 30.0 | 120.48 |
| IX-13 | 3.3 | 59.91 |
| | 10.0 | 86.54 |
| | 30.0 | 89.38 |
| IX-14 | 3.3 | 112.76 |
| | 10.0 | 111.2 |
| | 30.0 | 118.98 |
| IX-15 | 0.12 | 94.02 |
| | 0.37 | 101.54 |
| | 1.10 | 103.96 |
| IX-16 | 3.3 | 107.86 |
| | 10.0 | 108.67 |
| | 30.0 | 105.82 |
| IX-17 | 3.3 | 108.29 |
| | 10.0 | 111.39 |
| | 30.0 | 107.58 |
| IX-18 | 3.3 | 102.13 |
| | 10.0 | 125.18 |
| | 30.0 | 106.47 |

TABLE III-continued

ACTIVITY TABLE

HIV Protease Inhibitory Assay

| Code Number | HIV-1 Dose ($\mu$M) | HIV-1 Protease % Inhibition |
|---|---|---|
| IX-19 | 3.3 | 102.7 |
|  | 10.0 | 126.43 |
|  | 30.0 | 105.49 |
| IX-20 | 3.3 | 103.73 |
|  | 10.0 | 100.77 |
|  | 30.0 | 91.85 |
| IX-21 | 3.3 | 95.72 |
|  | 10.0 | 100.91 |
|  | 30.0 | 96.11 |
| IX-22 | 3.3 | 94.32 |
|  | 10.0 | 96.32 |
|  | 30.0 | 94.48 |
| IX-23 | 3.3 | 109.41 |
|  | 10.0 | 101.07 |
|  | 30.0 | 111.98 |
| IX-24 | 3.3 | 101.58 |
|  | 10.0 | 100.79 |
|  | 30.0 | 101.8 |
| IX-25 | 3.3 | 120.16 |
|  | 10.0 | 119.61 |
|  | 30.0 | 117.27 |
| IX-26 | 3.3 | 110.39 |
|  | 10.0 | 116.08 |
|  | 30.0 | 105.33 |
| IX-27 | 3.3 | 104.54 |
|  | 10.0 | 116.62 |
|  | 30.0 | 106.22 |
| IX-28 | 3.3 | 123.03 |
|  | 10.0 | 117.59 |
|  | 30.0 | 124.91 |
| IX-29 | 3.3 | 94.92 |
|  | 10.0 | 101.94 |
|  | 30.0 | 93.32 |
| IX-30 | 3.3 | 97.14 |
|  | 10.0 | 96.59 |
|  | 30.0 | 94.29 |
| IX-31 | 3.3 | 107.49 |
|  | 10.0 | 113.66 |
|  | 30.0 | 108.99 |
| IX-32 | 3.3 | 100.05 |
|  | 10.0 | 105.91 |
|  | 30.0 | 110.64 |
| IX-33 | 3.3 | 99 |
|  | 10.0 | 99.36 |
|  | 30.0 | 97.57 |
| IX-34 | 3.3 | 96.97 |
|  | 10.0 | 98.11 |
|  | 30.0 | 93.32 |
| IX-35 | 3.3 | 82.21 |
|  | 10.0 | 98.83 |
|  | 30.0 | 91.94 |
| IX-36 | 3.3 | 37.0 |
|  | 10.0 | 79.59 |
|  | 30.0 | 83.05 |
| IX-37 | 3.3 | 99.2 |
|  | 10.0 | 100.09 |
|  | 30.0 | 96.68 |
| IX-38 | 3.3 | 82.95 |
|  | 10.0 | 85.04 |
|  | 30.0 | 84.81 |
| IX-39 | 3.3 | 76.76 |
|  | 10.0 | 78.07 |
|  | 30.0 | 106.29 |
| IX-40 | 3.3 | 90.81 |
|  | 10.0 | 91.07 |
|  | 30.0 | 104.18 |
| IX-41 | 3.3 | 97.36 |
|  | 10.0 | 96.88 |
|  | 30.0 | 101.46 |
| IX-42 | 3.3 | 94.53 |
|  | 10.0 | 95.97 |
|  | 30.0 | 96.78 |
| IX-43 | 3.3 | 98.63 |
|  | 10.0 | 96.76 |
|  | 30.0 | 99.84 |
| IX-44 | 3.3 | 90.33 |
|  | 10.0 | 92.34 |
|  | 30.0 | 80.29 |
| IX-45 | 3.3 | 91.92 |
|  | 10.0 | 94.3 |
|  | 30.0 | 80.92 |
| IX-46 | 3.3 | 90.27 |
|  | 10.0 | 86.98 |
|  | 30.0 | 81.66 |
| IX-47 | 3.3 | 93.55 |
|  | 10.0 | 103.33 |
|  | 30.0 | 88.28 |
| IX-48 | 3.3 | 94.53 |
|  | 10.0 | 94.70 |
|  | 30.0 | 89.06 |
| IX-49 | 3.3 | 86.97 |
|  | 10.0 | 94.94 |
|  | 30.0 | 78.56 |
| IX-50 | 3.3 | 108.32 |
|  | 10.0 | 104.21 |
|  | 30.0 | 105.61 |
| IX-51 | 3.3 | 101.14 |
|  | 10.0 | 102.10 |
|  | 30.0 | 106.05 |
| IX-52 | 3.3 | 109.50 |
|  | 10.0 | 104.11 |
|  | 30.0 | 99.88 |
| IX-53 | 3.3 | 102.49 |
|  | 10.0 | 104.29 |
|  | 30.0 | 92.05 |
| IX-54 | 3.3 | 102.04 |
|  | 10.0 | 104.91 |
|  | 30.0 | 92.37 |
| IX-55 | 3.3 | 93.83 |
|  | 10.0 | 93.76 |
|  | 30.0 | 96.34 |
| IX-56 | 3.3 | 81.88 |
|  | 10.0 | 100.53 |
|  | 30.0 | 92.54 |
| IX-57 | 3.3 | — |
|  | 10.0 | — |
|  | 30.0 | — |
| IX-58 | 3.3 | 79.84 |
|  | 10.0 | 86.76 |
|  | 30.0 | 87.38 |
| JX-1 | 3.3 | 94.33 |
|  | 10.0 | 103.31 |
|  | 30.0 | 103.2 |
| JX-2 | 3.3 | 56.9 |
|  | 10.0 | 87.65 |
|  | 30.0 | 102.88 |
| JX-3 | 3.3 | 43.22 |
|  | 10.0 | 65.32 |
|  | 30.0 | 96.32 |
| JX-4 | 3.3 | 85.87 |
|  | 10.0 | 99.23 |
|  | 30.0 | 112.59 |
| OX-1 | 3.3 | 78.84 |
|  | 10.0 | 89.92 |
|  | 30.0 | 100.05 |
| OX-2 | 3.3 | 14.91 |
|  | 10.0 | 34.12 |
|  | 30.0 | 59.02 |

We claim:

1. A compound represented by the structure shown in formula 1,

Formula 1

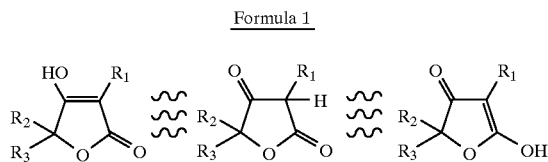

wherein 3 tautomers of the same structure are shown, wherein $R_1$ is a) —CH—($C_3$—$C_6$ cycloalkyl)$_2$,
b) diphenylmethyl,
c) diphenylethyl,
d) diphenylethenyl,
e) diphenylpropyl,
f) phenylcyclobutyl;
g) —CH($CH_2$-phenyl)$_2$,
h) -5,6,7,8,9-tetrahydro-5H-benzocycloheptenyl,
i) -1,2,3,4-tetrahydro-naphthalenyl, substituted with zero, one (1) or two (2) —O— ($C_{1-6}$ alkyl) or —$CH_3$, j)

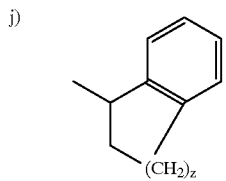

Formula 2, k)

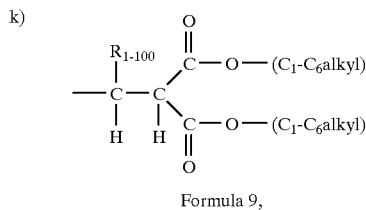

Formula 9, l)

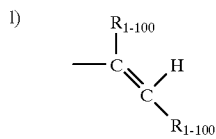

Formula 10, m)

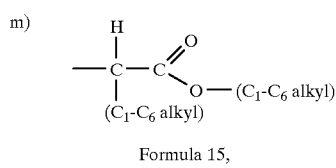

Formula 15, n)

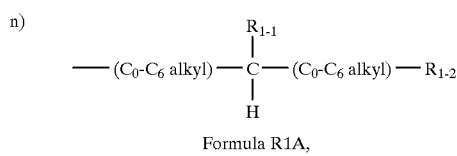

Formula R1A,

-continued o)

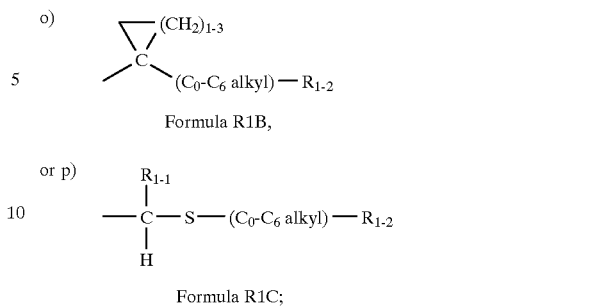

Formula R1B, or p)

—C(H)(R$_{1-1}$)—S—($C_0$-$C_6$ alkyl)—R$_{1-2}$

Formula R1C;

wherein $R_{1-1}$ is
a) —$C_{1-10}$ alkyl,
b) —$C_{2-10}$ alkenyl,
c) —$C_{3-7}$ cycloalkyl,
d) —($C_{1-6}$ alkyl)—($C_{3-7}$ cycloalkyl),
e) —$CH_2$—C(O)—O—((H or ($C_{1-6}$ alkyl)),
f) —($C_{0-6}$ alkyl)—$R_{1-100}$,
g) —($C_{0-6}$ alkyl)—$R_{1-500}$, or
h) —($C_{0-6}$ alkyl)—CH=CH—$R_{1-100}$;
wherein $R_{1-2}$ is
a) -halo,
b) -trifluoromethyl,
c) —$C_{3-7}$ cycloalkyl,
d) —$C_{2-10}$ alkenyl,
e) —($C_{0-6}$ alkyl)—(($CH_2$)$CH_2$—O—)$_q$—($C_{1-6}$ alkyl),
f) —$R_{1-100}$,
g) —C(O)—O—($C_{0-6}$ alkyl)—$R_{1-100}$,
h) —$R_{1-500}$,
i) —C(O)—$R_{1-500}$ or
j) —O—$R_{1-500}$;
wherein $R_{1-100}$ is
a) phenyl, substituted with zero (0) to three (3) of $RA_1$,
b) naphthyl, substituted with zero (0) to three (3) of $RA_1$,
c) biphenyl, substituted with zero (0) to three (3) of $RA_1$,
d) perhalophenyl;
wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
a) halo,
b) —H
c) —N-methyl-piperazino,
d) —$C_{1-8}$ alkyl, substituted with zero (0) to three (3) halo,
e) —$C_{2-8}$ alkenyl,
f) —$C_{3-7}$ cycloalkyl,
g) —($C_{0-6}$ alkyl)—$RA_{1-RA-12}$
h) —($C_{1-6}$ alkyl)-phenyl, substituted with zero (0) to three (3) $RA_{1-RA-120}$;
i) —($C_{0-6}$ alkyl)—$RA_{1-RA-15}$
j) —OH,
k) —O—($C_{1-6}$ alkyl), substituted with zero (0) to three (3) hydroxy, l) —($C_{1-6}$ alkyl)—O-($C_{1-6}$ alkyl), substituted with zero (0) to three (3) hydroxy,
m) —O—($C_{2-7}$ alkenyl), substituted with zero (0) to three (3) hydroxy,
n) —($C_{1-6}$ alkyl)—O-($C_{2-7}$ alkenyl), substituted with zero (0) to three (3) hydroxy,
o) (o-) or (m-)—O-($C_{1-6}$ alkyl)—CH=CH$_2$,
p) —(CH$_2$-O)$_q$—$C_{1-3}$ alkyl,
q) —O—(CH$_2$CH$_2$—O—)$_q$—CH$_3$,
r) —CH(O),
s) —C(O)—($C_{1-6}$ alkyl),
t) —C(O)—O—($C_{1-6}$ alkyl),
u) —C(O)—N(H or $C_{1-5}$ alkyl)$_2$,
v) —SO$_3$H,
w) —SO$_2$—RA$_{1\text{-}RA\text{-}12}$,
x) —($C_{0-6}$ alkyl)—SO$_2$-($C_{0-6}$ alkyl)—RA$_{1\text{-}RA\text{-}12}$,
y) —($C_{0-6}$ alkyl)—SO$_2$-($C_{0-6}$ alkyl)—RA$_{1\text{-}RA\text{-}15}$,
z) —CN,
a1) —NH$_2$,
b1) —NH—($C_{1-6}$ alkyl),
c1) -mono or -di($C_{1-6}$ alkyl)amino,
d1) -diethylamino,
e1) —($C_{0-6}$ alkyl)—NH—C(NH(H or $C_{1-5}$ alkyl))=NCN,
f1) —($C_{0-6}$ alkyl)—NH—C(NH(H or $C_{1-5}$ alkyl))=CHNO$_2$,
g1) —($C_{0-6}$ alkyl)—NH—C(O)—O—($C_{1-6}$ alkyl)—RA$_{1\text{-}RA\text{-}12}$
h1) —($C_{0-6}$ alkyl)—NH—C(O)—O—($C_{1-6}$ alkyl)—RA$_{1\text{-}RA\text{-}15}$,
i1) —($C_{0-6}$ alkyl)—NH—C(O)—N($C_{1-3}$ alkyl)$_2$,
j1) —($C_{0-6}$ alkyl)—NH—C(O)—NH—RA$_{1\text{-}RA\text{-}12}$,
k1) —($C_{0-6}$ alkyl)—NH—SO$_2$—NH—RA$_{1\text{-}RA\text{-}12}$,
l1) —NH—C(O)—NH—SO$_2$—RA$_{1\text{-}RA\text{-}12}$,
m1) —($C_{0-6}$ alkyl)—NH—C(SCH$_3$)=CHNO$_2$,
n1) —($C_{0-6}$ alkyl)—NH—C(SCH$_3$)=NCN),
o1) —NH—AA—P$_1$,
p1) —NO$_2$,
q1) —($C_{0-6}$ alkyl)—N$_3$,
r1)

—NH—SO$_2$
 \  /
 (CH$_2$)$_u$ s1) —N=C—(NH—CH($C_{2-6}$ alkyl)$_2$)$_2$,
t1) —NR$_{40}$R$_{41}$,
u1) —NH—P(O)($C_{1-4}$ alkyl)—RA$_{1\text{-}RA\text{-}12}$,
v1) —NH—P(O)(RA$_{1\text{-}RA\text{-}12}$-RA$_{1\text{-}RA\text{-}12}$,
w1) —NH—P(O)(O—R$_{11}$)—(RA$_{1\text{-}RA\text{-}12}$),
x1) —NH—C(S)—NH—R$_{42}$, or
y1) —NH—C(S)—CH$_2$—R$_{42}$;
z1) —($C_{1-6}$ alkyl)—G$_{1\text{-}1}$—CH=CH—RA$_{1\text{-}RA\text{-}12}$,
a2) —($C_{0-6}$ alkyl)—G$_{1\text{-}1}$—CH=CH—RA$_{1\text{-}RA\text{-}15}$,
b2) —($C_{0-6}$ alkyl)—G$_{1\text{-}1}$—($C_{1-10}$ alkyl), substituted with zero (0) to three (3) halo,
c2) —($C_{0-6}$ alkyl)—G$_{1\text{-}1}$—($C_{2-5}$ alkenyl),
d2) —G$_{1\text{-}1}$—CH(($C_{1-6}$ alkyl))—NH—C(O)—O—($C_{1-6}$ alkyl),
e2) —G$_{1\text{-}1}$—CH(($C_{1-6}$ alkyl)—RA$_{1\text{-}RA\text{-}15}$)—NH—C(O)—O—($C_{1-6}$ alkyl),
f2) —G$_{1\text{-}1}$—($C_{1-6}$ alkyl)—CH(NH—C(O)—O—($C_{1-6}$ alkyl)—RA$_{1\text{-}RA\text{-}12}$)—C(O)—O—($C_{1-6}$ alkyl)—RA$_{1\text{-}RA\text{-}12}$,
g2) —($C_{0-6}$ alkyl)—G$_{1\text{-}2}$—($C_{1-12}$ alkyl),
h2) —G$_{1\text{-}2}$—($C_{1-6}$ alkyl)-halo,
i2) —G$_{1\text{-}2}$—($C_{1-6}$ alkyl)—NH$_2$.

j2) —G$_{1\text{-}2}$—($C_{1-6}$ alkyl)—NH—C(O)—O—($C_{1-6}$ alkyl),
k2) —G$_{1\text{-}2}$—($C_{1-6}$ alkyl)—CH(NH—C(O)—O—($C_{1-6}$ alkyl))—C(O)—O—($C_{1-6}$ alkyl),
l2) —G$_{1\text{-}2}$—($C_{0-6}$ alkyl)—CH(NH—C(O)—O—($C_{1-6}$ alkyl))—($C_{1-6}$ alkyl)—RA$_{1\text{-}RA\text{-}15}$,
m2) —G$_{1\text{-}2}$—($C_{1-6}$ alkyl)—CH(NH$_2$)—C(O)—OH,
n2) —G$_{1\text{-}2}$—($C_{1-6}$ alkyl)—C(O)—O—($C_{1-6}$ alkyl),
o2) —G$_{1\text{-}2}$—($C_{1-6}$ alkyl)—($C_{3-6}$ cycloalkyl),
p2) —($C_{0-6}$ alkyl)—G$_{1\text{-}2}$—($C_{O\text{-}6}$ alkyl)—RA$_{1\text{-}RA\text{-}12}$,
q2) —($C_{0-6}$ alkyl)—G$_{1\text{-}2}$—($C_{0-6}$ alkyl)—RA$_{1\text{-}RA\text{-}15}$,
r2) —G$_{1\text{-}2}$—($C_{0-6}$ alkyl)—O—RA$_{1\text{-}RA\text{-}12}$,
s2) —($C_{0-6}$ alkyl)—G$_{1\text{-}2}$—($C_{0-6}$ alkyl)—O—($C_{1-6}$ alkyl),
t2) —G$_{1\text{-}2}$—($C_{1-6}$ alkyl)—C(O)—RA$_{1\text{-}RA\text{-}15}$,
u2) —G$_{1\text{-}2}$—($C_{1-6}$ alkyl)—C(O)—NH—($C_{1-6}$ alkyl)—RA$_{1\text{-}RA\text{-}15}$,
v2) —G$_{1\text{-}2}$—($C_{1-6}$ alkyl)—S—RA$_{1\text{-}RA\text{-}15}$,
w2) —($C_{0-6}$ alkyl)—G$_{1\text{-}2}$—O—($C_{1-6}$ alkyl)—RA$_{1\text{-}RA\text{-}12}$,
x2) —($C_{0-6}$ alkyl)—G$_{1\text{-}2}$—O—($C_{1-6}$ alkyl)—RA$_{1\text{-}RA\text{-}15}$,
y2) —G$_{1\text{-}2}$—CH=CH$_2$,
z2) —G$_{1\text{-}2}$—CH=CH—RA$_{1\text{-}RA\text{-}12}$,
a3) —G$_{1\text{-}2}$—N(R$_{42}$)$_2$,
b3) —G$_{1\text{-}2}$—NH$_2$,
c3) —G$_{1\text{-}2}$—($C_{1-6}$ alkyl)-phthalimido,
d3) —G$_{1\text{-}2}$-(pentafluoro)-phenyl,
e3) —G$_{1\text{-}2}$—($C_{1-6}$ alkyl)-bicyclo[2.2.1]heptane,
f3) —G$_{1\text{-}2}$—H, or
g3) —($C_{2-6}$ alkyl)—R$_{30}$;
wherein G$_{1\text{-}1}$ is
a) —NH—C(O)—,
b) —NH—SO$_2$—,
c) —NH—C(O)—NH—, or
d) —SO$_2$—NH—;
wherein G$_{1\text{-}2}$ is
a) —NH—C(O)—,
b) —C(O)—NH—,
c) —NH—SO$_2$—,
d) —SO$_2$—NH—,
e) —NH—SO$_2$—NH—,
f) —C(O)—O—,
g) —O—C(O)—,
h) —N(($C_{1-6}$ alkyl)—RA$_{1\text{-}RA\text{-}12}$)—C(O)—,
i) —NH—C(O)—NH,
j) —N(($C_{1-6}$ alkyl)—RA$_{1\text{-}RA\text{-}12}$)—SO$_2$—, or
k) —N(($C_{0-6}$ alkyl)—($C_{1-6}$ alkyl))—SO$_2$—;
wherein RA$_2$ and RA$_3$ are defined independently and are the same as RA$_1$;
wherein RA$_{1\text{-}RA\text{-}12}$ is
a) -phenyl, substituted with zero (0) to three (3) RA$_{1\text{-}RA\text{-}12\text{-}AXA}$, or
b) -naphthyl, substituted with zero (0) to three (3) RA$_{1\text{-}RA\text{-}12\text{-}AXA}$;
wherein RA$_{1\text{-}RA\text{-}15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) RA$_{1\text{-}RA\text{-}15\text{-}AXA}$;
wherein RA$_{1\text{-}RA\text{-}120}$, RA$_{2\text{-}RA\text{-}120}$ and RA$_{3\text{-}RA\text{-}120}$, are defined independently and are a) —$C_1$–$C_4$ alkyl,
b) —$C_1$–$C_3$ alkoxy,
c) -dimethylamino,
d) -diethylamino,
e) —$CF_3$,
f) —CN,
g) -halo,
h) —$NH_2$,
i) —OH,
j) —$SO_2$—$NH_2$, or
k) —C(O)—$NH_2$;

wherein $RA_{1\text{-}RA\text{-}12\text{-}AXA}$ or $RA_{1\text{-}RA\text{-}15\text{-}AXA}$ are independent and are,
a) —H
b) -halo,
c) —$NO_2$,
d) —CN,
e) —($C_{1\text{-}10}$ alkyl), substituted with zero (0) to three (3) halo,
f) —($C_{0\text{-}6}$ alkyl)-phenyl, substituted with zero (0) to three (3) halo or hydroxy,
g) —OH,
h) —O—$C_{1\text{-}5}$ alkyl,
i) —($C_{0\text{-}6}$ alkyl)—O—($C_{1\text{-}6}$ alkyl), substituted with zero (0) to three (3) halo or hydroxy,
j) —($C_{0\text{-}6}$ alkyl)—O—($C_{2\text{-}7}$ alkenyl), substituted with zero (0) to three (3) halo or hydroxy,
k) —CH(O),
l) —C(O)—($C_{1\text{-}6}$ alkyl),
m) —C(O)OH,
n) —C(O)O—($C_{1\text{-}5}$ alkyl),
o) —C(O)—N(H or $C_{1\text{-}6}$ alkyl)$_2$,
p) —$NH_2$,
q) —NH—($C_{1\text{-}6}$ alkyl),
r) -mono or di-($C_{1\text{-}6}$ alkyl)amino,
s) —NH—OH,
t) —NH—C(O)—($C_{1\text{-}3}$ alkyl),
u) —($C_{0\text{-}6}$ alkyl)—NH—C(O)—phenyl,
v) —($C_{0\text{-}6}$ alkyl)—NH—$SO_2$-phenyl,
w) —($C_{0\text{-}6}$ alkyl)—N═N—phenyl, substituted with zero (0) or one (1) —N($C_1$–$C_3$ alkyl)$_2$, or
x) —$SO_2$-phenyl, substituted with zero (0) to three (3) $C_1$–$C_5$ alkyl;

wherein $R_2$ is
a) —H,
b) —$C_{1\text{-}6}$ alkyl,
c) —($C_{1\text{-}6}$ alkyl)—$C_{3\text{-}7}$ cycloalkyl,
d) —($C_{2\text{-}10}$ alkenyl)
e) —($C_{1\text{-}6}$ alkyl)—$R_{2\text{-}100}$,
f) —($C_{1\text{-}6}$ alkyl)—$R_{2\text{-}500}$;

wherein $R_{2\text{-}100}$ is independent of and defined the same as $R_{1\text{-}100}$ wherein $RA_1$ is $RA_2$;
wherein $R_{2\text{-}500}$ is independent of and defined the same as $R_{1\text{-}500}$ wherein $RA_1$ is $RA_2$;
wherein $RA_2$ is independent of and defined the same as $RA_1$;
wherein $R_3$ is
a) —$C_{1\text{-}10}$ alkyl, substituted with zero (0) to five (5) halo,
b) —$C_{3\text{-}7}$ cycloalkyl,
c) —$C_{2\text{-}10}$ alkenyl,
d) —($C_{1\text{-}6}$ alkyl)—CH═$CH_2$
e) —($C_{0\text{-}6}$ alkyl)—C(O)—O—($C_{1\text{-}6}$ alkyl),
f) —($C_{0\text{-}6}$ alkyl)—($CH_2CH_2$—O—)$_q$—($C_{1\text{-}6}$ alkyl),
g) —($C_{1\text{-}6}$ alkyl)—$R_{3\text{-}4}$,
h) —($C_{0\text{-}6}$ alkyl)—CH═CH—$R_{3\text{-}4}$,
i) —($C_{2\text{-}10}$ alkenyl)—$R_{3\text{-}4}$,
j) —($C_{0\text{-}6}$ alkyl)—CH($R_{3\text{-}6}$)—($C_{0\text{-}6}$ alkyl)—$R_{3\text{-}4}$,
k) —($C_{0\text{-}6}$ alkyl)—CH($R_{3\text{-}6}$)—($C_{2\text{-}6}$ alkenyl)—$R_{3\text{-}4}$,
l) —($C_{0\text{-}6}$ alkyl)—C(O)—N(H or —$C_{1\text{-}5}$ alkyl)—($C_{0\text{-}6}$ alkyl)—$R_{3\text{-}4}$,
m) —($C_{1\text{-}6}$ alkyl)—N(H or —$C_{1\text{-}5}$ alkyl)—C(O)—$R_{3\text{-}4}$,
n) —($C_{1\text{-}6}$ alkyl)—N(H or —$C_{1\text{-}5}$ alkyl)—C(O)—($C_{0\text{-}6}$ alkyl)—$R_{3\text{-}4}$,
o) —$R_{3\text{-}100}$,
except when $R_{3\text{-}100}$ is phenyl and $R_1$ is 1-phenylpropyl,
p) —$R_{3\text{-}500}$,
q) —CH($R_{3\text{-}6}$)—CH($R_{3\text{-}6}$)—$R_{3\text{-}4}$,
r) —CH($C_{0\text{-}6}$ alkyl)—($C_{0\text{-}6}$ alkyl)—$G_{3\text{-}1}$—($C_{0\text{-}6}$ alkyl)—$RA_{3\text{-}RA\text{-}12}$, or
s) —CH($C_{0\text{-}6}$ alkyl)—($C_{0\text{-}6}$ alkyl)—$G_{3\text{-}1}$—($C_{0\text{-}6}$ alkyl)—$RA_{3\text{-}RA\text{-}15}$;

wherein $G_{3\text{-}1}$ is
a) —NH—C(O)—,
b) —NH—$SO_2$—,
c) —NH—CO—NH—, or
d) —$SO_2$—NH—;

wherein, $R_{3\text{-}4}$ is
a) -trifluoromethyl;
b) -halo,
c) —($C_{1\text{-}6}$ alkyl)
d) —$C_{3\text{-}7}$ cycloalkyl,
e) —$C_{2\text{-}10}$ alkenyl,
f) —($C_{0\text{-}6}$ alkyl)—($CH_2CH_2$—O—)$_q$—($C_{1\text{-}6}$ alkyl),
g) —OH,
h) —O—($C_{1\text{-}6}$ alkyl),
i) —O—$R_{3\text{-}500}$,
j) —C(O)—$R_{3\text{-}500}$,
k) —C(O)—OH,
l) —C(O)—O—($C_{1\text{-}6}$ alkyl),
m) —C(O)—O—($C_{0\text{-}6}$ alkyl)—$R_{3\text{-}100}$,
n) —$R_{3\text{-}100}$, or
o) —$R_{3\text{-}500}$;

wherein $R_{3\text{-}6}$ is
a) —OH,
b) —$C_{1\text{-}0}$ alkyl,
c) —($C_{0\text{-}6}$ alkyl)—$C_3$–$C_7$ cycloalkyl,
d) —($C_{1\text{-}6}$ alkyl)—CH═$CH_2$,
e) —($C_{0\text{-}6}$ alkyl)—$R_{3\text{-}4}$,
f) —($C_{1\text{-}6}$ alkyl)—$R_{3\text{-}100}$, or
g) —($C_{1\text{-}6}$ alkyl)—$R_{3\text{-}500}$;

wherein $R_{3\text{-}9}$ is
a) —($C_{1\text{-}6}$ alkyl),
b) —($C_{2\text{-}7}$ alkenyl),
c) —($C_{0\text{-}5}$ alkyl)—($C_{3\text{-}7}$ cycloalkyl),
d) —($C_{0\text{-}6}$ alkyl)—$RA_{3\text{-}RA\text{-}12}$, or
e) —($C_{0\text{-}6}$ alkyl)—$RA_{3\text{-}RA\text{-}15}$;

wherein $R_{3\text{-}100}$ is independent of and defined the same as $R_{1\text{-}100}$ wherein $RA_1$ is $RA_3$;
wherein $R_{3\text{-}500}$ is independent of and defined the same as $R_{1\text{-}100}$ wherein $RA_1$ is $RA_3$;
wherein $RA_3$ is independent of and defined the same as $RA_1$;
wherein $RA_{3\text{-}RA\text{-}12}$, $RA_{3\text{-}RA\text{-}15}$, $RA_{3\text{-}RA\text{-}12\text{-}AXA}$ and $RA_{3\text{-}RA\text{-}15\text{-}AXA}$, are all independent of and defined the same as the corresponding $R_1$ variables, which are: $RA_{1\text{-}RA\text{-}12}$, $RA_{1\text{-}RA\text{-}15}$, $RA_{1\text{-}RA\text{-}12\text{-}AXA}$ and $RA_{1\text{-}RA\text{-}15\text{-}AXA}$, respectively,
or wherein $R_2$ and $R_3$ can be taken together to form a ring comprised of the following groups,
a) —($C_{5\text{-}9}$ cycloalkyl), b) —(C$_{5-9}$ cycloalkyl) substituted with one to three: —OH, =N—OH, =O, R$_{3-9}$,
c) —(C$_{1-5}$ alkyl substituted with zero to two R$_{3-9}$)—R$_{23}$—(C$_{1-5}$ alkyl substituted with zero to two R$_{3-9}$)—,
d) a 5- or 6-membered saturated ring containing one (1) or two (2) oxygen atoms, or or
e) a double bond represented by the formula shown below;

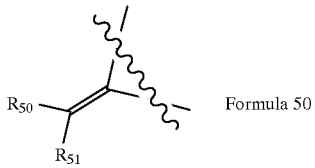

Formula 50 wherein R$_{3-9}$ is
a) —(C$_{1-6}$ alkyl),
b) —(C$_{2-7}$ alkenyl),
c) —(C$_{0-6}$ alkyl)—(C$_{3-7}$ cycloalkyl),
d) —(C$_{0-6}$ alkyl)—RA$_{3-RA-12}$, or
e) —(C$_{0-6}$ alkyl)—RA$_{3-RA-15}$;
wherein R$_{11}$ is
a) —H,
b) —C$_1$–C$_4$ alkyl,
c) —(RA$_{3-RA-12}$), or
d) pharmaceutically acceptable salts,
wherein R$_{23}$ is
a) —O—,
b) —C(O)—,
c) —N(H)—,
d) —N(R$_{3-9}$)—,
e) —N(C(O)—R$_{3-9}$)—, or
f) —N(C(O)—O—R$_{3-9}$);
wherein R$_{30}$ is
a) -morpholino,
b) -piperidino,
c) -piperazino,
d) —OR$_{40}$,
e) -halo,
f)

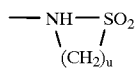

g) —NR$_{40}$R$_{41}$;
wherein R$_{40}$ and R$_{41}$ are defined independently and are,
a) —H,
b) —C$_1$–C$_4$ alkyl,
c) phenyl, substituted with zero (0) to three (3) RA$_{1-RA-120}$,
wherein R$_{42}$ is
a) —C$_1$–C$_4$ alkyl,
b) —phenyl, substituted with zero (0) to three (3) RA$_{1-RA-120}$, or
c) —(C$_{0-6}$ alkyl)-phenyl, substituted with zero (0) to three (3) RA$_{1-RA-120}$;
wherein RA$_{2-RA-120}$ and RA$_{3-RA-120}$ are independent of and defined the same as RA$_{1-RA-120}$;
wherein R$_{50}$ and R$_{51}$ are defined independently and are
a) —(H or C$_{1-6}$ alkyl),
b) —(C$_{0-6}$ alkyl)—RA$_{3-RA-12}$, or
c) —(C$_{0-6}$ alkyl)—RA$_{3-RA-15}$;

wherein AA is an amino acid residue,
wherein P$_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof,
with the proviso that when R$_1$ is 1-phenylpropyl and R$_2$ is H, then R$_3$ is not C$_{1-5}$ alkyl, and
with the proviso that when RA$_1$ or RA$_3$ is —G$_{1-2}$—(C$_{0-6}$ alkyl)—O—RA$_{1-RA-12}$, —(C$_{0-6}$ alkyl)—G$_{1-2}$—(C$_{0-6}$ alkyl)—O—(C$_{0-6}$ alkyl), —(C$_{0-6}$ alkyl)—G$_{1-2}$—O—(C$_{1-6}$ alkyl)—RA$_{1-RA-12}$, —(C$_{0-6}$ alkyl)—G$_{1-2}$—O—(C$_{1-6}$ alkyl)—RA$_{1-RA-15}$, —G$_{1-2}$—N(R$_{42}$)$_2$, or —G$_{1-2}$—NH$_2$, then G$_{1-2}$ is NOT, —C(O)—NH—, —NH—SO$_2$—, —SO$_2$—NH—, —NH—SO$_2$—NH—, —C(O)—O—, —NH—C(O)—NH, —N((C$_{1-6}$ alkyl)—RA$_{1-RA-12}$)—SO$_2$—, or —N((C$_{0-6}$ alkyl)—(C$_{1-6}$ alkyl))—SO$_2$—.

2. A compound selected from the following compounds
BX-1)
5H-Furan-2-one, 5-benzyl-3-cyclopropylphenylmethyl-4-hydroxy-,
BX-2)
2(5H)-Furanone, 3(cyclopropylphenylmethyl)—4-hydroxy-5-(2-phenylethyl)—,
BX-3)
2(5H)-Furanone, 3-(cyclopropylphenylmethyl)—4-hydroxy-5-(3-phenylpropyl)—,
BX-4)
2(5H)-Furanone, 3-(cyclopropylphenylmethyl)—4-hydroxy-5-propyl-,
BX-5)
2(5H)-Furanone, 5-(2-cyclohexylethyl)—3-(cyclopropylphenylmethyl)-4-hydroxy-,
BX-6)
2(5H)-Furanone, 3-(cyclopropylphenylmethyl)-4-hydroxy-5-(3-phenyl-2-propenyl)-,
BX-7)
2(5H)-Furanone, 3-(cyclopropylphenylmethyl)-4-hydroxy-5-(1-hydroxy-3-phenyl-2-propenyl)-,
BX-8)
2(5H)-Furanone, 3-(cyclopropylphenylmethy)-4-hydroxy-5-(1-hydroxy-3-phenylpropyl)—,
BX-9)
2(5H)-Furanone, 4-hydroxy-5-(phenylmethyl)-3-(1-phenylpropyl)-,
BX-10)
2(5H)-Furanone, 3-(cyclopropylphenylmethyl)-4-hydroxy-5-(1-methylethyl)-,
BX-11)
2(5H)-Furanone, 5-butyl-3-(cyclopropylphenylmethyl)-4-hydroxy-,
BX-12)
2(5H)-Furanone, 3-(cyclopropylphenylmethyl)-4-hydroxy-5,5-dipropyl-,
BX-13)
2(5H)-Furanone, 3-(cyclopropylphenylmethyl)-4-hydroxy-5,5-bis(1-methylethyl)-,
BX-14)

2(5H)-Furanone, 3-(cyclopropylphenylmethyl)-5,5-diethyl-4-hydroxy-,
BX-15) 2(5H)-Furanone, 5,5-dibutyl-3-(cyclopropyl phenylmethyl)-4-hydroxy-,
BX-16) 2(5H)-Furanone, 4-hydroxy-5-(2-phenylethyl)-3-(1-phenylpropyl)-.

3. A compound selected from the following compounds,
CX-1) 1-Oxaspiro[4.4]non-3-en-2-one, 3-(cyclopropylphenylnethyl)-4-hydroxy-,
CX-2) 1-Oxaspiro[4.7]dodec-3-en-2-one, 3-(cyclopropylphenylmethyl)-4-hydroxy-,
CX-3) 2(5H)-Furanone, 3-(cyclopropylphenylmethyl)-4-hydroxy-methyl-5-(2-phenylethyl)-.

4. A compound selected from the following compounds,
DX-1) 2(5H)-Furanone, 3-(cyclopropylphenylmethyl)-4-hydroxy-5-(3-phenylpropyl)-5-propyl-,
DX-2) 2(5H)-Furanone, 3-(cyclopropylphenylmethyl)-hydroxy-5-methyl-5-(phenylmethyl)-,
DX-3) 2(5H)-Furanone, 3-(cyclopropylphenylmethyl)-5-ethyl-4-hydroxy-5-(phenylmethyl)-,
DX-4) 2(5H)-Furanone, 3-(cyclopropylphenylmethyl)-4-hydroxy-5-(phenylmethyl)- 5-propyl-,
DX-5) 2(5H)-Furanone, 3-(cyclopropylphenylmethyl)-4-hydroxy-5,5-bis(phenylmethyl)-,
DX-6) 2(5H)-Furanone, 3-(cyclopropylphenylmethyl)-4-hydroxy-5-propyl-5-(3-pyridinylmethyl)-,
DX-7) 2(5H)-Furanone, 3-(cyclopropylphenylmethyl)-5-ethyl-4-hydroxy-5-(2-phenyl-ethyl)-,
DX-8) 2(5H)-Furanone, 3-(cyclopropylphenylmethyl)-4-hydroxy-5-(2-phenyl-ethyl)-5-propyl-,
DX-9) 2(5H)-Furanone, 3-(cyclopropylphenylmethyl)-4-hydroxy-5,5-bis(2-phenylethyl)-,
DX-10) 2(5H)-Furanone, 3-(cyclopropylphenylmethyl)-4-hydroxy-5-methyl-5-(3-phenylpropyl)-,
DX-1 1) 2(5H)-Furanone, 3-(cyclopropylphenylmethyl)-5-ethyl-4-hydroxy-5-(3-phenylpropyl)-,
DX-12) 2(5H)-Furanone, 5-butyl-3-(cyclopropylphenylmethyl)-4-hydroxy-5-(3-phenylpropyl)-,
DX-13) 2(5H)-Furanone, 3-(cyclopropylphenylmethyl)-4-hydroxy-5,5-bis(3-phenylpropyl)-,
DX-14) 2(5H)-Furanone, 5-(cyclopropylmethyl)-3-cyclopropylphenylmethyl)-hydroxy-5-(3-phenylpropyl)-,
DX-15) 2(5H)-Furanone, 3-(cyclopropylphenylmethyl) hydroxy-5-(phenylmethyl)-5-(3-phenylpropyl)-,
DX-16) 2(5H)-Furanone, 3-(cyclopropylphenylmethyl)-4-hydroxy-5-(3-phenylpropyl)-5-(2-propenyl)-,
DX-17) 2(5H)-Furanone, 3-(cyclopropylphenylmethyl)-4-hydroxy-5-(1 -methylethyl)-5-(3-phenylpropyl)-,
DX-18) 2(5H)-Furanone, 3-(cyclopropylphenylmethyl)4-hydroxy-5-(2-phenyl-ethyl)-5-(3-phenylpropyl)-,
DX-19) 2(5H)-Furanone, 3-(cyclopropylphenylmethyl) hydroxy-5-(1-methylpropyl)-5-(3-phenylpropyl)-,
DX-20) 2(5H)-Furanone, 3-(cyclopropylphenylmethyl)-4-hydroxy-5-(2-methylpropyl)-5-(3-phenylpropyl)-.

5. A compound selected from the following compounds,
FX-1) 2(5H)-Furanone, 3-(1,2-diphenylethyl)-4-hydroxy-5-(3-phenylpropyl)-,
FX-2) 2(5H)-Furanone, 3-(diphenylmethyl)-4-hydroxy-5-(3-phenylpropyl)-,
FX-3) 2(5H)-Furanone, 4-hydroxy-3-(1-phenyl-2-propenyl)-5-(3-phenylpropyl)-,
FX-4) 2(5H)-Furanone, 4-hydroxy-3-(2-methyl-1-phenylpropyl)-5-(3-phenylpropyl)-,
FX-5) 2(5H)-Furanone, 3-(2,2-dimethyl-1-phenylpropyl)-4-hydroxy-5-(3-phenylpropyl)-.

6. A compound selected from the following compounds,
GX-1) 2(5H)-Furanone, 3-(cyclopropylphenylmethyl)-4-hydroxy-5-(1-(2-phenylethyl)pentyl)-,
GX-2) 2(5H)-Furanone, 3-(cyclopropylphenylmethyl)-4-hydroxy-5-(1-(2-phenylethyl)pentyl)-,
GX-3) 2(5H)-Furanone, 3-(cyclopropylphenylmethyl)-4-hydroxy-5-(1-methyl-3-phenylpropyl)-,
GX-4) 2(5H)-Furanone, 3-(cyclopropylphenylmethyl)-5-(1,3-diphenylpropyl)-4-hydroxy-,
GX-5) 2(5H)-Furanone, 3-(cyclopropylphenylmethyl)-5-(1-ethylpentyl)-4-hydroxy-,
GX6) 2(5H)-Furanone, 3-(cyclopropylphenylmethyl)-4-hydroxy-5-(1-phenylpropyl)-,
GX-7) 2(5H)-Furanone, 3-(cyclopropylphenylmethyl)-4-hydroxy-5-(1-phenylbutyl)-,
GX-8) 2(5H)-Furanone, 3-(cyclopropylphenylmethyl)-5-(1-ethylpropyl)-4-hydroxy-.

7. A compound selected from the following compounds,
HX-1) 2-Furanpropanoic acid, 4(cyclopropylphenylmethyl)-2,5-dihydro-3-hydroxy-5-oxo-.beta.-(2-phenylethyl)-, methyl ester,
HX-2) 2(5H)-Furanone, 3-(cyclopropylphenylmethyl)-4-hydroxy-(1-(2-hydroxyethyl)-3-phenylpropyl)-.

8. A compound selected from the following compounds,
IX-1) 2(5H)-Furanone, 3-(cyclopropyl(3-nitrophenyl)methyl)-4-hydroxy-5,5-dipropyl-,
IX-2) 2(5H)-Furanone, 4-hydroxy-3-(1-(3-nitrophenyl)propyl)-5,5-dipropyl-,
IX-3) 1-Oxaspiro[4.5]dec-3-en-2-one, 3-(cyclopropylphenylmethyl)-4-hydroxy-,
IX-4) 1-Oxaspiro[4.5]dec-3-en-2-one, 3-(cyclopropylphenylmethyl)-4-hydroxy -6-(2-phenylethyl)-,
IX-5) 1-Oxaspiro[4.5]dec-3-en-2-one, 3-(cyclopropylphenylmethyl)-4-hydroxy-6-(2-phenylethyl)-,
IX-6) 1-Oxaspiro[4.5]dec-3-en-2-one, 3-(cyclopropylphenylmethyl)-4-hydroxy-6-(2-phenylmethyl)-,
IX-7) 1-Oxaspiro[4.5]dec-3-en-2-one, 3-(cyclopropylphenylmethyl)-4-hydroxy-6-(2-phenylmethyl)-,
IX-8) 1-Oxaspiro[4.6]undec-3-en-2-one, 3-(cyclopropylphenylmethyl)-4-hydroxy-,
IX-9) 2(5H)-Furanone, 5-ethyl-4-hydroxy-3-(2-methyl-1-phenylpropyl)-5-(phenylmethyl)-,
IX-10) 2(5H)-Furanone, 5-ethyl-4-hydroxy-5-(phenylmethyl)-3-(1-phenylpropyl)-,
IX-11) 2(5H)-Furanone, 3-((3-aminophenyl)cyclopropylmethyl)-4-hydroxy-5,5-dipropyl-,
IX-12) 2(5H)-Furanone, 3-((3-aminophenyl)cyclopropylmethyl)-4-hydroxy-5,5-dipropyl-hydrochloride,
IX-13) 2(5H)-Furanone, 3-(1-(3-aminophenyl)propyl)-4-hydroxy-5,5-dipropyl-,
IX-14) Benzenesulfonamide, 4-cyano-N-(3-(cyclopropyl(2,5-dihydro-4-hydroxy-2-oxo-5,5-dipropyl-3-furanyl)methyl)phenyl)-, IX-15) Benzenesulfonamide, N-(3-(cyclopropyl(2,5-dihydro-4-hydroxy-2-oxo-5,5-dipropyl-3-furanyl)methyl)phenyl)-, IX-16) Benzenesulfonamide, N-(3-(cyclopropyl(2,5-dihydro-4-hydroxy-2-oxo-5,5-dipropyl-3-furanyl)methyl)phenyl)-4-fluoro-, IX-17) 1H-Imidazole-4-sulfonamide, N-(3-(cyclopropyl(2,5-dihydro-4-hydroxy-2-oxo-5,5-dipropyl-3-furanyl)methyl)phenyl)-1-methyl-, IX-18) 8-Quinolinesulfonamide, N-(3-(cyclopropyl(2,5-dihydrohydroxy-2-oxo-5,5-dipropyl-3-furanyl)methyl)phenyl)-, IX-19) 1-Naphthalenesulfonamide, N-(3-(cyclopropyl(2,5-dihydro-4-hydroxy-2-oxo-5,5-dipropyl-3-furanyl)methyl)phenyl)-, IX-20) Benzenesulfonamide, N-(3-(1-(2,5-dihydro-4-hydroxy-2-oxo-5,5-ipropyl-3-furanyl)propyl)phenyl)-, IX-21) Benzenesulfonamide, 4-Cyano-N-(3-(1-(4-hydroxy-2-oxo-5,5-dipropyl-2,5-dihydrofuran- 3-yl)-3-methyl-butyl)-phenyl)-, IX-22) 1H-Imidazole-4-sulfonamide, N-(3-(1-(4-hydroxy-2-oxo-5,5-dipropyl-2,5-dihydrofuran-3-yl)-3-methyl-butyl)-phenyl)-1-methyl-, IX-23) Benzenesulfonamide, 4-Cyano-N-(3-(1-(4-hydroxy-2-oxo-5,5-dipropyl-2,5-dihydrofuran-3-yl)-2-methyl-propyl)-phenyl)-, IX-24) 1H-Imidazole-4-sulfonamide, N-(3-(1-(4-hydroxy-2-oxo-5,5-dipropyl-2,5-dihydrofuran-3-yl)-2-methyl-propyl)-phenyl)-1-methyl-, IX-25) Benzenesulfonamide, 4-Cyano-N-(3-(1-(4-hydroxy-2-oxo-5,5-dipropyl-2,5-dihydrofuran-3-yl)-2,2-dimethyl-propyl)-phenyl)-, IX-26) 1H-Imidazole-4-sulfonamide, N-(3-(1-(4-hydroxy-2-oxo-5,5-dipropyl-2,5-dihydrofuran-3-yl)-2,2-dimethyl-propyl)-phenyl)-1-methyl-, IX-27) Benzenesulfonamide, N-(3-(1-(2,5-dihydro-4-hydroxy-2-oxo-5-(phenylmethyl)-5-propyl-3-furanyl)-2-methylpropyl)phenyl)-, IX-28) Benzenesulfonamide, 4cyano-N-(3-(1-(2,5-dihydro-4-hydroxy-2-oxo-5-(phenylmethyl)-5-propyl-3-furanyl)-2-methylpropyl)phenyl)-, IX-29) Benzenesulfonamide, N-(3-(1-(2,5-dihydro-4-hydroxy-2-oxo-5-(phenylmethyl)-5-propyl-3-furanyl)-2-methylpropyl)phenyl)-4fluoro-, IX-30) 1H-Imidazole-4-sulfonamnide, N-(3-(1-(2,5-dihydro-4-hydroxy-2-oxo-5-(phenyl methyl)-5-propyl-3-furanyl)-2-methylpropyl)phenyl)-1-methyl-, IX-31) 8-Quinolinesulfonamide, N-(3-(1-(2,5-dihydro-4-hydroxy-2-oxo-5-(phenylmethyl)-5-propyl-3-furanyl)-2-methylpropyl)phenyl)-, IX-32) Carbamic acid, (3-(cyclopropyl(2,5-dihydro-4-hydroxy-2-oxo-5,5-dipropyl-3-furanyl)methyl)phenyl)-, phenylmethyl ester, IX-33) 1-Oxaspiro[4.5]dec-3-en-2-one, 3-(cyclopropylphenylmethyl)-4-hydroxy-6-ethyl-, IX-34) 1-Oxaspiro[4.5]dec-3-en-2-one, 3-(cyclopropylphenylmethyl)-4-hydroxy-6-etyl-, IX-35) 5-cyano-2-pyridinesulfonamide, N-(3-(cyclopropyl (2,5-dihydro-4-hydroxy-2-oxo-5,5-dipropyl-3-furanyl)methyl)phenyl)-, IX-36) 1H-Imidazole-2-sulfonamide, N-(3-(cyclopropyl(2,5-dihydro-4-hydroxy-2-oxo-5,5-dipropyl-3-furanyl)methyl)phenyl)-, IX-37) 1-Methyl-1H-imidazole-2-sulfonamide, N-(3-(cyclopropyl(2,5-dihydro-4-hydroxy-2-oxo-5,5-dipropyl-3-furanyl)methyl)phenyl)-, IX-38) 2-Quinolinesulfonamide, N-(3-(cyclopropyl(2,5-dihydro-4-hydroxy-2-oxo-5,5-dipropyl-3-furanyl)methyl)phenyl)-, IX-39) Benzenesulfonamide, 4-cyano-N-(3-(1-(4-hydroxy-2-oxo-5,5-dipropyl- 2,5-dihydro-furan-3-yl)-2-phenyl-ethyl)-phenyl)-, IX-40) 1H-Imidazole-4-sulfonamide, N-(3-(1-(4-hydroxy-2-oxo-5,5-dipropyl-2,5-dihydrofuran-3-yl)-2-phenyl-ethyl)-phenyl)-1-methyl-, IX-41) Benzenesulfonamide, 4-cyano-N-(3-(cyclopentyl (2,5-dihydro-4-hydroxy-2-oxo-5,5-dipropyl-3-furanyl)methyl)phenyl)-, IX-42) 1H-Imidazole-4-sulfonamide, N-(3-(cyclopentyl (2,5-dihydro-4-hydroxy-2-oxo-5,5-dipropyl-3-furanyl)methyl)phenyl)-1-methyl-, IX-43) Benzenesulfonamide, 4-cyano-N-(3-(cyclopropyl-(5,5-dibenzyl-4-hydroxy-2-oxo-2,5-dihydro-3-furanyl)methyl)phenyl)-, IX-44) Benzenesulfonamide, N-(3-(cyclopropyl-(5,5-dibenzyl-4-hydroxy-2-oxo-2,5-dihydro-3-furanyl)methyl)phenyl)-4-fluoro-, IX-45) 1H-Imidazole-4-sulfonamide, N-(3-(cyclopropyl-(5,5-dibenzyl-4-hydroxy-2-oxo-2,5-dihydro-3-furanyl)methyl)phenyl)-1-methyl-, IX-46) 8-Quinolinesulfonamide, N-(3-(cyclopropyl-(5,5-dibenzyl-4-hydroxy-2-oxo-2,5-dihydro-3-furanyl)methyl)phenyl)-, IX-47) Benzenesulfonamide, 4-cyano-N-(3-((5,5-dipropyl-4-hydroxy-2-oxo-2,5-dihydro-3-furanyl)-phenyl-methyl)phenyl)-, IX-48) 1H-Imidazole-4-sulfonamide, N-(3-((5,5-dipropyl-4-hydroxy-2-oxo-2,5-dihydro-3-furanyl)-phenyl-methyl)phenyl-1-methyl-, IX-49) Benzenesulfonamide, 4cyano-3-cyclopentyl-N-(3-(cyclopentyl(2,5-dihydro-4-hydroxy-2-oxo-5,5-dipropyl-3-furanyl)methyl)phenyl-, IX-50) 1H-Tetrazole-5-sulfonamide, N-(3-(cyclopropyl-(4-hydroxy-2-oxo-5,5-dipropyl-2,5-dihydro-furan-3-yl)-methyl)-phenyl)-1-phenyl-, IX-51) 1H-Benzoimidazole-2-sulfonamide, N-(3-(cyclopropyl-(4-hydroxy-2-oxo-5,5-dipropyl-2,5-dihydro-furan-3-yl)-methyl)-phenyl)-, IX-52) 2-Pyridinesulfonamide, N-(3-(cyclopropyl-(4-hydroxy-2-oxo-5,5-propyl-2,5-dihydro-furan-3-yl)-methyl)-phenyl)-, IX-53) 1H-Imidazole-4-sulfonamide, N-(3-(1-(4-hydroxy-2-oxo-5,5-dipropyl-2,5-dihydro-furan-3-yl)-2,2-dimethyl-propyl)-phenyl)-1-methyl-, IX-54) Benzenesulfonamide, 4-Cyano-N-(3-(1-(4-hydroxy-2-oxo-5,5-dipropyl-2,5-dihydro-furan-3-yl)-2,2-dimethyl-propyl)-phenyl)-, IX-55) 2-Pyrimidinesulfonamide, N-(3-(cyclopropyl-(4-hydroxy-2-oxo-5,5-dipropyl-2,5-dihydro-furan-3-yl)-methyl)-phenyl)-, IX-56) Benzenesulfonamide 4-Cyano-N-(3-(4-hydroxy-2-oxo- 5,5-dipropyl-2,5-dihydro-furan-3-ylmethyl)-phenyl)-, IX-57) 1H-Tetrazole-5-sulfonamide, N-(3-(cyclopropyl-(4-hydroxy-2-oxo-5,5-dipropyl-2,5-dihydro-furan-3-yl)-methyl)-phenyl)-1-methyl-, IX-58) 3-(Cyclopropyl-phenyl-methyl)-4-hydroxy-2-oxo-1-oxa-8-aza-spiro[4.5]dec-3-ene-8-carboxylic acid.

9. A compound selected from the following compounds,

JX-1) 3-(Cyclopropyl-phenyl-methyl)-4-hydroxy-5-(3-phenyl-propylidene)-5H-furan-2-one, JX-2) 5-Benzylidene-3-(cyclopropyl-phenyl-methyl)-4-hydroxy-5H-furan-2-one, JX-3) 3-(Cyclopropyl-phenyl-methyl)-4-hydroxy-5-propylidene-5H-furan-2-one, JX-4) 5-Butylidene-3-(cyclopropyl-phenyl-methyl)-4-hydroxy-5H-furan-2-one, or OX-1) 3-(Cyclopropyl-phenyl-methyl)-4-hydroxy-2-oxo-1-oxa-8-aza-spiro[4.5]dec-3-ene -8-carboxylic acid tert-butyl ester, OX-2) 3-(Cyclopropyl-phenyl-methyl)-4-hydroxy-1-oxa-8-aza-spiro[4.5]dec-3-en-2-one.

10. A compound selected from the following compounds, a) 2-Pyrimidinesulfonamide, N-(3-(cyclopropyl(2,5-dihydro-4-hydroxy-2-oxo-5,5-dipropyl-3-furanyl)methyl)phenyl)-, b) 2-Quinazolinesulfonamide, N-(3-(cyclopropyl(2,5-dihydro-4-hydroxy-2-oxo-5,5-dipropyl-3-furanyl)methyl)phenyl)-, c) 4-Thiazolesulfonamide, N-(3-(cyclopropyl(2,5-dihydro-4-hydroxy-2-oxo-5,5-dipropyl-3-furanyl)methyl)phenyl)-, d) 7H-Purine-6-sulfonamide, N-(3-(cyclopropyl(2,5-dihydro-4-hydroxy-2-oxo-5,5-dipropyl-3-furanyl)methyl)phenyl)-, e) Benzenesulfonamide, N-(3-(cyclopropyl-(5,5-dibenzyl-4-hydroxy-2-oxo-2,5-dihydro-3-furanyl)methyl)phenyl)-, f) 2-Pyridinesulfonamide, N-(3-(cyclopropyl-(5,5-dibenzyl-4-hydroxy-2-oxo-2,5-dihydro-3-furanyl)methyl)phenyl)-, g) 5-cyano-2-pyridinesulfonamide, N-(3-(cyclopropyl-(5,5-dibenzyl-4-hydroxy-2-oxo-2,5-dihydro-3-furanyl)methyl)phenyl)-, h) 2-Quinolinesulfonamide, N-(3-(cyclopropyl-(5,5-benzylhydroxy-2-oxo-2,5-dihydro-3-furanyl)methyl)phenyl)-, i) 2-Pyrimidinesulfonamide, N-(3-(cyclopropyl-(5,5-dibenzyl-4-hydroxy-2-oxo-2,5-dihydro-3-furanyl)methyl)phenyl)-, j) 2-Quinazolinesulfonamide, N-(3-(cyclopropyl-(5,5-dibenzyl-4-hydroxy-2-oxo-2,5-dihydro-3-furanyl)methyl)phenyl)-, k) 1H-Benzimidazole-2-sulfonamide, N-(3-(cyclopropyl-(5,5-dibenzyl-4-hydroxy-2-oxo-2,5-dihydro-3-furanyl)methyl)phenyl)-, l) 1H-Imidazole-2-sulfonamide, N-(3-(cyclopropyl-(5,5-dibenzyl-4-hydroxy-2-oxo-2,5-dihydro-3-furanyl)methyl)phenyl)-, m) 4-Thiazolesulfonamide, N-(3-(cyclopropyl-(5,5-dibenzyl-4-hydroxy-2-oxo-2,5-dihydro-3-furanyl)methyl)phenyl)-, n) 7H-Purine-6-sulfonamide, N-(3-(cyclopropyl-(5,5-dibenzyl-4-hydroxy-2-oxo-2,5-dihydro-3-furanyl)methyl)phenyl)-, o) Benzenesulfonamide, N-(3-(1-(4-hydroxy-2-oxo-5,5-dipropyl-2,5-dihydro-3-furanyl)-2,2-dimethyl-propyl)-phenyl)-, p) 2-Pyridinesulfonamide, N-(3-(1-(4-hydroxy-2-oxo-5,5-dipropyl-2,5-dihydro-3-furanyl)-2,2-dimethyl-propyl)-phenyl)-, q) 5-cyano-2-pyridinesulfonamide, N-(3-(1-(4-hydroxy-2-oxo-5,5-dipropyl-2,5-dihydro-3-furanyl)-2,2-dimethyl-propyl)-phenyl)-, r) 2-Quinolinesulfonamide, N-(3-(1-(4-hydroxy-2-oxo-5,5-dipropyl-2,5-dihydro-3-furanyl)-2,2-dimethyl-propyl)-phenyl)-, s) 2-Pyrimidinesulfonamide, N-(3-(1-(4-hydroxy-2-oxo-5,5-dipropyl-2,5-dihydro-3-furanyl)-2,2-dimethyl-propyl)-phenyl)-, t) 2-Quinazolinesulfonamide, N-(3-(1-(4-hydroxy-2-oxo-5,5-dipropyl-2,5-dihydro-3-furanyl)-2,2-dimethyl-propyl)-phenyl)-, u) 1H-Benzimidazole-2-sulfonamide, N-(3-(1-(4-hydroxy-2-oxo5,5-dipropyl-2,5-dihydro-3-furanyl)-2,2-dimethyl-propyl)-phenyl)-, v) 1H-Imidazole-2-sulfonamide, N-(3-(1-(4-hydroxy-2-oxo-5,5-dipropyl-2,5-dihydro-3-furanyl)-2,2-dimethyl-propyl)-phenyl)-, w) 4-Thiazolesulfonamide, N-(3-(1-(4-hydroxy-2-oxo-5,5-dipropyl-2,5-dihydro-3-furanyl)-2,2-dimethyl-propyl)-phenyl)-, x) 7H-Purine-6-sulfonamide, N-(3-(1-(4-hydroxy-2-oxo-5,5-ipropyl-2,5-dihydro-3-furanyl)-2,2-dimethyl-propyl)-phenyl)-, y) Benzenesulfonamide, N-3-(1-(5,5-dibenzyl-4-hydroxy-2-oxo-2,5-dihydro-3-furanyl)-2,2-dimethyl-propyl)-phenyl)-, z) Benzenesulfonamide, 4cyano-N-3-(1-(5,5-dibenzyl-4-hydroxy-2-oxo-2,5-dihydro-3-furanyl)-2,2-dimethyl-propyl)-phenyl)-, a1) 1H-Imidazole-4-sulfonamide, N-3-(1-(5,5-dibenzyl-4-hydroxy-2-oxo-2,5-dihydro-3-furanyl)-2,2-dimethyl-propyl)-phenyl)-1-methyl-, b1) 2-Pyridinesulfonamide, N-3-(1-(5,5-dibenzyl-4-hydroxy-2-oxo-2,5-dihydro-3-furanyl)-2,2-dimethyl-propyl)-phenyl)-, c1) 5-cyano-2-pyridinesulfonamide, N-3-(1-(5,5-dibenzyl-4-hydroxy-2-oxo-2,5-dihydro-3-furanyl)-2,2-dimethyl-propyl)-phenyl)-, d1) 2-Quinolinesulfonamide, N-3-(1-(5,5-dibenzyl-hydroxy-2-oxo-2,5-dihydro-3-furanyl)-2,2-dimethyl-propyl)-phenyl)-, e1) 2-Pyrimidinesulfonamide, N-3-(1-(5,5-dibenzyl-4-hydroxy-2-oxo-2,5-dihydro-3-furanyl)-2,2-dimethyl-propyl)-phenyl)-, f1) 2-Quinazolinesulfonamide, N-3-(1-(5,5-dibenzyl-4-hydroxy-2-oxo-2,5-dihydro-3-furanyl)-2,2-dimethyl-propyl)-phenyl)-, g1) 1H-Benzimidazole-2-sulfonamide, N-3-(1-(5,5-dibenzyl-4-hydroxy-2-oxo-2,5-dihydro-3-furanyl)-2,2-dimethyl-propyl)-phenyl)-, h1) 1H-Imidazole-2-sulfonamide, N-3-(1-(5,5-dibenzyl-4-hydroxy-2-oxo-2,5-dihydro-3-furanyl)-2,2-dimethyl-propyl)-phenyl)-, i1) 4-Thiazolesulfonamide, N-3-(1-(5,5-dibenzyl-4-hydroxy-2-oxo-2,5-dihydro-3-furanyl)-2,2-dimethyl-propyl)-phenyl)-, j1) 7H-Purine-6-sulfonamide, N-3-(1-(5,5-dibenzyl-hydroxy-2-oxo-2,5-dihydro-3-furanyl)-2,2-dimethyl-propyl)-phenyl)-.

11. A compound of claim 1 selected from the following compounds, a) N-(3-(Cyclopropyl-(4-hydroxy-2-oxo-5,5-dipropyl-2,5-dihydro-3-furanyl)-methyl)-phenyl)—N-methyl-benzenesulfonamide, b) 4-yano-N-(3-(cyclopropyl-(4-hydroxy-2-oxo-5,5-dipropyl-2,5-dihydro-3-furanyl)-methyl)-phenyl)—N-methyl-benzenesulfonamide, c) 1-Methyl-1H-imidazole-4-sulfonic acid (3-(cyclopropyl-(4-hydroxy-2-oxo-5,5-dipropyl-2,5-dihydro-3-furanyl)-methyl)-phenyl)-methyl-amide, d) Pyridine-2-sulfonic acid (3-(cyclopropyl-(4-hydroxy-2-oxo-5,5-dipropyl-2,5-dihydro-3-furanyl)-methyl)-phenyl)-methyl-amide, e) 5-Cyano-pyridine-2-sulfonic acid (3-(cyclopropyl-(4-hydroxy-2-oxo-5,5-dipropyl-2,5-dihydro-3-furanyl)-methyl)-phenyl)-methyl-amide, f) Quinoline-2-sulfonic acid (3-(cyclopropyl-(4-hydroxy-2-oxo-5,5-dipropyl-2,5-dihydro-3-furanyl)-methyl)-phenyl)-methyl-amide, g) Pyrimidine-2-sulfonic acid (3-(cyclopropyl-(4-hydroxy-2-oxo-5,5-dipropyl-2,5-dihydro-3-furanyl)-methyl)-phenyl)-methyl-amide, h) Quinazoline-2-sulfonic acid (3-(cyclopropyl-(4-hydroxy-2-oxo-5,5-dipropyl-2,5-dihydro-3-furanyl)-methyl)-phenyl)-methyl-amide, i) 1H-Benzimidazole-2-sulfonic acid (3-(cyclopropyl-(4-hydroxy-2-oxo-5,5-dipropyl-2,5-dihydro-3-furanyl)-methyl)-phenyl)-methyl-amide, j) 1H-Imidazole-2-sulfonic acid (3-(cyclopropyl-(4-hydroxy-2-oxo-5,5-dipropyl-2,5-dihydro-3-furanyl)-methyl)-phenyl)-methyl-amide, k) Thiazole-4-sulfonic acid (3-(cyclopropyl-(4-hydroxy-2-oxo-5,5-dipropyl-2,5-dihydro-3-furanyl)-methyl)-phenyl)-methyl-amide, l) 7H-Purine-6-sulfonic acid (3-(cyclopropyl-(4-hydroxy-2-oxo-5,5-dipropyl-2,5-dihydro-3-furanyl)-methyl)-phenyl)-methyl-amide, m) N-(3-(1-(4-hydroxy-2-oxo-5,5-dipropy-2,5-dihydro-3-furanyl)-2,2-ethyl-propyl)-phenyl)—N-methyl-benzenesulfonamide, n) 4-Cyano-N-(3-(1-(4-hydroxy-2-oxo-5,5-dipropyl-2,5-dihydro-3-furanyl)-2,2-dimethyl-propyl)-phenyl)-N-methyl-benzenesulfonamide, o) 1-Methyl-1H-imidazole-4-sulfonic acid (3-(1-(4-hydroxy-2-oxo-5,5-dipropyl-2,5-dihydro-3-furanyl)-2,2-dimethyl-propyl)-phenyl)-methyl-amide, p) Pyridine-2-sulfonic acid (3-(1-(4-hydroxy-2-oxo-5,5-dipropyl-2,5-dihydro-3-furanyl)-2,2-dimethyl-propyl)-phenyl)-methyl-amide, q) 5-Cyano-pyridine-2-sulfonic acid (3-(1-(4-hydroxy-2-oxo-5,5-dipropyl-2,5-dihydro-3-furanyl)-2,2-dimethyl-propyl)-phenyl)-methyl-amide, r) Quinoline-2-sulfonic acid (3-(1-(4-hydroxy-2-oxo-5,5-dipropyl-2,5-dihydro-3-furanyl)-2,2-dimethyl-propyl)-phenyl)-methyl-amide, s) Pyrimidine-2-sulfonic acid (3-(1-(4-hydroxy-2-oxo-5,5-dipropyl-2,5-dihydro-3-furanyl)-2,2-dimethyl-propyl)-phenyl)-methyl-amide, t) Quinazoline-2-sulfonic acid (3-(1-(4-hydroxy-2-oxo-5,5-dipropyl-2,5-dihydro-3-furanyl)-2,2-dimethyl-propyl)-phenyl)-methyl-amide, u) 1H-Benzimidazole-2-sulfonic acid (3-(1-(4-hydroxy-2-oxo-5,5-dipropyl-2,5-dihydro-3-furanyl)-2,2-dimethyl-propyl)-phenyl)-methyl-amide, v) 1H-Imidazole-2-sulfonic acid (3-(1-(4-hydroxy-2-oxo-5,5-dipropyl-2,5-dihydro-3-furanyl)-2,2-dimethyl-propyl)-phenyl)-methyl-amide, w) Thiazole-4-sulfonic acid (3-(1-(4-hydroxy-2-oxo-5,5-dipropyl-2,5-dihydro-3-furanyl)-2,2-dimethyl-propyl)-phenyl)-methyl-amide, x) 7H-Purine-6-sulfonic acid (3-(1-(4-hydroxy-2-oxo-5,5-dipropyl-2,5-dihydro-3-furanyl)-2,2-dimethyl-propyl)-phenyl)-methyl-amide, y) N-(3-(Cyclopropyl-(5,5-dibenzyl-4-hydroxy-2-oxo-2,5-dihydro-3-furanyl)-methyl)-phenyl)-N-methyl-benzenesulfonamide, z) 4-Cyano-N-(3-(cyclopropyl-(5,5-dibenzyl-4-hydroxy-2-oxo-2,5-dihydro-3-furanyl)-methyl)-phenyl)-N-methyl-benzenesulfonamide, a1) 1-Methyl-1H-imidazole-4-sulfonic acid (3-(cyclopropyl-(5,5-dibenzyl-4-hydroxy-2-oxo-2,5-dihydro-3-furanyl)-methyl)-phenyl)-methyl-amide, b1) Pyridine-2-sulfonic acid (3-(cyclopropyl-(5,5-dibenzyl-4-hydroxy-2-oxo-2,5-dihydro-3-furanyl)-methyl)-phenyl)-methyl-amide, c1) 5-Cyano-pyridine-2-sulfonic acid (3-(cyclopropyl-(5,5-dibenzyl-4-hydroxy-2-oxo-2,5-dihydro-3-furanyl)-methyl)-phenyl)-methyl-amide, d1) Quinoline-2-sulfonic acid (3-(cyclopropyl-(5,5-dibenzyl-4-hydroxy-2-oxo-2,5-dihydro-3-furanyl)-methyl)-phenyl)-methyl-amide, e1) Pyrimidine-2-sulfonic acid (3-(cyclopropyl-(5,5-dibenzyl-4-hydroxy-2-oxo-2,5-dihydro-3-furanyl)-methyl)-phenyl)-methyl-amide, f1) Quinazoline-2-sulfonic acid (3-(cyclopropyl-(5,5-dibenzyl-4-hydroxy-2-oxo-2,5-dihydro-3-furanyl)-methyl)-phenyl)-methyl-amide, g1) 1H-Benzimidazole-2-sulfonic acid (3-(cyclopropyl-(5,5-dibenzyl-4-hydroxy-2-oxo-2,5-dihydro-3-furanyl)-methyl)-phenyl)-methyl-amide, h1) 1H-Imidazole-2-sulfonic acid (3-(cyclopropyl-(5,5-dibenzyl-4-hydroxy-2-oxo-2,5-dihydro-3-furanyl)-methyl)-phenyl)-methyl-amide, i1) Thiazole-4-sulfonic acid (3-(cyclopropyl-(5,5-dibenzyl-4-hydroxy-2-oxo-2,5-hydro-3-furanyl)-methyl)-phenyl)-methyl-amide, j1) 7H-Purine-6-sulfonic acid (3-(cyclopropyl-(5,5-dibenzyl-4-hydroxy-2-oxo-2,5-dihydro-3-furanyl)-methyl)-phenyl)-methyl-amide, k1) N-(3-(1-(5,5-dibenzyl-4-hydroxy-2-oxo-2,5-dihydro-3-furanyl)-2,2-methyl-propyl)-phenyl)-N-methyl-benzenesulfonamide, l1) 4-yano-N-(3-(1-(5,5-dibenzyl-4-hydroxy-2-oxo-2,5-dihydro-3-furanyl)-2,2-dimethyl-propyl)-phenyl)-N-methyl-benzenesulfonamide, m1) 1-Methyl-1H-imidazole-4-sulfonic acid (3-(1-(5,5-dibenzyl-4-hydroxy-2-oxo-2,5-dihydro-3-furanyl)-2,2-dimethyl-propyl)-phenyl)-methyl-amide, n1) Pyridine-2-sulfonic acid (3-(1-(5,5-dibenzyl-4-hydroxy-2-oxo-2,5-dihydro-3-furanyl)-2,2-dimethyl-propyl)-phenyl)-methyl-amide, o1) 5-Cyano-pyridine-2-sulfonic acid (3-(1-(5,5-dibenzyl-4-hydroxy-2-oxo-2,5-dihydro-3-furanyl)-2,2-dimethyl-propyl)-phenyl)-methyl-amide, p1) Quinoline-2-sulfonic acid (3-(1-(5,5-dibenzyl-4-hydroxy-2-oxo-2,5-dihydro-3-furanyl)-2,2-dimethyl-propyl)-phenyl)-methyl-amide, q1) Pyrimidine-2-sulfonic acid (3-(1-(5,5-dibenzyl-4-hydroxy-2-oxo-2,5-dihydro-3-furanyl)-2,2-dimethyl-propyl)-phenyl)-methyl-amide, r1) Quinazoline-2-sulfonic acid (3-(1-(5,5-dibenzyl-4-hydroxy-2-oxo-2,5-dihydro-3-furanyl)-2,2-dimethyl-propyl)-phenyl)-methyl-amide, s1) 1H-Benzimidazole-2-sulfonic acid (3-(1-(5,5-dibenzyl-4-hydroxy-2-oxo-2,5-dihydro-3-furanyl)-2,2-dimethyl-propyl)-phenyl)-methyl-amide, t1) 1H-Imidazole-2-sulfonic acid (3-(1-(5,5-dibenzyl-4-hydroxy-2-oxo-2,5-dihydro-3-furanyl)-2,2-dimethyl-propyl)-phenyl)-methyl-amide, u1) Thiazole-4-sulfonic acid (3-(1-(5,5-dibenzyl-4-hydroxy-2-oxo-2,5-dihydro-3-furanyl)-2,2-dimethyl-propyl)-phenyl)-methyl-amide, v1) 7H-Purine-6-sulfonic acid (3-(1-(5,5-dibenzyl-4-hydroxy-2-oxo-2,5-dihydro-3-furanyl)-2,2-dimethyl-propyl)-phenyl)-methyl-amide.

12. A compound selected from the following compounds, a) 3-((3-Benzenesulfonylmethyl-phenyl)-cyclopropyl-methyl)-4-hydroxy-5,5-dipropyl-5H-furan-2-one, b) 4-(3-(Cyclopropyl-(4-hydroxy-2-oxo-5,5-dipropyl-2,5-dihydro-furan-3-yl)-methyl)-phenylmethanesulfonyl)-benzonitrile, c) 3-(Cyclopropyl-(3-(1-methyl-1H-imidazole-4-sulfonylmethyl)-phenyl)-methyl)-4-hydroxy-5,5-dipropyl-5H-furan-2-one, d) 3-(Cyclopropyl-(3-(pyridine-2-sulfonylmethyl)-phenyl)-methyl)4-hydroxy-5,5-dipropyl-5H-furan-2-one, e) 6-(3-(Cyclopropyl-(4-hydroxy-2-oxo-5,5-dipropyl-2,5-hydro-furan-3-yl)-methyl)-phenylmethanesulfonyl)-nicotinonitrile, f) 3-(Cyclopropyl-(3-(quinoline-2-sulfonylmethyl)-phenyl)-methyl)-4-hydroxy-5,5-dipropyl-5H-furan-2one, g) 3-(Cyclopropyl-(3-(pyrimidine-2-sulfonylmethyl)-phenyl)-methyl)-4-hydroxy-5,5-dipropyl-5H-furan-2-one, h) 3-(Cyclopropyl-(3-(quinazoline-2-sulfonylmethyl)-phenyl)-methyl)-4-hydroxy-5,5-dipropyl-5H-furan-2-one, i) 3-((3-(1H-Benzimidazole-2-sulfonylmethyl)-phenyl)-cyclopropyl-methyl)-4-hydroxy-5,5-dipropyl-5H-furan-2-one, j) 3-(Cyclopropyl-(3-(1H-imidazole-2-sulfonylmethyl)-phenyl)-methyl)-4-hydroxy-5,5-dipropyl-5H-furan-2-one, k) 3-(Cyclopropyl-(3-(thiazole-4-sulfonylmethyl)-phenyl)-methyl)-4-hydroxy-5,5-dipropyl-5H-furan-2-one, l) 3-(Cyclopropyl-(3-(7H-purine-6-sulfonylmethyl)-phenyl)-methyl)-4-hydroxy-5,5-dipropyl-5H-furan-2-one, m) 3-(1-(3-Benzenesulfonylmethyl-phenyl)-2,2-dimethyl-propyl)-4-hydroxy-5,5-dipropyl-5H-furan-2-one, n) 4(3-(1-(4-Hydroxy-2-oxo-5,5-dipropyl-2,5-dihydro-furan-3-yl)-2,2-dimethyl-propyl)-phenylmethanesulfonyl)-benzonitrile, o) 3-(2,2-Dimethyl-1-(3-(1-methyl-1H-imidazole-4-sulfonylmethyl)-phenyl)-propyl)-4-hydroxy-5,5-dipropyl-5H-furan-2-one, p) 3-(2,2-Dimethyl-1-(3-(pyridine-2-sulfonylmethyl)-phenyl)-propyl)-4-hydroxy-5,5-dipropyl-5H-furan-2-one, q) 6-(3-(1-(4-Hydroxy-2-oxo-5,5-dipropyl-2,5-dihydro-furan-3-yl)-2,2-dimethyl-propyl)-phenylmethanesulfonyl)-nicotinonitrile, r) 3-(2,2-Dimethyl-1-(3-(quinoline-2-sulfonylmethyl)-phenyl)-propyl)-4-hydroxy-5,5-dipropyl-5H-furan-2-one, s) 3-(2,2-Dimethyl-1-(3-(pyrimidine-2-sulfonylmethyl)-phenyl)-propyl)-4-hydroxy-5,5-dipropyl-5H-furan-2-one, t) 3-(2,2-Dimethyl-1-(3-(quinazoline-2-sulfonylmethyl)-phenyl)-propyl)-4-hydroxy-5,5-dipropyl-5H-furan-2-one, u) 3-(1-(3-(1H-Benzimidazole-2-sulfonylmethyl)-phenyl)-2,2-dimethyl-propyl)-hydroxy-5,5-dipropyl-5H-furan-2-one, v) 4-Hydroxy-3-(1-(3-(1H-imidazole-2-sulfonylmethyl)-phenyl)-2,2-dimethyl-propyl)-5,5-dipropyl-5H-furan-2-one, w) 3-(2,2-Dimethyl-1-(3-(thiazole-4-sulfonylmethyl)-phenyl)-propyl)-hydroxy-5,5-dipropyl-5H-furan-2-one, x) 3-(2,2-Dimethyl-1-(3-(7H-purine-6-sulfonylmethyl)-phenyl)-propyl)-4-hydroxy-5,5-dipropyl-5H-furan-2-one, y) 3-((3-Benzenesulfonylmethyl-phenyl)-cyclopropyl-methyl)-5,5-dibenzyl-4-hydroxy-5H-furan-2-one, z) 4-(3-(Cyclopropyl-(5,5-dibenzyl-4-hydroxy-2-oxo-2,5-dihydro-furan-3-yl)-methyl)-phenylmethanesulfonyl)-benzonitrile, a1) 5,5-Dibenzyl-3-(cyclopropyl-(3-(1-methyl-1H-imidazole-4-sulfonylmethyl)-phenyl)-methyl)-4-hydroxy-5H-furan-2-one, b1) 5,5-Dibenzyl-3-(cyclopropyl-(3-(pyridine-2-sulfonylmethyl)-phenyl)-methyl)-4-hydroxy-5H-furan-2-one, c1) 6-(3-(Cyclopropyl-(5,5-dibenzyl-4-hydroxy-2-oxo-2,5-ydro-furan-3-yl)-methyl)-phenylmethanesulfonyl)-nicotinonitrile, d1) 5,5-Dibenzyl-3-(cyclopropyl-(3-(quinoline-2-sulfonylmethyl)-phenyl)-methyl)-4-hydroxy-5H-furan-2-one, e1) 5,5-Dibenzyl-3-(cyclopropyl-(3-(pyrimidine-2-sulfonylmethyl)-phenyl)-methyl)-4-hydroxy-5H-furan-2-one, f1) 5,5-Dibenzyl-3-(cyclopropyl-(3-(quinazoline-2-sulfonylmethyl)-phenyl)-methyl)-4-hydroxy-5H-furan-2-one, g1) 3-((3-(1H-Benzimidazole-2-sulfonylmethyl)-phenyl)-cyclopropyl-methyl)-5,5-dibenzyl-4-hydroxy-5H-furan-2-one, h1) 5,5-Dibenzyl-3-(cyclopropyl-(3-(1H-imidazole-2-sulfonylmethyl)-phenyl)-methyl) hydroxy-5H-furan-2-one, i1) 5,5-Dibenzyl-3-(cyclopropyl-(3-(thiazole-4-sulfonylmethyl)-phenyl)-methyl)-4-hydroxy-5H-furan-2-one, j1) 5,5-Dibenzyl-3-(cyclopropyl-(3-(7H-purine-6-sulfonylmethyl)-phenyl)-methyl)-4-hydroxy-5H-furan-2-one, k1) 3-(1-(3-Benzenesulfonylmethyl-phenyl)-2,2dimethyl-propyl)-5,5-dibenzyl-4-hydroxy-5H-furan-2-one, l1) 4-(3-(1-(5,5-Dibenzyl-4-hydroxy-2-oxo-2,5-dihydro-furan-3-yl)-2,2-dimethyl-propyl)-phenylmethanesulfonyl)-benzonitrile, m1) 5,5-Dibenzyl-3-(2,2-dimethyl-1-(3-(1-methyl-1H-imidazole-4-sulfonylmethyl)-phenyl)-propyl)-4-hydroxy-5H-furan-2-one, n1) 5,5-Dibenzyl-3-(2,2-dimethyl-1-(3-(pyridine-2-sulfonylmethyl)-phenyl)-propyl)-4-hydroxy-5H-furan-2-one, o1) 6-(3-(1-(5,5-Dibenzyl-4-hydroxy-2-oxo-2,5-dihydro-furan-3-yl)-2,2-dimethyl-propyl)-phenylmethanesulfonyl)-nicotinonitrile, p1) 5,5-Dibenzyl-3-(2,2-dimethyl-1-(3-(quinoline-2-sulfonylmethyl)-phenyl)-propyl)-4-hydroxy-5H-furan-2-one, q1) 5,5-Dibenzyl-3-(2,2-dimethyl-1-(3-(pyrimidine-2-sulfonylmethyl)-phenyl)-propyl)-4-hydroxy-5H-furan-2-one, r1) 5,5-Dibenzyl-3-(2,2-dimethyl-1-(3-(quinazoline-2-sulfonylmethyl)-phenyl)-propyl)-4-hydroxy-5H-furan-2-one, s1) 3-(1-(3-(1H-Benzimidazole-2-sulfonylmethyl)-phenyl)-2,2-dimethyl-propyl)-5,5-dibenzyl-4-hydroxy-5H-furan-2-one, t1) 5,5-Dibenzyl-4-hydroxy-3-(1-(3-(1H-imidazole-2-sulfonylmethyl)-phenyl)-2,2-dimethyl-propyl)-5H-furan-2-one, u1) 5,5-Dibenzyl-3-(2,2-dimethyl-1-(3-(thiazole-4-sulfonylmethyl)-phenyl)-propyl)4-hydroxy-5H-furan-2-one, v1) 5,5-Dibenzyl-3-(2,2-dimethyl-1-(3-(7H-purine-6-sulfonylmethyl)-phenyl)-propyl)-4-hydroxy-5H-furan-2-one.

13. A pharmaceutical composition comprising a pharmaceutically acceptable carrier and an effective amount of a compound described in claim 1.

14. A method of administering an effective amount of a compound described by claim 1 to a patient in need thereof for the treatment of AIDS and diseases caused by all variants of HIV comprising administering an effective amount of said compound to said patient.

15. A compound represented by the structure shown in formula 1,

Formula 1

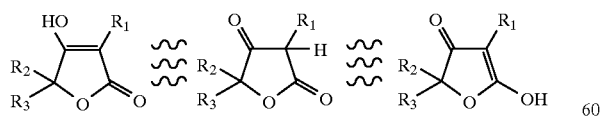

wherein 3 tautomers of the same structure are shown, wherein $R_1$ is a)

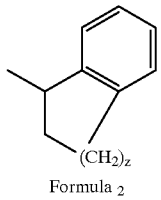

Formula 2 b)

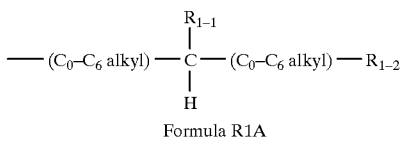

Formula R1A c)

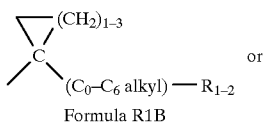

Formula R1B d)

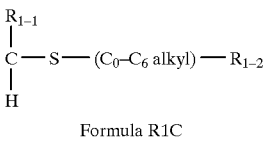

Formula R1C wherein $R_{1-1}$ is
a) —($C_{1-5}$ alkyl),
b) —($C_{2-5}$ alkenyl),
c) —($C_{3-7}$ cycloalkyl),
d) —($C_{3-5}$ cycloalkyl),
e) -cyclopropyl,
f) —($C_{1-5}$ alkyl)—($C_{3-7}$ cycloalkyl),
g) —$R_{1-100}$, or
h) —($C_1$–$C_5$ alkyl)—$R_{1-100}$;
wherein $R_{1-2}$ is —$R_{1-100}$, or —$R_{1-500}$;
wherein $R_{1-100}$ is
a) phenyl, substituted with zero (0) to three (3) of $RA_1$,
b) naphthyl, substituted with zero (0) to three (3) of $RA_1$,
c) biphenyl, substituted with zero (0) to three (3) of $RA_1$,
d) perhalophenyl;
wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
a) —H,
b) —($C_{1-5}$ alkyl),
c) —($C_{2-5}$ alkenyl),
d) —OH, e) —O—($C_{1-5}$ alkyl),
f) —O—($C_{2-5}$ alkenyl),
g) —C(O)OH,
h) —C(O)($C_{1-5}$ alkyl),
i) —C(O)—$RA_{1-3}$, wherein $RA_{1-3}$ is any N-terminus substituted amino acid,
j) —C(O)—N(H)$RA_{1-1}$,
k) —CN,
l) —$NH_2$ (para or meta positions),
m) —N(H)($C_{1-5}$ alkyl) (para or meta positions),
n) —N($C_{1-5}$ alkyl)$_2$,
o) —N(H)$RA_{1-4}$, wherein $RA_{1-4}$ is any C-terminus substituted amino acid,
p) —N(H)C(O)—$RA_{1-1}$ (para or meta positions),
q) —N(H)C(O)—O—$RA_{1-1}$ (para or meta positions),
r) —N(H)($SO_2$)—$RA_{1-2}$,
s) —N($C_{1-6}$ alkyl)($SO_2$)—$RA_{1-2}$,
t) —N($CH_3$)($SO_2$)—$RA_{1-2}$,
u) —$NO_2$,
v) —$PO_3H$,
w) —$SO_3H$,
x) —$SO_2NH_2$,
y) —($C_{0-6}$ alkyl)—$SO_2$—$RA_{1-RA-12}$,
z) —($C_{0-6}$ alkyl)—$SO_2$—$RA_{1-RA-15}$,
a1) -halo,
b1) —$RA_{1-RA-12}$, or
c1) —$RA_{1-RA-15}$;

wherein $RA_{1-1}$ is
a) —($C_{1-5}$ alkyl),
b) —($C_{1-5}$ alkyl)—C(O)—O—($C_{1-5}$ alkyl),
c) —($C_{1-5}$ alkyl)—$NH_2$,
d) —($C_{1-5}$ alkyl)—N(H)C(O)—O—($C_{1-5}$ alkyl),
e) —($C_{1-5}$ alkyl)—C((H)($NH_2$))—C(O)OH,
f) —$RA_{1-RA-12}$,
g) —$RA_{1-RA-15}$,
h) —($C_{1-5}$ alkyl)-RAX,
i) —($C_{1-5}$ alkyl)—O-RAX,
j) —C(O)—$RA_{1-1-3}$, wherein $RA_{1-1-3}$ is any N-terminus amino acid,
k) —N(H)—$RA_{1-1-4}$, or wherein $RA_{1-1-4}$ is any C-terminus amino acid,
l) —$R_{1-500}$;

wherein $RA_{1-2}$ is
a) -RAX,
b) —($C_{1-5}$ alkyl)-RAX,
c) —($C_{1-5}$ alkyl)—O-RAX,
d) —$RA_{1-RA-12}$,
e) —$RA_{1-RA-15}$,
f) —($C_1$–$C_5$ alkyl)—$R_{1-RA-12}$,
g) —($C_1$–$C_5$ alkyl)—$RA_{1-RA-15}$,
h) —($C_1$–$C_5$ alkyl)—O—$RA_{1-RA-12}$, or
i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
a) —NH—C(O)—,
b) —NH—$SO_2$—,
c) —NH—C(O)—NH—, or
d) —$SO_2$—NH—;

wherein $G_{1-2}$ is
a) —NH—C(O)—,
b) —C(O)—NH—,
c) —NH—$SO_2$—,
d) —$SO_2$—NH—,
e) —NH—$SO_2$—NH—,
f) —C(O)—O—, g) —O—C(O)—,
h) —N(($C_{1-6}$ alkyl)—$RA_{1-RA-12}$)—C(O)—,
i) —NH—C(O)—NH,
j) —N(($C_{1-6}$ alkyl)-$RA_{1-RA-12}$)—$SO_2$—, or
k) —N(($C_{0-6}$alkyl)—($C_{1-6}$ alkyl))—$SO_2$—;

wherein $RA_2$ and $RA_3$ are defined independently and are the same as $RA_1$;

wherein $RA_{1-RA-12}$ is
a) -phenyl, substituted with zero (0) to three (3) $RA_{1-RA-12-AXA}$, or
b) -naphthyl, substituted with zero (0) to three (3) $RA_{1-RA-12-AXA}$;

wherein $RA_{1-RA-15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;

wherein $RA_{1-RA-120}$, $RA_{2-RA-120}$ and $RA_{3-RA-120}$, are defined independently and are
a) —$C_1$–$C_4$ alkyl,
b) —$C_1$–$C_3$ alkoxy,
c) -dimethylamino,
d) -diethylamino,
e) —$CF_3$,
f) —CN,
g) -halo,
h) —$NH_2$,
i) —OH,
j) —$SO_2$—$NH_2$, or
k) —C(O)—$NH_2$;

wherein $RA_{1-RA-12-AXA}$ or $RA_{1-RA-15-AXA}$ are independent and are,
a) —H
b) -halo,
c) —$NO_2$,
d) —CN,
e) —($C_{1-10}$ alkyl), substituted with zero (0) to three (3) halo,
f) —($C_{0-6}$ alkyl)-phenyl, substituted with zero (0) to three (3) halo or hydroxy,
g) —OH,
h) —O—$C_{1-5}$ alkyl,
i) —($C_{0-6}$ alkyl)—O—($C_{1-6}$ alkyl), substituted with zero (0) to three (3) halo or hydroxy,
j) —($C_{0-6}$ alkyl)—O—($C_{2-7}$ alkenyl), substituted with zero (0) to three (3) halo or hydroxy,
k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —$NH_2$,
q) —NH—($C_{1-6}$ alkyl),
r) -mono or di-($C_{1-6}$ alkyl)amino,
s) —NH—OH,
t) —NH—C(O)—($C_{1-3}$ alkyl),
u) —($C_{0-6}$ alkyl)—NH—C(O)-phenyl,
v) —($C_{0-6}$ alkyl)—NH—$SO_2$-phenyl,
w) —($C_{0-6}$ alkyl)—N=N-phenyl, substituted with zero (0) or one (1) —N($C_1$–$C_3$ alkyl)$_2$, or
x) —$SO_2$-phenyl, substituted with zero (0) to three (3) $C_1$–$C_5$ alkyl;

wherein $R_2$ is
  a) —H,
  b) —$C_{1-6}$ alkyl,
  c) —($C_{1-6}$ alkyl)—$C_{3-7}$ cycloalkyl,
  d) —($C_{2-10}$ alkenyl)
  e) —($C_{1-6}$ alkyl)—$R_{2-100}$,
  f) —($C_{1-6}$ alkyl)—$R_{2-500}$,
wherein $R_{2-100}$ is independent of and defined the same as $R_{1-100}$ wherein $RA_1$ is $RA_2$;
wherein $R_{2-500}$ is independent of and defined the same as $R_{1-500}$ wherein $RA_1$ is $RA_2$;
wherein $RA_2$ is independent of and defined the same as $RA_1$;
wherein $R_3$ is
  a) —($C_{1-5}$ alkyl),
  b) —($C_{6-10}$ alkyl),
  c) —($C_{2-5}$ alkenyl),
  d) —($C_{6-10}$ alkenyl),
  e) —($C_{1-6}$ alkyl)—CH=CH$_2$,
  f) —($C_{1-5}$ alkyl)—($C_{3-7}$ cycloalkyl),
  g) —($C_{1-5}$ alkyl)—O—(CH$_2$CH$_2$O)$_q$—CH$_3$,
  h) —($C_{1-5}$ alkyl)—$R_{3-4}$,
  i) —($C_{2-6}$ alkenyl)—$R_{3-4}$,
  j) —CH($R_{3-6}$)—$R_{3-4}$,
  k) —CH($R_{3-6}$)—($C_{1-6}$ alkyl)—$R_{3-4}$,
  l) —CH($R_{3-6}$)—($C_{2-6}$ alkenyl)—$R_{3-4}$,
  m) —$R_{3-100}$,
  n) —($C_{1-5}$ alkyl)—$R_{3-100}$,
  o) —($C_{3-4}$ alkyl)-RAX
  p) —H or —($C_{1-5}$ alkyl),
  q) -n propyl-RAX,
  r) —3-phenylpropyl,
  s) —$R_{3-500}$,
  t) —($C_{1-5}$ alkyl)—$R_{3-500}$,
  u) —($C_{3-4}$ alkyl)—$R_{3-500}$,
  v) -n propyl-$R_{3-500}$,
  w) —C(H)(OH)—$R_{3-1}$,
  x) —($C_{1-5}$ alkyl)—C(H)(OH)—$R_{3-1}$,
  y) —C(O)—$R_{3-1}$,
  z) —($C_{1-5}$ alkyl)—C(O)—$R_{3-1}$,
  a1) —($C_{1-5}$ alkyl)—N(H)$R_{3-1}$,
  b1) —($C_{1-5}$ alkyl)—N(($C_{1-5}$ alkyl)(($C_{1-5}$ alkyl)—$R_{3-1}$),
  c1) —($C_{1-5}$ alkyl)—N(H)C(O)—$R_{3-1}$,
  d1) —C(O)—N(H)$R_{3-1}$, or
  e1) —($C_{1-5}$ alkyl)—C(O)—N(H)$R_{3-1}$;
wherein $R_{3-1}$ is
  a) —NH—C(O)—,
  b) —NH—SO$_2$—,
  c) —NH—CO—NH—, or
  d) —SO$_2$—NH—;
wherein, $R_{3-4}$ is
  a) —OH,
  b) —O—($C_{1-6}$ alkyl),
  c) —C(O)—OH,
  d) —C(O)—O—($C_{1-6}$ alkyl),
  e) —($C_{1-6}$ alkyl),
  f) —($C_{3-6}$ cycloalkyl),
  g) —$R_{3-100}$, or
  h) —$R_{3-500}$;
wherein $R_{3-6}$ is
  a) —OH,
  b) —$C_{1-10}$ alkyl,
  c) —($C_{0-6}$ alkyl)—$C_3$-$C_7$ cycloalkyl,
  d) —($C_{1-6}$ alkyl)—CH=CH$_2$,
  e) —($C_{0-6}$ alkyl)—$R_{3-4}$,
  f) —($C_{1-6}$ alkyl)—$R_{3-100}$, or
  g) —($C_{1-6}$ alkyl)—$R_{3-500}$;
wherein $R_{3-9}$ is
  a) —($C_{1-6}$ alkyl),
  b) —($C_{0-6}$ alkyl)—RA$_{3-RA-12}$, or
  c) —($C_{0-6}$ alkyl)—RA$_{3-RA-15}$;
wherein $R_{3-100}$ is independent of and defined the same as $R_{1-100}$;
wherein $R_{3-500}$ is independent of and defined the same as $R_{1-500}$;
wherein $RA_3$ is independent of and defined the same as $RA_1$;
wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively,
wherein $R_2$ and $R_3$ can be taken together to form a ring comprised of the following groups,
  a) ($C_{5-9}$ cycloalkyl),
  b) ($C_{5-9}$ cycloalkyl) substituted with one to two —$R_{3-9}$, or
  c) —($C_{1-5}$ alkyl substituted with zero to one $R_{3-9}$)—$R_{23}$—($C_{1-5}$ alkyl);
wherein $R_{3-9}$ is
  a) —($C_{1-6}$ alkyl),
  b) —($C_{0-6}$ alkyl)—RA$_{3-RA-12}$, or
  c) —($C_{0-6}$ alkyl)—RA$_{3-RA-15}$;
or wherein $R_2$ and $R_3$ can be taken together to form a double bond represented by formula 50, shown below,

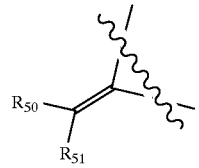

wherein $R_{11}$ is
  a) —H,
  b) —$C_1$-$C_4$ alkyl,
  c) —(RA$_{3-RA-12}$), or
  d) pharmaceutically acceptable salts,
wherein $R_{23}$ is
  a) —O—,
  b) —C(O)—,
  c) —N(H)—,
  d) —N($R_{3-9}$)—,
  e) —N(C(O)—$R_{3-9}$)—, or
  f) —N(C(O)—O—$R_{3-9}$);
wherein $R_{30}$ is
  a) -morpholino,
  b) -piperidino,
  c) -piperazino,
  d) —OR$_{40}$,
  e) -halo,
  f)

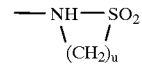

g) —NR$_{40}$R$_{41}$;
wherein $R_{40}$ and $R_{41}$ are defined independently and are,
  a) —H, b) —$C_1$–$C_4$ alkyl,
c) phenyl, substituted with zero (0) to three (3) $RA_{1\text{-}RA\text{-}120}$,
wherein $R_{42}$ is
  a) —$C_1$–$C_4$ alkyl,
  b) -phenyl, substituted with zero (0) to three (3) $RA_{1\text{-}RA\text{-}120}$, or
  c) —($C_{0\text{-}6}$ alkyl)-phenyl, substituted with zero (0) to three (3) $RA_{1\text{-}RA\text{-}120}$;
wherein $RA_{2\text{-}RA\text{-}120}$ and $RA_{3\text{-}RA\text{-}120}$ are independent of and defined the same as $RA_{1\text{-}RA\text{-}120}$;
wherein $R_{50}$ and $R_{51}$ are defined independently and are
  a) —(H or $C_{1\text{-}6}$ alkyl),
  b) —($C_{0\text{-}6}$ alkyl)—$RA_{3\text{-}RA\text{-}12}$, or
  c) —($C_{0\text{-}6}$ alkyl)—$RA_{3\text{-}RA\text{-}15}$;
wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof,
  with the proviso that when $R_1$ is 1-phenylpropyl and $R_2$ is H, then $R_3$ is not $C_{1\text{-}5}$ alkyl, and
  with the proviso that when $RA_1$ or $RA_3$ is —$G_{1\text{-}2}$—($C_{0\text{-}6}$ alkyl)—O—$RA_{1\text{-}RA\text{-}12}$, —($C_{0\text{-}6}$ alkyl)—$G_{1\text{-}2}$—($C_{0\text{-}6}$ alkyl)—O—($C_{1\text{-}6}$ alkyl)—$RA_{1\text{-}RA\text{-}12}$, —($C_{0\text{-}6}$ alkyl)—$G_{1\text{-}2}$—O—($C_{1\text{-}6}$ alkyl)—$RA_{1\text{-}RA\text{-}15}$, —$G_{1\text{-}2}$—N($R_{42}$)$_2$, or —$G_{1\text{-}2}$—$NH_2$, then $G_{1\text{-}2}$ is NOT, —C(O)—NH—, —NH—$SO_2$—, —$SO_2$—NH—, —NH—$SO_2$—NH—, —C(O)—O—, —NH—C(O)—NH, —N(($C_{1\text{-}6}$ alkyl)—$RA_{1\text{-}RA\text{-}12}$)—$SO_2$—, or —N(($C_{0\text{-}6}$ alkyl)—($C_{1\text{-}6}$ alkyl))—$SO_2$—.

16. A compound represented by the structure shown in formula 1,

Formula 1

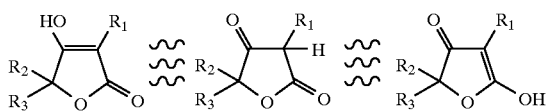

wherein 3 tautomers of the same structure are shown,
wherein $R_1$ is (a)

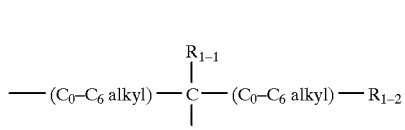

Formula R1A wherein $R_{1\text{-}1}$ is
  a) —($C_{1\text{-}5}$ alkyl),
  b) —($C_{2\text{-}5}$ alkenyl),
  c) —($C_{3\text{-}7}$ cycloalkyl),
  d) —($C_{3\text{-}5}$ cycloalkyl),
  e) -cyclopropyl,
  f) —($C_{1\text{-}5}$ alkyl)—($C_{3\text{-}7}$ cycloalkyl),
  g) —$R_{1\text{-}100}$, or
  h) —($C_1$–$C_5$ alkyl)—$R_{1\text{-}100}$;
wherein $R_{1\text{-}2}$ is —$R_{1\text{-}100}$, or —$R_{1\text{-}500}$;
wherein $R_{1\text{-}100}$ is
  a) phenyl, substituted with zero (0) to three (3) of $RA_1$,
  b) naphthyl, substituted with zero (0) to three (3) of $RA_1$,
  c) biphenyl, substituted with zero (0) to three (3) of $RA_1$,
  d) perhalophenyl;
wherein $R_{1\text{-}500}$ is
  a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
  a) —H,
  b) —($C_{1\text{-}5}$ alkyl),
  c) —($C_{2\text{-}5}$ alkenyl),
  d) —OH,
  e) —O—($C_{1\text{-}5}$ alkyl),
  f) —O—($C_{2\text{-}5}$ alkenyl),
  g) —C(O)OH,
  h) —C(O)($C_{1\text{-}5}$ alkyl),
  i) —C(O)—$RA_{1\text{-}3}$,
wherein $RA_{1\text{-}3}$ is any N-terminus substituted amino acid,
  j) —C(O)—N(H)$RA_{1\text{-}1}$,
  k) —CN,
  l) —$NH_2$ (para or meta positions),
  m) —N(H)($C_{1\text{-}5}$ alkyl) (para or meta positions),
  n) —N($C_{1\text{-}5}$ alkyl)$_2$,
  o) —N(H)$RA_{1\text{-}4}$,
wherein $RA_{1\text{-}4}$ is any C-terminus substituted amino acid,
  p) —N(H)C(O)—$RA_{1\text{-}1}$ (para or meta positions),
  q) —N(H)C(O)—O—$RA_{1\text{-}1}$ (para or meta positions),
  r) —N(H)($SO_2$)—$RA_{1\text{-}2}$,
  s) —N($C_{1\text{-}6}$ alkyl)($SO_2$)—$RA_{1\text{-}2}$,
  t) —N($CH_3$)($SO_2$)—$RA_{1\text{-}2}$,
  u) —$NO_2$,
  v) —$PO_3H$,
  w) —$SO_3H$,
  x) —$SO_2NH_2$,
  y) —($C_{0\text{-}6}$ alkyl)—$SO_2$—$RA_{1\text{-}RA\text{-}12}$,
  z) —($C_{0\text{-}6}$ alkyl)—$SO_2$—$RA_{1\text{-}RA\text{-}15}$,
  a1) -halo,
  b1) —$RA_{1\text{-}RA\text{-}12}$, or
  c1) —$RA_{1\text{-}RA\text{-}15}$;
wherein $RA_{1\text{-}1}$ is
  a) —($C_{1\text{-}5}$ alkyl),
  b) —($C_{1\text{-}5}$ alkyl)—C(O)—O—($C_{1\text{-}5}$ alkyl),
  c) —($C_{1\text{-}5}$ alkyl)—$NH_2$,
  d) —($C_{1\text{-}5}$ alkyl)—N(H)C(O)—O—($C_{1\text{-}5}$ alkyl),
  e) —($C_{1\text{-}5}$ alkyl)—C((H)($NH_2$))—C(O)OH,
  f) —$R_{1\text{-}RA\text{-}12}$,
  g) —$R_{1\text{-}RA\text{-}15}$,
  h) —($C_{1\text{-}5}$ alkyl)-RAX,
  i) —($C_{1\text{-}5}$ alkyl)—O-RAX,
  j) —C(O)—$RA_{1\text{-}1\text{-}3}$,
wherein $RA_{1\text{-}1\text{-}3}$ is any N-terminus amino acid,
  k) —N(H)—$RA_{1\text{-}1\text{-}4}$, or wherein $RA_{1-1-4}$ is any C-terminus amino acid,
l) —$R_{1-500}$;
wherein $RA_{1-2}$ is
a) -RAX,
b) —($C_{1-5}$ alkyl)-RAX,
c) —($C_{1-5}$ alkyl)—O-RAX,
d) —$RA_{1-RA-12}$,
e) —$RA_{1-RA-15}$,
f) —($C_1$–$C_5$ alkyl)—$RA_{1-RA-12}$,
g) —($C_1$–$C_5$ alkyl)—$RA_{1-RA-15}$,
h) —($C_1$–$C_5$ alkyl)—O—$RA_{1-RA-12}$, or
i) —($C_1$–$C_5$ alkyl)—O—$RA_{1-RA-15}$;
wherein $RA_2$ and $RA_3$ are defined independently and are independent of and defined the same as $RA_1$;
wherein $G_{1-1}$ is
a) —NH—C(O)—,
b) —NH—$SO_2$—,
c) —NH—C(O)—NH—, or
d) —$SO_2$—NH—;
wherein $G_{1-2}$ is
a) —NH—C(O)—,
b) —C(O)—NH—,
c) —NH—$SO_2$—,
d) —$SO_2$—NH—,
e) —NH—$SO_2$—NH—,
f) —C(O)—O—,
g) —O—C(O)—,
h) —N(($C_{1-6}$ alkyl)—$RA_{1-RA-12}$)—C(O)—,
i) —NH—C(O)—NH,
j) —N(($C_{1-6}$ alkyl)—$RA_{1-RA-12}$)—$SO_2$—, or
k) —N(($C_{0-6}$ alkyl)—($C_{1-6}$ alkyl))—$SO_2$—;
wherein $RA_2$ and $RA_3$ are defined independently and are the same as $RA_1$;
wherein $RA_{1-RA-12}$ is
a) -phenyl, substituted with zero (0) to three (3) $RA_{1-RA-12-AXA}$, or
b) -naphthyl, substituted with zero (0) to three (3) $RA_{1-RA-12-AXA}$,
wherein $RA_{1-RA-15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;
wherein $RA_{1-RA-120}$, $RA_{2-RA-120}$ and $RA_{3-RA-120}$, are defined independently and are
a) —$C_1$–$C_4$ alkyl,
b) —$C_1$–$C_3$ alkoxy,
c) -dimethylamino,
d) -diethylamino,
e) —$CF_3$,
f) —CN,
g) -halo,
h) —$NH_2$,
i) —OH,
j) —$SO_2$—$NH_2$, or
k) —C(O)—$NH_2$;
wherein $RA_{1-RA-12-AXA}$ or $RA_{1-RA-15-AXA}$ are independent and are,
a) —H
b) -halo,
c) —$NO_2$,
d) —CN,
e) —($C_{1-10}$ alkyl), substituted with zero (0) to three (3) halo,
f) —($C_{0-6}$ alkyl)-phenyl, substituted with zero (0) to three (3) halo or hydroxy,
g) —OH,
h) —O—$C_{1-5}$ alkyl,
i) —($C_{0-6}$ alkyl)—O—($C_{1-6}$ alkyl), substituted with zero (0) to three (3) halo or hydroxy,
j) —($C_{0-6}$ alkyl)—O—($C_{2-7}$ alkenyl), substituted with zero (0) to three (3) halo or hydroxy,
k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —$NH_2$,
q) —NH—($C_{1-6}$ alkyl),
r) -mono or di-($C_{1-6}$ alkyl)amino,
s) —NH—OH,
t) —NH—C(O)—($C_{1-3}$ alkyl),
u) —($C_{0-6}$ alkyl)—NH—C(O)-phenyl,
v) —($C_{0-6}$ alkyl)—NH—$SO_2$-phenyl,
w) —($C_{0-6}$ alkyl)—N=N-phenyl, substituted with zero (0) or one (1) —N($C_1$–$C_3$ alkyl)$_2$, or
x) —$SO_2$-phenyl, substituted with zero (0) to three (3) $C_1$–$C_5$ alkyl;
wherein $R_2$ is
a) —H,
b) —$C_{1-6}$ alkyl,
c) —($C_{1-6}$ alkyl)—$C_{3-7}$ cycloalkyl,
d) —($C_{2-10}$ alkenyl)
e) —($C_{1-6}$ alkyl)—$R_{2-100}$,
f) —($C_{1-6}$ alkyl)—$R_{2-500}$,
wherein $R_{2-100}$ is independent of and defined the same as $R_{1-100}$ wherein $RA_1$ is $RA_2$;
wherein $R_{2-500}$ is independent of and defined the same as $R_{1-500}$ wherein $RA_1$ is $RA_2$;
wherein $RA_2$ is independent of and defined the same as $RA_1$;
wherein $R_3$ is
a) —($C_{1-5}$ alkyl),
b) —($C_{6-10}$ alkyl),
c) —($C_{2-5}$ alkenyl),
d) —($C_{6-10}$ alkenyl),
e) —($C_{1-6}$ alkyl)—CH=$CH_2$,
f) —($C_{1-5}$ alkyl)—($C_{3-7}$ cycloalkyl),
g) —($C_{1-5}$ alkyl)—O—($CH_2CH_2O)_q$—$CH_3$,
h) —($C_{1-6}$ alkyl)—$R_{3-4}$,
i) —($C_{2-6}$ alkenyl)—$R_{3-4}$,
j) —CH($R_{3-6}$)—$R_{3-4}$,
k) —CH($R_{3-6}$)—($C_{1-6}$ alkyl)—$R_{3-4}$,
l) —CH($R_{3-6}$)—($C_{2-6}$ alkenyl)—$R_{3-4}$,
m) —$R_{3-100}$,
n) —($C_{1-5}$ alkyl)—$R_{3-100}$,
o) —($C_{3-4}$ alkyl)-RAX
p) —H or —($C_{1-5}$ alkyl),
q) -n propyl-RAX,
r) —3-phenylpropyl,
s) —$R_{3-500}$,
t) —($C_{1-5}$ alkyl)—$R_{3-500}$,
u) —($C_{3-4}$ alkyl)—$R_{3-500}$,
v) -n propyl-$R_{3-500}$,
w) —C(H)(OH)—$R_{3-1}$,
x) —($C_{1-5}$ alkyl)—C(H)(OH)—$R_{3-1}$,
y) —C(O)—$R_{3-1}$,
z) —$C_{1-5}$ alkyl)—C(O)—$R_{3-1}$, a1) —(C$_{1-5}$ alkyl)—N(H)R$_{3-1}$,
b1) —(C$_{1-5}$ alkyl)-N((C$_{1-5}$ alkyl)((C$_{1-5}$ alkyl)—R$_{3-1}$),
c1) —(C$_{1-5}$ alkyl)—N(H)C(O)—R$_{3-1}$,
d1) —C(O)—N(H)R$_{3-1}$, or
e1) —(C$_{1-5}$ alkyl)—C(O)—N(H)R$_{3-1}$;

wherein R$_{3-1}$ is
  a) —NH—C(O)—,
  b) —NH—SO$_2$—,
  c) —NH—CO—NH—, or
  d) —SO$_2$—NH—;

wherein, R$_{3-4}$ is
  a) —OH,
  b) —O—(C$_{1-6}$alkyl),
  c) —C(O)—OH,
  d) —C(O)—O—(C$_{1-6}$ alkyl),
  e) —(C$_{1-6}$ alkyl),
  f) —(C$_{3-6}$ cycloalkyl),
  g) —R$_{3-100}$, or
  h) —R$_{3-500}$;

wherein R$_{3-6}$ is
  a) —OH,
  b) —C$_{1-10}$ alkyl,
  c) —(C$_{0-6}$ alkyl)—C$_3$–C$_7$ cycloalkyl,
  d) —(C$_{1-6}$ alkyl)—CH=CH$_2$,
  e) —(C$_{0-6}$ alkyl)—R$_{3-4}$,
  f) —(C$_{1-6}$ alkyl)—R$_{3-100}$, or
  g) —(C$_{1-6}$ alkyl)—R$_{3-500}$;

wherein R$_{3-9}$ is
  a) —(C$_{1-6}$ alkyl),
  b) —(C$_{0-6}$ alkyl)—RA$_{3\text{-}RA\text{-}12}$, or
  c) —(C$_{0-6}$ alkyl)—RA$_{3\text{-}RA\text{-}15}$;

wherein R$_{3-100}$ is independent of and defined the same as R$_{1-100}$;

wherein R$_{3-500}$ is independent of and defined the same as R$_{1-500}$;

wherein RA$_3$ is independent of and defined the same as RA$_1$;

wherein RA$_{3\text{-}RA\text{-}12}$, RA$_{3\text{-}RA\text{-}15}$, RA$_{3\text{-}RA\text{-}12\text{-}AXA}$ and RA$_{3\text{-}RA\text{-}15\text{-}AXA}$, are all independent of and defined the same as the corresponding R$_1$ variables, which are: RA$_{1\text{-}RA\text{-}12}$, RA$_{1\text{-}RA\text{-}15}$, RA$_{1\text{-}RA\text{-}12\text{-}AXA}$ and RA$_{1\text{-}RA\text{-}15\text{-}AXA}$, respectively, wherein R$_2$ and R$_3$ can be taken together to form a ring comprised of the following groups,
  a) (C$_{5-9}$ cycloalkyl),
  b) (C$_{5-9}$ cycloalkyl) substituted with one to two —R$_{3-9}$, or
  c) —(C$_{1-5}$ alkyl substituted with zero to one R$_{3-9}$)—R$_{23}$—(C$_{1-5}$ alkyl);

wherein R$_{3-9}$ is
  a) —(C$_{1-6}$ alkyl),
  b) —(C$_{0-6}$ alkyl)—RA$_{3\text{-}RA\text{-}12}$, or
  c) —(C$_{0-6}$ alkyl)—RA$_{3\text{-}RA\text{-}15}$;

or wherein R$_2$ and R$_3$ can be taken together to form a double bond represented by formula 50, shown below,

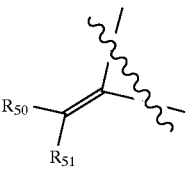

wherein R$_{11}$ is
  a) —H,
  b) —C$_1$–C$_4$ alkyl,
  c) —(RA$_{3\text{-}RA\text{-}12}$), or
  d) pharmaceutically acceptable salts, wherein R$_{23}$ is
  a) —O—,
  b) —C(O)—,
  c) —N(H)—,
  d) —N(R$_{3-9}$)—,
  e) —N(C(O)—R$_{3-9}$)—, or
  f) —N(C(O)—O—R$_{3-9}$);

wherein R$_{30}$ is
  a) -morpholino,
  b) -piperidino,
  c) -piperazino,
  d) —OR$_{40}$,
  e) -halo,
  f) 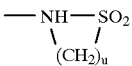

g) —NR$_{40}$R$_{41}$;

wherein R$_{40}$ and R$_{41}$ are defined independently and are,
  a) —H,
  b) —C$_1$–C$_4$ alkyl,
  c) phenyl, substituted with zero (0) to three (3) RA$_{1\text{-}RA\text{-}120}$, wherein R$_{42}$ is
  a) —C$_1$–C$_4$ alkyl,
  b) -phenyl, substituted with zero (0) to three (3) RA$_{1\text{-}RA\text{-}120}$, or
  c) —(C$_{0-6}$ alkyl)-phenyl, substituted with zero (0) to three (3) RA$_{1\text{-}RA\text{-}120}$;

wherein RA$_{2\text{-}RA\text{-}120}$ and R$_{3\text{-}RA\text{-}120}$ are independent of and defined the same as RA$_{1\text{-}RA\text{-}120}$;

wherein R$_{50}$ and R$_{51}$ are defined independently and are
  a) —(H or C$_{1-6}$ alkyl),
  b) —(C$_{0-6}$ alkyl)—RA$_{3\text{-}RA\text{-}12}$, or
  c) —(C$_{0-6}$ alkyl)—RA$_{3\text{-}RA\text{-}15}$;

wherein AA is an amino acid residue,
wherein P$_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof, with the proviso that when R$_1$ is 1-phenylpropyl and R$_2$ is H, then R$_3$ is not C$_{1-5}$ alkyl, and with the proviso that when RA$_1$ or RA$_3$ is —G$_{1-2}$—(C$_{0-6}$ alkyl)—O—RA$_{1\text{-}RA\text{-}12}$, —(C$_{0-6}$ alkyl)—G$_{1-2}$—(C$_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42}$)$_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$RA_{1-RA-12}$)—$SO_2$—, or —N(($C_{0-6}$ alkyl)—($C_{1-6}$ alkyl))—$SO_2$—.

17. A compound represented by the structure shown in formula 1,

Formula 1

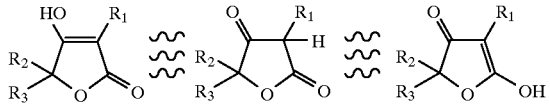

wherein 3 tautomers of the same structure are shown, wherein $R_1$ is (a)

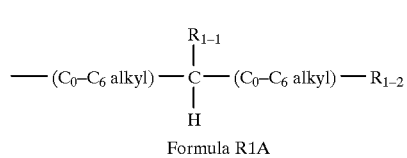

Formula R1A wherein $R_{1-1}$ is
 a) —($C_{1-5}$ alkyl),
 b) —($C_{2-5}$ alkenyl),
 c) —($C_{3-7}$ cycloalkyl),
 d) —($C_{3-5}$ cycloalkyl),
 e) -cyclopropyl,
 f) —($C_{1-5}$ alkyl)—($C_{3-7}$ cycloalkyl),
 g) —$R_{1-100}$, or
 h) —($C_1$–$C_5$ alkyl)—$R_{1-100}$;
wherein $R_{1-2}$ is —$R_{1-100}$, or —$R_{1-500}$;
wherein $R_{1-100}$ is
 a) phenyl, substituted with zero (0) to three (3) of $RA_1$,
 b) naphthyl, substituted with zero (0) to three (3) of $RA_1$,
 c) biphenyl, substituted with zero (0) to three (3) of $RA_1$,
 d) perhalophenyl;
wherein $R_{1-500}$ is
 a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
 a) —H,
 b) —($C_{1-5}$ alkyl),
 c) —O—($C_{1-5}$ alkyl),
 d) —C(O)—$RA_{1-3}$,
wherein $RA_{1-3}$ is any N-terminus substituted amino acid,
 e) —C(O)—N(H)$RA_1$,,
 f) —$NH_2$ (para or meta positions),
 g) —N(H)($C_{1-5}$ alkyl) (para or meta positions),
 h) —N($C_{1-5}$ alkyl)$_2$,
 i) —N(H)$RA_{1-4}$,
wherein $RA_{1-4}$ is any C-terminus substituted amino acid,
 j) —N(H)C(O)—$RA_{1-1}$ (para or meta positions),
 k) —N(H)C(O)—O—$RA_{1-1}$ (para or meta positions),
 l) —N(H)($SO_2$)—$RA_{1-2}$,
 m) —N($CH_3$)($SO_2$—$RA_{1-2}$,
 n) —$NO_2$,
 o) —$SO_2NH_2$,
 p) —($C_{1-3}$ alkyl)—$SO_2$—$RA_{1-RA-12}$,
 q) —($C_{1-3}$ alkyl)—$SO_2$—$RA_{1-RA-15}$,
 r) -halo,
wherein $RA_{1-1}$ is
 a) —($C_{1-5}$ alkyl),
 b) —($C_{1-5}$ alkyl)—C(O)—O—($C_{1-5}$ alkyl),
 c) —($C_{1-5}$ alkyl)—$NH_2$,
 d) —($C_{1-5}$ alkyl)—N(H)C(O)—O—($C_{1-5}$ alkyl),
 e) —($C_{1-5}$ alkyl)—C((H)($NH_2$))—C(O)OH,
 f) —$RA_{1-RA-12}$,
 g) $RA_{1-RA-15}$,
 h) —($C_{1-5}$ alkyl)-RAX,
 i) —($C_{1-5}$ alkyl)—O-RAX,
 j) —C(O)—$RA_{1-1-3}$,
wherein $RA_{1-1-3}$ is any N-terminus amino acid,
 k) —N(H)—$RA_{1-1-4}$, or
wherein $RA_{1-1-4}$ is any C-terminus amino acid,
 l) —$R_{1-500}$;
wherein $RA_{1-2}$ is
 a) -RAX,
 b) —($C_{1-5}$ alkyl)-RAX,
 c) —($C_{1-5}$ alkyl)—O-RAX,
 d) —$RA_{1-RA-12}$,
 e) —$RA_{1-RA-15}$,
 f) —($C_1$–$C_5$ alkyl)—$RA_{1-RA-12}$,
 g) —($C_1$–$C_5$ alkyl)—$RA_{1-RA-15}$,
 h) —($C_1$–$C_5$ alkyl)—O—$RA_{1-RA-12}$, or
 i) —($C_1$–$C_5$ alkyl)—O—$RA_{1-RA-15}$;
wherein $RA_2$ and $RA_3$ are defined independently and are independent of and defined the same as $RA_1$;
wherein $G_{1-1}$ is
 a) —NH—C(O)—,
 b) —NH—$SO_2$—,
 c) —NH—C(O)—NH—, or
 d) —$SO_2$—NH—;
wherein $G_{1-2}$ is
 a) —NH—C(O)—,
 b) —C(O)—NH—,
 c) —NH—$SO_2$—,
 d) —$SO_2$—NH—,
 e) —NH—$SO_2$—NH—,
 f) —C(O)—O—,
 g) —O—C(O)—,
 h) —N(($C_{1-6}$ alkyl)—$RA_{1-RA-12}$)—C(O)—,
 i) —NH—C(O)—NH,
 j) —N(($C_{1-6}$alkyl)—$RA_{1-RA-12}$)—$SO_2$—, or
 k) —N(($C_{0-6}$ alkyl)—($C_{1-6}$ alkyl))—$SO_2$—;
wherein $RA_2$ and $RA_3$ are defined independently and are the same as $RA_1$;
wherein $RA_{1-RA-12}$ is
 a) -phenyl, substituted with zero (0) to three (3) $RA_{1-RA-12-AXA}$, or
 b) -naphthyl, substituted with zero (0) to three (3) $RA_{1-RA-12-AXA}$;
wherein $RA_{1-RA-15}$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;

wherein $RA_{1-RA-120}$, $RA_{2-RA-120}$ and $RA_{3-RA-120}$, are defined independently and are
- a) —$C_1$–$C_4$ alkyl,
- b) —$C_1$–$C_3$ alkoxy,
- c) -dimethylamino,
- d) -diethylamino,
- e) —$CF_3$,
- f) —CN,
- g) -halo,
- h) —$NH_2$,
- i) —OH,
- j) —$SO_2$—$NH_2$, or
- k) —C(O)—$NH_2$;

wherein $RA_{1-RA-12-AXA}$ or $RA_{1-RA-15-AXA}$ are independent and are,
- a) —H
- b) -halo,
- c) —$NO_2$,
- d) —CN,
- e) —($C_{1-10}$ alkyl), substituted with zero (0) to three (3) halo,
- f) —($C_{0-6}$ alkyl)-phenyl, substituted with zero (0) to three (3) halo or hydroxy,
- g) —OH,
- h) —O—$C_{1-5}$ alkyl,
- i) —($C_{0-6}$ alkyl)—O—($C_{1-6}$ alkyl), substituted with zero (0) to three (3) halo or hydroxy,
- j) —($C_{0-6}$ alkyl)—O—($C_{2-7}$ alkenyl), substituted with zero (0) to three (3) halo or hydroxy,
- k) —CH(O),
- l) —C(O)—($C_{1-6}$ alkyl),
- m) —C(O)OH,
- n) —C(O)O—($C_{1-5}$ alkyl),
- o) —C(O)—N(H or $C_{1-6}$ alkyl)$_2$,
- p) —$NH_2$,
- q) —NH—($C_{1-6}$ alkyl),
- r) -mono or di—($C_{1-6}$alkyl)amino,
- s) —NH—OH,
- t) —NH—C(O)—($C_{1-3}$alkyl),
- u) —($C_{0-6}$alkyl)—NH—C(O)-phenyl,
- v) —($C_{0-6}$ alkyl)—NH—$SO_2$-phenyl,
- w) —($C_{0-6}$ alkyl)—N=N-phenyl, substituted with zero (0) or one (1) —N($C_1$–$C_3$ alkyl)$_2$, or
- x) —$SO_2$-phenyl, substituted with zero (0) to three (3) $C_1$–$C_5$ alkyl;

wherein $R_2$ is
- a) —H,
- b) —$C_{1-6}$ alkyl,
- c) —($C_{1-6}$ alkyl)—$C_{3-7}$ cycloalkyl,
- d) —($C_{2-10}$ alkenyl)
- e) —($C_{1-6}$ alkyl)—$R_{2-100}$,
- f) —($C_{1-4}$ alkyl)—$R_{2-500}$;

wherein $R_{2-100}$ is independent of and defined the same as $R_{1-100}$ wherein $RA_1$ is $RA_2$;

wherein $R_{2-500}$ is independent of and defined the same as $R_{1-500}$ wherein $RA_1$ is $RA_2$;

wherein $RA_2$ is independent of and defined the same as $RA_1$;

wherein $R_3$ is
- a) —($C_{1-5}$ alkyl),
- b) —($C_{6-10}$ alkyl),
- c) —($C_{2-5}$ alkenyl),
- d) —($C_{6-10}$ alkenyl),
- e) —($C_{1-6}$ alkyl)—CH=$CH_2$,
- f) —($C_{1-5}$ alkyl)—($C_{3-7}$ cycloalkyl),
- g) —($C_{1-5}$ alkyl)—O—($CH_2CH_2O)_q$—$CH_3$,
- h) —($C_{1-6}$ alkyl)—$R_{3-4}$,
- i) —($C_{2-6}$ alkenyl)—$R_{3-4}$,
- j) —CH($R_{3-6}$)—$R_{3-4}$),
- k) —CH($R_{3-6}$)—($C_{1-6}$ alkyl)—$R_{3-4}$,
- l) —CH($R_{3-6}$)—($C_{2-6}$ alkenyl)—$R_{3-4}$,
- m) —$R_{3-100}$,
- n) —($C_{1-5}$ alkyl)—$R_{3-100}$,
- o) —($C_{3-4}$ alkyl)-RAX
- p) —H or —($C_{1-5}$ alkyl),
- q) -n propyl-RAX,
- r) —3-phenylpropyl,
- s) —$R_{3-500}$,
- t) —($C_{1-5}$ alkyl)—$R_{3-500}$,
- u) —($C_{3-4}$ alkyl)—$R_{3-500}$,
- v) -n propyl—$R_{3-500}$,
- w) —C(H)(OH)—$R_{3-1}$,
- x) —($C_{1-5}$ alkyl)—C(H)(OH)—$R_{3-1}$,
- y) —C(O)—$R_{3-1}$,
- z) —($C_{1-5}$ alkyl)—C(O)—$R_{3-1}$,
- a1) —($C_{1-5}$ alkyl)—N(H)$R_{3-1}$,
- b1) —($C_{1-5}$ alkyl)—N(($C_{1-5}$ alkyl)(($C_{1-5}$ alkyl)—$R_{3-1}$),
- c1) —($C_{1-5}$ alkyl)—N(H)C(O)—$R_{3-1}$,
- d1) —C(O)—N(H)$R_{3-1}$, or
- e1) —($C_{1-5}$ alkyl)—C(O)—N(H)$R_{3-1}$;

wherein $R_{3-1}$ is
- a) —NH—C(O)—,
- b) —NH—$SO_2$—,
- c) —NH—CO—NH—, or
- d) —$SO_2$—NH—;

wherein, $R_{3-4}$ is
- a) —OH,
- b) —O—($C_{1-6}$alkyl),
- c) —C(O)—OH,
- d) —C(O)—O—($C_{1-6}$alkyl),
- e) —($C_{1-6}$ alkyl),
- f) —($C_{3-6}$ cycloalkyl),
- g) —$R_{3-100}$, or
- h) —$R_{3-500}$;

wherein $R_{3-6}$ is
- a) —OH,
- b) —$C_{1-10}$ alkyl,
- c) —($C_{0-6}$ alkyl)—$C_3$–$C_7$ cycloalkyl,
- d) —($C_{1-6}$ alkyl)—CH=$CH_2$,
- e) —($C_{0-6}$ alkyl)—$R_{3-4}$,
- f) —($C_{1-6}$ alkyl)—$R_{3-100}$, or
- g) —($C_{1-6}$ alkyl)—$R_{3-500}$;

wherein $R_{3-9}$ is
- a) —($C_{1-6}$ alkyl),
- b) —($C_{0-6}$ alkyl)—$RA_{3-RA-12}$, or
- c) —($C_{0-6}$ alkyl)—$RA_{3-RA-15}$;

wherein $R_{3-100}$ is independent of and defined the same as $R_{1-100}$;

wherein $R_{3-500}$ is independent of and defined the same as $R_{1-500}$;

wherein $RA_3$ is independent of and defined the same as $RA_1$;

wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively, wherein $R_2$ and $R_3$ can be taken together to form a ring comprised of the following groups,
a) ($C_{5-9}$ cycloalkyl),
b) ($C_{5-9}$ cycloalkyl) substituted with one to two —$R_{3-9}$, or
c) —($C_{1-5}$ alkyl substituted with zero to one $R_{3-9}$)—$R_{23}$—($C_{1-5}$ alkyl);

wherein $R_{3-9}$ is
a) —($C_{1-6}$ alkyl),
b) —($C_{0-6}$ alkyl)—$RA_{3-RA-12}$, or
c) —($C_{0-6}$ alkyl)—$RA_{3-RA-15}$;

or
wherein $R_2$ and $R_3$ can be taken together to form a double bond represented by formula 50, shown below,

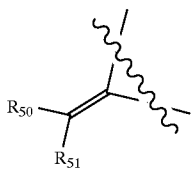

wherein $R_{11}$ is
a) —H,
b) —$C_1$–$C_4$ alkyl,
c) —($RA_{3-RA-12}$), or
d) pharmaceutically acceptable salts, wherein $R_{23}$ is
a) —O—,
b) —C(O)—,
c) —N(H)—,
d) —N($R_{3-9}$)—,
e) —N(C(O)—$R_{3-9}$)—, or
f) —N(C(O)—O—$R_{3-9}$);

wherein $R_{30}$ is
a) -morpholino,
b) -piperidino,
c) -piperazino,
d) —$OR_{40}$,
e) -halo,
f)

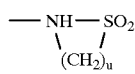

g) —$NR_{40}R_{41}$;

wherein $R_{40}$ and $R_{41}$ are defined independently and are,
a) —H,
b) —$C_1$–$C_4$ alkyl,
c) phenyl, substituted with zero (0) to three (3) $RA_{1-RA-120}$, wherein $R_{42}$ is
a) —$C_1$–$C_4$ alkyl,
b) -phenyl, substituted with zero (0) to three (3) $RA_{1-RA-120}$, or
c) —($C_{0-6}$ alkyl)-phenyl, substituted with zero (0) to three (3) $RA_{1-RA-120}$;

wherein $RA_{2-RA-120}$ and $RA_{3-RA-120}$ are independent of and defined the same as $RA_{1-RA-120}$;

wherein $R_{50}$ and $R_{51}$ are defined independently and are a) —(H or $C_{1-6}$ alkyl),
b) —($C_{0-6}$ alkyl)—$RA_{3-RA-12}$, or
c) —($C_{0-6}$ alkyl)-$RA_{3-RA-15}$;

wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42})_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$RA_{1-RA-12}$)—$SO_2$—, or —N(($C_{0-6}$ alkyl)—($C_{1-6}$ alkyl))—$SO_2$—.

18. A compound represented by the structure shown in formula 1,

Formula 1

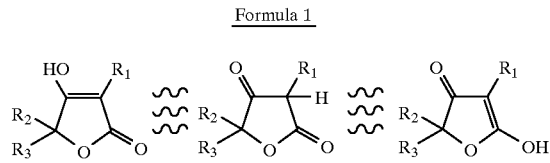

wherein 3 tautomers of the same structure are shown,
wherein $R_1$ is

Formula R1A

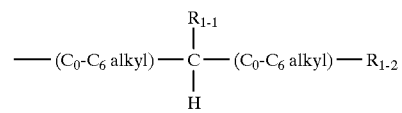

(a)

wherein $R_{1-1}$ is
a) —($C_{1-5}$ alkyl),
b) —($C_{2-5}$ alkenyl),
c) —($C_{3-7}$ cycloalkyl),
d) —($C_{3-5}$ cycloalkyl),
e) -cyclopropyl,
f) —($C_{1-5}$ alkyl)—($C_{3-7}$ cycloalkyl),
g) —$R_{1-100}$, or
h) —($C_1$–$C_5$ alkyl)—$R_{1-100}$;

wherein $R_{1-2}$ is —$R_{1-100}$, or —$R_{1-500}$;

wherein $R_{1-100}$ is
a) phenyl, substituted with zero (0) to three (3) of $RA_1$,
b) naphthyl, substituted with zero (0) to three (3) of $RA_1$,
c) biphenyl, substituted with zero (0) to three (3) of $RA_1$,
d) perhalophenyl;

wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is
- a) —H,
- b) —($C_{1-5}$ alkyl),
- c) —O—($C_{1-5}$ alkyl),
- d) —C(O)—$RA_{1-3}$, wherein $RA_{1-3}$ is any N-terminus substituted amino acid,
- e) —C(O)—N(H)$RA_{1-1}$,
- f) —$NH_2$ (para or meta positions),
- g) —N(H)($C_{1-5}$ alkyl) (para or meta positions),
- h) —N(($C_{1-5}$ alkyl))$_2$,
- i) —N(H)$RA_{1-4}$, wherein $RA_{1-4}$ is any C-terminus substituted amino acid,
- j) —N(H)C(O)—$RA_{1-1}$ (para or meta positions),
- k) —N(H)C(O)—O—$RA_{1-1}$ (para or meta positions),
- l) —N(H)($SO_2$)—$RA_{1-2}$,
- m) —N($CH_3$)($SO_2$)—$RA_{1-2}$,
- n) —$NO_2$,
- o) —$SO_2NH_2$,
- p) —($C_{1-3}$ alkyl)—$SO_2$—$RA_{1\text{-}RA\text{-}12}$,
- q) —($C_{1-3}$ alkyl)—$SO_2$—$RA_{1\text{-}RA\text{-}15}$,
- r) -halo, wherein $RA_{1-1}$ is
- a) —($C_{1-5}$ alkyl),
- b) —($C_{1-5}$ alkyl)—C(O)—O—($C_{1-5}$ alkyl),
- c) —($C_{1-5}$ alkyl)—$NH_2$,
- d) —($C_{1-5}$ alkyl)—N(H)C(O)—O—($C_{1-5}$ alkyl),
- e) —($C_{1-5}$ alkyl)—C((H)($NH_2$))—C(O)OH,
- f) —$RA_{1\text{-}RA\text{-}12}$,
- g) —$RA_{1\text{-}RA\text{-}15}$,
- h) —($C_{1-5}$ alkyl)-RAX,
- i) —($C_{1-5}$ alkyl)—O-RAX,
- j) —C(O)—$RA_{1-1-3}$, wherein $RA_{1-1-3}$ is any N-terminus amino acid,
- k) —N(H)—$RA_{1-1-4}$, or wherein $RA_{1-1-4}$ is any C-terminus amino acid,
- l) —$R_{1-500}$;

wherein $RA_{1-2}$ is
- a) -RAX,
- b) —($C_{1-5}$ alkyl)-RAX,
- c) —($C_{1-5}$ alkyl)—O-RAX,
- d) —$RA_{1\text{-}RA\text{-}12}$,
- e) —$RA_{1\text{-}RA\text{-}15}$,
- f) —($C_1$–$C_5$ alkyl)—$RA_{1\text{-}RA\text{-}12}$,
- g) —($C_1$–$C_5$ alkyl)—$RA_{1\text{-}RA\text{-}15}$,
- h) —($C_1$–$C_5$ alkyl)—O—$RA_{1\text{-}RA\text{-}12}$, or
- i) —($C_1$–$C_5$ alkyl)—O—$RA_{1\text{-}RA\text{-}15}$;

wherein $RA_2$ and $RA_3$ are defined independently and are independent of and defined the same as $RA_1$;

wherein $G_{1-1}$ is
- a) —NH—C(O)—,
- b) —NH—$SO_2$—,
- c) —NH—C(O)—NH—, or
- d) —$SO_2$—NH—;

wherein $G_{1-2}$ is
- a) —NH—C(O)—,
- b) —C(O)—NH—,
- c) —NH—$SO_2$—,
- d) —$SO_2$—NH—,
- e) —NH—$SO_2$—NH—,
- f) —C(O)—O—,
- g) —O—C(O)—,
- h) —N(($C_{1-6}$ alkyl)—$RA_{1\text{-}RA\text{-}12}$)—C(O)—,
- i) —NH—C(O)—NH,
- j) —N(($C_{1-6}$ alkyl)—$RA_{1\text{-}RA\text{-}12}$)—$SO_2$—, or
- k) —N(($C_{0-6}$ alkyl)—($C_{1-6}$ alkyl))—$SO_2$—;

wherein $RA_2$ and $RA_3$ are defined independently and are the same as $RA_1$;

wherein $RA_{1\text{-}RA\text{-}12}$ is
- a) -phenyl, substituted with zero (0) to three (3) $RA_{1\text{-}RA\text{-}12\text{-}AXA}$, or
- b) -naphthyl, substituted with zero (0) to three (3) $RA_{1\text{-}RA\text{-}12\text{-}AXA}$;

wherein $RA_{1\text{-}RA\text{-}15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1\text{-}RA\text{-}15\text{-}AXA}$;

wherein $RA_{1\text{-}RA\text{-}120}$, $RA_{2\text{-}RA\text{-}120}$ and $RA_{3\text{-}RA\text{-}120}$, are defined independently and are
- a) —$C_1$–$C_4$ alkyl,
- b) —$C_1$–$C_3$ alkoxy,
- c) -dimethylamino,
- d) -diethylamino,
- e) —$CF_3$,
- f) —CN,
- g) -halo,
- h) —$NH_2$,
- i) —OH,
- j) —$SO_2$—$NH_2$, or
- k) —C(O)—$NH_2$;

wherein $RA_{1\text{-}RA\text{-}12\text{-}AXA}$ or $RA_{1\text{-}RA\text{-}15\text{-}AXA}$ are independent and are,
- a) —H
- b) -halo,
- c) —$NO_2$,
- d) —CN,
- e) —($C_{1-10}$ alkyl), substituted with zero (0) to three (3) halo,
- f) —($C_{0-6}$ alkyl)-phenyl, substituted with zero (0) to three (3) halo or hydroxy,
- g) —OH,
- h) —O—$C_{1-5}$ alkyl,
- i) —($C_{0-6}$ alkyl)—O—($C_{1-6}$ alkyl), substituted with zero (0) to three (3) halo or hydroxy,
- j) —($C_{0-6}$ alkyl)—O—($C_{2-7}$ alkenyl), substituted with zero (0) to three (3) halo or hydroxy,
- k) —CH(O),
- l) —C(O)—($C_{1-6}$ alkyl),
- m) —C(O)OH,
- n) —C(O)O—($C_{1-5}$ alkyl),
- o) —C(O)—N(H or $C_{1-6}$ alkyl)$_2$,
- p) —$NH_2$,
- q) —NH—($C_{1-6}$ alkyl),
- r) -mono or di —($C_{1-6}$ alkyl)amino,
- s) —NH—OH,
- t) —NH—C(O)—($C_{1-3}$ alkyl),
- u) —($C_{0-6}$ alkyl)—NH—C(O)-phenyl,
- v) —($C_{0-6}$ alkyl)—NH—$SO_2$-phenyl,
- w) —($C_{0-6}$ alkyl)—N=N-phenyl, substituted with zero (0) or one (1) —N($C_1$–$C_3$ alkyl)$_2$, or x) —SO$_2$-phenyl, substituted with zero (0) to three (3) C$_1$–C$_5$ alkyl;

wherein R$_2$ is
a) —C$_{3-4}$ alkyl,
b) -n-propyl,
c) —(C$_{1-5}$ alkyl)—C$_{3-5}$ cycloalkyl,
d) —(C$_{2-5}$ alkenyl)
e) —(C$_{1-5}$ alkyl)—R$_{2-100}$,
f) —(C$_{1-5}$ alkyl)—R$_{2-500}$, wherein R$_{2-100}$ is independent of and defined the same as R$_{1-100}$ wherein RA$_1$ is RA$_2$;

wherein R$_{2-500}$ is independent of and defined the same as R$_{1-500}$ wherein RA$_1$ is RA$_2$;

wherein RA$_2$ is independent of and defined the same as RA$_1$;

wherein R$_3$ is
a) —(C$_{1-5}$ alkyl),
b) —(CH$_2$—CH=CH$_2$),
c) —(C$_{1-5}$ alkyl)—(C$_{3-5}$ cycloalkyl),
d) —(C$_{1-5}$ alkyl)—O—(CH$_2$CH$_2$O)$_q$—CH$_3$,
e) —(C$_{1-6}$ alkyl)—R$_{3-4}$,
f) —(C$_{2-6}$ alkenyl)—R$_{3-4}$,
g) —R$_{3-100}$,
h) —(C$_{1-4}$ alkyl)—R$_{3-100}$,
i) —H or —(C$_{1-5}$ alkyl),
j) —CH$_2$-RAX
k) -n propyl-RAX,
l) —3-phenylpropyl,
m) —R$_{3-500}$,
n) —CH$_2$-RAX
o) -n propyl-R$_{3-500}$,
p) —C(H)(OH)—R$_{3-1}$,
q) —(C$_{1-5}$ alkyl)—C(H)(OH)—R$_{3-1}$,
r) —C(O)—R$_{3-1}$,
s) —(C$_{1-4}$ alkyl)—C(O)—R$_{3-1}$,
t) —(C$_{1-4}$alkyl)—N(H)R$_{3-1}$,
u) —(C$_{1-4}$alkyl)—N((C$_{1-4}$ alkyl)((C$_{1-4}$ alkyl)—R$_{3-1}$),
v) —(C$_{1-4}$ alkyl)—N(H)C(O)—R$_{3-1}$,
w) —C(O)—N(H)R$_{3-1}$, or
x) —(C$_{1-4}$ alkyl)—C(O)—N(H)R$_{3-1}$;

wherein R$_{3-1}$ is
a) —NH—C(O)—,
b) —NH—SO$_2$—,
c) —NH—CO—NH—, or
d) —SO$_2$—NH—;

wherein, R$_{3-4}$ is
a) —OH,
b) —O—(C$_{1-6}$ alkyl),
c) —C(O)—OH,
d) —C(O)—O—(C$_{1-6}$ alkyl),
e) —(C$_{1-6}$ alkyl),
f) —(C$_{3-6}$ cycloalkyl),
g) —R$_{3-100}$, or
h) —R$_{3-500}$;

wherein R$_{3-6}$ is
a) —OH,
b) —C$_{1-10}$ alkyl,
c) —(C$_{0-6}$ alkyl)—C$_3$–C$_7$ cycloalkyl,
d) —(C$_{1-6}$ alkyl)—CH=CH$_2$,
e) —(C$_{0-6}$ alkyl)—R$_{3-4}$,
f) —(C$_{1-6}$ alkyl)—R$_{3-100}$, or
g) —(C$_{1-6}$ alkyl)—R$_{3-500}$;

wherein R$_{3-9}$ is
a) —(C$_{1-6}$ alkyl),
b) —(C$_{0-6}$ alkyl)—RA$_{3-RA-12}$, or
c) —(C$_{0-6}$ alkyl)—RA$_{3-RA-15}$;

wherein R$_{3-100}$ is independent of and defined the same as R$_{1-100}$;

wherein R$_{3-500}$ is independent of and defined the same as R$_{1-500}$;

wherein RA$_3$ is independent of and defined the same as RA$_1$;

wherein RA$_{3-RA-12}$, RA$_{3-RA-15}$, RA$_{3-RA-12-AXA}$ and RA$_{3-RA-15-AXA}$, are all independent of and defined the same as the corresponding R$_1$ variables, which are: RA$_{1-RA-12}$, RA$_{1-RA-15}$, RA$_{1-RA-12-AXA}$ and RA$_{1-RA-15-AXA}$, respectively, wherein R$_2$ and R$_3$ can be taken together to form a ring comprised of the following groups,
a) (C$_{5-9}$ cycloalkyl),
b) (C$_{5-9}$ cycloalkyl) substituted with one to two —R$_{3-9}$, or
c) —(C$_{1-5}$ alkyl substituted with zero to one R$_{3-9}$)—R$_{23}$—(C$_{1-5}$ alkyl);

wherein R$_{3-9}$ is
a) —(C$_{1-6}$ alkyl),
b) —(C$_{0-6}$ alkyl)—RA$_{3-RA-12}$, or
c) —(C$_{0-6}$ alkyl)—RA$_{3-RA-15}$;

or wherein R$_2$ and R$_3$ can be taken together to form a double bond represented by formula 50, shown below,

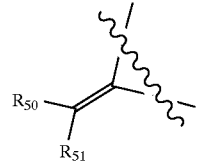

wherein R$_{11}$ is
a) —H,
b) —C$_1$–C$_4$ alkyl
c) —(RA$_{3-RA-12}$), or
d) pharmaceutically acceptable salts, wherein R$_{23}$ is
a) —O—,
b) —C(O)—,
c) —N(H)—,
d) —N(R$_{3-9}$)—,
e) —N(C(O)—R$_{3-9}$)—, or
f) —N(C(O)—O—R$_{3-9}$);

wherein R$_{30}$ is
a) -morpholino,
b) -piperidino,
c) -piperazino,
d) —OR$_{40}$,
e) -halo,
f)

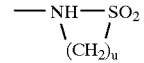

g) —NR$_{40}$R$_{41}$;

wherein R$_{40}$ and R$_{41}$ are defined independently and are,
a) —H,
b) —C$_1$–C$_4$ alkyl,
c) phenyl, substituted with zero (0) to three (3) RA$_{1-RA-120}$, wherein R$_{42}$ is a) —$C_1$–$C_4$ alkyl,
b) -phenyl, substituted with zero (0) to three (3) $RA_{1-RA-120}$, or
c) —($C_{0-6}$ alkyl)-phenyl, substituted with zero (0) to three (3) $RA_{1-RA-120}$;

wherein $RA_{2-RA-120}$ and $RA_{3-RA-120}$ are independent of and defined the same as $RA_{1-RA-120}$;

wherein $R_{50}$ and $R_{51}$ are defined independently and are
a) —(H or $C_{1-6}$ alkyl),
b) —($C_{0-6}$ alkyl)—$RA_{3-RA-12}$, or
c) —($C_{0-6}$ alkyl)—$RA_{3-RA-15}$;

wherein AA is an amino acid residue, wherein $P_1$ is hydrogen or a nitrogen protecting group, wherein m and n are independently zero (0) to five (5) inclusive, wherein p and q are independently one (1) to five (5) inclusive, wherein z is one (1) to three (3) inclusive; and pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42}$)$_2$, or —$G_{1-2}$—NH$_2$, then $G_{1-2}$ is NOT, —C(O)—NH—, —NH—SO$_2$—, —SO$_2$—NH—, —NH—SO$_2$—NH—, -C(O)—O—, —NH—C(O)—NH, —N(($C_{1-6}$ alkyl)—$R_{1-RA-12}$)—SO$_2$—, or —N(($C_{0-6}$ alkyl)—($C_{1-6}$ alkyl))—SO$_2$—.

19. A compound represented by the structure shown in formula 1,

Formula 1

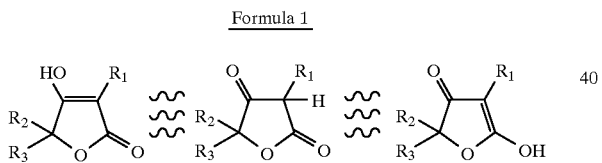

wherein 3 tautomers of the same structure are shown,
wherein $R_1$ is

Formula R1A

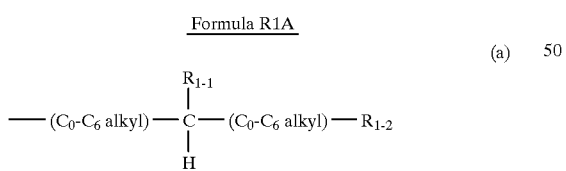

(a)

wherein $R_{1-1}$ is
a) —($C_{1-5}$ alkyl),
b) —($C_{2-5}$ alkenyl),
c) —($C_{3-7}$ cycloalkyl),
d) —($C_{3-5}$ cycloalkyl),
e) -cyclopropyl,
f) —($C_{1-5}$ alkyl)—($C_{3-7}$ cycloalkyl),
g) —$R_{1-100}$, or
h) —($C_1$–$C_5$ alkyl)—$R_{1-100}$;

wherein $R_{1-2}$ is —$R_{1-100}$, or —$R_{1-500}$;

wherein $R_{1-100}$ is a) phenyl, substituted with zero (0) to three (3) of $RA_1$, wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is
a) —H,
b) —($C_{1-5}$ alkyl),
c) —O—($C_{1-5}$ alkyl),
d) —C(O)—$RA_{1-3}$, wherein $RA_{1-3}$ is any N-terminus substituted amino acid,
e) —C(O)—N(H)$RA_{1-1}$,
f) —NH$_2$ (para or meta positions),
g) —N(H)($C_{1-5}$ alkyl) (para or meta positions),
h) —N($C_{1-5}$ alkyl)$_2$,
i) —N(H)$RA_{1-4}$, wherein $RA_{1-4}$ is any C-terminus substituted amino acid,
j) —N(H)C(O)—$RA_{1-1}$ (para or meta positions),
k) —N(H)C(O)—O—$RA_{1-1}$ (para or meta positions),
l) —N(H)(SO$_2$)—$RA_{1-2}$,
m) —N(CH$_3$)(SO$_2$)—$RA_{1-2}$,
n) —NO$_2$,
o) —SO$_2$NH$_2$,
p) —($C_{1-3}$ alkyl)—SO$_2$—$RA_{1-RA-12}$,
q) —($C_{1-3}$ alkyl)—SO$_2$—$RA_{1-RA-15}$,
r) -halo, wherein $RA_{1-1}$ is
a) —($C_{1-5}$ alkyl),
b) —($C_{1-5}$ alkyl)—C(O)—O—($C_{1-5}$ alkyl),
c) —($C_{1-5}$ alkyl)—NH$_2$,
d) —($C_{1-5}$ alkyl)—N(H)C(O)—O—($C_{1-5}$ alkyl),
e) —($C_{1-5}$ alkyl)—C((H)(NH$_2$))—C(O)OH,
f) —$RA_{1-RA-12}$,
g) —$RA_{1-RA-15}$,
h) —($C_{1-5}$ alkyl)-RAX,
i) —($C_{1-5}$ alkyl)—O-RAX,
j) —C(O)—$RA_{1-1-3}$, wherein $RA_{1-1-3}$ is any N-terminus amino acid,
k) —N(H)—$RA_{1-1-4}$, or wherein $RA_{1-2}$ is any C-terminus amino acid,
l) —$R_{1-500}$;

wherein $RA_{1-2}$ is
a) -RAX,
b) —($C_{1-5}$ alkyl)-RAX,
c) —($C_{1-5}$ alkyl)—O-RAX,
d) —$RA_{1-RA-12}$,
e) —$RA_{1-RA-15}$,
f) —($C_1$–$C_5$ alkyl)—$RA_{1-RA-12}$,
g) —($C_1$–$C_5$ alkyl)—$RA_{1-RA-15}$,
h) —($C_1$–$C_5$ alkyl)—O—$RA_{1-RA-12}$, or
i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
a) —NH—C(O)—,
b) —NH—SO$_2$—,
c) —NH—C(O)—NH—, or
d) —SO$_2$—NH—;

wherein $G_{1-2}$ is
  a) —NH—C(O)—,
  b) —C(O)—NH—,
  c) —NH—SO$_2$—,
  d) —SO$_2$—NH—,
  e) —NH—SO$_2$—NH—,
  f) —C(O)—O—,
  g) —O—C(O)—,
  h) —N((C$_{14}$ alkyl)—RA$_{1\text{-}RA\text{-}12}$)—C(O)—,
  i) —NH—C(O)—NH,
  j) —N((C$_{1-6}$ alkyl)—RA$_{1\text{-}RA\text{-}12}$)—SO$_2$—, or
  k) —N((C$_{0-6}$ alkyl)—(C$_{1-6}$ alkyl))—SO$_2$—;
wherein RA$_2$ and RA$_3$ are defined independently and are the same as RA$_1$;
wherein RA$_{1\text{-}RA\text{-}12}$ is
  a) -phenyl, substituted with zero (0) to three (3) RA$_{1\text{-}RA\text{-}12\text{-}AXA}$, or
  b) -naphthyl, substituted with zero (0) to three (3) RA$_{1\text{-}RA\text{-}12\text{-}AXA}$;
wherein RA$_{1\text{-}RA\text{-}15}$ is
  a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, C$_3$-C$_8$ cycloalkyl, or another heterocycle; and substituted with zero (0) to three (3) RA$_{1\text{-}RA\text{-}15\text{-}AXA}$;
wherein RA$_{1\text{-}RA\text{-}120}$, RA$_{2\text{-}RA\text{-}120}$ and RA$_{3\text{-}RA\text{-}120}$, are defined independently and are
  a) —C$_1$-C$_4$ alkyl,
  b) —C$_1$-C$_3$ alkoxy,
  c) -dimethylamino,
  d) -diethylamino,
  e) —CF$_3$,
  f) —CN,
  g) -halo,
  h) —NH$_2$,
  i) —OH,
  j) —SO$_2$—NH$_2$, or
  k) —C(O)—NH$_2$;
wherein RA$_{1\text{-}RA\text{-}12\text{-}AXA}$ or RA$_{1\text{-}RA\text{-}15\text{-}AXA}$ are independent and are,
  a) —H
  b) -halo,
  c) —NO$_2$,
  d) —CN,
  e) —(C$_{1-10}$ alkyl), substituted with zero (0) to three (3) halo,
  f) —(C$_{0-6}$ alkyl)-phenyl, substituted with zero (0) to three (3) halo or hydroxy,
  g) —OH,
  h) —O—C$_{1-5}$ alkyl,
  i) —(C$_{0-6}$ alkyl)—O—(C$_{1-6}$ alkyl), substituted with zero (0) to three (3) halo or hydroxy,
  j) —(C$_{0-6}$ alkyl)—O—(C$_{2-7}$ alkenyl), substituted with zero (0) to three (3) halo or hydroxy,
  k) —CH(O), l) —C(O)—(C$_{1-6}$ alkyl),
  m) —C(O)OH,
  n) —C(O)O—(C$_{1-5}$ alkyl),
  o) —C(O)—N(H or C$_{1-6}$ alkyl)$_2$,
  p) —NH$_2$,
  q) —NH—(C$_{1-6}$ alkyl),
  r) -mono or di —(C$_{1-6}$ alkyl)amino,
  s) —NH—OH,
  t) —NH—C(O)—(C$_{1-3}$ alkyl),
  u) —(C$_{0-6}$ alkyl)—NH—C(O)-phenyl,
  v) —(C$_{0-6}$ alkyl)—NH—SO$_2$-phenyl, w) —(C$_{0-6}$ alkyl)—N=N-phenyl, substituted with zero (0) or one (1) —N(C$_1$-C$_3$ alkyl)$_2$, or
  x) —SO$_2$-phenyl, substituted with zero (0) to three (3) C$_1$-C$_5$ alkyl;
wherein R$_2$ is
  a) —C$_{3-4}$ alkyl,
  b) -n-propyl,
  c) —C$_{1-5}$ alkyl)—C$_{3-5}$ cycloalkyl,
  d) —(C$_{2-5}$ alkenyl)
  e) —(C$_{1-5}$ alkyl)—R$_{2-100}$,
  f) —(C$_{1-5}$ alkyl)—R$_{2-500}$,
wherein R$_{2-100}$ is independent of and defined the same as R$_{1-100}$ wherein RA$_1$ is RA$_2$;
wherein R$_{2-500}$ is independent of and defined the same as R$_{1-500}$ wherein RA$_1$ is RA$_2$;
wherein RA$_2$ is independent of and defined the same as RA$_1$;
wherein R$_3$ is
  a) —(C$_{1-5}$ alkyl),
  b) —(CH$_2$—CH=CH$_2$),
  c) —(C$_{1-5}$ alkyl)—(C$_{3-5}$ cycloalkyl),
  d) —(C$_{1-5}$ alkyl)—O—(CH$_2$CH$_2$O)$_q$—CH$_3$,
  e) —(C$_{1-6}$ alkyl)—R$_{3-4}$,
  f) —(C2-6 alkenyl)—R$_{3-4}$,
  g) —R$_{3-100}$,
  h) —(C$_{1-4}$ alkyl)—R$_{3-100}$,
  i) —H or —(C$_{1-5}$ alkyl),
  j) —CH$_2$-RAX
  k) -n propyl-RAX,
  l) —3-phenylpropyl,
  m) —R$_{3-500}$,
  n) —CH$_2$-RAX
  o) -n propyl-R$_{3-500}$,
  p) —C(H)(OH)—R$_{3-1}$,
  q) —(C$_{1-5}$ alkyl)—C(H)(OH)—R$_{3-1}$,
  r) —C(O)—R$_{3-1}$,
  s) —(C$_{1-4}$ alkyl)—C(O)—R$_{3-1}$,
  t) —(C$_{1-4}$ alkyl)—N(H)R$_{3-1}$,
  u) —(C$_{1-4}$ alkyl)—N((C$_{1-4}$ alkyl)((C$_{1-4}$ alkyl)—R$_{3-1}$),
  v) —(C$_{1-4}$ alkyl)—N(H)C(O)—R$_{3-1}$,
  w) —C(O)—N(H)R$_{3-1}$, or
  x) —(C$_{1-4}$ alkyl)—C(O)—N(H)R$_{3-1}$;
wherein R$_{3-1}$ is
  a) —NH—C(O)—,
  b) —NH—SO$_2$—,
  c) —NH—CO—NH—, or
  d) —SO$_2$—NH—;
wherein, R$_{3-4}$ is
  a) —OH,
  b) —O—(C$_{1-6}$ alkyl),
  c) —C(O)—OH,
  d) —C(O)—O—(C$_{1-6}$ alkyl),
  e) —(C$_{1-6}$ alkyl),
  f) —(C$_{3-6}$ cycloalkyl),
  g) —R$_{3-100}$, or
  h) —R$_{3-500}$;
wherein R$_{3-6}$ is
  a) —OH,
  b) —C$_{1-10}$ alkyl,
  c) —(C$_{0-6}$ alkyl)—C$_3$-C$_7$ cycloalkyl,
  d) —(C$_{1-6}$ alkyl)—CH=CH$_2$,
  e) —(C$_{0-6}$ alkyl)—R$_{3-4}$,
  f) —(C$_{1-6}$ alkyl)—R$_{3-100}$, or
  g) —(C$_{1-6}$ alkyl)—R$_{3-500}$;

wherein $R_{3-9}$ is
   a) —($C_{1-6}$ alkyl),
   b) —($C_{0-6}$ alkyl)—$RA_{3-RA-12}$, or
   c) —($C_{0-6}$ alkyl)—$RA_{3-RA-15}$;
wherein $R_{3-100}$ is independent of and defined the same as $R_{1-100}$;
wherein $R_{3-500}$ is independent of and defined the same as $R_{1-500}$;
wherein $RA_3$ is independent of and defined the same as $RA_1$;
wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively,
wherein $R_2$ and $R_3$ can be taken together to form a ring comprised of the following groups,
   a) ($C_{5-9}$ cycloalkyl),
   b) ($C_{5-9}$ cycloalkyl) substituted with one to two —$R_{3-9}$, or
   c) —$C_{1-5}$ alkyl substituted with zero to one $R_{3-9}$)—$R_{23}$—($C_{1-5}$ alkyl);
wherein $R_{3-9}$ is
   a) —($C_{1-6}$ alkyl),
   b) —($C_{0-6}$ alkyl)—$RA_{3-RA-12}$, or
   c) —($C_{0-6}$ alkyl)—$RA_{3-RA-15}$;
or
wherein $R_2$ and $R_3$ can be taken together to form a double bond represented by formula 50, shown below,

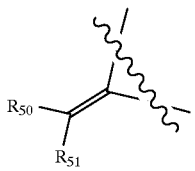

wherein $R_{11}$ is
   a) —H,
   b) —$C_1$–$C_4$ alkyl,
   c) —($RA_{3-RA-12}$), or
   d) pharmaceutically acceptable salts,
wherein $R_{23}$ is
   a) —O—,
   b) —C(O)—,
   c) —N(H)—,
   d) —N($R_{3-9}$)—,
   e) —N(C(O)—R—$_{3-9}$)—, or
   f) —N(C(O)—O—$R_{3-9}$);
wherein $R_{30}$ is
   a) -morpholino,
   b) -piperidino,
   c) -piperazino,
   d) —$OR_{40}$,
   e) -halo,
   f)

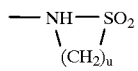

g) —$NR_{40}R_{41}$;
wherein $R_{40}$ and $R_{41}$ are defined independently and are,
   a) —H,
   b) —$C_1$–$C_4$ alkyl,
   c) phenyl, substituted with zero (0) to three (3) $RA_{1-RA-120}$,
wherein $R_{42}$ is
   a) —$C_1$–$C_4$ alkyl,
   b) -phenyl, substituted with zero (0) to three (3) $RA_{1-RA-120}$, or
   c) —($C_{0-6}$ alkyl)-phenyl, substituted with zero (0) to three (3) $RA_{1-RA-120}$;
wherein $RA_{2-RA-120}$ and $RA_{3-RA-120}$ are independent of and defined the same as $RA_{1-RA-120}$;
wherein $R_{50}$ and $R_{51}$ are defined independently and are
   a) —(H or $C_{1-6}$ alkyl),
   b) —($C_{0-6}$ alkyl)—$RA_{3-RA-12}$, or
   c) —($C_{0-6}$ alkyl)—$RA_{3-RA-15}$;
wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof,
   with the proviso that when $R_1$ is 1-phenylpropyl and $R_2$ is H, then $R_3$ is not $C_{1-5}$ alkyl, and
   with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—$N(R_{42})_2$, or —$G_{1-2}$—$NH_2$, then $G_{1-2}$ is NOT, —C(O)—NH—, —NH—$SO_2$—, —$SO_2$—NH—, —NH—$SO_2$—NH—, -C(O)—O—, —NH—C(O)—NH, —N(($C_{1-6}$ alkyl)—$RA_{1-RA-12}$)—$SO_2$—, or —N(($C_{0-6}$ alkyl)—($C_{1-6}$ alkyl))—$SO_2$—.

20. A compound represented by the structure shown in formula 1,

Formula 1

HO   $R_1$         O   $R_1$              O   $R_1$
  \\_//             \\_//—H               \\_//
$R_2$              $R_2$                  $R_2$
$R_3$   O   O      $R_3$   O   O          $R_3$   O   OH wherein 3 tautomers of the same structure are shown,
wherein $R_1$ is —CH($R_{1-1}$)—$R_{1-2}$;
wherein $R_{1-1}$ is
   a) —($C_{1-5}$ alkyl),
   b) —($C_{2-5}$ alkenyl),
   c) —($C_{3-7}$ cycloalkyl),
   d) —($C_{3-5}$ cycloalkyl),
   e) -cyclopropyl,
   f) —($C_{1-5}$ alkyl)—($C_{3-7}$ cycloalkyl),
   g) —$R_{1-100}$, or
   h) —($C_{1-5}$ alkyl)—$R_{1-100}$;
wherein $R_{1-2}$ is —$R_{1-100}$, or —$R_{1-500}$;
wherein $R_{1-100}$ is
   a) phenyl, substituted with zero (0) to three (3) of $RA_1$,
wherein $R_{1-500}$ is
   a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is
- a) —H,
- b) —($C_{1-5}$ alkyl),
- c) —O—($C_{1-5}$ alkyl),
- d) —C(O)—$RA_{1-3}$, wherein $RA_{1-3}$ is any N-terminus substituted amino acid,
- e) —C(O)—N(H)$RA_{1-1}$,
- f) —$NH_2$ (para or meta positions),
- g) —N(H)($C_{1-5}$ alkyl) (para or meta positions),
- h) —N($C_{1-5}$ alkyl)$_2$,
- i) —N(H)$RA_{1-4}$, wherein $RA_{1-4}$ is any C-terminus substituted amino acid,
- j) —N(H)C(O)—$RA_{1-1}$ (para or meta positions),
- k) —N(H)C(O)—O—$RA_{1-1}$ (para or meta positions),
- l) —N(H)($SO_2$)—$RA_{1-2}$,
- m) —N($CH_3$)($SO_2$)—$RA_{1-2}$,
- n) —$NO_2$,
- o) —$SO_2NH_2$,
- p) —($C_{1-3}$ alkyl)—$SO_2$—$RA_{1-RA-12}$,
- q) —($C_{1-3}$ alkyl)—$SO_2$—$RA_{1-RA-15}$,
- r) -halo, wherein $RA_{1-1}$ is
- a) —($C_{1-5}$ alkyl),
- b) —($C_{1-5}$ alkyl)—C(O)—O—($C_{1-5}$ alkyl),
- c) —($C_{1-5}$ alkyl)—$NH_2$,
- d) —($C_{1-5}$ alkyl)—N(H)C(O)—O—($C_{1-5}$ alkyl),
- e) —($C_{1-5}$ alkyl)—C((H)($NH_2$))—C(O)OH,
- f) —$RA_{1-RA-12}$,
- g) —$RA_{1-RA-15}$,
- h) —($C_{1-5}$ alkyl)-RAX,
- i) —($C_{1-5}$ alkyl)—O-RAX,
- j) —C(O)—$RA_{1-1-3}$, wherein $RA_{1-1-3}$ is any N-terminus amino acid,
- k) —N(H)—$RA_{1-1-4}$, or wherein $RA_{1-1-4}$ is any C-terminus amino acid,
- l) —$R_{1-500}$;

wherein $RA_{1-2}$ is
- a) -RAX
- b) —($C_{1-5}$ alkyl)-RAX,
- c) —($C_{1-5}$ alkyl)—O-RAX,
- d) —$RA_{1-RA-12}$,
- e) —$RA_{1-RA-15}$,
- f) —($C_1$–$C_5$ alkyl)—$RA_{1-RA-12}$,
- g) —($C_1$–$C_5$ alkyl)—$RA_{1-RA-15}$,
- h) —($C_1$–$C_5$ alkyl)—O—$RA_{1-RA-12}$, or
- i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
- a) —NH—C(O)—,
- b) —NH—$SO_2$—,
- c) —NH—C(O)—NH—, or
- d) —$SO_2$—NH—;

wherein $G_{1-2}$ is
- a) —NH—C(O)—,
- b) —C(O)—NH—,
- c) —NH—$SO_2$—,
- d) —$SO_2$—NH—,
- e) —NH—$SO_2$—NH—,
- f) —C(O)—O—,
- g) —O—C(O)—,
- h) —N(($C_{1-6}$ alkyl)—$RA_{1-RA-12}$)—C(O)—,
- i) —NH—C(O)—NH,
- j) —N(($C_{1-6}$ alkyl)—$RA_{1-RA-12}$)—$SO_2$—, or
- k) —N(($C_{0-6}$ alkyl)—($C_{1-6}$ alkyl))—$SO_2$—;

wherein $RA_2$ and $RA_3$ are defined independently and are the same as $RA_1$;

wherein $RA_{1-RA-12}$ is
- a) -phenyl, substituted with zero (0) to three (3) $RA_{1-RA-12-AXA}$, or
- b) -naphthyl, substituted with zero (0) to three (3) $RA_{1-RA-12-AXA}$;

wherein $RA_{1-RA-15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;

wherein $RA_{1-RA-120}$, $RA_{2-RA-120}$ and $RA_{3-RA-120}$, are defined independently and are
- a) —$C_1$–$C_4$ alkyl,
- b) —$C_1$–$C_3$ alkoxy,
- c) -dimethylamino,
- d) -diethylamino,
- e) —$CF_3$,
- f) —CN,
- g) -halo,
- h) —$NH_2$,
- i) —OH,
- j) —$SO_2$—$NH_2$, or
- k) —C(O)—$NH_2$;

wherein $RA_{1-RA-12-AXA}$ or $RA_{1-RA-15-AXA}$ are independent and are,
- a) —H
- b) -halo,
- c) —$NO_2$,
- d) —CN,
- e) —($C_{1-10}$ alkyl), substituted with zero (0) to three (3) halo,
- f) —($C_{0-6}$ alkyl)-phenyl, substituted with zero (0) to three (3) halo or hydroxy,
- g) —OH,
- h) —O—$C_{1-5}$ alkyl,
- i) —($C_{0-6}$ alkyl)—O—($C_{1-6}$alkyl), substituted with zero (0) to three (3) halo or hydroxy,
- j) —($C_{0-6}$ alkyl)—O—($C_{2-7}$ alkenyl), substituted with zero (0) to three (3) halo or hydroxy,
- k) —CH(O),
- l) —C(O)—($C_{1-6}$ alkyl),
- m) —C(O)OH,
- n) —C(O)O—($C_{1-5}$ alkyl),
- o) —C(O)—N(H or $C_{1-6}$ alkyl)$_2$,
- p) —$NH_2$,
- q) —NH—($C_{1-6}$ alkyl),
- r) -mono or di —($C_{1-6}$ alkyl)amino,
- s) —NH—OH,
- t) —NH—C(O)—($C_{1-3}$ alkyl),
- u) —($C_{0-6}$ alkyl)—NH—C(O)-phenyl,
- v) —($C_{0-6}$ alkyl)—NH—$SO_2$-phenyl,
- w) —($C_{0-6}$ alkyl)—N=N-phenyl, substituted with zero (0) or one (1) —N($C_1$–$C_3$ alkyl)$_2$, or x) —SO$_2$-phenyl, substituted with zero (0) to three (3) C$_1$–C$_5$ alkyl;

wherein R$_2$ is
a) —C$_{3-4}$ alkyl,
b) -n-propyl,
c) —(C$_{1-5}$ alkyl)—C$_{3-5}$ cycloalkyl,
d) —(C$_{2-5}$ alkenyl)
e) —C$_{1-5}$ alkyl)—R$_{2-100}$,
f) —(C$_{1-5}$ alkyl)—R$_{2-500}$, wherein R$_{2-100}$ is independent of and defined the same as R$_{1-100}$ wherein RA$_1$ is RA$_2$;

wherein R$_{2-500}$ is independent of and defined the same as R$_{1-500}$ wherein RA$_1$ is RA$_2$;

wherein RA$_2$ is independent of and defined the same as RA$_1$;

wherein R$_3$ is
a) —(C$_{1-5}$ alkyl),
b) —(CH$_2$—CH=CH$_2$),
c) —(C$_{1-5}$ alkyl)—(C$_{3-5}$ cycloalkyl),
d) —(C$_{1-5}$ alkyl)—O—(CH$_2$CH$_2$O)$_q$—CH$_3$,
e) —(C$_{1-6}$ alkyl)—R$_{3-4}$,
f) —(C$_{2-6}$ alkenyl)—R$_{3-4}$,
g) —R$_{3-100}$)
h) —(C$_{1-4}$ alkyl)—R$_{3-100}$,
i) —H or —(C$_{1-5}$ alkyl),
j) —CH$_2$-RAX
k) -n propyl-RAX,
l) —3-phenylpropyl,
m) —R$_{3-500}$,
n) —CH$_2$-RAX
o) -n propyl-R$_{3-500}$,
p) —C(H)(OH)—R$_{3-1}$,
q) —(C$_{1-5}$ alkyl)—C(H)(OH)—R$_{3-1}$,
r) —C(O)—R$_{3-1}$,
s) —(C$_{1-4}$ alkyl)—C(O)—R$_{3-1}$,
t) —(C$_{1-4}$ alkyl)—N(H)R$_{3-1}$,
u) —(C$_{1-4}$ alkyl)—N((C$_{1-4}$ alkyl)((C$_{1-4}$ alkyl)—R$_{3-1}$),
v) —(C$_{1-4}$ alkyl)—N(H)C(O)—R$_{3-1}$,
w) —C(O)—N(H)R$_{3-1}$, or
x) —(C$_{1-4}$ alkyl)—C(O)—N(H)R$_{3-1}$;

wherein R$_{3-1}$ is
a) —NH—C(O)—,
b) —NH—SO$_2$—,
c) —NH—CO—NH—, or
d) —SO$_2$—NH—;

wherein, R$_{3-4}$ is
a) —OH,
b) —O—(C$_{1-6}$alkyl),
c) —C(O)—OH,
d) —C(O)—O—(C$_{1-6}$ alkyl),
e) —(C$_{1-6}$ alkyl),
f) —(C$_{3-6}$ cycloalkyl),
g) —R$_{3-100}$, or wherein R$_{3-6}$ is
a) —OH,
b) —C$_{1-10}$ alkyl,
c) —(C$_{0-6}$ alkyl)—C$_3$–C$_7$ cycloalkyl,
d) —(C$_{1-6}$ alkyl)—CH=CH$_2$,
e) —(C$_{0-6}$ alkyl)—R$_{3-4}$,
f) —(C$_{1-6}$ alkyl)—R$_{3-100}$, or
g) —(C$_{1-6}$ alkyl)—R$_{3-500}$;

wherein R$_{3-9}$ is
a) —(C$_{1-6}$ alkyl),
b) —(C$_{0-6}$ alkyl)—RA$_{3-RA-12}$, or
c) —(C$_{0-6}$ alkyl)—RA$_{3-RA-15}$;

wherein R$_{3-100}$ is independent of and defined the same as R$_{1-100}$;

wherein R$_{3-500}$ is independent of and defined the same as R$_{1-500}$;

wherein RA$_3$ is independent of and defined the same as RA$_1$;

wherein RA$_{3-RA-12}$, RA$_{3-RA-15}$, RA$_{3-RA-12-AXA}$ and RA$_{3-RA-15-AXA}$, are all independent of and defined the same as the corresponding R$_1$ variables, which are: RA$_{1-RA-12}$, RA$_{1-RA-15}$, RA$_{1-RA-12-AXA}$ and RA$_{1-RA-15-AXA}$, respectively, wherein R$_2$ and R$_3$ can be taken together to form a ring comprised of the following groups,
a) (C$_{5-9}$ cycloalkyl),
b) (C$_{5-9}$ cycloalkyl) substituted with one to two —R$_{3-9}$, or
c) —(C$_{1-5}$ alkyl substituted with zero to one R$_{3-9}$)—R$_{23}$—(C$_{1-5}$ alkyl);

wherein R$_{3-9}$ is
a) —(C$_{1-6}$ alkyl),
b) —(C$_{0-6}$ alkyl)—RA$_{3-RA-12}$, or
c) —(C$_{0-6}$ alkyl)-RA$_{3-RA-15}$;
or
wherein R$_2$ and R$_3$ can be taken together to form a double bond represented by formula 50, shown below,

R$_{50}$—⧸=⧹
R$_{51}$ wherein R$_{11}$ is
a) —H,
b) —C$_1$–C$_4$ alkyl,
c) —(RA$_{3-RA-12}$), or
d) pharmaceutically acceptable salts, wherein R$_{23}$ is
a) —O—,
b) —C(O)—,
c) —N(H)—,
d) —N(R$_{3-9}$)—,
e) —N(C(O)—R$_{3-9}$)—, or
f) —N(C(O)—O—R$_{3-9}$);

wherein R$_{30}$ is
a) -morpholino,
b) -piperidino,
c) -piperazino,
d) —OR$_{40}$,
e) -halo,
f)

—NH—SO$_2$
\    /
(CH$_2$)$_u$ g) —NR$_{40}$R$_{41}$;

wherein R$_{40}$ and R$_{41}$ are defined independently and are,
a) —H,
b) —C$_1$–C$_4$ alkyl,
c) phenyl, substituted with zero (0) to three (3) RA$_{1-RA-120}$, wherein R$_{42}$ is
a) —C$_1$–C$_4$ alkyl,
b) -phenyl, substituted with zero (0) to three (3) RA$_{1-RA-120}$, or c) —($C_{0-6}$ alkyl)-phenyl, substituted with zero (0) to three (3) $RA_{1-RA-120}$;

wherein $RA_{2-RA-120}$ and $RA_{3-RA-120}$ are independent of and defined the same as $RA_{1-RA-120}$;

wherein $R_{50}$ and $R_{51}$ are defined independently and are
a) —(H or $C_{1-6}$ alkyl),
b) —($C_{0-6}$ alkyl)—$RA_{3-RA-12}$, or
c) —($C_{0-6}$ alkyl)—$RA_{3-RA-15}$;

wherein AA is an amino acid residue, wherein $P_1$ is hydrogen or a nitrogen protecting group, wherein m and n are independently zero (0) to five (5) inclusive, wherein p and q are independently one (1) to five (5) inclusive, wherein z is one (1) to three (3) inclusive; and pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42}$)$_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$RA_{1-RA-12}$)—$SO_2$—, or —N(($C_{0-6}$ alkyl)—($C_{1-6}$ alkyl))—$SO_2$—.

21. A compound represented by the structure shown in formula 1,

Formula 1

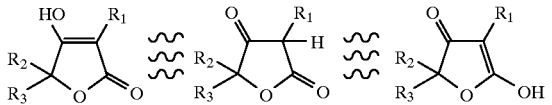

wherein 3 tautomers of the same structure are shown, wherein $R_1$ is —CH($R_{1-1}$)—$R_{1-2}$;

wherein $R_{1-1}$ is
a) —($C_{1-5}$ alkyl),
b) —($C_{3-5}$ cycloalkyl),
c) -cyclopropyl, wherein $R_{1-2}$ is —$R_{1-100}$ or —$R_{1-500}$;

wherein $R_{1-100}$ is
a) phenyl, substituted with zero (0) to three (3) of $RA_1$, wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is
a) —H,
b) —($C_{1-5}$ alkyl),
c) —O—($C_{1-5}$ alkyl), wherein $RA_{1-4}$ is any C-terminus substituted amino acid,
j) —N(H)C(O)—$RA_{1-1}$ (para or meta positions),
k) —N(H)C(O)—O—$RA_{1-1}$ (para or meta positions),
l) —N(H)($SO_2$)—$RA_{1-2}$,
m) —N($CH_3$)($SO_2$)—$RA_{1-2}$,
n) —$NO_2$,
o) —$SO_2NH_2$,
p) —($C_{1-3}$ alkyl)—$SO_2$—$RA_{1-RA-12}$,
q) —($C_{1-3}$ alkyl)—$SO_2$—$RA_{1-RA-15}$,
r) -halo, wherein $RA_{1-1}$ is
a) —$C_{1-5}$ alkyl),
b) —($C_{1-5}$ alkyl)—C((H)($NH_2$))—C(O)OH, wherein $RA_{1-2}$ is
a) -RAX,
b) —($C_{1-5}$ alkyl)-RAX,
c) —($C_{1-5}$ alkyl)—O-RAX,
d) —$RA_{1-RA-12}$,
e) —$RA_{1-RA-15}$,
f) —($C_1$–$C_5$ alkyl)—$R_{1-RA-12}$,
g) —($C_1$–$C_5$ alkyl)—$RA_{1-RA-15}$,
h) —($C_1$–$C_5$ alkyl)—O—$RA_{1-RA-12}$, or
i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
a) —NH—C(O)—,
b) —NH—$SO_2$—,
c) —NH—C(O)—NH—, or
d) —$SO_2$—NH—;

wherein $G_{1-2}$ is
a) —NH—C(O)—,
b) —C(O)—NH—,
c) —NH—$SO_2$—,
d) —$SO_2$—NH—,
e) —NH—$SO_2$—NH—,
f) —C(O)—O—,
g) —O—C(O)—,
h) —N(($C_{1-6}$ alkyl)—$RA_{1-RA-12}$)—C(O)—,
i) —NH—C(O)—NH,
j) —N(($C_{1-6}$ alkyl)—$R_{1-RA-12}$)—$SO_2$—, or
k) —N(($C_{0-6}$ alkyl)—($C_{1-6}$ alkyl))—$SO_2$—;

wherein $RA_2$ and $RA_3$ are defined independently and are the same as $RA_1$;

wherein $RA_{1-RA-12}$ is
a) -phenyl, substituted with zero (0) to three (3) $RA_{1-RA-12}$-AXA, or
b) -naphthyl, substituted with zero (0) to three (3) $RA_{1-RA-12-AXA}$;

wherein $RA_{1-RA-15}$ is
a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{1-RA-15-AXA}$;

wherein $RA_{1-RA-120}$, $RA_{2-RA-120}$ and $RA_{3-RA-120}$, are defined independently and are
a) —$C_1$–$C_4$ alkyl,
b) —$C_1$–$C_3$ alkoxy,
c) -dimethylamino,
d) -diethylamino,
e) —$CF_3$,
f) —CN, g) -halo,
h) —$NH_2$,
i) —OH,
j) —$SO_2$—$NH_2$, or
k) —C(O)—$NH_2$;

wherein $RA_{1-RA-12-AXA}$ or $RA_{1-RA-15-AXA}$ are independent and are,
a) —H
b) -halo,
c) —$NO_2$,
d) —CN,
e) —($C_{1-10}$ alkyl), substituted with zero (0) to three (3) halo,
f) —($C_{0-6}$ alkyl)-phenyl, substituted with zero (0) to three (3) halo or hydroxy,
g) —OH,
h) —O—$C_{1-5}$ alkyl,
i) —($C_{0-6}$ alkyl)—O—($C_{1-6}$ alkyl), substituted with zero (0) to three (3) halo or hydroxy,
j) —($C_{0-6}$ alkyl)—O—($C_{2-7}$ alkenyl), substituted with zero (0) to three (3) halo or hydroxy,
k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —$NH_2$,
q) —NH—($C_{1-6}$ alkyl),
r) -mono or di-($C_{1-6}$ alkyl)amino,
s) —NH—OH,
t) —NH—C(O)—($C_{1-3}$alkyl),
u) —($C_{0-6}$ alkyl)—NH—C(O)-phenyl,
v) —($C_{0-6}$ alkyl)—NH—$SO_2$-phenyl,
w) —($C_{0-6}$ alkyl)—N=N-phenyl, substituted with zero (0) or one (1) —N($C_1$–$C_3$ alkyl)$_2$, or
x) —$SO_2$-phenyl, substituted with zero (0) to three (3) $C_1$–$C_5$ alkyl;

wherein $R_2$ is
a) —$C_{3-4}$ alkyl,
b) -n-propyl,
c) —($C_{1-5}$ alkyl)—$C_{3-5}$ cycloalkyl,
d) —($C_{2-5}$ alkenyl)
e) —($C_{1-5}$ alkyl)—$R_{2-100}$,
f) —($C_{1-5}$ alkyl)—$R_{2-500}$, wherein $R_{2-100}$ is independent of and defined the same as $R_{1-100}$ wherein $RA_1$ is $RA_2$;

wherein $R_{2-500}$ is independent of and defined the same as $R_{1-500}$ wherein $RA_1$ is $RA_2$;

wherein $RA_2$ is independent of and defined the same as $RA_1$;

wherein $R_3$ is
a) —($C_{1-5}$ alkyl),
b) —($CH_2$—CH=$CH_2$),
c) —($C_{1-5}$ alkyl)—($C_{3-5}$ cycloalkyl),
d) —($C_{1-5}$ alkyl)—O—($CH_2CH_2O)_q$—$CH_3$,
e) —($C_{1-6}$ alkyl)—$R_{3-4}$,
f) —($C_{2-6}$ alkenyl)—$R_{3-4}$,
g) —$R_{3-100}$,
h) —($C_{1-4}$ alkyl)—$R_{3-100}$,
i) —H or —($C_{1-5}$ alkyl),
j) —$CH_2$-RAX
k) -n propyl-RAX,
l) —3-phenylpropyl,
m) —$R_{3-500}$,
n) —$CH_2$-RAX
o) -n propyl-$R_{3-500}$,
p) -benzyl, wherein $R_{3-1}$ is
a) —NH—C(O)—,
b) —NH—$SO_2$—,
c) —NH—CO—NH—, or
d) —$SO_2$—NH—;

wherein, $R_{3-4}$ is
a) —OH,
b) —O—($C_{1-6}$ alkyl),
c) —C(O)—OH,
d) —C(O)—O—($C_{1-6}$ alkyl),
e) —($C_{1-6}$ alkyl),
f) —($C_{3-6}$ cycloalkyl),
g) —$R_{3-100}$, or
h) —$R_{3-500}$;

wherein $R_{3-6}$ is
a) —OH,
b) —$C_{1-10}$ alkyl,
c) —($C_{0-6}$ alkyl)—$C_3$–$C_7$ cycloalkyl,
d) —($C_{1-6}$ alkyl)—CH=$CH_2$,
e) —($C_{0-6}$ alkyl)—$R_{3-4}$,
f) —($C_{1-6}$ alkyl)—$R_{3-100}$, or
g) —($C_{1-6}$ alkyl)—$R_{3-500}$;

wherein $R_{3-9}$ is
a) —($C_{1-6}$ alkyl),
b) —($C_{0-6}$ alkyl)—$RA_{3-RA-12}$, or
c) —($C_{0-6}$ alkyl)—$RA_{3-RA-15}$;

wherein $R_{3-100}$ is independent of and defined the same as $R_{1-100}$;

wherein $R_{3-500}$ is independent of and defined the same as $R_{1-500}$;

wherein $RA_3$ is independent of and defined the same as $RA_1$;

wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively, wherein $R_2$ and $R_3$ can be taken together to form a ring comprised of the following groups,
a) ($C_{5-9}$ cycloalkyl),
b) ($C_{5-9}$ cycloalkyl) substituted with one to two —$R_{3-9}$, or
c) —($C_{1-5}$ alkyl substituted with zero to one $R_{3-9}$)—$R_{23}$—($C_{1-5}$ alkyl);

wherein $R_{3-9}$ is
a) —($C_{1-6}$ alkyl),
b) —($C_{0-4}$ alkyl)—$RA_{3-RA-12}$, or
c) —($C_{0-6}$ alkyl)—$RA_{3-RA-15}$;

or wherein $R_2$ and $R_3$ can be taken together to form a double bond represented by formula 50, shown below, wherein $R_{11}$ is
a) —H,
b) —$C_1$–$C_4$ alkyl,
c) —($RA_{3-RA-12}$), or d) pharmaceutically acceptable salts,
wherein $R_{23}$ is
  a) —O—,
  b) —C(O)—,
  c) —N(H)—,
  d) —N($R_{3-9}$)—,
  e) —N(C(O)—$R_{3-9}$)—, or
  f) —N(C(O)—O—$R_{3-9}$);
wherein $R_{30}$ is
  a) -morpholino,
  b) -piperidino,
  c) -piperazino,
  d) —O$R_{40}$,
  e) -halo,
  f)

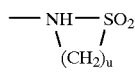

g) —N$R_{40}R_{41}$;
wherein $R_{40}$ and $R_{41}$ are defined independently and are,
  a) —H,
  b) —$C_1$–$C_4$ alkyl,
  c) phenyl, substituted with zero (0) to three (3) $RA_{1\text{-}RA\text{-}120}$,
wherein $R_{42}$ is
  a) —$C_1$–$C_4$ alkyl,
  b) -phenyl, substituted with zero (0) to three (3) $RA_{1\text{-}RA\text{-}120}$, or
  c) —($C_{0-6}$ alkyl)-phenyl, substituted with zero (0) to three (3) $RA_{1\text{-}RA\text{-}120}$;
wherein $R_{2\text{-}RA\text{-}120}$ and $RA_{3\text{-}RA\text{-}120}$ are independent of and defined the same as $RA_{1\text{-}RA\text{-}120}$;
wherein $R_{50}$ and $R_{51}$ are defined independently and are
  a) —(H or $C_{1-6}$ alkyl),
  b) —($C_{0-6}$ alkyl)—$RA_{3\text{-}RA\text{-}12}$, or
  c) —($C_{0-6}$ alkyl)—$RA_{3\text{-}RA\text{-}15}$;
wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof, with the proviso that when $R_1$ is 1-phenylpropyl and $R_2$ is H, then $R_3$ is not $C_{1-5}$ alkyl, and
with the proviso that when $RA_1$ or $RA_3$ is —$G_{1-2}$—($C_{0-6}$ alkyl)—O—$R_{1\text{-}RA\text{-}12}$, —($C_{0-6}$ alkyl)—$G_{1-2}$—($C_{0-6}$ alkyl)—O—($C_{0-6}$ alkyl), —($C_{0-6}$ alkyl)-$G_{1-2}$—O—($C_{1-6}$ alkyl)—$RA_{1\text{-}RA\text{-}12}$, —($C_{0-6}$ alkyl)—$G_{1-2}$—O—($C_{1-6}$ alkyl)—$RA_{1\text{-}RA\text{-}15}$, —$G_{1-2}$—N($R_{42})_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$RA_{1\text{-}RA\text{-}12}$)—$SO_2$—, or —N(($C_{0-6}$ alkyl)—($C_{1-6}$ alkyl))—$SO_2$—.

22. A compound represented by the structure shown in formula 1,

Formula 1

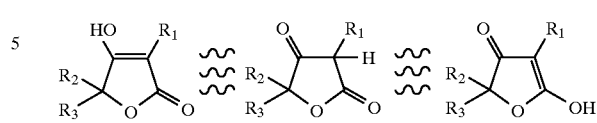

Formula 1
wherein 3 tautomers of the same structure are shown,
wherein $R_1$ is —CH($R_{1-1}$)—$R_{1-2}$;
wherein $R_{1-1}$ is
  a) —($C_{1-5}$ alkyl),
  b) —($C_{3-5}$ cycloalkyl),
  c) -cyclopropyl,
wherein $R_{1-2}$ is —$R_{1-100}$, or —$R_{1-500}$;
wherein $R_{1-100}$ is
  a) phenyl, substituted with zero (0) to three (3) of $RA_1$,
wherein $R_{1-500}$ is
  a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
  a) —H,
  b) —($C_{1-5}$ alkyl),
  c) —O—($C_{1-5}$ alkyl),
wherein $RA_{1-4}$ is any C-terminus substituted amino acid,
  j) —N(H)C(O)—$RA_{1-1}$ (para or meta positions),
  k) —N(H)C(O)—O—$RA_{1-1}$ (para or meta positions),
  l) —N(H)($SO_2$)—$RA_{1-2}$,
  m) —N($CH_3$)($SO_2$)—$RA_{1-2}$,
  n) —$NO_2$,
  o) —$SO_2NH_2$,
  p) —($C_{1-3}$ alkyl)—$SO_2$—$RA_{1\text{-}RA\text{-}12}$,
  q) —($C_{1-3}$ alkyl)—$SO_2$—$RA_{1\text{-}RA\text{-}15}$,
  r) -halo,
wherein $RA_{1-1}$ is
  a) —($C_{1-5}$ alkyl),
  b) —($C_{1-5}$ alkyl)—C((H)($NH_2$))—C(O)OH,
wherein $RA_{1-2}$ is
  a) -RAX,
  b) —($C_{1-5}$ alkyl)-RAX,
  c) —($C_{1-5}$ alkyl)—O-RAX,
  d) —$RA_{1\text{-}RA\text{-}12}$)
  e) —$RA_{1\text{-}RA\text{-}15}$)
  f) —($C_1$–$C_5$ alkyl)—$RA_{1\text{-}RA\text{-}12}$,
  g) —($C_1$–$C_5$ alkyl)—$RA_{1\text{-}RA\text{-}15}$,
  h) —($C_1$–$C_5$ alkyl)—O—$RA_{1\text{-}RA\text{-}12}$, or
  i) —($C_1$–$C_5$ alkyl)—O—$RA_{1\text{-}RA\text{-}15}$;
wherein $RA_2$ and $RA_3$ are defined independently and are independent of and defined the same as $RA_1$;
wherein $G_{1-1}$ is
  a) —NH—C(O)—,
  b) —NH—$SO_2$—,
  c) —NH—C(O)—NH—, or
  d) —$SO_2$—NH—;
wherein $G_{1-2}$ is a) —NH—C(O)—,
b) —C(O)—NH—,
c) —NH—SO$_2$—,
d) —SO$_2$—NH—,
e) —NH—SO$_2$—NH—,
f) —C(O)—O—,
g) —O—C(O)—,
h) —N((C$_{1-6}$ alkyl)—RA$_{1-RA-12}$)—C(O)—,
i) —NH—C(O)—NH,
j) —N((C$_{1-6}$ alkyl)—RA$_{1-RA-12}$)—SO$_2$—, or
k) —N((C$_{0-6}$ alkyl)—(C$_{1-6}$ alkyl))—SO$_2$—;

wherein RA$_2$ and RA$_3$ are defined independently and are the same as RA$_1$;

wherein —RA$_{1-RA-12}$, —RA$_{2-RA-12}$, and —RA$_{3-RA-12}$ are defined independently as phenyl, cyanophenyl, fluorophenyl, naphthyl; or phenyl or naphthyl— substituted with 1 to 3 groups of —(C$_{1-6}$ alkyl), cyano, halo, hydroxy or —(C$_{1-6}$ alkoxy);

wherein —RA$_{1-RA-15}$, —RA$_{2-RA-15}$, and —RA$_{3-RA-15}$ are defined independently as pyridinyl, cyano-pyridinyl, quinolinyl, pyrimidinyl, quinazolinyl, benzimidazolyl, imidazolyl, methyl-imidazolyl, thiazolyl or purinyl; or pyridinyl, quinolinyl, pyrimidinyl, quinazolinyl, benzimidazolyl, imidazolyl, thiazolyl, or purinyl— substituted with 1 to 3 groups of —(C$_{1-6}$ alkyl), cyano, halo, hydroxy or —(C$_{1-6}$ alkoxy);

wherein R$_2$ and R$_3$ can be taken together to form a ring comprised of the following groups,
a) (C$_6$ cycloalkyl),
b) (C$_6$ cycloalkyl)—R$_{3-9}$, or
c) —(C$_2$ alkyl substituted with zero to one R$_{3-9}$)—R$_{23}$—(C$_2$ alkyl substituted with zero to one R$_{3-9}$)—.

wherein RA$_{1-RA-120}$, R$_{2-RA-120}$ and RA$_{3-RA-120}$, are defined independently and are
a) —C$_1$-C$_4$ alkyl,
b) —C$_1$-C$_3$ alkoxy,
c) -dimethylamino,
d) -diethylamino,
e) —CF$_3$,
f) —CN,
g) -halo,
h) —NH$_2$,
i) —OH,
j) —SO$_2$—NH$_2$, or
k) —C(O)—NH$_2$;

wherein RA$_{1-RA-12-AXA}$ or RA$_{1-RA-15-AXA}$ are independent and are,
a) —H
b) -halo,
c) —NO$_2$,
d) —CN,
e) —(C$_{1-10}$ alkyl), substituted with zero (0) to three (3) halo,
f) —(C$_{0-6}$ alkyl)-phenyl, substituted with zero (0) to three (3) halo or hydroxy,
g) —OH,
h) —O—C$_{1-5}$ alkyl,
i) —(C$_{0-6}$ alkyl)—O—(C$_{1-6}$ alkyl), substituted with zero (0) to three (3) halo or hydroxy,
j) —(C$_{0-6}$ alkyl)—O—(C$_{2-7}$ alkenyl), substituted with zero (0) to three (3) halo or hydroxy,
k) —CH(O),
l) —C(O)—(C$_{1-6}$ alkyl),
m) —C(O)OH,
n) —C(O)O—(C$_{1-5}$ alkyl),
o) —C(O)—N(H or C$_{1-6}$ alkyl)$_2$,
p) —NH$_2$,
q) —NH—(C$_{1-6}$ alkyl),
r) -mono or di-(C$_{1-6}$ alkyl)amino,
s) —NH—OH,
t) —NH—C(O)—(C$_{1-3}$ alkyl),
u) —(C$_{0-6}$ alkyl)—NH—C(O)-phenyl,
v) —(C$_{0-6}$ alkyl)—NH—SO$_2$-phenyl,
w) —(C$_{0-6}$ alkyl)—N=N-phenyl, substituted with zero (0) or one (1) —N(C$_1$–C$_3$ alkyl)$_2$, or
x) —SO$_2$-phenyl, substituted with zero (0) to three (3) C$_1$–C$_5$ alkyl;

wherein R$_2$ is
a) —C$_{3-4}$ alkyl,
b) -n-propyl,
c) —(C$_{1-5}$ alkyl)—C$_{3-5}$ cycloalkyl,
d) —(C$_{2-5}$ alkenyl)
e) —(C$_{1-5}$ alkyl)—R$_{2-100}$,
f) —(C$_{1-5}$ alkyl)—R$_{2-500}$, wherein R$_{2-100}$ is independent of and defined the same as R$_{1-100}$ wherein RA$_1$ is RA$_2$;

wherein R$_{2-500}$ is independent of and defined the same as R$_{1-500}$ wherein RA$_1$ is RA$_2$;

wherein RA$_2$ is independent of and defined the same as RA$_1$;

wherein R$_3$ is
a) —(C$_{1-5}$ alkyl),
b) —(CH$_2$—CH=CH$_2$),
c) —(C$_{1-5}$ alkyl)—(C$_{3-5}$ cycloalkyl),
d) —(C$_{1-5}$ alkyl)—O—(CH$_2$CH$_2$O)$_q$—CH$_3$,
e) —(C$_{1-6}$ alkyl)—R$_{3-4}$,
f) —(C$_{2-6}$ alkenyl)—R$_{3-4}$,
g) —R$_{3-100}$,
h) —(C$_{1-4}$ alkyl)—R$_{3-100}$,
i) —H or —(C$_{1-5}$ alkyl),
j) —CH$_2$-RAX
k) -n propyl-RAX,
l) —3-phenylpropyl,
m) —R$_{3-500}$,
n) —CH$_2$-RAX
o) -n propyl-R$_{3-500}$,
p) -benzyl, wherein R$_{3-1}$ is
a) —NH—C(O)—,
b) —NH—SO$_2$—,
c) —NH—CO—NH—, or
d) —SO$_2$—NH—;

wherein, R$_{3-4}$ is
a) —OH,
b) —O—(C$_{1-6}$ alkyl),
c) —C(O)—OH,
d) —C(O)—O—(C$_{1-6}$ alkyl),
e) —(C$_{1-6}$ alkyl),
f) —(C$_{3-6}$ cycloalkyl),
g) —R$_{3-100}$, or
h) —R$_{3-500}$;

wherein R$_{3-6}$ is
a) —OH,
b) —C$_{1-10}$ alkyl,
c) —(C$_{0-6}$ alkyl)—C$_3$-C$_7$ cycloakyl
d) —(C$_{1-6}$ alkyl)—CH=CH$_2$,
e) —(C$_{0-6}$ alkyl)—R$_{3-4}$,
f) —(C$_{1-6}$ alkyl)—R$_{3-100}$, or
g) —(C$_{1-6}$ alkyl)—R$_{3-500}$;

wherein R$_{3-9}$ is
a) —(C$_{1-6}$ alkyl),
b) —(C$_{0-6}$ alkyl)—RA$_{3-RA-12}$, or c) —($C_{0-6}$ alkyl)—$RA_{3-RA-15}$;

wherein $R_{3-100}$ is independent of and defined the same as $R_{1-100}$;

wherein $R_{3-500}$ is independent of and defined the same as $R_{1-500}$;

wherein $RA_3$ is independent of and defined the same as $RA_1$;

wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively, wherein $R_2$ and $R_3$ can be taken together to form a ring comprised of the following groups,
a) ($C_{5-9}$ cycloalkyl),
b) ($C_{5-9}$ cycloalkyl) substituted with one to two —$R_{3-9}$, or
c) —($C_{1-5}$ alkyl substituted with zero to one $R_{3-9}$)—$R_{23}$—($C_{1-5}$ alkyl);

wherein $R_{3-9}$ is
a) —($C_{1-6}$ alkyl),
b) —($C_{0-6}$ alkyl)—$RA_{3-RA-12}$, or
c) —($C_{0-6}$ alkyl)—$RA_{3-RA-15}$;

or
wherein $R_2$ and $R_3$ can be taken together to form a double bond represented by formula 50, shown below,

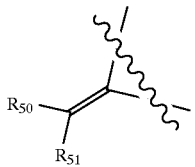

wherein $R_{11}$ is
a) —H,
b) —$C_1$–$C_4$ alkyl,
c) —($RA_{3-RA-12}$), or
d) pharmaceutically acceptable salts, wherein $R_{23}$ is
a) —O—,
b) —C(O)—,
c) —N(H)—,
d) —N($R_{3-9}$)—,
e) —N(C(O)—$R_{3-9}$)—, or
f) —N(C(O)—O—$R_{3-9}$);

wherein $R_{30}$ is
a) -morpholino,
b) -piperidino,
c) -piperazino,
d) -$OR_{40}$,
e) -halo,
f)

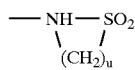

g) —$NR_{40}R_{41}$;

wherein $R_{40}$ and $R_{41}$ are defined independently and are,
a) —H,
b) —$C_1$–$C_4$ alkyl,
c) phenyl, substituted with zero (0) to three (3) $RA_{1-RA-120}$, wherein $R_{42}$ is
a) —$C_1$–$C_4$ alkyl,
b) -phenyl, substituted with zero (0) to three (3) $RA_{1-RA-120}$, or
c) —($C_{0-6}$ alkyl)-phenyl, substituted with zero (0) to three (3) $RA_{1-RA-120}$;

wherein $RA_{2-RA-120}$ and $RA_{3-RA-120}$ are independent of and defined the same as $RA_{1-RA-120}$;

wherein $R_{50}$ and $R_{51}$ are defined independently and are
a) —(H or $C_{1-6}$ alkyl),
b) —($C_{0-6}$ alkyl)—$RA_{3-RA-12}$, or
c) —($C_{0-6}$ alkyl)—$RA_{3-RA-15}$;

wherein AA is an amino acid residue, wherein $P_1$ is hydrogen or a nitrogen protecting group, wherein m and n are independently zero (0) to five (5) inclusive, wherein p and q are independently one (1) to five (5) inclusive, wherein z is one (1) to three (3) inclusive; and pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—N($R_{42}$)$_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$RA_{1-RA-12}$)—$SO_2$—, or —N(($C_{0-6}$ alkyl)—($C_{1-6}$ alkyl))—$SO_2$—.

23. A compound represented by the structure shown in formula 1,

Formula 1

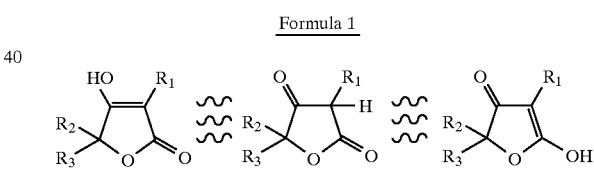

wherein 3 tautomers of the same structure are shown, wherein $R_1$ is —CH($R_{1-1}$)—$R_{1-2}$;

wherein $R_{1-1}$ is
a) —($C_{1-5}$ alkyl),
b) —($C_{3-5}$ cycloalkyl),
c) -cyclopropyl, wherein $R_{1-2}$ is —$R_{1-100}$, or —$R_{1-500}$;

wherein $R_{1-100}$ is
a) phenyl, substituted with zero (0) to three (3) of $RA_1$, wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is a) —H,
b) —($C_{1-5}$ alkyl),
c) —O—($C_{1-5}$ alkyl), wherein $RA_{1-4}$ is any C-terminus substituted amino acid,
j) —N(H)C(O)—$RA_{1-1}$ (para or meta positions),
k) —N(H)C(O)—O—$RA_{1-1}$ (para or meta positions),
l) —N(H)($SO_2$)—$RA_{1-2}$,
m) —N($CH_3$)($SO_2$)—$RA_{1-2}$,
n) —$NO_2$,
o) —$SO_2NH_2$,
p) —($C_{1-3}$ alkyl)—$SO_2$—$RA_{1-RA-12}$,
q) —($C_{1-3}$ alkyl)—$SO_2$—$RA_{1-RA-15}$,
r) -halo, wherein $RA_{1-1}$ is
a) —($C_{1-5}$ alkyl),
b) —($C_{1-5}$ alkyl)—C((H)($NH_2$))—C(O)OH, wherein $RA_{1-2}$ is
a) -RAX
b) —($C_{1-5}$ alkyl)-RAX,
c) —($C_{1-5}$ alkyl)—O-RAX,
d) —$RA_{1-RA-12}$,
e) —$RA_{1-RA-15}$,
f) —($C_1$–$C_5$ alkyl)—$RA_{1-RA-12}$,
g) —($C_1$–$C_5$ alkyl)—$RA_{1-RA-15}$,
h) —($C_1$–$C_5$ alkyl)—O—$RA_{1-RA-12}$, or
i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
a) —NH—C(O)—,
b) —NH—$SO_2$—,
c) —NH—C(O)—NH—, or
d) —$SO_2$—NH—;

wherein $G_{1-2}$ is
a) —NH—C(O)—,
b) —C(O)—NH—,
c) —NH—$SO_2$—,
d) —$SO_2$—NH—,
e) —NH—$SO_2$—NH—,
f) —C(O)—O—,
g) —O—C(O)—,
h) —N(($C_{1-6}$ alkyl)—$RA_{1-RA-12}$)—C(O)—,
i) —NH—C(O)—NH,
j) —N(($C_{1-6}$ alkyl)—$RA_{1-RA-12}$)—$SO_2$—, or
k) —N(($C_{0-6}$ alkyl)—($C_{1-6}$ alkyl))—$SO_2$—;

wherein $RA_2$ and $RA_3$ are defined independently and are the same as $RA_1$;

wherein —$RA_{1-RA-12}$, is phenyl, fluorophenyl or cyanophenyl;

wherein —$RA_{1-RA-15}$, is
1-methyl-4-imidazolyl, 2-pyridinyl, 5-cyano-2-pyridinyl, 2-quinolinyl, 8-quinolinyl, 2-pyrimidinyl, 2-quinazolinyl, 2-benzimidazolyl, 2-imidazolyl, 4-thiazolyl, 6-purinyl;

wherein $R_{2-100}$ and $R_{3-100}$ are defined independently and are,
phenyl,
benzyl, or
phenyl or benzyl, substituted with one, two, or three of the following, —($C_{1-5}$ alkyl), -hydroxy, —O—($C_{1-5}$ alkyl), or -halo;

wherein —$RA_{2-RA-12}$, and —$RA_{3-RA-12}$ are defined independently as phenyl, cyanophenyl, fluorophenyl, naphthyl; or phenyl or naphthyl—substituted with 1 to 3 groups of —($C_{1-6}$ alkyl), cyano, halo, hydroxy or —($C_{1-6}$ alkoxy);

wherein —$RA_{2-RA-15}$, and —$RA_{3-RA-15}$ are defined independently as pyridinyl, cyano-pyridinyl, quinolinyl, pyrimidinyl, quinazolinyl, benzimidazolyl, imidazolyl, methylimidazolyl, thiazolyl or purinyl; or pyridinyl, quinolinyl, pyrimidinyl, quinazolinyl, benzimidazolyl, imidazolyl, thiazolyl, or purinyl—substituted with 1 to 3 groups of —($C_{1-6}$ alkyl), cyano, halo, hydroxy or —($C_{1-6}$ alkoxy);

wherein $R_2$ and $R_3$ can be taken together to form a ring comprised of the following groups,
a) ($C_6$ cycloalkyl),
b) ($C_6$ cycloalkyl)—$R_{3-9}$, or
c) —($C_2$ alkyl substituted with zero to one $R_{3-9}$)—$R_{23}$—($C_2$ alkyl substituted with zero to one $R_{3-9}$)—.

wherein $RA_{1-RA-120}$, $RA_{2-RA-120}$ and $RA_{3-RA-120}$, are defined independently and are
a) —$C_1$–$C_4$ alkyl,
b) —$C_1$–$C_3$ alkoxy,
c) -dimethylamino,
d) -diethylamino,
e) —$CF_3$,
f) —CN,
g) -halo,
h) —$NH_2$,
i) —OH,
j) —$SO_2$—$NH_2$, or
k) —C(O)—$NH_2$;

wherein $RA_{1-RA-12-AXA}$ or $RA_{1-RA-15-AXA}$ are independent and are,
a) —H
b) -halo,
c) —$NO_2$,
d) —CN,
e) —($C_{1-10}$ alkyl), substituted with zero (0) to three (3) halo,
f) —($C_{0-6}$ alkyl)-phenyl, substituted with zero (0) to three (3) halo or hydroxy,
g) —OH,
h) —O—$C_{1-5}$ alkyl,
i) —($C_{0-6}$ alkyl)—O—($C_{1-6}$ alkyl), substituted with zero (0) to three (3) halo or hydroxy,
j) —($C_{0-6}$ alkyl)—O—($C_{2-7}$ alkenyl), substituted with zero (0) to three (3) halo or hydroxy,
k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —$NH_2$,
q) —NH—($C_{1-6}$ alkyl),
r) -mono or di-($C_{1-6}$ alkyl)amino,
s) —NH—OH,
t) —NH—C(O)—($C_{1-3}$ alkyl),
u) —($C_{0-6}$ alkyl)—NH—C(O)-phenyl,
v) —($C_{0-4}$ alkyl)—NH—$SO_2$-phenyl,
w) —($C_{0-6}$ alkyl)—N=N-phenyl, substituted with zero (0) or one (1) —N($C_1$–$C_3$ alkyl)$_2$, or
x) —$SO_2$-phenyl, substituted with zero (0) to three (3) $C_1$–$C_5$ alkyl;

wherein $R_2$ is
a) —$C_{3-4}$ alkyl
b) -n-propyl,
c) —($C_{1-5}$ alkyl)—$C_{3-5}$ cycloalkyl,
d) —($C_{2-5}$ alkenyl)
e) —($C_{1-5}$ alkyl)—$R_{2-100}$,
f) —($C_{1-5}$ alkyl)—$R_{2-500}$, wherein $R_{2-100}$ is independent of and defined the same as $R_{1-100}$ wherein $RA_1$ is $RA_2$;

wherein $R_{2\text{-}500}$ is independent of and defined the same as $R_{1\text{-}500}$ wherein $RA_1$ is $RA_2$;
wherein $RA_2$ is independent of and defined the same as $RA_1$;
wherein $R_3$ is
   a) —($C_{1\text{-}5}$ alkyl),
   b) —($CH_2$—$CH=CH_2$),
   c) —$C_{1\text{-}5}$ alkyl—($C_{3\text{-}5}$ cycloalkyl),
   d) —($C_{1\text{-}5}$ alkyl)—O—($CH_2CH_2O)_q$—$CH_3$,
   e) —($C_{1\text{-}6}$ alkyl)—$R_{3\text{-}4}$,
   f) —($C_{2\text{-}6}$ alkenyl)—$R_{3\text{-}4}$,
   g) —$R_{3\text{-}100}$,
   h) —($C_{1\text{-}4}$ alkyl)—$R_{3\text{-}100}$,
   i) —H or —($C_{1\text{-}5}$ alkyl),
   j) —$CH_2$-RAX
   k) -n propyl-RAX,
   l) —3-phenylpropyl,
   m) —$R_{3\text{-}500}$,
   n) —$CH_2$-RAX
   o) -n propyl-$R_{3\text{-}500}$,
   p) -benzyl,
wherein $R_{3\text{-}1}$ is
   a) —NH—C(O)—,
   b) —NH—$SO_2$—,
   c) —NH—CO—NH—, or
   d) —$SO_2$—NH—;
wherein, $R_{3\text{-}4}$ is
   a) —OH)
   b) —O—($C_{1\text{-}6}$ alkyl),
   c) —C(O)—OH,
   d) —C(O)—O—($C_{1\text{-}6}$ alkyl),
   e) —($C_{1\text{-}6}$ alkyl),
   f) —($C_{3\text{-}6}$ cycloalkyl),
   g) —$R_{3\text{-}100}$, or
   h) —$R_{3\text{-}500}$;
wherein $R_{3\text{-}6}$ is
   a) —OH,
   b) —$C_{1\text{-}10}$ alkyl,
   c) —($C_{0\text{-}6}$ alkyl)—$C_3$-$C_7$ cycloalkyl,
   d) —($C_{1\text{-}6}$ alkyl)—$CH=CH_2$,
   e) —($C_{0\text{-}6}$ alkyl)—$R_{3\text{-}4}$,
   f) —($C_{1\text{-}6}$ alkyl)—$R_{3\text{-}100}$, or
   g) —($C_{1\text{-}6}$ alkyl)—$R_{3\text{-}500}$;
wherein $R_{3\text{-}9}$ is
   a) —($C_{1\text{-}6}$ alkyl),
   b) —($C_{0\text{-}6}$ alkyl)—$RA_{3\text{-}RA\text{-}12}$, or
   c) —($C_{0\text{-}6}$ alkyl)—$RA_{3\text{-}RA\text{-}15}$;
wherein $R_{3\text{-}100}$ is independent of and defined the same as $R_{1\text{-}100}$;
wherein $R_{3\text{-}500}$ is independent of and defined the same as $R_{1\text{-}500}$;
wherein $RA_3$ is independent of and defined the same as $RA_1$;
wherein $RA_{3\text{-}RA\text{-}12}$, $RA_{3\text{-}RA\text{-}15}$, $RA_{3\text{-}RA\text{-}12\text{-}AXA}$ and $RA_{3\text{-}RA\text{-}15\text{-}AXA}$, are all independent of and defined the same as the corresponding $R_1$ variables, which are: $RA_{1\text{-}RA\text{-}12}$, $RA_{1\text{-}RA\text{-}15}$, $RA_{1\text{-}RA\text{-}12\text{-}AXA}$ and $RA_{1\text{-}RA\text{-}15\text{-}AXA}$, respectively,
wherein $R_2$ and $R_3$ can be taken together to form a ring comprised of the following groups,
   a) ($C_{5\text{-}9}$ cycloalkyl),
   b) ($C_{5\text{-}9}$ cycloalkyl) substituted with one to two —$R_{3\text{-}9}$, or
   c) —($C_{1\text{-}5}$ alkyl substituted with zero to one $R_{3\text{-}9}$)—$R_{23}$—($C_{1\text{-}5}$ alkyl);

wherein $R_{3\text{-}9}$ is
   a) —($C_{1\text{-}6}$ alkyl),
   b) —($C_{0\text{-}6}$ alkyl)—$RA_{3\text{-}RA\text{-}12}$, or
   c) —($C_{0\text{-}6}$ alkyl)—$RA_{3\text{-}RA\text{-}15}$;
or
wherein $R_2$ and $R_3$ can be taken together to form a double bond represented by formula 50, shown below,

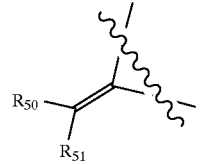

wherein $R_{11}$ is
   a) —H,
   b) —$C_1$-$C_4$ alkyl,
   c) —($RA_{3\text{-}RA\text{-}12}$), or
   d) pharmaceutically acceptable salts,
wherein $R_{23}$ is
   a) —O—,
   b) —C(O)—,
   c) —N(H)—,
   d) —N($R_{3\text{-}9}$)—,
   e) —N(C(O)—$R_{3\text{-}9}$)—, or
   f) —N(C(O)—O—$R_{3\text{-}9}$);
wherein $R_{30}$ is
   a) -morpholino,
   b) -piperidino,
   c) -piperazino,
   d) —$OR_{40}$,
   e) -halo,
   f)

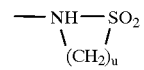

g) —$NR_{40}R_{41}$;
wherein $R_{40}$ and $R_{41}$ are defined independently and are,
   a) —H,
   b) —$C_1$-$C_4$ alkyl,
   c) phenyl, substituted with zero (0) to three (3) $RA_{1\text{-}RA\text{-}120}$,
wherein $R_{42}$ is
   a) —$C_1$-$C_4$ alkyl,
   b) -phenyl, substituted with zero (0) to three (3) $RA_{1\text{-}RA\text{-}120}$, or
   c) —($C_{0\text{-}6}$ alkyl)-phenyl, substituted with zero (0) to three (3) $RA_{1\text{-}RA\text{-}120}$;
wherein $RA_{2\text{-}RA\text{-}120}$ and $RA_{3\text{-}RA\text{-}120}$ are independent of and defined the same as $RA_{1\text{-}RA\text{-}120}$;
wherein $R_{50}$ and $R_{51}$ are defined independently and are
   a) —(H or $C_{1\text{-}6}$ alkyl),
   b) —($C_{0\text{-}6}$ alkyl)—$RA_{3\text{-}RA\text{-}12}$, or
   c) —($C_{0\text{-}6}$ alkyl)—$RA_{3\text{-}RA\text{-}15}$;
wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and pharmaceutically acceptable salts, including bis salts, thereof, with the proviso that when $R_1$ is 1-phenylpropyl and $R_2$ is H, then $R_3$ is not $C_{1-5}$ alkyl, and with the proviso that when $RA_1$ or $RA_3$ is —$G_{1-2}$—($C_{0-6}$ alkyl)—O—$R_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$RA_{1-RA-15}$, —$G_{1-2}$—$N(R_{42})_2$, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$R_{1-RA-12}$)—$SO_2$—, or —N(($C_{0-6}$ alkyl)—($C_{1-6}$ alkyl))—$SO_2$—.

24. A compound represented by the structure shown in formula 1,

Formula 1

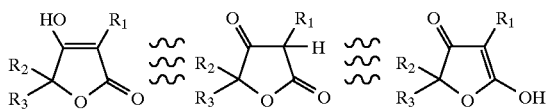

wherein 3 tautomers of the same structure are shown, wherein $R_1$ is —CH($R_{1-1}$)—$R_{1-2}$;

wherein $R_{1-1}$ is
 a) —($C_{1-5}$ alkyl),
 b) —($C_{3-5}$ cycloalkyl),
 c) -cyclopropyl, wherein $R_{1-2}$ is —$R_{1-100}$, or —$R_{1-500}$;

wherein $R_{1-100}$ is
 a) phenyl, substituted with zero (0) to three (3) of $RA_1$, wherein $R_{1-500}$ is
 a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;

wherein $RA_1$ is
 a) —H,
 b) —($C_{1-5}$ alkyl),
 c) —O—($C_{1-5}$ alkyl), wherein $RA_{1-4}$ is any C-terminus substituted amino acid,
 j) —N(H)C(O)—$RA_{1-1}$ (para or meta positions),
 k) —N(H)C(O)—O—$RA_{1-1}$ (para or meta positions),
 l) —N(H)($SO_2$)—$RA_{1-2}$,
 m) —N($CH_3$)($SO_2$)—$RA_{1-2}$,
 n) —$NO_2$,
 o) —$SO_2NH_2$,
 p) —($C_{1-3}$ alkyl)—$SO_2$—$RA_{1-RA-12}$,
 q) —($C_{1-3}$ alkyl)—$SO_2$—$RA_{1-RA-15}$,
 r) -halo, wherein $RA_{1-1}$ is
 a) —($C_{1-5}$ alkyl),
 b) —($C_{1-5}$ alkyl)—C((H)($NH_2$))—C(O)OH, wherein $RA_{1-2}$ is
 a) -RAX,
 b) —($C_{1-5}$ alkyl)-RAX,
 c) —($C_{1-5}$ alkyl)—O-RAX,
 d) —$RA_{1-RA-12}$,
 e) —$RA_{1-RA-15}$,
 f) —($C_1$–$C_5$ alkyl)—$RA_{1-RA-12}$,
 g) —($C_1$–$C_5$ alkyl)—$RA_{1-RA-15}$,
 h) —($C_1$–$C_5$ alkyl)—O—$R_{1-RA-12}$, or
 i) —($C_1$–$C_5$ alkyl)—O—$RA_{1-RA-15}$;

wherein $RA_2$ and $RA_3$ are defined independently and are independent of and defined the same as $RA_1$;

wherein $G_{1-1}$ is
 a) —NH—C(O)—,
 b) —NH—$SO_2$—,
 c) —NH—C(O)—NH—, or
 d) —$SO_2$—NH—;

wherein $G_{1-2}$ is
 a) —NH—C(O)—,
 b) —C(O)—NH—,
 c) —NH—$SO_2$—,
 d) —$SO_2$—NH—,
 e) —NH—$SO_2$—NH—,
 f) —C(O)—O—,
 g) —O—C(O)—,
 h) —N(($C_{1-6}$ alkyl)—$R_{1-RA-12}$)—C(O)—,
 i) —NH—C(O)—NH,
 j) —N(($C_{1-6}$alkyl)—$RA_{1-RA-12}$)—$SO_2$—, or
 k) —N(($C_{0-6}$ alkyl)—($C_{1-6}$ alkyl))—$SO_2$—;

wherein $RA_2$ and $RA_3$ are defined independently and are the same as $RA_1$;

wherein —$RA_{1-RA-12}$, is phenyl, fluorophenyl or cyanophenyl;

wherein —$RA_{1-RA-15}$, is
 1-methyl-4-imidazolyl, 2-pyridinyl, 5-cyano-2-pyridinyl, 2-quinolinyl, 8-quinolinyl, 2-pyrimidinyl, 2-quinazolinyl, 2-benzimidazolyl, 2-imidazolyl, 4-thiazolyl, 6-purinyl;

wherein $R_{2-500}$ and $R_{3-100}$ are defined independently and are,
 a) phenyl, substituted with zero (0) to three (3) $RA_{2-RA-12-AXA}$, or
 b) naphthyl, substituted with zero (0) to three (3) $RA_{2-RA-12-AXA}$;

wherein $R_{2-500}$ and $R_{3-500}$ are defined independently and are,
 a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{2-RA-15-AXA}$;

wherein $RA_{2-RA-12-AXA}$, $RA_{2-RA-15-AXA}$ are are defined independently and are,
 a) —H,
 b) -halo,
 c) —$NO_2$,
 d) —CN,
 e) —$C_{1-10}$ alkyl, substituted with zero (0) to three (3) halo,
 f) —($C_{0-6}$ alkyl)-phenyl, substituted with zero (0) to three (3) hydroxy or halo,
 g) —OH,
 h) —O—$C_{1-5}$ alkyl,
 i) —($C_{0-6}$ alkyl)—O—($C_{1-6}$ alkyl), substituted with zero (0) to three (3) hydroxy or halo,
 j) —($C_{0-6}$ alkyl)—O—($C_{2-7}$ alkenyl), substituted with zero (0) to three (3) hydroxy or halo, k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —NH$_2$,
q) —NH—($C_{1-6}$ alkyl),
r) mono or di-($C_{1-6}$ alkyl)amino,
s) —NH—OH,
t) —NH—C(O)—($C_{1-3}$ alkyl),
u) —($C_{0-6}$ alkyl)—NH—C(O)-phenyl,
v) —($C_{0-6}$ alkyl)—NH—SO$_2$-phenyl,
w) —($C_{0-6}$ alkyl)—N=N-phenyl, substituted by zero (0) or one (1) —N($C_1$–$C_3$ alkyl)$_2$, or
x) —SO$_2$-phenyl, substituted with zero (0) to three (3) $C_1$–$C_5$ alkyl;

wherein $R_2$ and $R_3$ can be taken together to form a ring comprised of the following groups,
a) ($C_{5-9}$ cycloalkyl),
b) ($C_{5-9}$ cycloalkyl) substituted with one $R_{3-9}$,
c) —($C_{1-5}$ alkyl substituted with zero to one $R_{3-9}$)—$R_3$—($C_{1-5}$ alkyl).

wherein $RA_{1-RA-120}$, $RA_{2-RA-120}$ and $RA_{3-RA-120}$, are defined independently and are
a) —$C_1$–$C_4$ alkyl,
b) —$C_1$–$C_3$ alkoxy,
c) -dimethylamino,
d) -diethylamino,
e) —CF$_3$,
f) —CN,
g) -halo,
h) —NH$_2$,
i) —OH,
j) —SO$_2$—NH$_2$, or
k) —C(O)—NH$_2$;

wherein $RA_{1-RA-12-AXA}$ or $RA_{1-RA-15-AXA}$ are independent and are,
a) —H
b) -halo,
c) —NO$_2$,
d) —CN,
e) —($C_{1-10}$ alkyl), substituted with zero (0) to three (3) halo,
f) —($C_{0-6}$ alkyl)-phenyl, substituted with zero (0) to three (3) halo or hydroxy,
g) —OH,
h) —O—$C_{1-5}$ alkyl,
i) —($C_{0-6}$ alkyl)—O—($C_{1-6}$ alkyl), substituted with zero (0) to three (3) halo or hydroxy,
j) —($C_{0-6}$ alkyl)—O—($C_{2-7}$ alkenyl), substituted with zero (0) to three (3) halo or hydroxy,
k) —CH(O),
l) —C(O)—($C_{1-6}$ alkyl),
m) —C(O)OH,
n) —C(O)O—($C_{1-5}$ alkyl),
o) —C(O)—N(H or $C_{1-6}$ alkyl)$_2$,
p) —NH$_2$,
q) —NH—($C_{1-6}$ alkyl),
r) -mono or di —($C_{1-6}$ alkyl)amino,
s) —NH—OH,
t) —NH—C(O)—($C_{1-3}$ alkyl),
u) —($C_{0-6}$ alkyl)—NH—C(O)-phenyl,
v) —($C_{0-6}$ alkyl)—NH—SO$_2$-phenyl,
w) —($C_{0-6}$ alkyl)—N=N-phenyl, substituted with zero (0) or one (1) —N($C_1$–$C_3$ alkyl)$_2$, or
x) —SO$_2$-phenyl, substituted with zero (0) to three (3) $C_1$–$C_5$ alkyl;

wherein $R_2$ is
a) —$C_{3-4}$ alkyl,
b) -n-propyl,
c) —($C_{1-5}$ alkyl)—$C_{3-5}$ cycloalkyl,
d) —($C_{2-5}$ alkenyl)
e) —($C_{1-5}$ alkyl)—$R_{2-100}$,
f) —$C_{1-5}$ alkyl)—$R_{2-500}$,
wherein $R_{2-100}$ is independent of and defined the same as $R_{1-100}$ wherein $RA_1$ is $RA_2$;
wherein $R_{2-500}$ is independent of and defined the same as $R_{1-500}$ wherein $RA_1$ is $RA_2$;
wherein $RA_2$ is independent of and defined the same as $RA_1$;
wherein $R_3$ is
a) —($C_{1-5}$ alkyl),
b) —(CH$_2$—CH=CH$_2$),
c) —($C_{1-5}$ alkyl)—($C_{3-5}$ cycloalkyl),
d) —($C_{1-5}$ alkyl)—O—(CH$_2$CH$_2$O)$_q$—CH$_3$,
e) —($C_{1-6}$ alkyl)—$R_{3-4}$,
f) —($C_{2-6}$ alkenyl)—$R_{3-4}$,
g) —$R_{3-100}$,
h) —($C_{1-4}$ alkyl)—$R_{3-100}$,
i) —H or —($C_{1-5}$ alkyl),
j) —CH$_2$-RAX,
k) -n propyl-RAX,
l) —3-phenylpropyl,
m) —$R_{3-500}$,
n) —CH$_2$-RAX
o) -n propyl-$R_{3-500}$,
p) -benzyl,
wherein $R_{3-1}$ is
a) —NH—C(O)—,
b) —NH—SO$_2$—,
c) —NH—CO—NH—, or
d) —SO$_2$—NH—;
wherein, $R_{3-4}$ is
a) —OH,
b) —O—($C_{1-6}$ alkyl),
c) —C(O)—OH,
d) —C(O)—O—($C_{1-6}$ alkyl),
e) —($C_{1-6}$ alkyl),
f) —($C_{3-6}$ cycloalkyl),
g) —$R_{3-100}$, or
h) —$R_{3-500}$;
wherein $R_{3-6}$ is
a) —OH,
b) —$C_{1-10}$ alkyl,
c) —($C_{0-6}$ alkyl)—$C_3$–$C_7$ cycloalkyl,
d) —($C_{1-6}$ alkyl)—CH=CH$_2$,
e) —($C_{0-6}$ alkyl)—$R_{3-4}$,
f) —($C_{1-6}$ alkyl)—$R_{3-100}$, or
g) —($C_{1-6}$ alkyl)—$R_{3-500}$;
wherein $R_{3-9}$ is
a) —($C_{1-6}$ alkyl),
b) —($C_{0-6}$ alkyl)—$RA_{3-RA-12}$, or
c) —($C_{0-6}$ alkyl)—$RA_{3-RA-15}$;
wherein $R_{3-100}$ is independent of and defined the same as $R_{1-100}$;
wherein $R_{3-500}$ is independent of and defined the same as $R_{1-500}$;
wherein $RA_3$ is independent of and defined the same as $RA_1$;
wherein $RA_{3-RA-12}$, $RA_{3-RA-15}$, $RA_{3-RA-12-AXA}$ and $RA_{3-RA-15-AXA}$, are all independent of and defined the same as the corresponding $R_1$ variables, which are: $RA_{1-RA-12}$, $RA_{1-RA-15}$, $RA_{1-RA-12-AXA}$ and $RA_{1-RA-15-AXA}$, respectively, wherein R₂ and R₃ can be taken together to form a ring comprised of the following groups,
a) ($C_{5-9}$ cycloalkyl),
b) ($C_{5-9}$ cycloalkyl) substituted with one to two —$R_{3-9}$, or
c) —($C_{1-5}$ alkyl substituted with zero to one $R_{3-9}$)—$R_{23}$—($C_{1-5}$ alkyl);

wherein $R_{3-9}$ is
a) —($C_{1-6}$ alkyl),
b) —($C_{0-6}$ alkyl)—$RA_{3-RA-12}$, or
c) —($C_{0-6}$ alkyl)—$RA_{3-RA-15}$;
or
wherein R₂ and R₃ can be taken together to form a double bond represented by formula 50, shown below,

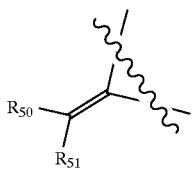

wherein $R_{11}$ is
a) —H,
b) —$C_1$–$C_4$ alkyl,
c) —($RA_{3-RA-12}$), or
d) pharmaceutically acceptable salts, wherein $R_{23}$ is
a) —O—,
b) —C(O)—,
c) —N(H)—,
d) —N($R_{3-9}$)—,
e) —N(C(O)—$R_{3-9}$)—, or
f) —N(C(O)—O—$R_{3-9}$);

wherein $R_{30}$ is
a) -morpholino,
b) -piperidino,
c) -piperazino,
d) —$OR_{40}$,
e) -halo,
f)

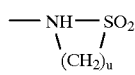

g) —$NR_{40}R_{41}$;
wherein $R_{40}$ and $R_{41}$ are defined independently and are,
a) —H,
b) —$C_1$–$C_4$ alkyl,
c) phenyl, substituted with zero (0) to three (3) $RA_{1-RA-120}$, wherein $R_{42}$ is
a) —$C_1$–$C_4$ alkyl,
b) -phenyl, substituted with zero (0) to three (3) $RA_{1-RA-120}$, or
c) —($C_{0-6}$ alkyl)-phenyl, substituted with zero (0) to three (3) $RA_{1-RA-120}$;

wherein $RA_{2-RA-120}$ and $RA_{3-RA-120}$ are independent of and defined the same as $RA_{1-RA-120}$;

wherein $R_{50}$ and $R_{51}$ are defined independently and are
a) —(H or $C_{1-6}$ alkyl),
b) —($C_{0-6}$ alkyl)—$RA_{3-RA-12}$, or
c) —($C_{0-6}$ alkyl)—$RA_{3-RA-15}$;

wherein AA is an amino acid residue,
wherein $P_1$ is hydrogen or a nitrogen protecting group,
wherein m and n are independently zero (0) to five (5) inclusive,
wherein p and q are independently one (1) to five (5) inclusive,
wherein z is one (1) to three (3) inclusive; and
pharmaceutically acceptable salts, including bis salts, thereof,
with the proviso that when $R_1$ is 1-phenylpropyl and $R_2$ is H, then $R_3$ is not $C_{1-5}$ alkyl, and
with the proviso that when $RA_1$ or $RA_3$ is —$G_{1-2}$—($C_{0-6}$ alkyl)—O—$RA_{1-RA-12}$, —($C_{0-6}$ alkyl)—$G_{1-2}$—($C_{0-6}$ alkyl)—O—($C_{0-6}$ alkyl), —($C_{0-6}$ alkyl)—$G_{1-2}$—O—($C_{1-6}$ alkyl)—$RA_{1-RA-12}$, —($C_{0-6}$ alkyl)—$G_{1-2}$—O—($C_{1-6}$ alkyl)—$R_{1-RA-15}$, —$G_{1-2}$—N($R_{42}$)₂, or —$G_{1-2}$—$NH_2$, then $G_{1-2}$ is NOT, —C(O)—NH—, —NH—$SO_2$—, —$SO_2$—NH—, —NH—$SO_2$—NH—, —C(O)—O—, —NH—C(O)—NH, —N(($C_{1-6}$ alkyl)—$R_{1-RA-12}$)—$SO_2$—, or —N(($C_{0-6}$ alkyl)—($C_{1-6}$ alkyl))—$SO_2$—.

25. A compound represented by the structure shown in formula 1,

Formula 1

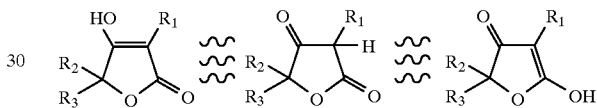

wherein 3 tautomers of the same structure are shown,
wherein $R_1$ is —CH($R_{1-1}$)—$R_{1-2}$;
wherein $R_{1-1}$ is
a) —($C_{1-5}$ alkyl),
b) —($C_{3-5}$ cycloalkyl),
c) -cyclopropyl,
wherein $R_{1-2}$ is —$R_{1-100}$, or —$R_{1-500}$;
wherein $R_{1-100}$ is
a) phenyl, substituted with zero (0) to three (3) of $RA_1$,
wherein $R_{1-500}$ is
a 5- or 6-membered saturated or unsaturated ring containing from one (1) to four (4) heteroatoms selected from the group consisting of nitrogen, oxygen and sulfur; and substituted with zero (0) to three (3) $RA_1$; and including any bicyclic group in which any of the above heterocyclic rings is fused to a benzene ring, $C_3$–$C_8$ cycloalkyl, or another heterocycle; and substituted with zero (0) to three (3) $RA_1$; and if chemically feasible, the nitrogen and sulfur atoms may be in the oxidized forms;
wherein $RA_1$ is
a) —H,
b) —($C_{1-5}$ alkyl),
c) —O—($C_{1-5}$ alkyl),
wherein $RA_{1-4}$ is any C-terminus substituted amino acid,
j) —N(H)C(O)—$RA_{1-1}$ (para or meta positions),
k) —N(H)C(O)—O—$RA_{1-1}$ (para or meta positions),
l) —N(H)($SO_2$)—$RA_{1-2}$,
m) —N($CH_3$)($SO_2$)—$RA_{1-2}$,
n) —$NO_2$,
o) —$SO_2NH_2$,
p) —($C_{1-3}$ alkyl)—$SO_2$—$RA_{1-RA-12}$,
q) —($C_{1-3}$ alkyl)—$SO_2$—$RA_{1-RA-15}$, r) -halo,
wherein $RA_{1-1}$ is
  a) —($C_{1-5}$ alkyl),
  b) —($C_{1-5}$ alkyl)—C((H)(NH$_2$))—C(O)OH,
wherein $RA_{1-2}$ is
  a) -RAX,
  b) —($C_{1-5}$ alkyl)-RAX,
  c) —($C_{1-5}$ alkyl)—O-RAX,
  d) —$RA_{1\text{-}RA\text{-}12}$,
  e) —$RA_{1\text{-}RA\text{-}15}$,
  f) —($C_1$–$C_5$ alkyl)—$RA_{1\text{-}RA\text{-}12}$,
  g) —($C_{1-5}$ alkyl)—$RA_{1\text{-}RA\text{-}15}$,
  h) —($C_1$–$C_5$ alkyl)—O—$RA_{1\text{-}RA\text{-}12}$, or
  i) —($C_1$–$C_5$ alkyl)—O—$R_{1\text{-}RA\text{-}15}$;
wherein $RA_2$ and $RA_3$ are defined independently and are independent of and defined the same as $RA_1$;
wherein $G_{1-1}$ is
  a) —NH—C(O)—,
  b) —NH—SO$_2$—,
  c) —NH—C(O)—NH—, or
  d) —SO$_2$—NH—;
wherein $G_{1-2}$ is
  a) —NH—C(O)—,
  b) —C(O)—NH—,
  c) —NH—SO$_2$—,
  d) —SO$_2$—NH—,
  e) —NH—SO$_2$—NH—,
  f) —C(O)—O—,
  g) —O—C(O)—,
  h) —N(($C_{1-6}$ alkyl)—$RA_{1\text{-}RA\text{-}12}$)—C(O)—,
  i) —NH—C(O)—NH,
  j) —N(($C_{1-6}$ alkyl)—$R_{1\text{-}RA\text{-}12}$)—SO$_2$—, or
  k) —N(($C_{0-6}$ alkyl)—($C_{1-6}$ alkyl))—SO$_2$—;
wherein $RA_2$ and $RA_3$ are defined independently and are the same as $RA_1$; wherein —$RA_{1\text{-}RA\text{-}12}$, is phenyl, fluorophenyl or cyanophenyl;
wherein —$RA_{1\text{-}RA\text{-}15}$, is
  1-methyl-4-imidazolyl, 2-pyridinyl, 5-cyano-2-pyridinyl, 2-quinolinyl, 8-quinolinyl, 2-pyrimidinyl, 2-quinazolinyl, 2-benzimidazolyl, 2-imidazolyl, 4-thiazolyl, 6-purinyl;
wherein $R_{2\text{-}100}$ and $R_{3\text{-}100}$ are defined independently and are,
  a) phenyl, substituted with zero (0) to three (3) $RA_{2\text{-}RA\text{-}12\text{-}AXA}$, or
  b) naphthyl, substituted with zero (0) to three (3) $RA_{2\text{-}RA\text{-}12\text{-}AXA}$;
wherein $R_{2\text{-}500}$ and $R_{3\text{-}500}$ are defined independently and are,
  a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and substituted with zero (0) to three (3) $RA_{2\text{-}RA\text{-}15\text{-}AXA}$;
wherein $RA_{2\text{-}RA\text{-}12\text{-}AXA}$ or $RA_{2\text{-}RA\text{-}15\text{-}AXA}$ are are defined independently and are,
  a) —H,
  b) -halo,
  c) —NO$_2$,
  d) —CN,
  e) —$C_{1-10}$ alkyl, substituted with zero (0) to three (3) halo,
  f) —($C_{0-6}$ alkyl)-phenyl, substituted with zero (0) to three (3) hydroxy or halo,
  g) —OH,
  h) —O—$C_{1-5}$ alkyl,
  i) —($C_{0-6}$ alkyl)—O—($C_{1-6}$ alkyl), substituted with zero (0) to three (3) hydroxy or halo,
  j) —($C_{0-6}$ alkyl)—O—($C_{2-7}$ alkenyl), substituted with zero (0) to three (3) hydroxy or halo,
  k) —CH(O),
  l) —C(O)—($C_{1-6}$ alkyl),
  m) —C(O)OH,
  n) —C(O)O—($C_{1-5}$ alkyl),
  o) —C(O)—N(H or $C_{1-6}$ alkyl)$_2$,
  p) —NH$_2$,
  q) —NH—($C_{1-6}$ alkyl),
  r) mono or di —($C_{1-6}$ alkyl)amino,
  s) —NH—OH,
  t) —NH—C(O)—($C_{1-3}$ alkyl),
  u) —($C_{0-6}$ alkyl)—NH—C(O)-phenyl,
  v) —($C_{0-4}$ alkyl)—NH—SO$_2$-phenyl,
  w) —($C_{0-6}$ alkyl)—N=N-phenyl, substituted by zero (0) or one (1) —N($C_1$–$C_3$ alkyl)$_2$, or
  x) —SO$_2$-phenyl, substituted with zero (0) to three (3) $C_1$–$C_5$ alkyl;
wherein $R_2$ and $R_3$ can be taken together to form a ring comprised of the following groups,
  a) ($C_{5-9}$ cycloalkyl),
  b) ($C_{5-9}$ cycloalkyl) substituted with one $R_{3-9}$,
  c) —($C_{1-5}$ alkyl substituted with zero to one $R_{3-9}$)—$R_{23}$—($C_{1-5}$ alkyl).
wherein $RA_{1\text{-}RA\text{-}120}$, $RA_{2\text{-}RA\text{-}120}$ and $RA_{3\text{-}RA\text{-}120}$, are defined independently and are
  a) —$C_1$–$C_4$ alkyl,
  b) —$C_1$–$C_3$ alkoxy,
  c) -dimethylamino,
  d) -diethylamino,
  e) —CF$_3$,
  f) —CN,
  g) -halo,
  h) —NH$_2$,
  i) —OH,
  j) —SO$_2$—NH$_2$, or
  k) —C(O)—NH$_2$;
wherein $RA_{1\text{-}RA\text{-}12\text{-}AXA}$ or $RA_{1\text{-}RA\text{-}15\text{-}AXA}$ are independent and are,
  a) —H
  b) -halo,
  c) —NO$_2$,
  d) —CN,
  e) —($C_{1-10}$ alkyl), substituted with zero (0) to three (3) halo,
  f) —($C_{0-6}$ alkyl)-phenyl, substituted with zero (0) to three (3) halo or hydroxy,
  g) —OH,
  h) —O—$C_{1-5}$ alkyl,
  i) —($C_{0-6}$ alkyl)—O—($C_{1-6}$ alkyl), substituted with zero (0) to three (3) halo or hydroxy,
  j) —($C_{0-6}$ alkyl)—O—($C_{2-7}$ alkenyl), substituted with zero (0) to three (3) halo or hydroxy,
  k) —CH(O),
  l) —C(O)—($C_{1-6}$ alkyl),
  m) —C(O)OH,
  n) —C(O)O—($C_{1-5}$ alkyl),
  o) —C(O)—N(H or $C_{1-6}$ alkyl)$_2$,
  p) —NH$_2$,
  q) —NH—($C_{1-6}$ alkyl),
  r) -mono or di —($C_{1-6}$ alkyl)amino,

225 s) —NH—OH,
t) —NH—C(O)—(C$_{1-3}$ alkyl),
u) —(C$_{0-6}$ alkyl)—NH—C(O)-phenyl,
v) —(C$_{0-6}$ alkyl)—NH—SO$_2$-phenyl,
w) —(C$_{0-6}$alkyl)—N=N-phenyl, substituted with zero (0) or one (1) —N(C$_1$–C$_3$ alkyl)$_2$, or
x) —SO$_2$-phenyl, substituted with zero (0) to three (3) C$_1$–C$_5$ alkyl;

wherein R$_2$ is
a) —C$_{3-4}$ alkyl,
b) -n-propyl,
c) —(C$_{1-5}$ alkyl)—C$_{3-5}$ cycloalkyl,
d) —(C$_{2-5}$ alkenyl)
e) —(C$_{1-5}$ alkyl)—R$_{2-100}$,
f) —(C$_{1-5}$ alkyl)—R$_{2-500}$, wherein R$_{2-100}$ is independent of and defined the same as R$_{1-100}$ wherein RA$_1$ is RA$_2$;
wherein R$_{2-500}$ is independent of and defined the same as R$_{1-500}$ wherein RA$_1$ is RA$_2$;
wherein RA$_2$ is independent of and defined the same as RA$_1$;

wherein R$_3$ is
a) —(C$_{1-5}$ alkyl),
b) —(CH$_2$—CH=CH$_2$),
c) —C$_{1-5}$ alkyl)—(C$_{3-5}$ cycloalkyl),
d) —(C$_{1-5}$ alkyl)—O—(CH$_2$CH$_2$O)$_q$—CH$_3$,
e) —(C$_{1-6}$ alkyl)—R$_{3-4}$,
f) —(C$_{1-6}$ alkenyl)—R$_{3-4}$,
g) —R$_{3-100}$,
h) —(C$_{1-4}$ alkyl)—R$_{3-100}$,
i) —H or —(C$_{1-5}$ alkyl),
j) —CH$_2$-RAX
k) -n propyl-RAX,
l) —3-phenylpropyl,
m) —R$_{3-500}$,
n) —CH$_2$-RAX
o) -n propyl-R$_{3-500}$,
p) -benzyl, wherein R$_{3-1}$ is
a) —NH—C(O)—,
b) —NH—SO$_2$—,
c) —NH—CO—NH—, or
d) —SO$_2$—NH—;
e) —(C$_{1-5}$ alkyl),
f) —(C$_{2-5}$ alkenyl),
g) —(C$_{1-2}$ alkyl)—(C$_{3-7}$ cycloalkyl),
h) —(C$_{1-2}$ alkyl)—R$_{3-100}$, or
i) —(C$_{1\ 2}$ alkyl)—R$_{3-500}$;

wherein, R$_{3-4}$ is
a) —OH,
b) —O—(C$_{1-6}$ alkyl),
c) —C(O)—OH,
d) —C(O)—O—(C$_{1-6}$ alkyl),
e) —(C$_{1-6}$ alkyl),
f) —(C$_{3-4}$ cycloalkyl),
g) —R$_{3-100}$, or
h) —R$_{3-500}$;

wherein R$_{3-6}$ is
a) —OH,
b) —C$_{1-10}$ alkyl,
c) —(C$_{0-6}$ alkyl)—C$_3$–C$_7$ cycloalkyl,
d) —(C$_{1-4}$ alkyl)—CH=CH$_2$,
e) —(C$_{0-6}$ alkyl)—R$_{3-4}$,
f) —(C$_{1-6}$ alkyl)—R$_{3-100}$, or
g) —(C$_{1-4}$ alkyl)—R$_{3-500}$;

wherein R$_{3-9}$ is

226 a) —(C$_{1-6}$ alkyl),
b) —(C$_{0-6}$ alkyl)—RA$_{3\text{-}RA\text{-}12}$, or
c) —(C$_{0-4}$ alkyl)—RA$_{3\text{-}RA\text{-}15}$;

wherein R$_{3-100}$ is independent of and defined the same as R$_{1-100}$;

wherein R$_{3-500}$ is independent of and defined the same as R$_{1-500}$;

wherein RA$_3$ is independent of and defined the same as RA$_1$;

wherein RA$_{3\text{-}RA\text{-}12}$, RA$_{3\text{-}RA\text{-}15}$, RA$_{3\text{-}RA\text{-}12\text{-}AXA}$ and RA$_{3\text{-}RA\text{-}15\text{-}AXA}$, are all independent of and defined the same as the corresponding R$_1$ variables, which are: RA$_{1\text{-}RA\text{-}12}$, RA$_{1\text{-}RA\text{-}15}$, RA$_{1\text{-}RA\text{-}12\text{-}AXA}$ and RA$_{1\text{-}RA\text{-}15\text{-}AXA}$, respectively, wherein R$_{2-100}$ and R$_{3-100}$ are defined independently and are,
phenyl,
benzyl, or
phenyl or benzyl, substituted with one, two, or three of the following, —(C$_{1-5}$ alkyl), -hydroxy, —O—(C$_{1-5}$ alkyl), or -halo;

or wherein R$_2$ and R$_3$ can be taken together to form a ring comprised of the following groups,
a) (C$_6$ cycloalkyl),
b) (C$_6$ cycloalkyl) substituted with one R$_{3-9}$, or
c) —(C$_2$ alkyl substituted with zero to one R$_{3-9}$)—R$_{23}$—(C$_2$ alkyl);

wherein R$_{3-9}$ is
a) —(C$_{1-6}$ alkyl),
b) —(C$_{0-6}$ alkyl)—RA$_{3\text{-}RA\text{-}12}$, or
c) —(C$_{0-6}$ alkyl)—RA$_{3\text{-}RA\text{-}15}$;

or wherein R$_2$ and R$_3$ can be taken together to form a double bond represented by formula 50, shown below,

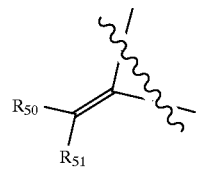

wherein R$_{11}$ is
a) —H,
b) —C$_1$–C$_4$ alkyl,
c) —(RA$_{3\text{-}RA\text{-}12}$), or
d) pharmaceutically acceptable salts, wherein R$_{23}$ is
a) —O—,
b) —C(O)—,
c) —N(H)—,
d) —N(R$_{3-9}$)—,
e) —N(C(O)—R$_{3-9}$)—, or
f) —N(C(O)—O—R$_{3-9}$);

wherein R$_{30}$ is
a) -morpholino,
b) -piperidino,
c) -piperazino,
d) -OR$_{40}$,
e) -halo, f)

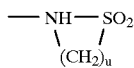

g) —NR$_{40}$R$_{41}$;

wherein R$_{40}$ and R$_{41}$ are defined independently and are,
a) —H,
b) —C$_1$–C$_4$ alkyl,
c) phenyl, substituted with zero (0) to three (3) RA$_{1\text{-}RA\text{-}120}$, wherein R$_4$ is
a) —C$_1$–C$_4$ alkyl,
b) -phenyl, substituted with zero (0) to three (3) RA$_{1\text{-}RA\text{-}120}$, or
c) —(C$_{0\text{-}6}$ alkyl)-phenyl, substituted with zero (0) to three (3) RA$_{1\text{-}RA\text{-}120}$;

wherein RA$_{2\text{-}RA\text{-}120}$ and RA$_{3\text{-}RA\text{-}120}$ are independent of and defined the same as RA$_{1\text{-}RA\text{-}120}$;

wherein R$_{50}$ and R$_{51}$ are defined independently and are
a) —(H or C$_{1\text{-}6}$ alkyl),
b) —(C$_{0\text{-}6}$ alkyl)—RA$_{3\text{-}RA\text{-}12}$, or
c) —(C$_{0\text{-}6}$ alkyl)—RA$_{3\text{-}RA\text{-}15}$;

wherein AA is an amino acid residue, wherein P$_1$ is hydrogen or a nitrogen protecting group, wherein m and n are independently zero (0) to five (5) inclusive, wherein p and q are independently one (1) to five (5) inclusive, wherein z is one (1) to three (3) inclusive; and pharmaceutically acceptable salts, including bis salts, thereof, with the proviso that when R$_1$ is 1-phenylpropyl and R$_2$ is H, then R$_3$ is not C$_{1\text{-}5}$ alkyl, and with the proviso that when RA$_1$ or RA$_3$ is —G$_{1\text{-}2}$—(C$_{0\text{-}6}$ alkyl)—O—RA$_{1\text{-}RA\text{-}12}$, —(C$_{0\text{-}6}$ alkyl)—G$_{1\text{-}2}$—(C$_{0\text{-}6}$ alkyl)—O—(C$_{0\text{-}6}$ alkyl), —(C$_{0\text{-}6}$ alkyl)—G$_{1\text{-}2}$—O—(C$_{1\text{-}6}$ alkyl)—R$_{1\text{-}RA\text{-}12}$, —(C$_{0\text{-}6}$ alkyl)—G$_{1\text{-}2}$—O—(C$_{1\text{-}6}$ alkyl)—RA$_{1\text{-}RA\text{-}15}$, —G$_{1\text{-}2}$—N(R$_{42}$)$_2$, or —G$_{1\text{-}2}$—NH$_2$, then G$_{1\text{-}2}$ is NOT, —C(O)—NH—, —NH—SO$_2$—, —SO$_2$—NH—, —NH—SO$_2$—NH—, —C(O)—O—, —NH—C(O)—NH, —N((C$_{1\text{-}6}$ alkyl)—RA$_{1\text{-}RA\text{-}12}$)—SO$_2$—, or —N((C$_{0\text{-}6}$ alkyl)—(C$_{1\text{-}6}$ alkyl))—SO$_2$—.

\* \* \* \* \*